US008637497B2

(12) United States Patent
Yao et al.

(10) Patent No.: US 8,637,497 B2
(45) Date of Patent: Jan. 28, 2014

(54) AZA SPIRO ALKANE DERIVATIVES AS INHIBITORS OF METALLOPROTEASES

(75) Inventors: Wenqing Yao, Kennett Square, PA (US);
Jincong Zhuo, Boothwyn, PA (US);
Meizhong Xu, Hockessin, DE (US);
Fenglei Zhang, Lansdale, PA (US);
Brian Metcalf, Moraga, CA (US)

(73) Assignee: Incyte Corporation, Wilmington, DE (US)

( * ) Notice: Subject to any disclaimer, the term of this patent is extended or adjusted under 35 U.S.C. 154(b) by 92 days.

(21) Appl. No.: 13/184,860

(22) Filed: Jul. 18, 2011

(65) Prior Publication Data
US 2011/0288068 A1 Nov. 24, 2011

Related U.S. Application Data

(63) Continuation of application No. 12/327,313, filed on Dec. 3, 2008, now Pat. No. 8,039,471, which is a continuation of application No. 10/831,265, filed on Apr. 23, 2004, now Pat. No. 7,723,349.

(60) Provisional application No. 60/466,159, filed on Apr. 24, 2003, provisional application No. 60/534,501, filed on Jan. 6, 2004.

(51) Int. Cl.
*A61K 31/03* (2006.01)
*A61K 31/44* (2006.01)
*A61K 31/50* (2006.01)
*A61K 31/4965* (2006.01)
*A61K 31/40* (2006.01)
*C07D 241/04* (2006.01)
*C07D 221/20* (2006.01)
*C07D 471/20* (2006.01)
*C07D 209/54* (2006.01)

(52) U.S. Cl.
USPC ............... 514/210.18; 514/250; 514/253.06; 514/255.01; 514/278; 514/409; 544/230; 546/15; 546/16; 546/17; 548/407

(58) Field of Classification Search
USPC .......... 514/210.18, 253.13, 278, 250, 253.06, 514/255.01, 409; 544/230; 546/15, 16, 17; 548/407
See application file for complete search history.

(56) References Cited

U.S. PATENT DOCUMENTS

| | | | |
|---|---|---|---|
| 4,879,315 A | 11/1989 | Magarian et al. |
| 4,973,593 A | 11/1990 | Brubaker |
| 5,157,034 A | 10/1992 | Bright et al. |
| 5,182,288 A | 1/1993 | Murray et al. |
| 5,494,919 A | 2/1996 | Morriello et al. |
| 5,536,727 A | 7/1996 | Witzel et al. |
| 5,610,162 A | 3/1997 | Witzel et al. |
| 5,763,471 A | 6/1998 | Fourtillan et al. |
| 5,872,152 A | 2/1999 | Brown |
| 5,892,112 A | 4/1999 | Levy et al. |
| 5,945,430 A | 8/1999 | Doll et al. |
| 5,968,795 A | 10/1999 | Dixon et al. |
| 5,972,925 A | 10/1999 | Hohlweg et al. |
| 6,071,901 A | 6/2000 | Dorwald et al. |
| 6,110,913 A | 8/2000 | Dorwald et al. |
| 6,114,300 A | 9/2000 | Bourdin et al. |
| 6,235,764 B1 | 5/2001 | Larson et al. |
| 6,239,148 B1 | 5/2001 | Dorwald et al. |
| 6,268,379 B1 | 7/2001 | Xue et al. |
| 6,372,754 B1 | 4/2002 | Kulagowski |
| 6,387,371 B1 | 5/2002 | Hudziak et al. |
| 6,414,130 B1 | 7/2002 | Doherty et al. |
| 6,429,213 B1 | 8/2002 | Xue et al. |
| 6,455,472 B1 | 9/2002 | Fischer et al. |
| 6,482,838 B2 | 11/2002 | Pratt |
| 6,489,352 B2 | 12/2002 | Bryans et al. |
| 6,500,847 B2 | 12/2002 | Van Zandt et al. |
| 6,528,538 B1 | 3/2003 | Zeiller et al. |

(Continued)

FOREIGN PATENT DOCUMENTS

| | | |
|---|---|---|
| CA | 2114178 | 7/1994 |
| EA | 006815 | 4/2006 |

(Continued)

OTHER PUBLICATIONS

Amour et al., "The in Vitro Activity of ADAM-10 is Inhibited by TIMP-1 and TIMP-3," *FEBS Letters*, 473(3):275-279, 2000.

(Continued)

*Primary Examiner* — James O Wilson
*Assistant Examiner* — Ebenezer O Sackey
(74) *Attorney, Agent, or Firm* — Fish & Richardson P.C.

(57) ABSTRACT

The present invention provides a compound of Formula I or Formula II:

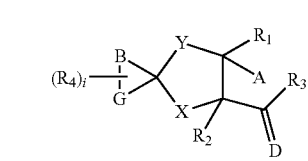

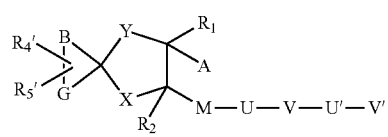

enantiomer, diastereomer, prodrug, solvate, metabolite, or pharmaceutically acceptable salt thereof, wherein constituent variables are provided herein. The compounds of Formula I and II are modulators of metalloproteases and are useful in treating diseases associated with metalloprotease activity such as arthritis, cancer, cardiovascular disorders, skin disorders, inflammation and allergic conditions.

10 Claims, No Drawings

(56) References Cited

U.S. PATENT DOCUMENTS

| | | | |
|---|---|---|---|
| 6,593,344 | B1 | 7/2003 | Biedermann et al. |
| 6,608,104 | B2 | 8/2003 | Noe |
| 6,653,312 | B1 | 11/2003 | Auvin et al. |
| 6,713,487 | B2 | 3/2004 | Yu et al. |
| 6,727,247 | B2 | 4/2004 | Flohr et al. |
| 6,858,626 | B2 | 2/2005 | Xue et al. |
| 2002/0182702 | A1 | 12/2002 | Ruben et al. |
| 2004/0006073 | A1 | 1/2004 | Dooley |
| 2004/0034019 | A1 | 2/2004 | Tomlinson et al. |
| 2004/0247602 | A1 | 12/2004 | Friedman et al. |
| 2005/0113344 | A1 | 5/2005 | Li et al. |
| 2005/0250789 | A1 | 11/2005 | Burns et al. |
| 2007/0117809 | A1 | 5/2007 | Fridman |
| 2007/0280943 | A1 | 12/2007 | Friedman et al. |

FOREIGN PATENT DOCUMENTS

| | | |
|---|---|---|
| EA | 006964 | 6/2006 |
| EP | 0 431 197 | 6/1991 |
| EP | 550025 | 7/1993 |
| EP | 456183 | 10/1995 |
| EP | 937459 | 8/1999 |
| EP | 1415986 | 5/2004 |
| GB | 908986 | 10/1962 |
| GB | 1 596 030 | 8/1981 |
| JP | A-53-84947 | 7/1978 |
| JP | A-3-287562 | 12/1991 |
| JP | 07300460 | 11/1995 |
| JP | A-10-502067 | 2/1998 |
| WO | WO 93/23040 | 11/1993 |
| WO | WO 93/23041 | 11/1993 |
| WO | WO 94/17038 | 8/1994 |
| WO | WO 96/00727 | 1/1996 |
| WO | WO 96/11924 | 4/1996 |
| WO | WO 96/31470 | 10/1996 |
| WO | WO 96/31473 | 10/1996 |
| WO | WO 96/31474 | 10/1996 |
| WO | WO 96/31498 | 10/1996 |
| WO | WO 96/31500 | 10/1996 |
| WO | WO 96/31503 | 10/1996 |
| WO | WO 96/33176 | 10/1996 |
| WO | WO 98/08850 | 3/1998 |
| WO | WO 98/51665 | 11/1998 |
| WO | WO 98/57932 | 12/1998 |
| WO | WO 99/58528 | 11/1999 |
| WO | WO 99/65867 | 12/1999 |
| WO | WO 00/08046 | 2/2000 |
| WO | WO 00/17158 | 3/2000 |
| WO | WO 00/32193 | 6/2000 |
| WO | WO 00/35451 | 6/2000 |
| WO | WO 00/35453 | 6/2000 |
| WO | WO 00/35876 | 6/2000 |
| WO | WO 00/43383 | 7/2000 |
| WO | WO 00/55143 | 9/2000 |
| WO | WO 00/75137 | 12/2000 |
| WO | WO 01/08669 | 2/2001 |
| WO | WO 01/00616 | 4/2001 |
| WO | WO 01/46166 | 6/2001 |
| WO | WO 01/58891 | 8/2001 |
| WO | WO 01/70673 | 9/2001 |
| WO | WO 01/98306 | 12/2001 |
| WO | WO 02/40481 | 5/2002 |
| WO | WO 02/055491 | 7/2002 |
| WO | WO 02/055516 | 7/2002 |
| WO | WO 02/074738 | 9/2002 |
| WO | WO 02/074754 | 9/2002 |
| WO | WO 02/096426 | 12/2002 |
| WO | WO 03/024456 | 3/2003 |
| WO | WO 03/031431 | 4/2003 |
| WO | WO 03/032914 | 4/2003 |
| WO | WO 03/051840 | 6/2003 |
| WO | WO 03/063845 | 8/2003 |
| WO | WO 03/076430 | 9/2003 |
| WO | WO 03/091220 | 11/2003 |
| WO | WO 03/092606 | 11/2003 |
| WO | WO 2004/024462 | 3/2004 |
| WO | WO 2004/018453 | 4/2004 |
| WO | WO 2004/034963 | 4/2004 |
| WO | WO 2004/037240 | 5/2004 |
| WO | WO 2004/043349 | 5/2004 |
| WO | WO 2004/056353 | 7/2004 |
| WO | WO 2004/065361 | 8/2004 |
| WO | WO 2004/089294 | 10/2004 |
| WO | WO 2004/104086 | 12/2004 |
| WO | WO 2005/037826 | 4/2005 |
| WO | WO 2005/117882 | 12/2005 |

OTHER PUBLICATIONS

Arribas et al., "Protein Ectodomain Shedding", *Chem. Rev.*, 102(12):4627-4638, 2002.

Babine at al., "Molecular Recognition of Protein minus sign Ligand Complexes: Applications to Drug Design", *Chem. Rev.*, 97,(5):1359-1472, 1997.

Baselga, et al. Phase II Study of weekly intravenous recombinant humanized anti-p185 Her2 monoclonal antibody in patients with HER2/neu-overexpressing metastic breast cancer. J. of Clin. Oncol. 14(3): 737-744, Mar. 1996.

Baselga et al., "Mechanism of Action of anti-HER2 Monoclonal Antibodies", *Annals of Oncology*, 12/Suppl 1):S35-S41, 2001.

Baselga et al., "Mechanism of Action of Trastuzumab and Scientific Updated", *Seminars in Oncology*, 28(5/Suppl 16):4-11, 2001.

Burns, D. M. et al. Bioorganic & Medicinal Chemistry Letters 18 (2008) 560-564.

Carney et al., "Potential Clinical Utility of Serum HER-2/neu Oncoprotein Concentrations in Patients with Breast Cancer", *Clinical Chemistry*, 49(10):1579-1598, 2003.

Chandler et al., "Matrix Metalloproteinases Degrade Myelin Basic Protein", *Neuroscience Lett.*, 201(3):223-226, 1995.

Codony-Servat et al., "Cleavage of the HER2 Ectodomain is a Pervanadate-activable Process that is Inhibited by the tissue Inhibitor of Metalloproteases-1 in Brest Cancer Cells", *Cancer Research*, 59(6):1196-1201, 1999.

Coussens et al., "Matrix Metalloproteinase Inhibitors and Cancer: Trials and Tribulations", *Science*, 1295:2387-2392, 2002.

Fridman, J. et al. "Preclinical characterization of INCB7839, a potent and selective inhibitor of ErbB ligand and HER2 receptor shedding: inhibition of ADAM10 and ADAM17 for the treatment of breast cancer," 30th Annual San Antonio Breast Cancer Symposium, Dec. 13-16, 2007.

Fridman, J.S. et al., "Selective Inhibition of ADAM Metalloproteases as a Novel Approach for Modulating ErbB pathways in Cancer", *Clin Cancer res*, 13, (6) pp. 1892-1901, 2007.

Infante, J. et al. "A multicenter phase Ib study of the safety, pharmacokinetics, biological activity and clinical efficacy of INCB7839, a potent and selective inhibitor of ADAM10 and ADAM17," 30th Annual San Antonio Breast Cancer Symposium, Dec. 13-16, 2007.

Kuipers et al., "N4-unsubstituted N1-arylpiperazines as High-affinity 5-HT1A Receptor Ligands", J. Med. Chem., 38(11):1942-1954, 1995.

Liu, P.C.C. et al., "Identification of ADAM10 as a Major Source of HER2 Ectodomain Sheddase Activity in HER2 Overexpressing Breast Cancer Cells", *Cancer Biology & Therapy*, 5:6 pp. 657-664, 2006.

Liu, X. et al., "Selective Inhibition of ADAM Metalloproteases blocks HER-2 Extracellular Domain (ECD) Cleavage and Potentiates the Anti-Tumor Effects of Trastuzumab", *Cancer Biology & Therapy*, 5:6 pp. 648-655, 2006.

Liu, X. et al. "Selective inhibition of ADAM metalloproteases blocks Her-2 extracellular domain (ECD) cleavage and potentiates trastuzumab in blocking the growth of Her-2 overexpressing breast cancer cells" Poster/Abst #6051, 28th Annual San Antonio Breast Cancer Symposium, Dec. 8-11, 2005, San Antonio, TX.

Liu X. et al. "INCB3619, a Novel Potent and Selective ADAM Protease Inhibitor, Blocks HER-2 Extracellular Domain (ECD) Shedding and Enhances Antitumor Activities of Trastuzumab" Poster #B193, San Antonio Breast Cancer Symposium, Dec. 2005.

(56) References Cited

OTHER PUBLICATIONS

Molina et al., "NH(2) Terminal Truncated HER-2 Protein but not Full-Length Receptor is associated with Nodal Metastasis in Human Breast Cancer", *Clinical Cancer Research*, 8(2):347-353, 2002.

Molina et al., "Trastuzumab (herceptin) a Humanized anti-Her2 Receptor Monoclonal Antibody, Inhibits Basal and Activated Her2 Ectodomain Cleavage in Breast Cancer Cells", *Cancer Research*, 61(12):4744-4749, 2001.

Muller, A.J. and Scherle, P.A., "Targeting the Mechanisms of Tumoral Immune Tolerance with Small-molecule Inhibitors" *Nature Reviews Cancer*, 6, pp. 613-626, 2006.

Parikh, B. et al. "Development of a Sustained Release Formulation for a Novel Anti-Cancer Agent" Poster #T3378 (Nov. 2007).

Pharmaceutical Drugs (Guide for Physicians) Part I, $12^{th}$ ed. M.S. Mashkovskiy, ed., "Meditsina," Moscow, 1993, p. 8.

Rosendahl et al., "Identification and Characterization of a Pro-tumor Necrosis Factor-alpha-Processing Enzyme from the ADAM Family of Zinc Metalloproteases", *Biol. Chem.*, 272(39):24588-24593, 1997.

Saus et al., "The Complete Primary Structure of Human Matrix Metalloproteinase-3. Identity with Stromelysin", *J. Biol. Chem.*, 263(14):6742-6745, 1988.

Shepherd, et al. Proceedings of the American Association of Cancer Research Annual Meeting 43: 1167 and 1168, Mar. 2002.

Templeton et al., "Cloning and Characterization of Human Tumor Cell Interstitial Collagenase", *Cancer Research*, 50(17),:5431-5437, 1990.

Xue et al. CAS132:49888 (2 pages).

Xue et al., "Rational Design, Synthesis and Structure-activity Relationships of a Cyclic Succinate Series of TNF-alpha Converting Enzyme Inhibitors. Part 1: Lead Identification", *Biorg. Med. Chem. Lett.*, 13(24):4293-4297, 2003.

Xue et al., "Rational Design, Synthesis and Structure-activity Relationships of a Cyclic Succinate Series of TNF-alpha Converting Enzyme Inhibitors. Part 2: Lead Optimization", *Biorg. Med. Chem. Lett.*, 13(24):4299-4304, 2003.

Yao, W. et al. Bioorganic & Medicinal Chemistry Letters 18 (2008) 159-163.

Yao, W. et al., "Discovery of Potent, Selective, and Orally Active Human Epidermal Growth Factor Receptor-2 Sheddase Inhibitor for the Treatment of Cancer", *J. Med. Chem.* 50:603-606, 2007.

Yoshiizumi et al., "Synthesis and Structure-activity Relationship of 5,67,8-tetrahydropyrido[3,4- b]pyrazine-based Hydroxamic Acids as HB-EGF Shedding Inhibitors", *Biorg Med. Chem. Lett.*, 11(3):433:450, 2003.

Zhou, Bin-Bing S. et al., "Targeting ADAM-mediated Ligand Cleavage to Inhibit HER3 and EGFR Pathways in Non-small Cell Lung Cancer", *Cancer Cell*, 10:39-50, 2006.

Zhou, J. et al., "Asymmetric Synthesis of Conformationally Constrained *trans*-2,3-Piperidine-Dicarboxylic Acid Derivatives", *SYNLETT*, No. 3, pp. 460-464, 2007.

Zhou, B.B., et al., *Expert Opin. Investig. Drugs*, 14(6):591-606, 2005.

Search Report and Written Opinion received for corresponding Singaporean Application No. 200717125-9, mailed Apr. 14, 2010, and based upon International Appl. No. PCT/US04/012672, filed Apr. 23, 2004 (11 pgs.).

Official Action dated Jun. 1, 2010 for Japanese Patent Appln. No. 2006-513288 (3 pgs.).

Official Action dated Feb. 20, 2008 in connection with Russian Pat. App. No. 2005136429/04(040664), three pages, translated.

Chemical Encyclopedic Dictionary, I.L. Knunyants, ed. "Sovetskaya Entsiklopedia,", Moscow, 1983, pp. 130-131 (terms Getianks-Hydrogenolysis), translated.

Search Report from Eurasian Patent Office dated Jan. 30, 2008.

Office Action dated Apr. 8, 2008 in connection with U.S. Appl. No. 10/817,718.

Office Action dated Oct. 9, 2007 in connection with U.S. Appl. No. 10/817,718.

Amendment in Reply to Office Action dated Jan. 7, 2008 in connection with U.S. Appl. No. 10/817,718.

Non-final Office Action dated Mar. 20, 2007 in connection with U.S. Appl. No. 10/965,215.

Response to Office Action of Mar. 20, 2007 dated Jul. 19, 2007 in connection with U.S. Appl. No. 10/965,215.

Final Office Action dated Sep. 25, 2007 in connection with U.S. Appl. No. 10/965,215.

Amendment and Reply to Office Action dated Nov. 19, 2007, filed in connection with U.S. Appl. No. 10/965,215.

Amendment dated Jan. 14, 2008 filed in connection with U.S. Appl. No. 10/965,215.

Notice of Allowance and Notice of Allowability dated Jan. 17, 2008 in connection with U.S. Appl. No. 10/965,215.

Reply in Connection with a Request for Continued Examination dated Apr. 15, 2008 filed in connection with U.S. Appl. No. 10/965,215.

Office Action for corresponding Colombian Application No. 05-106.414, mailed Feb. 27, 2009, and based upon International Appl. No. PCT/US2004/012672, filed Apr. 23, 2004.

U.S. Appl. No. 60/460,678, filed Apr. 4, 2003.

AZA SPIRO ALKANE DERIVATIVES AS INHIBITORS OF METALLOPROTEASES

CROSS REFERENCE TO RELATED APPLICATIONS

This application is a continuation of U.S. Ser. No. 12/327,313, filed Dec. 3, 2008, U.S. Pat. No. 8,039,471 which is a continuation of U.S. Ser. No. 10/831,265, filed Apr. 23, 2004, now U.S. Pat. No. 7,723,349 which claims the benefit of U.S. Ser. No. 60/466,159, filed Apr. 24, 2003, and U.S. Ser. No. 60/534,501, filed Jan. 6, 2004, the disclosures of each of which are incorporated herein by reference in their entireties.

FIELD OF THE INVENTION

The present invention relates to aza spiro alkane compounds which are useful in treating diseases, pathologic conditions and disorders associated with metalloprotease activity, including activity of sheddases and adamalysins (ADAMs).

BACKGROUND OF THE INVENTION

Most tissues exist in a highly regulated dynamic equilibrium wherein new tissue is formed and existing tissue is degraded and eliminated. The degradation of the extracellular matrix (ECM), including connective tissue and basement membranes, is effected by the metalloproteinases which are released from connective tissue and invading inflammatory cells. Excessive unregulated activity of these enzymes can result in undesirable tissue destruction and their activity is regulated at the transcription level, by controlled activation of the latent proenzyme and, after translation, by intracellular specific inhibitory factors such as TIMP ("Tissue Inhibitors of MetalloProteinase") or by more general proteinase inhibitors such as α2-macroglobulins.

Several structurally related metalloproteases (MPs) are known to play an important role in the breakdown of structural proteins. These metalloproteases typically act on the intercellular matrix, and thus are involved in tissue breakdown and remodeling. Such proteins have been referred to as metalloproteases or MPs. There are several different families of MPs, classified by sequence homology. Several families of known MPs, as well as examples thereof, are disclosed in the art.

These MPs include Matrix-Metallo Proteases [MMPs], zinc metalloproteases, many of the membrane bound metalloproteases, TNF converting enzymes, angiotensin-converting enzymes (ACEs), disintegrins, including ADAMs (See Wolfsberg et al, 131 J. Cell Bio. 275-78 Oct. 25, 1995), and the enkephalinases. Examples of MPs include human skin fibroblast collagenase, human skin fibroblast gelatinase, human sputum collagenase, aggrecanse and gelatinase, and human stromelysin. Collagenase, stromelysin, aggrecanase and related enzymes are thought to be important in mediating the symptomatology of a number of diseases.

Zinc proteases are subdivided according to the primary structure of their catalytic sites and include gluzincin, metzincin, inuzincin, carboxypeptidase, and DD carboxypeptidase subgroups (Hooper N M, 1994, FEBS Lett, 354:1-6). The metzincin subgroup is further divided into serralysins, astacins, matrixins, and adamalysins (Stocker W and Bode W, 1995, Curr Opin Struct Biol, 5:383-390).

The matrixins include the matrix metalloproteases, or MMPs. MMPs constitute a family of structurally similar zinc-containing metalloproteases, which are involved in the remodeling and degradation of extracellular matrix proteins, both as part of normal physiological processes and in pathological conditions. For a review see Bode, W et al., 1996, Adv Exp Med Biol, 389:1-11. Connective tissue, extracellular matrix constituents and basement membranes are the biological materials that provide rigidity, differentiation, attachment sites and, in some cases, elasticity to biological systems. Connective tissues components include, for example, collagen, elastin, proteoglycans, fibronectin and laminin that form the scaffold for all human tissues. Under normal conditions, connective tissue turnover and/or repair processes are controlled and in equilibrium. The loss of this balance, for whatever reason, leads to a number of disease states. Inhibition of the enzymes responsible loss of equilibrium provides a control mechanism for this tissue decomposition and, therefore, a treatment for these diseases. The uncontrolled breakdown of connective tissue by metalloproteases is a feature of many pathological conditions.

Besides a role in the regulation of extracellular matrix, there is also evidence to suggest that MMPs mediate the migration of inflammatory cells into tissues (Moscatelli D and Rifkin D B, 1988, Biochim Biophys Acta, 948: 67-85). Several reports have demonstrated that various MMPs can activate a variety of important non-matrix proteins, including cytokines, chemokines, integrins, and antimicrobial peptides (see Parks W C, 2002, J Clin Invest, 110:613-4). Many of the human MMPs are over expressed in human tumors and are associated with peritumor tissue degradation and metastasis formation. Another important function of certain MMPs is to activate various enzymes, including other MMPs, by cleaving the pro-domains from their protease domains. Thus some MMPs act to regulate the activities of other MMPs, so that over-production of one MMP may lead to excessive proteolysis of extracellular matrix by another. It has also been reported that MMPs can cleave and thereby inactivate the endogenous inhibitors of other proteinases such as elastase (Winyard P G et al., 1991, FEBS Letts, 279: 91-94) Inhibitors of MMPs could thus influence the activity of other destructive proteinases by modifying the level of their endogenous inhibitors. In addition, increasing or maintaining the levels of an endogenous or administered serine protease inhibitor supports the treatment and prevention of diseases such as emphysema, pulmonary diseases, inflammatory diseases and diseases of aging such as loss of skin or organ stretch and resiliency. Thus, MMPs should not be viewed solely as proteinases of ECM catabolism, but rather as extracellular processing enzymes involved in regulating cell-cell and cell-ECM signaling events.

The adamalysins include the reprolysins, snake venom metalloproteases and the ADAMs. The ADAMs (a disintegrin and metalloprotease domain) are a family of type I transmembrane glycoproteins that are important in diverse biologic processes, such as cell adhesion and the proteolytic shedding of cell surface receptors. ADAM family members have been identified from mammalian and nonmammalian sources, including *Xenopus, Drosophila*, and *Caenorhabditis elegans*. Members of the family have a modular design, characterized by the presence of metalloprotease and integrin receptor-binding activities, and a cytoplasmic domain that in many family members specifies binding sites for various signal-transducing proteins. The ADAMs family has been implicated in the control of membrane fusion, cytokine, growth factor and growth factor receptor shedding, and cell migration, as well as processes such as muscle development, fertilization, neurogenesis, and cell fate determination. Loss of regulation can lead to disease and pathology. Pathologies such as infertility, inflammation and cancer have been shown to involve ADAMs family members. For a review, see Wolfsberg T G and White J M, 1998, ADAM metalloproteinases. In Handbook of Proteolytic Enzymes (Barrett A J, Rawlings N D and Woessner J F eds), p. 1310-1313, Academic Press, London as well as Seals D F and Courtneidge S A, 2003, Genes and Development, 17:7-30.

Some specific examples of important ADAM metalloproteases include the TNFα-converting enzyme, TACE or ADAM17, that is currently an important target for anti-inflammatory drugs (Moss M L et al., 2001, Drug Discov Today, 6:417-426 and Black R A, 2002, Int J Biochem Cell Biol, 34:1-5). Other members of the family are also likely to be good therapeutic targets. ADAM8 has been reported to be expressed almost exclusively in cells of the immune system, particularly B-cells, monocytes, eosinophils and granulocytes. ADAM8 therefore represents a therapeutic target for human immunological-based diseases. ADAM15 is found in human aortic smooth muscle and cultured umbilical vein endothelial cells. While ADAM15 is not expressed in normal blood vessels, it has been detected in developing atherosclerotic lesions (Herren B et al., 1997, FASEB J, 11:173-180), and has also been shown to be upregulated in osteoarthritic versus normal human cartilage (Bohm B B et al., 1999, Arthritis Rheum, 42:1946-1950). Thus ADAM15 may play a role in atherosclerosis and cartilage degeneration diseases. The lymphocyte-specific expression of the ADAM28 suggests that it may have an important immunological function.

Excessive production of IgE is believed to be a major mediator of allergic responses. CD23, the low affinity receptor for IgE, is subject to ADAM type metalloprotease-dependent proteolytic release of soluble extracellular fragments, which have been shown to cause upregulation of IgE production and induction of inflammatory cytokines (see Novak N et al, 2001, Curr Opin Immunol, 13:721-726 and Mayer R J et al., 2002, Inflamm Res, 51:85-90). Increased levels of soluble CD23 have been observed in allergic asthma, in chronic B-lymphocytic leukemia and in rheumatoid arthritis Inhibition of the enzyme(s) responsible for CD23 processing may offer a therapeutic approach for the treatment of various immune based diseases. ADAM metalloproteases also appear to be responsible for the release or shedding of soluble receptors (for example, CD30 and receptors for TNF), adhesion molecules (for example, L-selectin, ICAM-1, fibronectin), growth factors and cytokines (for example Fas ligand, TGF-α, EGF, HB-EGF, SCF IL-6, IL-1, TSH and M-CSF), and growth factor receptors (for example EGFR family members, such as Her-2 and Her-4, which have been implicated in the pathogenesis of different types of cancer (Yarden Y and Sliwkowski M X, 2001, Nature Reviews 2:127-137). For example, Her-2 is over expressed in 25-30% of human breast cancers and is associated with an increased risk of relapse and death (Slamon D J et al, 1987, Science, 235:177-182). ADAM17 has recently been shown to be critical for the regulated shedding of Her-4 (Rio C et al, 2000, J Biol Chem, 275:10379-10387). The protease responsible for Her-2 cleavage, known as Her-2 sheddase, is an unknown MMP that may also be a member of the ADAM family (Codony-Servat J et al, 1999, Cancer Res 59:1196-1201). Modulation of this activity might therefore have an important role in the modulation of human disease. For a review of the sheddase activity of ADAMs see Moss M L and Lambert M H, 2002, Essays Biochem, 38:141-153.

ADAM-TS proteases have been identified as members of the ADAM family. These proteins are novel in that they contain unique thrombospondin (TS) type I motifs in addition to some of the structurally conserved domains of other ADAM family members. The ADAMTSs are also distinguished from the ADAMs by their lack of cysteine-rich, EGF-like, transmembrane, and cytoplasmic domains. ADAM-TS proteins have also been shown to be associated with a number of pathological or human disease states. For example, ADAMTS-1 is a tumor-selective gene expressed in colon tumor cells and is also an inflammation-associated protein. A human ortholog of ADAMTS-1, known as METH-1, and the related protein METH-2 have been recently shown to have antiangiogenic activity, and these or other ADAMTS family members may play important roles in regulating vascular development. ADAMTS-2 has been implicated in the normal development of the skin. This enzyme was long known as procollagen N-proteinase, a proteinase that proteolytically removes amino peptides in the processing of type I and type II procollagens to collagens, and it was shown to be deficient in the skin of individuals with the inherited connective tissue disorder type VIIC Ehlers-Danros syndrome. ADAMTS-4 and ADAMTS-11 are known as aggrecanase-1 and -2 because of their ability to cleave specific sites in aggrecan, a proteoglycan that maintains the mechanical properties of cartilage. Progressive degradation and depletion of aggrecan has been implicated in degenerative joint diseases such as osteoarthritis and inflammatory joint diseases such as rheumatoid arthritis. For a review of the ADAM-TS metalloproteases see Tang B L, 2001, Int J Biochem Cell Biol, 33:33-44 and Kaushal G P and S V Shah, 2000, J Clin Invest 105:1335-1337.

The metalloproteases are one of the older classes of proteinases and are found in bacteria, fungi as well as in higher organisms. Many enzymes contain the sequence HEXXH, which provides two histidine ligands for the zinc whereas the third ligand is either a glutamic acid (thermolysin, neprilysin, alanyl aminopeptidase) or a histidine (astacin). Other families exhibit a distinct mode of binding of the Zn atom. Metalloproteases have therefore been isolated from a number of prokaryotic and eukaryotic sources. Acidic metalloproteases have been isolated from broad-banded copperhead and rattlesnake venoms. Neutral metalloproteases, specifically those having optimal activity at neutral pH have, for example, been isolated from *Aspergillus sojae*. Alkaline metalloproteases, for example, have been isolated from *Pseudomonas aeruginosa* and the insect pathogen *Xenorhabdus luminescens*. Inhibition of microbial metalloproteases may lead to growth inhibition and represent an antibiotic strategy. Inhibition of metalloproteases associated with snake venom or insect toxicity may also lead to new therapeutic strategies.

Potential therapeutic indications of MP inhibitors have been discussed in the literature. See for example, U.S. Pat. No. 6,500,847 (Bayer Corporation), U.S. Pat. No. 6,268,379 (DuPont Pharmaceuticals Company), U.S. Pat. No. 5,968,795 (Bayer Corporation), U.S. Pat. No. 5,892,112 (Glycomed Incorporated and The University of Florida), and U.S. Pat. No. 5,872,152 (British Biotech Pharmaceuticals Limited). Some examples where inhibition of metalloprotease activity would be of benefit include: a) osteoarthritis, b) rheumatic diseases and conditions such as autoimmune disease, rheumatoid arthritis, c) septic arthritis, d) cancer including tumor growth, tumor metastasis and angiogenesis, e) periodontal diseases, f) corneal, epidermal or gastric ulceration (ulcerative conditions can result in the cornea as the result of alkali burns or as a result of infection by *Pseudomonas aeruginosa, Acanthamoeba*, Herpes simplex and vaccinia viruses), g) proteinuria, h) various cardiovascular and pulmonary diseases such as atherosclerosis, thrombotic events, atheroma, hemodynamic shock, unstable angina, restenosis, heart failure, i) aneurysmal diseases including those of the aorta, heart or brain, j) birth control, k) dystrophobic epidermolysis bullosa, l) degenerative cartilage loss following traumatic joint injury, m) osteopenias and other diseases of abnormal bone loss including osteoporosis, n) tempero mandibular joint disease, o) pulmonary diseases such as chronic obstructive pulmonary disease, p) demyelinating diseases of the nervous system such as multiple sclerosis, q) metabolic diseases including diabetes (with enhanced collagen degradation) and obesity mediated by insulin resistance, macular degeneration and diabetic retinopathy mediated by angiogenesis, cachexia, premature skin aging, r) impaired wound healing including burns, s) decubital ulcers, t) acute and chronic neurodegenerative disorders including stroke, spinal cord and traumatic brain injury, amyotrophic lateral sclerosis, cerebral amyloid angiopathy, CNS injuries in AIDS, Parkinson's disease, Alzheimer's disease, Huntington's diseases, prion diseases, myasthenia gravis, and Duchenne's muscular dystrophy, u) pain, v) autoimmune encephalomyelitis and w) diseases linked to TNFα production and/or signaling such as a wide variety of inflammatory and/or immunomodulatory diseases, including acute rheumatic fever, rheumatoid arthritis, multiple sclerosis, allergy, periodontal diseases, hepatitis, bone resorption, sepsis, gram negative sepsis, septic shock, endotoxic shock, toxic shock syndrome, systemic inflammatory response syndrome, inflammatory bowel diseases including Crohn's disease and ulcerative colitis, Jarisch-Herxheimer reactions, asthma, adult respiratory distress syndrome, acute pulmonary fibrotic diseases, pulmonary sarcoidosis, allergic respiratory diseases, silicosis, coal worker's pneumoconiosis, alveolar injury, hepatic failure, liver disease during acute inflammation, severe alcoholic hepatitis, malaria including *Plasmodium falciparum* malaria and cerebral malaria, congestive heart failure, damage following heart disease, arteriosclerosis including atherosclerosis, Alzheimer's disease, acute encephalitis, brain injury, pancreatitis including systemic complications in acute pancreatitis, impaired wound healing and immune responses in infection inflammation and cancer, myelodysplastic syndromes, systemic lupus erythematosus, biliary cirrhosis, non-insulin dependent diabetes mellitus, bowel necrosis, psoriasis, cachexia and anorexia, radiation injury, and toxicity following administration of monoclonal antibodies such as OKT3, host-versus-graft reactions including ischemia reperfusion injury and allograft rejections including those of the kidney, liver, heart, and skin, lung allograft rejection including chronic lung allograft rejection (obliterative bronchitis), as well as complications due to total hip replacement, infectious diseases including Mycobacterial infection, meningitis, *Helicobacter pylori* infection during peptic ulcer disease, Chaga's disease resulting from *Trypanosoma cruzi* infection, effects of Shiga-like toxin resulting from *E. coli* infection, the effects of enterotoxin A resulting from *Staphylococcus* infection, meningococcal infection, and infections from *Borrelia burgdorferi, Treponema pallidum*, cytomegalovirus, influenza virus, Sendai virus, Theiler's encephalomyelitis virus, and the human immunodeficiency virus (HIV). Defective injury repair processes also occur. This can produce improper wound healing leading to weak repairs, adhesions and scarring. These latter defects can lead to disfigurement and/or permanent disabilities as with post-surgical adhesions.

Matrix metalloprotease inhibitors are useful in treating diseases caused, at least in part, by breakdown of structural proteins. Though a variety of inhibitors have been prepared, there is a continuing need for potent matrix metalloprotease inhibitors useful in treating such diseases. Applicants have found that, surprisingly, the compounds of the present invention are potent metalloprotease inhibitors.

SUMMARY OF THE INVENTION

The present invention provides a compound of Formula I or II:

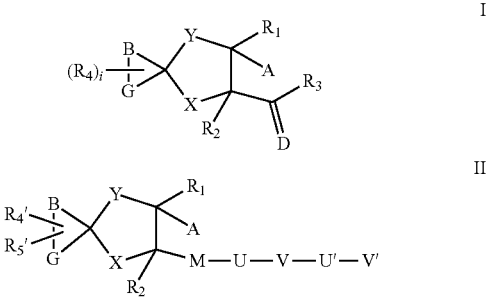

or enantiomer, diastereomer, prodrug, solvate, metabolite, or pharmaceutically acceptable salt thereof, wherein constituent members are provided hereinbelow.

The present invention further provides compositions comprising a compound of Formula I or II and a pharmaceutically acceptable carrier.

The present invention further provides a method for treating a disease associated with unwanted metalloprotease activity.

The present invention further provides a method for treating a disease modulated by a metalloprotease in a mammalian subject, wherein the disease is selected from the group consisting of arthritis, cancer, cardiovascular disorders, skin disorders, inflammation and allergic conditions.

The present invention further provides a method for treating cancer, including but not limited to breast cancer, in a mammal.

The present invention further provides a method of inhibiting pathological changes mediated by elevated levels of matrix metalloproteases in mammals comprising administering to said mammal in need thereof a therapeutically effective amount of a compound of the invention.

The present invention further provides a method for treating a disease associated with unwanted TNF-α converting enzyme activity.

The present invention further provides a method for treating a disease associated with unwanted matrix metalloprotease activity wherein said matix metalloprotease is selected from the group consisiting of MMP12, MMP14, MMP3, MMP2, and MMP9 in a mammalian subject.

The present invention further provides a method for treating a disease associated with unwanted activity of Her-2 sheddase, growth factor sheddases, or cytokine sheddases in a mammalian subject.

The present invention further provides a method for treating a disease associated with activity of Her-2 sheddase in a mammal.

The present invention further provides a method for treating a disease associated with unwanted ADAM10, ADAM15, or ADAM17 activity in a mammalian subject.

DETAILED DESCRIPTION

The instant invention provides, inter alia, compounds and pharmaceutical compositions of matter for treating pathological conditions which are associated with metalloprotease activity such as the rapid, unregulated breakdown of extracellular matrix tissue by MMPs including, but not limited to, MMP 12 and MMP 13. Some of these conditions include rheumatoid arthritis, osteoarthritis, septic arthritis, corneal, epidermal or gastric ulceration; periodontal disease, proteinuria, coronary thrombosis associated with atherosclerotic plaque rupture and bone disease. The compounds of the invention are also useful for treating cancer including, for example, tumor metastasis and angiogenesis which also appears to be associated withe metalloprotease activity. Also, since the cycle of tissue damage and response is associated with a worsening of the disease state, limiting metalloprotease-induced tissue damage due to elevated levels of the proteinases with the compounds of the instant invention can be a generally useful therapeutic approach to many of these debilitating diseases and others. The compounds of the invention are also inhibitors TNFα converting enzyme and sheddases including Her-2 sheddase and HB-EGF sheddase and other growth factor and cytokine sheddases.

The present invention provides a compound of Formula I or II:

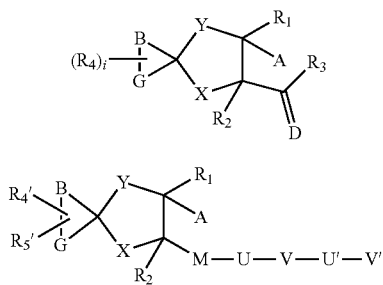

or enantiomer, diastereomer, prodrug, solvate, metabolite, or pharmaceutically acceptable salt thereof, wherein:

A is CWOH, CWNHOH, CWNHOR$_5$, N(OH)CHO, N(OH)CWR$_6$, SH, SR$_7$ or hydantoinyl;

B is $(CH_2)_m$, $(CH_2)_nC=W$, $(CR_dR_f)_nNR_8$, $NR_8(CR_dR_f)_n$, $(CR_dR_f)_nO(CR_dR_f)_r$, $(CR_dR_f)_nS(CR_dR_f)_r$, $O(C=W)NR_8$, O, N, NR$_8$, S(O)$_m$, S, C(O)NR$_8$(CR$_d$R$_f$)$_n$, C(O)CR$_d$R$_f)_n$ or combinations thereof;

G is $(CH_2)_m$, $(CH_2)_nC=W$, $(CR_dR_f)_nNR_8$, $NR_8(CR_dR_f)_n$, $(CR_dR_f)_nO(CR_dR_f)_r$, $(CR_dR_f)_nS(CR_dR_f)_r$, $O(C=W)NR_8$, O, N, NR$_8$, S(O)$_m$, S, C(O)NR$_8$(CR$_d$R$_f$)$_n$, C(O)(CR$_d$R$_f$)$_n$ or combinations thereof;

D is oxygen or sulfur;

X is absent, $(CH_2)_j$, $C_{1-10}$ alkylene substituted with 0 to 3 R$_a$, $C_{2-10}$ alkenylene substituted with 0 to 2 R$_a$, N, O, NR$_b$, S(O)$_m$, C=O, NR$_b$C(O), NR$_b$C(O)O, NR$_b$C(O)NR$_b$, C(O)O, OC(O), S(O)$_m$NR$_b$, NR$_b$S(O)$_m$, NR$_b$S(O)$_m$NR$_b$, $(CR_dR_f)_j$ NR$_b$, NR$_b$(CR$_d$R$_f$)$_j$, or combinations thereof;

Y is absent, $(CH_2)_j$, $C_{1-10}$ alkylene substituted with 0 to 3 R$_a$, $C_{2-10}$ alkenylene substituted with 0 to 2 R$_a$, N, O, NR$_b$, S(O)$_m$, C=O, NR$_b$C(O), NR$_b$C(O)O, NR$_b$C(O)NR$_b$, C(O)O, OC(O), S(O)$_m$NR$_b$, NR$_b$S(O)$_m$, NR$_b$S(O)$_m$NR$_b$, $(CR_dR_f)_j$ NR$_b$, NR$_b$(CR$_d$R$_f$)$_j$, or combinations thereof;

M is CO or S(O)$_i$;

U is absent, $C_{1-10}$ alkylene substituted with 0 to 5 R$_a$, $C_{2-10}$ alkenylene substituted with 0 to 2 R$_a$, N, O, NR$_b$, NR$_b$C(O), NR$_b$C(O)O, NR$_b$C(O)NR$_b$, NR$_b$S(O)$_m$, NR$_b$S(O)NR$_b$ or combinations thereof;

V is absent, H, $C_{3-13}$ carbocyclyl substituted with 0-5 R$_e$ or heterocyclyl substituted with 0-5 R$_e$;

U' is absent, $C_{1-10}$ alkylene substituted with 0 to 5 R$_a$, $C_{2-10}$ alkenylene substituted with 0 to 2 R$_a$, N, O, NR$_b$S(O)$_m$, C=O, NR$_b$C(O), NR$_b$C(O)O, NR$_b$C(O)NR$_b$, C(O)O, OC(O), S(O)$_m$NR$_b$, NR$_b$S(O)$_m$, NR$_b$S(O)NR$_b$ or combinations thereof;

V' is H, $C_{1-8}$ alkyl, NR$_b$R$_c$, $C_{3-13}$ carbocyclyl substituted with 0-5 R$_e$ or heterocyclyl substituted with 0-5 R$_e$;

R$_a$ and R$_e$ are each, independently, H, T, $C_{1-8}$alkylene-T, $C_{2-8}$alkenylene-T, $C_{2-6}$alkynylene-T, C(O)NR$_a$'(CR$_b$'R$_c$')$_r$-T, C(O)O(CR$_b$'R$_c$')$_r$-T, S(O)$_p$(CR$_b$'R$_c$')$_r$-T, (CR$_b$'R$_c$')$_r$—O—(CR$_b$'R$_c$')$_r$-T, OH, Cl, F, Br, I, CN, NO$_2$, NR$^I$R$^{II}$, COR$^{III}$, COOR$^{IV}$, OR$^{IV}$, CONR$^I$R$^{II}$, NR$^I$CONR$^I$R$^{II}$, OCONR$^I$R$^{II}$, NR$^I$COR$^{II}$, SO$_2$NR$^I$R$^{II}$, NR$^I$SO$_2$R$^{II}$, NR$^I$SO$_2$NR$^I$R$^{II}$, OSO$_2$NR$^I$R$^{II}$, SO$_p$R$^V$, $C_{1-8}$ haloalkyl, $C_{3-13}$ carbocyclyl, heterocyclyl, carbocyclylalkyl, or heterocyclylalkyl, wherein each of said carbocyclyl, heterocyclyl, carbocyclylalkyl, and heterocylcylalkyl groups is optionally substituted by one or more $C_{1-8}$ alkyl, alkoxy, halo, haloalkyl, haloalkoxy, cyano, nitro, amino, alkylamino, dialkylamino, carboxy, carboxy alkyl ester, carboxy aryl ester, aminocarbonyl, alkylaminocarbonyl, dialkylaminocarbonyl, sulfonyl, aminosulfonyl, alkylaminosulfonyl, dialkylaminosulfonyl, arylsulfonyl, arylsulfinyl, alkylsulfonyl or arylsufonyl;

R$_b$ and R$_c$ are each, independently, H, T, $C_{1-6}$alkylene-T, $C_{2-8}$alkenylene-T, $C_{2-6}$alkynylene-T, C(O)NR$_a$'(CR$_c$'R$_b$')$_r$-T, C(O)O(CR$_b$'R$_c$')$_r$-T, C(O)(CR$_b$'R$_c$')$_r$-T, S(O)$_p$(CR$_b$'R$_c$')$_r$-T, (CR$_c$'R$_b$')$_r$—O—(CR$_c$'R$_b$')$_r$-T, C(NR$_a$'R$_a$')(=N—CN) or C(NR$_a$'R$_a$')(=CHNO$_2$);

R$_d$ and R$_f$ are each, independently, H, $C_{1-6}$ alkyl, $C_{2-6}$ alkenyl, $C_{2-6}$ alkynyl, T, $C_{1-6}$alkylene-T, $C_{2-8}$alkenylene-T, $C_{2-6}$alkynylene-T, C(O)NR$_a$'(CR$_c$'R$_b$')$_r$-T, C(O)O(CR$_b$'R$_c$')$_r$-T, S(O)$_p$(CR$_b$'R$_c$')$_r$-T or (CR$_c$'R$_b$')$_r$—O—(CR$_c$'R$_b$')$_r$-T, OH, Cl, F, Br, I, CN, NO$_2$, NR$^I$R$^{II}$, COR$^{III}$, COOR$^{IV}$, OR$^{IV}$, CONR$^I$R$^{II}$, R$^I$NCONR$^I$R$^{II}$, OCONR$^I$R$^{II}$, R$^I$NCOR$^{II}$, SO$_2$NR$^I$R$^{II}$, NR$^I$SO$_2$R$^{II}$, NR$^I$SO$_2$NR$^I$R$^{II}$, OSO$_2$NR$^I$R$^{II}$, SO$_p$R$^V$, $C_{1-8}$ haloalkyl, carbocyclyl, heterocyclyl, carbocyclylalkyl, heterocyclylalkyl, carbocyclyloxy or heterocarbocyclyloxy, wherein each of said carbocyclyl, heterocyclyl, carbocyclylalkyl, heterocyclylalkyl, carbocyclyloxy or heterocarbocyclyloxy groups is optionally substituted by one or more $C_{1-8}$ alkyl, alkoxy, halo, haloalkyl, haloalkoxy, cyano, nitro, amino, alkylamino, dialkylamino, carboxy, carboxy alkyl ester, carboxy aryl ester, aminocarbonyl, alkylaminocarbonyl, dialkylaminocarbonyl, sulfonyl, aminosulfonyl, alkylaminosulfonyl, dialkylaminosulfonyl, arylsulfonyl, arylsulfinyl, alkylsulfonyl or arylsufonyl;

T is H, $C_{1-10}$ alkyl substituted with 0 to 5 R$_b$'; $C_{2-10}$ alkenyl substituted with 0 to 5 R$_b$', $C_{2-10}$ alkynyl substituted with 0 to 5 R$_b$', $C_{3-13}$ carbocyclyl substituted with 0-3 R$_b$', heterocyclyl substituted with 0-5 R$_b$';

R$_a$', R$_b$' and R$_c$' are each, independently, H, $C_{1-6}$ alkyl, $C_{2-6}$ alkenyl, $C_{2-6}$ alkynyl, OH, Cl, F, Br, I, CN, NO$_2$, NR$^I$R$^{II}$, COR$^{III}$, COOR$^{IV}$, OR$^{IV}$, CONR$^I$R$^{II}$, R$^I$NCONR$^I$R$^{II}$, OCONR$^I$R$^{II}$, R$^I$NCOR$^{II}$, SO$_2$NR$^I$R$^{II}$, NR$^I$SO$_2$R$^{II}$, NR$^I$SO$_2$NR$^I$R$^{II}$, OSO$_2$NR$^I$R$^{II}$, SO$_p$R$^V$, $C_{1-8}$ haloalkyl, carbocyclyl, heterocyclyl, carbocyclylalkyl, heterocyclylalkyl, carbocyclyloxy or heterocarbocyclyloxy, wherein each of said carbocyclyl, heterocyclyl, carbocyclylalkyl, heterocyclylalkyl, carbocyclyloxy or heterocarbocyclyloxy groups is optionally substituted by one or more $C_{1-8}$ alkyl, alkoxy, halo, haloalkyl, haloalkoxy, cyano, nitro, amino, alkylamino, dialkylamino, carboxy, carboxy alkyl ester, carboxy aryl ester, aminocarbonyl, alkylaminocarbonyl, dialkylaminocarbonyl, sulfonyl, aminosulfonyl, alkylaminosulfonyl, dialkylaminosulfonyl, arylsulfonyl, arylsulfinyl, alkylsulfonyl or arylsufonyl;

R$_1$ is hydrogen, $C_{1-6}$ alkyl, SR$_{10}$, OR$_{10}$ or NR$_{11}$R$_{12}$;

R$_2$ is hydrogen, $C_{1-6}$ alkyl, SR$_{10}$, OR$_{10}$ or NR$_{11}$R$_{12}$;

$R_3$ is:

(i) $C_{10-10}$alkyl, $C_{2-8}$ alkenyl or $C_{2-8}$ alkynyl;

(ii) $C_{3-13}$ carbocyclyl optionally substituted with one or more substituents selected from halogen, $C_{1-6}$ alkyl, $SR_{13}$, $NR_{11}R_{12}$, $OR_{13}$, heterocyclyl, aryl, $=S$, $=O$, CN, $NO_2$, $NR_\beta R_\beta'$, $COR_\gamma$, $R_\gamma NC(O)NR_\gamma R_\gamma'$, $OC(O)NR_\gamma R_\gamma'$, $C(O)OR_\gamma$, $C(O)NR_\gamma R_\gamma'$, or $R_\gamma NC(O)O$;

(iii) aryl optionally substituted with one or more substituents selected from halogen, $C_{1-6}$ alkyl, $SR_{13}$, $NR_{11}R_{12}$, $OR_{13}$, heterocyclyl, aryl, $=S$, $=O$, CN, $NO_2$, $NR_\beta R_\beta'$, $COR_\gamma$, $R_\gamma NC(O)NR_\gamma R_\gamma'$, $OC(O)NR_\gamma R_\gamma'$, $C(O)OR_\gamma$, $C(O)NR_\gamma R_\gamma'$, or $R_\gamma NC(O)O$;

(iv) heterocyclyl optionally substituted with one or more substituents selected from halogen, $C_{1-6}$ alkyl, $SR_{13}$, $NR_{11}R_{12}$, $OR_{13}$, heterocyclyl, aryl, $=S$, $=O$, CN, $NO_2$, $NR_\beta R_\beta'$, $COR_\gamma$, $R_\gamma NC(O)NR_\gamma R_\gamma'$, $OC(O)NR_\gamma R_\gamma'$, $C(O)OR_\gamma$, $C(O)NR_\gamma R_\gamma'$, and $R_\gamma NC(O)O$;

(v) $NR_{14}(CH_2)_j NR_{14}R_{15}$; or (vi) $NR_{16}R_{17}$;

$R_4$ and $R_5$ are each, independently, H, halogen, T, $C_{1-6}$alkylene-T, $C_{2-6}$alkynylene-T, $C(O)NR_a'(CR_c'R_b')_r$-T, $CO(CR_bR_c)_r$-T, $C(O)O(CR_b'R_c')_r$-T, $S(O)_p(CR_b'R_c')_r$-T, $(CR_c'R_b')_r$—O—$(CR_c'R_b')_r$-T, $NR_{11}R_{12}$, $SR_{18}$ or $OR_{18}$;

$R_4'$ is H, halogen, T, $C_{1-6}$alkylene-T, $C_{2-6}$alkynylene-T, $C(O)NR_a'(CR_c'R_b')_r$-T, $CO(CR_bR_c)_r$-T, $C(O)O(CR_b'R_c')_r$-T, $S(O)_p(CR_b'R_c')_r$-T, or $(CR_c'R_b')_r$—O—$(CR_c'R_b')_r$-T, $NR_{11}R_{12}$, $SR_{18}$, or $OR_{18}$;

$R_5'$ is H, halogen, T, $C_{1-6}$alkylene-T, $C_{2-6}$alkynylene-T, $C(O)NR_a'(CR_c'R_b')_r$-T, $CO(CR_bR_c)_r$-T, $C(O)O(CR_b'R_c')_r$-T, $S(O)_p(CR_b'R_c')_r$-T, or $(CR_c'R_b')_r$—O—$(CR_c'R_b')_r$-T, $NR_{11}R_{12}$, $SR_{18}$, or $OR_{18}$;

or $R_4'$ and $R_5'$ together with the atoms to which they are attached form a ring selected from $C_{3-13}$ carbocyclyl and 3-14 membered heterocyclyl;

W is oxygen or sulfur;

$R_6$ and $R_7$ are each, independently, hydrogen, $C_{1-6}$ alkyl, $C_{2-8}$ alkenyl or $C_{2-8}$ alkynyl;

$R_8$ is H, $C_{1-10}$ alkylene-T, $C_{2-10}$ alkenylene-T, and $C_{2-10}$ alkynylene-T, $(CR_b'R_c)_rO(CR_b'R_c')_r$-T,
$(CR_b'R_c)_rNR_a'(CR_b'R_c')_r$-T,
$(CR_b'R_c)_rC(O)(CR_b'R_c')_r$-T,
$(CR_b'R_c)_rC(O)O(CR_b'R_c')_r$-T,
$(CR_b'R_c)_rOC(O)(CR_b'R_c')_r$-T,
$(CR_b'R_c)_rC(O)NR_a'(CR_b'R_c')_r$-T,
$(CR_b'R_c)_rNR_a'C(O)(CR_b'R_c')_r$-T,
$(CR_b'R_c)_rOC(O)O(CR_b'R_c')_r$-T,
$(CR_b'R_c)_rOC(O)NR_a'(CR_b'R_c')_r$-T,
$(CR_b'R_c)_rNR_a'C(O)O(CR_b'R_c')_r$-T,
$(CR_b'R_c)_rNR_a'C(O)NR_a'(CR_b'R_c')_r$-T,
$(CR_b'R_c)_rS(O)_p(CR_b'R_c')_r$-T,
$(CR_b'R_c)_rSO_2NR_a'(CR_b'R_c')_r$-T,
$(CR_b'R_c)_rNR_a'SO_2(CR_b'R_c')_r$-T, or
$(CR_b'R_c)_rSO_2NR_a'SO_2(CR_b'R_c')_r$-T;

$R_{10}$ is H or $C_1$-$C_6$ alkyl;

$R_{11}$ and $R_{12}$ are each, independently, hydrogen or $C_1$-$C_8$ alkyl, or $R_{11}$ and $R_{12}$ together with the N atom to which they are attached form a 3-14 member heterocyclic ring;

$R_{13}$ is $C_1$-$C_6$ alkyl, $C_1$-$C_6$ haloalkyl, $C_{3-13}$ carbocyclyl, carbocyclylalkyl, heterocyclyl, heterocyclylalkyl, each of which is optionally substituted by one or more halo, $C_{1-4}$ alkyl, $C_{1-4}$ alkoxy, $C_{1-4}$ haloalkyl, $C_{1-4}$ haloalkoxy, CN, $NO_2$, OH, COOH, amino, alkylamino, or dialkylamino;

$R_{14}$ and $R_{15}$ are each, independently, hydrogen, $C_{1-10}$ alkyl, $C_{3-13}$ carbocyclyl substituted with one or more heterocyclyl, or $R_{14}$ and $R_{15}$ together with the N atom to which they are attached form a 3-14 membered heterocyclic system;

$R_{16}$ and $R_{17}$ are each, independently, hydrogen, $C_1$-$C_{10}$ alkyl, $C_3$-$C_{13}$ carbocyclyl, aryl, $C_3$-$C_{13}$ carbocyclylalkyl or arylalkyl, wherein said $C_1$-$C_{10}$ alkyl, $C_3$-$C_{13}$ carbocyclyl, aryl, $C_3$-$C_{13}$ carbocyclylalkyl or arylalkyl are each optionally substituted with one or more halo, $C_{1-4}$ alkyl, $C_{1-4}$ haloalkyl, $OR_{17}'$, $SR_{17}'$, $COOR_{17}'$, amino, alkylamino, dialkylamino or heterocyclyl;

or $R_{16}$ and $R_{17}$ together with the N atom to which they are attached form a 3-14 membered heterocycle substituted with 0-5 $R_\alpha$ or are substituted by one or more heterocyclyl, heterocyclylalkyl, $C_3$-$C_{13}$ carbocyclyl or carbocyclylalkyl, wherein said heterocyclyl, heterocyclylalkyl, $C_3$-$C_{13}$ carbocyclyl or carbocyclylalkyl are each optionally substituted by one or more $R_\alpha$;

$R_{17}'$ is H, $C_{1-4}$ alkyl, $C_{1-4}$ haloalkyl, $C_{3-13}$ carbocyclyl, carbocyclylalkyl, heterocyclyl or heterocyclylalkyl, wherein said $C_{3-13}$ carbocyclyl, carbocyclylalkyl, heterocyclyl or heterocyclylalkyl are each optionally substituted by halo or $C_{1-4}$ alkyl;

$R_{18}$ is $C_{1-6}$ alkyl;

$R_\alpha$ is halogen, $C_{1-6}$ alkyl, $C_{2-8}$ alkyloxyalkyl, $C_{1-6}$ haloalkyl, $SR_{13}$, $NR_{11}R_{12}$, OH, $OR_{13}$, $C_{3-13}$ carbocyclyl, heterocyclyl, aryl, $=S$, $=O$, CN, $NO_2$, $NR_\beta R_\beta'$, $COR_\gamma$, $NR_\beta C(O)NR_\beta R_\beta'$, $OC(O)NR_\beta R_\beta'$, $C(O)NR_\beta R_\beta'$, $C(O)OR_\gamma$, $NR_\beta C(O)OR_\gamma$ or $NR_\beta C(O)R_\gamma$, or two $R_\alpha$ together with a carbon atom to which they are both attached form a $C_{3-13}$ carbocycle;

$R_\beta$, $R_\beta'$, $R_\gamma$, and $R_\gamma'$ are each, independently, H, $C_{1-4}$ alkyl, phenyl or benzyl;

$R^I$ and $R^{II}$ are each, independently, H, $C_{1-6}$ alkyl or $C_{3-13}$ carbocyclyl;

$R^{III}$ and $R^{IV}$ are each, independently, H, $C_{1-6}$ alkyl, haloalkyl, carbocyclyl, heterocyclyl, carbocyclylalkyl or heterocyclylalkyl, wherein said carbocyclyl, heterocyclyl, carbocyclylalkyl or heterocyclylalkyl are each optionally substituted by one or more halo, $C_{1-4}$ alkyl or $C_{1-4}$ alkoxy;

$R^V$ is $C_{1-6}$ alkyl, haloalkyl, carbocyclyl or heterocyclyl;

j=1, 2, 3 or 4;

i=0, 1 or 2;

l=2, 3, 4, 5, 6, 7 or 8;

n=0, 1, 2, 3, 4, 5, 6, 7, 8, 9, 10, 11 or 12;

m=0,1 or 2;

p=1 or 2; and r=0, 1, 2, 3, 4 or 5.

The spiro ring is preferably a stable chemical entity.

In some embodiments, $NR_8$ and $NR_b$ have no N—N or N—O bonds.

In some embodiments, A is CWNHOH, $CWNHOR_5$, N(OH)CHO or $N(OH)CWR_6$.

In some embodiments, A is CWNHOH or $CWNHOR_5$.

In some embodiments, A is C(O)NHOH.

In some embodiments, B is $(CH_2)_n$, $(CH_2)_nC=W$, $(CR_dR_f)_n NR_8$, $NR_8(CR_dR_f)_n$, $(CR_dR_f)_nO(CR_dR_f)_r$, $(CR_dR_f)_n S(CR_dR_f)_r$, $O(C=W)NR_8$, O, $NR_8$, $S(O)_m$, S, $C(O)NR_8(CR_dR_f)_n$ or $C(O)(CR_dR_f)_n$.

In some embodiments, B is $(CH_2)_n$, $(CH_2)_nC=W$, $(CR_dR_f)_n NR_8$, $NR_8(CR_dR_f)_n$, $O(C=W)NR_8$, O, $NR_8$, $S(O)_m$, S, $C(O)NR_8(CR_dR_f)_n$ or $C(O)(CR_dR_f)_n$.

In some embodiments, B is $(CH_2)_n$, $(CH_2)_nC=W$, $(CR_dR_f)_n NR_8$, $NR_8(CR_dR_f)_n$, $O(C=W)NR_8$, $C(O)NR_8(CR_dR_f)_n$ or $C(O)(CR_dR_f)_n$.

In some embodiments, B is $(CH_2)_n$, $(CH_2)_nC=W$, $(CR_dR_f)_n NR_8$ or $NR_8(CR_dR_f)_n$.

In some embodiments, B is $(CH_2)_n$.

In some embodiments, B is $CH_2$.

In some embodiments, G is $(CH_2)_n$, $(CH_2)_nC=W$, $(CR_dR_f)_n$ $NR_8$, $NR_8(CR_dR_f)_n$, $(CR_dR_f)_nO(CR_dR_f)_r$, $(CR_dR_f)_n$ $S(CR_dR_f)_r$, $O(C=W)NR_8$, O, $NR_8$, $S(O)_n$, S, $C(O)NR_8$ $(CR_dR_f)_n$ or $C(O)(CR_dR_f)_n$.

In some embodiments, G is $(CH_2)_n$, $(CH_2)_nC=W$, $(CR_dR_f)_n$ $NR_8$, $NR_8(CR_dR_f)_n$, $O(C=W)NR_8$, O, $NR_8$, $S(O)_m$, S, $C(O)NR_8(CR_dR_f)_n$ or $C(O)(CR_dR_f)_n$.

In some embodiments, G is $(CH_2)_n$, $(CH_2)_nC=W$, $(CR_dR_f)_n$ $NR_8$, $NR_8(CR_dR_f)_n$, $O(C=W)NR_8$, $C(O)NR_8$ $(CR_dR_f)_n$ or $C(O)(CR_dR_f)_n$.

In some embodiments, G is $(CH_2)_n$, $(CH_2)_nC=W$, $(CR_dR_f)_n$ $NR_8$, $NR_8(CR_dR_f)_n$.

In some embodiments, G is $(CH_2)_n$.

In some embodiments, G is $CH_2$.

In some embodiments, B and G are both $CH_2$.

In some embodiments, D is oxygen.

In some embodiments, X is $(CH_2)_j$, $C_{1-10}$ alkylene substituted with 0 to 3 $R_a$, $NR_b$, $S(O)_m$, $C=O$, $NR_bC(O)$, $NR_bC(O)O$, $NR_bC(O)NR_b$, $C(O)O$, $OC(O)$, $S(O)_mNR_b$, $NR_b$ $S(O)_m$, $NR_bS(O)NR_b$, or $(CR_dR_f)_jNR_b$, $NR_b(CR_dR_f)_j$.

In some embodiments, X is $(CH_2)_j$, $NR_b$, $(CR_dR_f)_jNR_b$ or $NR_b(CR_dR_f)_j$.

In some embodiments, X is $(CH_2)_j$, $(CR_dR_f)_jNR_b$ or $NR_b$ $(CR_dR_f)_j$.

In some embodiments, X is $CH_2NR_b$, $CH_2CH_2$ or $NR_bCH_2CH_2$.

In some embodiments, X is $CH_2NR_b$.

In some embodiments, Y is absent, $(CH_2)_j$, $C_{1-10}$ alkylene substituted with 0 to 3 $R_a$, $NR_b$, $S(O)_m$, $C=O$, $NR_bC(O)$, $NR_bC(O)O$, $NR_bC(O)NR_b$, $C(O)O$, $OC(O)$, $S(O)_mNR_b$, $NR_bS(O)_m$, $NR_bS(O)NR_b$, or $(CR_dR_f)_jNR_b$, $NR_b(CR_dR_f)_j$.

In some embodiments, Y is absent, $(CH_2)_j$, $NR_b$, $(CR_dR_f)_j$ $NR_b$ or $NR_b(CR_dR_f)_j$.

In some embodiments, Y is absent, $(CH_2)_j$, $(CR_dR_f)_jNR_b$ or $NR_b(CR_dR_f)_j$.

In some embodiments, Y is absent, $CH_2$, $CH_2NR_b$, $CH_2CH_2$ or $NR_bCH_2CH_2$.

In some embodiments, Y is absent or $CH_2$.

In some embodiments, Y is $CH_2$.

In some embodiments, $R_1$ is H.

In some embodiments, $R_2$ is H.

In some embodiments, $R_4$ is H.

In some embodiments, $R_4'$ is H.

In some embodiments, $R_5'$ is H.

In some embodiments, $R_3$ is $NR_{16}R_{17}$.

In some embodiments, M is CO.

In some embodiments, U is absent.

In some embodiments, V is heterocyclyl substituted with 0-5 $R_e$.

In some embodiments, V is azetidin-1-yl, 2,5-dihydro-1H-pyrrol-1-yl, piperindin-1yl, piperazin-1-yl, pyrrolidin-1-yl, isoquinol-2-yl, pyridin-1-yl, 3,6-dihydropyridin-1-yl, 2,3-dihydroindol-1-yl, 1,3,4,9-tetrahydrocarbolin-2-yl, thieno[2,3-c]pyridin-6-yl, 3,4,10,10a-tetrahydro-1H-pyrazino[1,2-a]indol-2-yl, 1,2,4,4a,5,6-hexahydro-pyrazino[1,2-a]quinolin-3-yl, pyrazino[1,2-a]quinolin-3-yl, diazepan-1-yl, 1,4,5,6-tetrahydro-2H-benzo[f]isoquinolin-3-yl, 1,4,4a,5,6,10b-hexahydro-2H-benzo[f]isoquinolin-3-yl, 3,3a,8,8a-tetrahydro-1H-2-aza-cyclopenta[a]inden-2-yl, or 2,3,4,7-tetrahydro-1H-azepin-1-yl, azepan-1-yl.

In some embodiments, U' is absent, O or $C_{1-10}$alkylene substituted with 0 to 5 $R_a$.

In some embodiments, U' is absent.

In some embodiments, V' is $C_{3-13}$ carbocyclyl substituted with 0-5 $R_e$ or heterocyclyl substituted with 0-5 $R_e$.

In some embodiments, V' is $C_{3-13}$ carbocyclyl substituted with 0-5 $R_e$.

In some embodiments, V' is phenyl substituted with 0-5 $R_e$.

In some embodiments, V' is phenyl substituted with 0-5 T, $C_{1-8}$alkylene-T, $(CR_b'R_c')_r$—O—$(CR_b'R_c')_r$-T, OH, Cl, F, Br, I, CN, $NO_2$, $OR^{IV}$, $CONR^IR^{II}$ or $NR^ICOR^{II}$.

In some embodiments, V' is phenyl.

In some embodiments, V' is heterocyclyl substituted with 0-5 $R_e$.

In some embodiments, V' is thiazolyl, benzothiazolyl, thienyl, quinolinyl, pyridinyl, pyarazinyl, benzimidazolyl, indazolyl, 3,6-dihydropyridinyl, piperidinyl or 2,3-dihydro-benzofuran-5-yl.

In some embodiments, U' is O or $C_{1-10}$ alkylene and V' is $C_{3-13}$ carbocyclyl substituted with 0-5 $R_e$ or heterocyclyl substituted with 0-5 $R_e$.

In some embodiments, M is CO, U is absent, V is heterocyclyl substituted with 0-5 $R_e$, U' is absent, and V' is $C_{3-13}$ carbocyclyl substituted with 0-5 $R_e$ or heterocyclyl substituted with 0-5 $R_e$.

In some embodiments, M is CO, U is absent, V is absent, U' is absent and V' is $NR_bR_c$.

In some embodiments, $R_b$ and $R_c$ are each, independently, H, $C_{1-6}$alkylene-T, $C(O)NR_a'(CR_c'R_b')_r$-T, $C(O)O(CR_b'R_c')_r$-T, $C(O)(CR_b'R_c')_r$-T, $S(O)_p(CR_b'R_c')_r$-T, $(CR_c'R_b')_r$—O—$(CR_c'R_b')_r$-T, $C(NR_a'R_a')(=N-CN)$ or $C(NR_a'R_a')(=CHNO_2)$.

In some embodiments, $R_b$ and $R_c$ are each, independently, H, $C_{1-4}$ alkyl, $C(O)NR_a'(CR_c'R_b')_r$-T, $C(O)O(CR_b'R_c')_r$-T, $S(O)_p(CR_b'R_c')_r$-T, $(CR_c'R_b')_r$—O—$(CR_c'R_b')_r$-T, $C(NR_a'R_a')(=N-CN)$ or $C(NR_a'R_a')(=CHNO_2)$.

In some embodiments, $R_b$ is H, $C_{1-4}$ alkyl, $C(O)(CR_b'R_c')_r$-T, $C(O)O(CR_b'R_c')_r$-T, $S(O)_p(CR_b'R_c')_r$-T or $(CR_c'R_b')_r$—O—$(CR_c'R_b')_r$-T.

In some embodiments, $R_b$ is H.

In some embodiments, $R_b$ is $C_{1-4}$ alkyl.

In some embodiments, $R_b$ is $C(O)(CR_b'R_c')_r$-T.

In some embodiments, $R_b$ is $C(O)O(CR_b'R_c')_r$-T.

In some embodiments, $R_b$ is $S(O)_p(CR_b'R_c')_r$-T.

In some embodiments, $R_b$ is $(CR_c'R_b')_r$—O—$(CR_c'R_b')_r$-T.

In some embodiments, $R_c$ is H or $C_{1-4}$ alkyl.

In some embodiments, $R_e$ is H, T, $C_{1-8}$alkylene-T, $C(O)$ $NR_a'(CR_b'R_c')_r$-T, $(CR_b'R_c')_r$—O—$(CR_b'R_c')_r$-T, OH, Cl, F, Br, I, CN, $NO_2$, $OR^{IVi}$, $NR^IR^{II}$, $CONR^IR^{II}$, $NR^ICOR^{II}$, $SO_2NR^IR^{II}$, $C_{1-8}$ haloalkyl, $C_{3-13}$ carbocyclyl, heterocyclyl, carbocyclylalkyl, or heterocyclylalkyl, wherein each of said carbocyclyl, heterocyclyl, carbocyclylalkyl, and heterocyclyalkyl groups is optionally substituted by one or more $C_{1-8}$ alkyl, alkoxy, halo, haloalkyl, haloalkoxy, cyano, nitro, amino, alkylamino, dialkylamino, carboxy, carboxy alkyl ester, carboxy aryl ester, aminocarbonyl, alkylaminocarbonyl, dialkylaminocarbonyl, sulfonyl, aminosulfonyl, alkylaminosulfonyl, dialkylaminosulfonyl, arylsulfonyl, arylsulfinyl, alkylsulfonyl or arylsufonyl.

In some embodiments, wherein $R_e$ is H, $C_{1-6}$ alkyl, OH, Cl, F, Br, I, CN, $NO_2$, methoxy, ethoxy, n-propoxy, isopropoxy, phenoxy, benzyloxy, amino, $(C_{1-4}$ alkyl)amino, $(C_{2-8})$dialkylamino, $C(O)O(C_{1-4}$ alkyl), $CONH_2$, $CONH(C_{1-4}$ alkyl), $CON(C_{1-4}$ alkyl)$_2$, $C_{1-6}$ haloalkyl, phenyl, cyclopropyl, cyclobutyl, cyclopentyl, cyclohexyl, cycloheptyl, benzyl, or phenethyl.

In some embodiments, $R_4'$ is $C(O)NR_a'(CR_c'R_b')_r$-T, $C(O)$ $O(CR_b'R_c')_r$-T or $S(O)_p(CR_b'R_c')_r$-T.

In some embodiments, $R_5'$ is $C(O)NR_a'(CR_c'R_b')_r$-T, $C(O)$ $O(CR_b'R_c')_r$-T or $S(O)_p(CR_b'R_c')_r$-T.

In some embodiments, r is 0, 1 or 2.

In some embodiments, n is 0, 1 or 2.

In some embodiments, j is 1 or 2.

In some embodiments, said compound has Formula II.

In some embodiments, the compound has Formula II wherein:
A is CWNHOH,
B is $(CH_2)_n$, $(CH_2)_nC=W$, $(CR_dR_f)_nNR_8$, $NR_8(CR_dR_f)_n$, $(CR_dR_f)_nO(CR_dR_f)_r$, $(CR_dR_f)_nS(CR_dR_f)_r$, $OC(O)NR_8$, O, $NR_8$, $S(O)_m$, S, $C(O)NR_8CR_dR_f)_n$ or $C(O)(CR_dR_f)_n$;
G is $(CH_2)_n$, $(CH_2)_nC=W$, $(CR_dR_f)_nNR_8$, $NR_8(CR_dR_f)_n$, $(CR_dR_f)_nO(CR_dR_f)_r$, $(CR_dR_f)_nS(CR_dR_f)_r$, $OC(O)NR_8$, O, $NR_8$, $S(O)_m$, S, $C(O)NR_8(CR_dR_f)_n$ or $C(O)(CR_dR_f)_n$;
X is absent, $(CH_2)_j$, $C_{1-10}$ alkylene substituted with 0 to 3 $R_a$, O, $NR_b$, $S(O)_m$, C=O, $NR_bC(O)$, $NR_bC(O)O$, $NR_bC(O)NR_b$, C(O)O, OC(O), $S(O)_mNR_b$, $NR_bS(O)_m$, $NR_bS(O)NR_b$, $(CR_dR_f)_jNR_b$ or $NR_b(CR_dR_f)_j$;
Y is absent, $(CH_2)_j$, $C_{1-10}$ alkylene substituted with 0 to 3 $R_a$, O, $NR_b$, $S(O)_m$, C=O, $NR_bC(O)$, $NR_bC(O)O$, $NR_bC(O)NR_b$, C(O)O, OC(O), $S(O)_mNR_b$, $NR_bS(O)_m$, $NR_bS(O)NR_b$, $(CR_dR_f)_jNR_b$ or $NR_b(CR_dR_f)_j$;
M is CO;
U is absent, $C_{1-10}$ alkylene substituted with 0 to 5 $R_a$, O, $NR_b$, $S(O)_m$, C=O, $NR_bC(O)$, $NR_bC(O)O$, $NR_bC(O)NR_b$, C(O)O, OC(O), $S(O)_mNR_b$, $NR_bS(O)_m$ or $NR_bS(O)NR_b$;
V is absent, $C_{3-13}$ carbocyclyl substituted with 0-5 $R_e$ or heterocyclyl substituted with 0-5 $R_e$;
U' is absent, $C_{1-10}$ alkylene substituted with 0 to 5 $R_a$, O, $NR_bS(O)_m$, C=O, $NR_bC(O)$, $NR_bC(O)O$, $NR_bC(O)NR_b$, C(O)O, OC(O), $S(O)_mNR_b$, $NR_bS(O)_m$, or $NR_bS(O)NR_b$;
V' is H, $C_{1-8}$ alkyl, $NR_bR_c$, $C_{3-13}$ carbocyclyl substituted with 0-5 $R_c$ or heterocyclyl substituted with 0-5 $R_e$;
$R_1$ is hydrogen;
$R_2$ is hydrogen;
$R_3$ is $NR_{16}R_{17}$;
$R_4'$ is H, $C(O)NR_a'(CR_c'R_b')_r$-T, $C(O)O(CR_b'R_c')_r$-T or $S(O)_p(CR_b'R_c')_r$-T;
$R_5'$ is H, $C(O)NR_a'(CR_c'R_b')_r$-T, $C(O)O(CR_b'R_c')_r$-T or $S(O)_p(CR_b'R_c')_r$-T; and
W is oxygen.

In some embodiments, the compound has Formula II wherein:
A is C(O)NHOH;
B is $(CH_2)_n$, $(CH_2)_nC=W$, $(CR_dR_f)_nNR_8$, $NR_8(CR_dR_f)_n$, $(CR_dR_f)_nO(CR_dR_f)_r$, $(CR_dR_f)_nS(CR_dR_f)_r$, $OC(O)NR_8$, O, $NR_8$, $S(O)_m$, S, $C(O)NR_8(CR_dR_f)_n$ or $C(O)(CR_dR_f)_n$;
G is $(CH_2)_n$, $(CH_2)_nC=W$, $(CR_dR_f)_nNR_8$, $NR_8(CR_dR_f)_n$, $(CR_dR_f)_nO(CR_dR_f)_r$, $(CR_dR_f)_nS(CR_dR_f)_r$, $OC(O)NR_8$, O, $NR_8$, $S(O)_m$, S, $C(O)NR_8(CR_dR_f)_n$ or $C(O)(CR_dR_f)_n$;
X is absent, $(CH_2)_j$, $NR_b$, $(CR_dR_f)_jNR_b$ or $NR_b(CR_dR_f)_j$;
Y is absent, $(CH_2)_j$, $NR_b$, $(CR_dR_f)_jNR_b$ or $NR_b(CR_dR_f)_j$;
M is CO;
U is absent;
V is absent, $C_{3-13}$ carbocyclyl substituted with 0-5 $R_e$ or heterocyclyl substituted with 0-5 $R_e$;
U' is absent, $C_{1-10}$ alkylene substituted with 0 to 5 $R_a$, O, $NR_bS(O)_m$, C=O, $NR_bC(O)$, $NR_bC(O)O$, $NR_bC(O)NR_b$, C(O)O, OC(O), $S(O)_mNR_b$, $NR_bS(O)_m$, or $NR_bS(O)NR_b$;
V' is H, $C_{1-8}$ alkyl, $NR_bR_c$, $C_{3-13}$ carbocyclyl substituted with 0-5 $R_e$ or heterocyclyl substituted with 0-5 $R_e$;
$R_b$ and $R_c$ are each, independently, H, $C(O)O(CR_b'R_c')_r$-T or $S(O)_p(CR_b'R_c')_r$-T; $C(O)(CR_b'R_c')_r$-T, $(CR_c'R_b')_r$—O—$(CR_c'R_b')_r$-T, $C(O)NR_a'(CR_c'R_b')_r$-T, $C(NR_a'R_a')(=N-CN)$ or $C(NR_a'R_a')(=CHNO_2)$;
$R_d$ and $R_f$ are each, independently, H or $C_{1-6}$ alkyl;
$R_a'$ is H or $C_{1-6}$ alkyl;
$R_b'$ and $R_c'$ are each, independently, H, $C_{1-6}$ alkyl, OH, Cl, F, Br, I, CN, $NO_2$, $NR^IR^{II}$, $OR^{IV}$ or haloalkyl;
$R_1$ is hydrogen;
$R_2$ is hydrogen;
$R_4'$ is H, $C(O)NR_a'(CR_c'R_b')_r$-T, $C(O)O(CR_b'R_c')_r$-T or $S(O)_p(CR_b'R_c')_r$-T;
$R_5'$ is H, $C(O)NR_a'(CR_c'R_b')_r$-T, $C(O)O(CR_b'R_c')_r$-T or $S(O)_p(CR_b'R_c')_r$-T;
j=1 or 2;
l=2, 3 or 4;
n=0, 1, 2, 3 or 4; and
r=0, 1 or 2.

In some embodiments, the compound has Formula II wherein:
A is CONHOH;
B is $(CH_2)_n$, $(CH_2)_nC=W$, $(CR_dR_f)_nNR_8$, $NR_8(CR_dR_f)_n$, $(CR_dR_f)_nO(CR_dR_f)_r$, $(CR_dR_f)_nS(CR_dR_f)_r$, $OC(O)NR_8$, O, $NR_8$, $S(O)_m$, S, $C(O)NR_8(CR_dR_f)_n$ pr $C(O)(CR_dR_f)_n$;
G is $(CH_2)_n$, $(CH_2)_nC=W$, $(CR_dR_f)_nNR_8$, $NR_8(CR_dR_f)_n$, $(CR_dR_f)_nO(CR_dR_f)_r$, $(CR_dR_f)_nS(CR_dR_f)_r$, $OC(O)NR_8$, O, $NR_8$, $S(O)_m$, S, $C(O)NR_8(CR_dR_f)_n$ or $C(O)(CR_dR_f)_n$;
X is absent, $(CH_2)_j$, $CH_2NR_b$ or $NR_bCH_2CH_2$;
Y is absent, $(CH_2)_j$, $CH_2NR_b$ or $NR_bCH_2CH_2$;
M is CO;
U is absent;
V is heterocyclyl substituted with 0-5 $R_e$;
U' is absent, $C_{1-10}$ alkylene substituted with 0 to 5 $R_a$, or O;
V' is H, $C_{1-8}$ alkyl, $NR_bR_c$, $C_{3-13}$ carbocyclyl substituted with 0-5 $R_e$ or heterocyclyl substituted with 0-5 $R_e$;
$R_b$ is H, $C(O)O(CR_b'R_c')_r$-T or $S(O)_p(CR_b'R_c')_r$-T; $C(O)(CR_b'R_c')_r$-T, $(CR_c'R_b')_r$—O—$(CR_c'R_b')_r$-T, $C(O)NR_a'(CR_c'R_b')_r$-T, $C(NR_a'R_a')(=N-CN)$ or $C(NR_a'R_a')(=CHNO_2)$;
$R_c$ is H, T, $C_{1-6}$alkylene-T, $C_{2-8}$alkenylene-T or $C_{2-6}$alkynylene-T;
$R_d$ and $R_f$ are each, independently, H or $C_{1-6}$ alkyl;
$R_a'$ is H or $C_{1-6}$ alkyl;
$R_b'$ and $R_c'$ are each, independently, H, $C_{1-6}$ alkyl, OH, Cl, F, Br, I, CN, $NO_2$, $NR^IR^{II}$, $OR^{IV}$ or haloalkyl;
$R_1$ is hydrogen;
$R_2$ is hydrogen;

$R_4'$ is H;
$R_5'$ is H;
j=1 or 2;
j=2, 3 or 4;
n=0, 1, 2, 3 or 4; and
r=0, 1 or 2.

In some embodiments, the compound has Formula II wherein:
A is CONHOH;
B is $(CH_2)_n$, $(CH_2)_nC=W$, $(CR_dR_f)_nNR_8$ or $NR_8(CR_dR_f)_n$;
G is $(CH_2)_n$, $(CH_2)_nC=W$, $(CR_dR_f)_nNR_8$ or $NR_8(CR_dR_f)_n$;
X is absent, $(CH_2)_j$, $CH_2NR_b$ or $NR_bCH_2CH_2$;
Y is absent, $(CH_2)_j$, $CH_2NR_b$ or $NR_bCH_2CH_2$;
M is CO;
U is absent;
V is heterocyclyl substituted with 0-5 $R_e$;
U' is absent, $C_{1-10}$alkylene substituted with 0 to 5 $R_a$, or O;
V' is H, $C_{1-8}$ alkyl, $NR_bR_c$, $C_{3-13}$ carbocyclyl substituted with 0-5 $R_e$ or heterocyclyl substituted with 0-5 $R_e$;
$R_b$ is H, $C(O)O(CR_b'R_c')_r$-T or $S(O)_p(CR_b'R_c')_r$-T; $C(O)(CR_b'R_c')_r$-T, $(CR_c'R_b')_r$—O—$(CR_c'R_b')_r$-T, $C(O)NR_a'(CR_c'R_b')_r$-T, $C(NR_a'R_a')(=N—CN)$ or $C(NR_a'R_a')(=CHNO_2)$;
$R_c$ is H, T, $C_{1-6}$alkylene-T, $C_{2-8}$alkenylene-T or $C_{2-6}$alkynylene-T;
$R_d$ and $R_f$ are each, independently, H or $C_{1-6}$ alkyl;
$R_a'$ is H or $C_{1-6}$ alkyl;
$R_b'$ and $R_c'$ are each, independently, H, $C_{1-6}$ alkyl, OH, Cl, F, Br, I, CN, $NO_2$, $NR^JR^{JJ}$, $OR^{JV}$ or haloalkyl;
$R_1$ is hydrogen;
$R_2$ is hydrogen;
$R_4'$ is H;
$R_5'$ is H;
j=1 or 2;
l=2, 3 or 4;
n=0, 1, 2, 3 or 4; and
r=0, 1 or 2.

In some embodiments, the compound has Formula II wherein:
A is CONHOH;
B is $(CH_2)_n$;
G is $(CH_2)_n$;
X is absent, $(CH_2)_j$, $CH_2NR_b$ or $NR_bCH_2CH_2$;
Y is absent, $(CH_2)_j$, $CH_2NR_b$ or $NR_bCH_2CH_2$;
M is CO;
U is absent;
V is heterocyclyl substituted with 0-5 $R_e$;
U' is absent, $C_{1-10}$alkylene substituted with 0 to 5 $R_a$, or O;
V' is H, $C_{1-8}$ alkyl, $NR_bR_c$, $C_{3-13}$ carbocyclyl substituted with 0-5 $R_e$ or heterocyclyl substituted with 0-5 $R_e$;
$R_b$ is H, $C(O)O(CR_b'R_c')_r$-T or $S(O)_p(CR_b'R_c')_r$-T; $C(O)(CR_b'R_c')_r$-T, $(CR_c'R_b')_r$—O—$(CR_c'R_b')_r$-T, $C(O)NR_a'(CR_c'R_b')_r$-T, $C(NR_a'R_a')(=N—CN)$ or $C(NR_a'R_a')(=CHNO_2)$;
$R_c$ is H, T, $C_{1-6}$alkylene-T, $C_{2-8}$alkenylene-T or $C_{2-6}$alkynylene-T;
$R_a'$ is H or $C_{1-6}$ alkyl;
$R_b'$ and $R_c'$ are each, independently, H, $C_{1-6}$ alkyl, OH, Cl, F, Br, I, CN, $NO_2$, $NR^JR^{JJ}$, $OR^{JV}$ or haloalkyl;
$R_1$ is hydrogen;
$R_2$ is hydrogen;
$R_4'$ is H;
$R_5'$ is H;
j=1 or 2;
l=2, 3 or 4;
n=0, 1, 2, 3 or 4; and
r=0, 1 or 2.

In some embodiments, the compound has Formula II wherein:
A is CONHOH;
B is $CH_2$;
G is $CH_2$;
X is $CH_2NR_b$;
Y is $(CH_2)_j$;
M is CO;
U is absent;
V is azetidin-1-yl, 2,5-dihydro-1H-pyrrol-1-yl, piperindin-1yl, piperazin-1-yl, pyrrolidin-1-yl, isoquinol-2-yl, pyridin-1-yl, 3,6-dihydropyridin-1-yl, 2,3-dihydroindol-1-yl, 1,3,4,9-tetrahydrocarbolin-2-yl, thieno[2,3-c]pyridin-6-yl, 3,4,10,10a-tetrahydro-1H-pyrazino[1,2-a]indol-2-yl, 1,2,4,4a,5,6-hexahydro-pyrazino[1,2-a]quinolin-3-yl, pyrazino[1,2-a]quinolin-3-yl, diazepan-1-yl, 1,4,5,6-tetrahydro-2H-benzo[f]isoquinolin-3-yl, 1,4,4a,5,6,10b-hexahydro-2H-benzo[f]isoquinolin-3-yl, 3,3a,8,8a-tetrahydro-1H-2-aza-cyclopenta[a]inden-2-yl, or 2,3,4,7-tetrahydro-1H-azepin-1-yl, azepan-1-yl;
U' is absent;
V' is $C_{3-13}$ carbocyclyl substituted with 0-5 $R_e$;
$R_b$ is H, $C(O)O(CR_b'R_c')_r$-T or $C(O)(CR_b'R_c')_r$-T;
$R_a'$ is H or $C_{1-6}$ alkyl;
$R_b'$ and $R_c'$ are both H;
$R_1$ is hydrogen;
$R_2$ is hydrogen;
$R_4'$ is H;
$R_5'$ is H;
j=1 or 2; and
r=0, 1 or 2.

In some embodiments, the compound has Formula II wherein:
A is CONHOH;
B is $CH_2$;
G is $CH_2$;
X is $CH_2NR_b$;
Y is $(CH_2)_j$;
M is CO;
U is absent;
V is piperindin-1yl, piperazin-1-yl, pyrrolidin-1-yl, pyridin-1-yl or 3,6-dihydropyridin-1-yl;
U' is absent;
V' is $C_{3-13}$ aryl substituted with 0-5 $R_e$;
$R_b$ is H, $C(O)O(CR_b'R_c')_r$-T or $C(O)(CR_b'R_c')_r$-T;
$R_b'$ and $R_c'$ are both H;
$R_1$ is hydrogen;
$R_2$ is hydrogen;
$R_4'$ is H;
$R_5'$ is H;
j is 1 or 2; and
r is 0, 1 or 2.

In some embodiments, the compound has Formula II wherein:
A is CONHOH;
B is $CH_2$;
G is $CH_2$;
X is $CH_2NR_b$;
Y is $(CH_2)_j$;
M is CO;
U is absent;
V is piperindin-1yl, piperazin-1-yl, pyrrolidin-1-yl, pyridin-1-yl or 3,6-dihydropyridin-1-yl;
U' is absent;
V' is phenyl substituted with 0-3 $R_e$;
$R_b$ is H, $C(O)O(CR_b'R_c')_r$-T or $C(O)(CR_b'R_c')_r$-T;
$R_b'$ and $R_c'$ are both H;

R₁ is hydrogen;
R₂ is hydrogen;
R₄' is H;
R₅' is H;
j is 1 or 2; and
r is 0, 1 or 2.

At various places in the present specification substituents of compounds of the invention are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

For compounds of the invention in which a variable appears more than once, each variable can be a different moiety selected from the Markush group defining the variable. For example, where a structure is described having two $R^1$ groups that are simultaneously present on the same compound; the two R groups can represent different moieties selected from the Markush group defined for R.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

As used herein, the term "alkyl" is meant to refer to a saturated hydrocarbon group which is straight-chained or branched. Example alkyl groups include methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like. An alkyl group can contain from 1 to about 20, from 2 to about 20, from 1 to about 10, from 1 to about 8, from 1 to about 6, from 1 to about 4, or from 1 to about 3 carbon atoms.

As used herein, "alkenyl" refers to an alkyl group having one or more double carbon-carbon bonds. Example alkenyl groups include ethenyl, propenyl, cyclohexenyl, and the like.

As used herein, "alkynyl" refers to an alkyl group having one or more triple carbon-carbon bonds. Example alkynyl groups include ethynyl, propynyl, and the like.

As used herein, "haloalkyl" refers to an alkyl group having one or more halogen substituents. Example haloalkyl groups include $CF_3$, $C_2F_5$, $CHF_2$, $CCl_3$, $CHCl_2$, $C_2Cl_5$, and the like. An alkyl group in which all of the hydrogen atoms are replaced with halogen atoms can be referred to as "perhaloalkyl."

As used herein, "alkylene" or "alkylenyl" refers to a bivalent alkyl group. An example alkylene group is methylene or ethylene.

As used herein, "alkenylene" or "alkenylenyl" refers to a bivalent alkenyl group.

As used herein, "carbocyclyl" groups are saturated (i.e., containing no double or triple bonds) or unsaturated (i.e., containing one or more double or triple bonds) cyclic hydrocarbon moieties. Carbocyclyl groups can be mono- or polycyclic (e.g., having 2, 3 or 4 fused rings) or spirocyclic. Example carbocyclyl groups include cyclopropyl, cyclobutyl, cyclopentyl, cyclohexyl, cycloheptyl, cyclopentenyl, 1,3-cyclopentadienyl, cyclohexenyl, norbornyl, norpinyl, norcarnyl, adamantyl, phenyl, and the like. Carbocyclyl groups can be aromatic (e.g., "aryl") or non-aromatic (e.g., "cycloalkyl"). In some embodiments, carbocyclyl groups can have from about 3 to about 30 carbon atoms, about 3 to about 20, about 3 to about 10, or about 3 to about 7 carbon atoms.

As used herein, "aryl" refers to an aromatic carbocyclyl group including monocyclic or polycyclic (e.g., having 2, 3 or 4 fused rings) aromatic hydrocarbons such as, for example, phenyl, naphthyl, anthracenyl, phenanthrenyl, indanyl, indenyl, and the like. In some embodiments, aryl groups have from 6 to about 20 carbon atoms.

As used herein, "cycloalkyl" refers to non-aromatic carbocyclyl groups including cyclized alkyl, alkenyl, and alkynyl groups. Cycloalkyl groups can include bi- or polycyclic (e.g., having 2, 3 or 4 fused rings) ring systems as well as spiro ring systems. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, adamantyl, and the like. Also included in the definition of cycloalkyl are moieties that have one or more aromatic rings fused (i.e., having a bond in common with) to the cycloalkyl ring, for example, benzo derivatives of pentane, pentene, hexane, and the like.

As used herein, "heterocyclyl" or "heterocycle" refers to a saturated or unsaturated carbocyclyl group wherein one or more of the ring-forming carbon atoms of the carbocyclyl group is replaced by a heteroatom such as O, S, or N. Heterocyclyl groups can be aromatic (e.g., "heteroaryl") or non-aromatic (e.g., "heterocycloalkyl"). Heterocyclyl groups can also correspond to hydrogenated and partially hydrogenated heteroaryl groups. Heterocyclyl groups can be characterized as having 3-14 ring-forming atoms. In some embodiments, heterocyclyl groups can contain, in addition to at least one heteroatom, from about 1 to about 20, about 2 to about 10, or about 2 to about 7 carbon atoms and can be attached through a carbon atom or heteroatom. In further embodiments, the heteroatom can be oxidized (e.g., have an oxo or sulfindo substituent) or a nitrogen atom can be quaternized. Examples of heterocyclyl groups include morpholino, thiomorpholino, piperazinyl, tetrahydrofuranyl, tetrahydrothienyl, 2,3-dihydrobenzofuryl, 1,3-benzodioxole, benzo-1,4-dioxane, piperidinyl, pyrrolidinyl, isoxazolidinyl, isothiazolidinyl, pyrazolidinyl, oxazolidinyl, thiazolidinyl, imidazolidinyl, and the like, as well as any of the groups listed below for "heteroaryl" and "heterocycloalkyl." Further example heterocycles include pyrimidinyl, phenanthridinyl, phenanthrolinyl, phenazinyl, phenothiazinyl, phenoxathiinyl, phenoxazinyl, phthalazinyl, piperazinyl, piperidinyl, 3,6-dihydropyridyl, 1,2,3,6-tetrahydropyridyl, 1,2,5,6-tetrahydropyridyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, tetrazolyl, 6H-1,2,5-thia-diazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, xanthenyl, octahydro-isoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, quinazolinyl, quinolinyl, 4H-quinolizinyl, quinoxalinyl, quinuclidinyl, acridinyl, azocinyl, benzimidazolyl, benzofuranyl, benzothiofuranyl, benzo-thiophenyl, benzoxazolyl, benzthiazolyl, benztriazolyl, benztetrazolyl, benzisoxazolyl, benzisothiazolyl, benzimidazolinyl, methylenedioxyphenyl, morpholinyl, naphthyridinyl, deca-hydroquinolinyl, 2H,6H-1,5,2dithiazinyl, dihydrofuro[2,3-b]tetrahydrofuran, furanyl, furazanyl, carbazolyl, 4aH-carbazolyl, carbolinyl, chromanyl, chromenyl, cinnolinyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl and isoxazolyl. Further examples of heterocycles include azetidin-1-yl, 2,5-dihydro-1H-pyrrol-1-yl, piperindin-1yl, piperazin-1-yl, pyrrolidin-1-yl, isoquinol-2-yl, pyridin-1-yl, 3,6-dihydropyridin-1-yl, 2,3-dihydroindol-1-yl, 1,3,4,9-tetrahydrocarbolin-2-yl, thieno[2,3-c]pyridin-6-yl, 3,4,10,10a-tetrahydro-1H-pyrazino[1,2-a]indol-2-yl, 1,2,4,4a,5,6-hexahydro-pyrazino[1,2-a]quinolin-3-yl, pyrazino[1,2-a]quinolin-3-yl, diazepan-1-yl, 1,4,5,6-tetrahydro-2H-benzo[f] isoquinolin-3-yl, 1,4,4a,5,6,10b-hexahydro-2H-benzo[f]isoquinolin-3-yl, 3,3a,8,8a-tetrahydro-1H-2-aza-cyclopenta[a]inden-2-yl, and 2,3,4,7-tetrahydro-1H-azepin-1-yl, azepan-1-yl. Also included are fused ring and spiro compounds containing, for example, the above heterocycles.

As used herein, "heteroaryl" groups are aromatic heterocyclyl groups and include monocyclic and polycyclic (e.g., having 2, 3 or 4 fused rings) aromatic hydrocarbons that have at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl, and the like. In some embodiments, the heteroaryl group has from 1 to about 20 carbon atoms, and in further embodiments from about 3 to about 20 carbon atoms. In some embodiments, the heteroaryl group contains 3 to about 14, 3 to about 7, or 5 to 6 ring-forming atoms. In some embodiments, the heteroaryl group has 1 to about 4, 1 to about 3, or 1 to 2 heteroatoms.

As used herein, "heterocycloalkyl" refers to non-aromatic heterocyclyl groups including cyclized alkyl, alkenyl, and alkynyl groups where one or more of the ring-forming carbon atoms is replaced by a heteroatom such as an O, N, or S atom. Example heterocycloalkyl" groups include morpholino, thiomorpholino, piperazinyl, tetrahydrofuranyl, tetrahydrothienyl, 2,3-dihydrobenzofuryl, 1,3-benzodioxole, benzo-1,4-dioxane, piperidinyl, pyrrolidinyl, isoxazolidinyl, isothiazolidinyl, pyrazolidinyl, oxazolidinyl, thiazolidinyl, imidazolidinyl, and the like. Also included in the definition of heterocycloalkyl are moieties that have one or more aromatic rings fused (i.e., having a bond in common with) to the non-aromatic heterocyclic ring, for example phthalimidyl, naphthalimidyl, and benzo derivatives of heterocycles such as indolene and isoindolene groups. In some embodiments, the heterocycloalkyl group has from 1 to about 20 carbon atoms, and in further embodiments from about 3 to about 20 carbon atoms. In some embodiments, the heterocycloalkyl group contains 3 to about 14, 3 to about 7, or 5 to 6 ring-forming atoms. In some embodiments, the heterocycloalkyl group has 1 to about 4, 1 to about 3, or 1 to 2 heteroatoms. In some embodiments, the heterocycloalkyl group contains 0 to 3 double bonds. In some embodiments, the heterocycloalkyl group contains 0 to 2 triple bonds.

As used herein, "halo" or "halogen" includes fluoro, chloro, bromo, and iodo.

As used herein, "alkoxy" refers to an —O-alkyl group. Example alkoxy groups include methoxy, ethoxy, propoxy (e.g., n-propoxy and isopropoxy), t-butoxy, and the like.

As used herein, "aryloxy" refers to an —O-aryl group. An example aryloxy group is phenoxy.

As used here, "haloalkoxy" refers to an —O-haloalkyl group. An example haloalkoxy group is $OCF_3$.

As used herein, "carbocyclylalkyl" refers to an alkyl moiety substituted by a carbocyclyl group. Example carbocyclylalkyl groups include "aralkyl" (alkyl substituted by aryl ("arylalkyl")) and "cycloalkylalkyl" (alkyl substituted by cycloalkyl). In some embodiments, carbocyclylalkyl groups have from 4 to 24 carbon atoms.

As used herein, "heterocyclylalkyl" refers to an alkyl moiety substituted by a heterocarbocyclyl group. Example heterocarbocyclylalkyl groups include "heteroarylalkyl" (alkyl substituted by heteroaryl) and "heterocycloalkylalkyl" (alkyl substituted by heterocycloalkyl). In some embodiments, heterocyclylalkyl groups have from 3 to 24 carbon atoms in addition to at least one ring-forming heteroatom.

As used herein, "amino" refers to an $NH_2$ group. "Alkylamino" refers to an amino group substituted by an alkyl group and "dialkylamino" refers to an amino group substituted by two alkyl groups.

As used herein, "aminocarbonyl" refers to $CONH_2$.

As used herein, "alkylaminocarbonyl" refers to CONH (alkyl).

As used herein, "alkylaminocarbonyl" refers to CON (alkyl)$_2$.

As used herein, "carboxy" or "carboxyl" refers to COOH.

As used herein, "carboxy alkyl ester" refers to COO-alkyl.

As used herein, "carboxy aryl ester" refers to COO-aryl.

As used herein, "hydroxy" refers to OH.

As used herein, "mercapto" refers to SH.

As used herein, "sulfinyl" refers to SO.

As used herein, "sulfonyl" refers to $SO_2$.

As used herein, "aminosulfonyl" refers to $SO_2NH_2$.

As used herein, "alkylaminosulfonyl" refers to $SO_2NH$ (alkyl).

As used herein, "dialkylaminosulfonyl" refers to $SO_2N$ (alkyl)$_2$.

As used herein, "arylsulfonyl" refers to $SO_2$-aryl.

As used herein, "arylsulfinyl" refers to SO-aryl.

As used herein, "alkylsulfonyl" refers to $SO_2$-alkyl.

As used herein, "alkylsulfinyl" refers to SO-alkyl.

As used herein, "combinations thereof" is meant to refer to concatenation of two or more moieties recited for a given variable. For example, "$CH_2$, NH, CO, and combinations thereof" would include $CH_2NH$, $CH_2CO$, CONH, $CH_2NHCO$, and other stable combinations.

Unless otherwise indicated, the compounds provided in the above formula are meant to include pharmaceutically acceptable salts, prodrugs, enantiomers, diastereomers, racemic mixtures, crystalline forms, non-crystalline forms, amorphous forms, hydrates and solvates thereof.

The term "pharmaceutically acceptable salt" is meant to refer to salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, phosphoric, partially neutralized phosphoric acids, sulfuric, partially neutralized sulfuric, hydroiodic, or phosphorous acids and the like, as well as the salts derived from relatively nontoxic organic acids like acetic, propionic, isobutyric, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the present invention may contain both basic and acidic functionalities that allow the compounds to be converted into either base or acid addition salts.

The neutral forms of the compounds of the present invention may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

As noted above, some of the compounds of the present invention possess chiral or asymmetric carbon atoms (optical centers) or double bonds; the racemates, diastereomers, geometric isomers and individual optical isomers are all intended to be encompassed within the scope of the present invention.

Compounds of the invention can also include all isotopes of atoms occurring in the intermediates or final compounds. Isotopes include those atoms having the same atomic number but different mass numbers. For example, isotopes of hydrogen include tritium and deuterium.

Compounds of the invention can also include tautomeric forms, such as keto-enol tautomers. Tautomeric forms can be in equilibrium or sterically locked into one form by appropriate substitution.

Some of the compounds of the invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

In addition to salt forms, the present invention provides compounds may be in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex-vivo environment. For example, prodrugs can be slowly converted to the compounds of the present invention when placed in a transdermal patch reservoir with a suitable enzyme or chemical reagent.

In some embodiments, the present invention provides a compound selected from:

N-hydroxy-5-methyl-6-{[4-(3-methylphenyl)piperazin-1-yl]carbonyl}-5-azaspiro[2.5]octane-7-carboxamide;
N-hydroxy-5-methyl-6-[(4-phenylpiperazin-1-yl)carbonyl]-5-azaspiro[2.5]octane-7-carboxamide;
N-hydroxy-5-methyl-6-({4-[3-(trifluoromethyl)phenyl]piperazin-1-yl}carbonyl)-5-azaspiro[2.5]octane-7-carboxamide;
N-hydroxy-5-methyl-6-{[4-(2-methylphenyl)piperazin-1-yl]carbonyl}-5-azaspiro[2.5]octane-7-carboxamide;
6-{[4-(4-chlorophenyl)piperazin-1-yl]carbonyl}-N-hydroxy-5-methyl-5-azaspiro[2.5]octane-7-carboxamide;
N-hydroxy-5-methyl-6-{[4-(2-methyl-4-nitrophenyl)piperazin-1-yl]carbonyl}-5-azaspiro[2.5]octane-7-carboxamide;
N-hydroxy-5-methyl-6-[(4-phenylpiperidin-1-yl)carbonyl]-5-azaspiro[2.5]octane-7-carboxamide;
N-hydroxy-6-[(4-hydroxy-4-phenylpiperidin-1-yl)carbonyl]-5-methyl-5-azaspiro[2.5]octane-7-carboxamide;
N-hydroxy-5-methyl-6-[(4-phenyl-3,6-dihydropyridin-1(2H)-yl)carbonyl]-5-azaspiro[2.5]octane-7-carboxamide;
N-hydroxy-5-methyl-6-[(4-quinolin-2-ylpiperazin-1-yl)carbonyl]-5-azaspiro[2.5]octane-7-carboxamide;
6-{[4-(2,3-dichlorophenyl)piperazin-1-yl]carbonyl}-N-hydroxy-5-methyl-5-azaspiro[2.5]octane-7-carboxamide;
N-hydroxy-5-methyl-6-[(4-quinolin-4-ylpiperazin-1-yl)carbonyl]-5-azaspiro[2.5]octane-7-carboxamide;
N-hydroxy-5-methyl-6-{[4-(2-methylquinolin-4-yl)piperazin-1-yl]carbonyl}-5-azaspiro[2.5]octane-7-carboxamide;
N-hydroxy-5-methyl-6-{[4-(2-phenylethyl)piperazin-1-yl]carbonyl}-5-azaspiro[2.5]octane-7-carboxamide;
N-hydroxy-5-methyl-6-[(4-pyridin-4-ylpiperidin-1-yl)carbonyl]-5-azaspiro[2.5]octane-7-carboxamide;
N-hydroxy-5-methyl-6-{[4-(4-nitrophenyl)piperazin-1-yl]carbonyl}-5-azaspiro[2.5]octane-7-carboxamide;
N-hydroxy-6-{[4-(2-methoxyphenyl)piperazin-1-yl]carbonyl}-5-methyl-5-azaspiro[2.5]octane-7-carboxamide;
N-hydroxy-5-methyl-6-[(4-phenoxypiperidin-1-yl)carbonyl]-5-azaspiro[2.5]octane-7-carboxamide;
6-(3,4-dihydroisoquinolin-2(1H)-ylcarbonyl)-N-hydroxy-5-methyl-5-azaspiro[2.5]octane-7-carboxamide;
6-(4,7-dihydrothieno[2,3-c]pyridin-6(5H)-ylcarbonyl)-N-hydroxy-5-methyl-5-azaspiro[2.5]octane-7-carboxamide;
6-[(3-benzylpyrrolidin-1-yl)carbonyl]-N-hydroxy-5-methyl-5-azaspiro[2.5]octane-7-carboxamide;
N-hydroxy-5-methyl-6-[(4-pyridin-2-ylpiperazin-1-yl)carbonyl]-5-azaspiro[2.5]octane-7-carboxamide;
N-hydroxy-5-methyl-6-{[4-(2-pyridin-4-ylethyl)piperidin-1-yl]carbonyl}-5-azaspiro[2.5]octane-7-carboxamide;
N-hydroxy-5-methyl-6-({4-[5-(trifluoromethyl)pyridin-2-yl]piperazin-1-yl}carbonyl)-5-azaspiro[2.5]octane-7-carboxamide;
N-hydroxy-5-methyl-6-({4-[3-(trifluoromethyl)pyridin-2-yl]piperazin-1-yl}carbonyl)-5-azaspiro[2.5]octane-7-carboxamide;
6-(1,4'-bipiperidin-1'-ylcarbonyl)-N-hydroxy-5-methyl-5-azaspiro[2.5]octane-7-carboxamide;
N-hydroxy-5-methyl-6-{[4-(pyridin-2-ylmethyl)piperazin-1-yl]carbonyl}-5-azaspiro[2.5]octane-7-carboxamide;
N-hydroxy-5-methyl-6-{[4-(pyridin-4-ylmethyl)piperazin-1-yl]carbonyl}-5-azaspiro[2.5]octane-7-carboxamide;
N-hydroxy-5-methyl-6-{[4-(pyridin-3-ylmethyl)piperazin-1-yl]carbonyl}-5-azaspiro[2.5]octane-7-carboxamide;
N-hydroxy-5-methyl-6-{[4-(2-methylphenyl)-3,6-dihydropyridin-1(2H)-yl]carbonyl}-5-azaspiro[2.5]octane-7-carboxamide;
N-hydroxy-6-{[4-(3-methylphenyl)piperazin-1-yl]carbonyl}-5-azaspiro[2.5]octane-7-carboxamide;
N-hydroxy-5-methyl-6-(1,3,4,9-tetrahydro-2H-β-carbolin-2-ylcarbonyl)-5-azaspiro[2.5]octane-7-carboxamide;
N-hydroxy-5-methyl-6-[(9-methyl-1,3,4,9-tetrahydro-2H-β-carbolin-2-yl)carbonyl]-5-azaspiro[2.5]octane-7-carboxamide;
6-{[4-(2-fluorophenyl)-3,6-dihydropyridin-1(2H)-yl]carbonyl}-N-hydroxy-5-methyl-5-azaspiro[2.5]octane-7-carboxamide;
6-{[4-(2-chlorophenyl)-3,6-dihydropyridin-1(2H)-yl]carbonyl}-N-hydroxy-5-methyl-5-azaspiro[2.5]octane-7-carboxamide;

6-{[4-(4-nitrophenyl)-3,6-dihydropyridin-1(2H)-yl]carbonyl}-N-hydroxy-5-methyl-5-azaspiro[2.5]octane-7-carboxamide;
6-{[4-phenyl-3,6-dihydropyridin-1(2H)-yl]carbonyl}-N-hydroxy-5-methyl-5-azaspiro[2.5]octane-7-carboxamide;
6-{[4-(2-methyl-4-nitrophenyl)-3,6-dihydropyridin-1(2H)-yl]carbonyl}-N-hydroxy-5-methyl-5-azaspiro[2.5]octane-7-carboxamide;
N(7)-hydroxy-N(6),5-dimethyl-N(6)-(3-phenylpropyl)-5-azaspiro[2.5]octane-6,7-dicarboxamide;
N(7)-hydroxy-N(6)-isobutyl-5-methyl-5-azaspiro[2.5]octane-6,7-dicarboxamide;
N-hydroxy-5-methyl-6-{[4-(2-nitrophenyl)piperazin-1-yl]carbonyl}-5-azaspiro[2.5]octane-7-carboxamide;
N(7)-hydroxy-N(6)-isobutyl-N(6),5-dimethyl-5-azaspiro[2.5]octane-6,7-dicarboxamide;
N(7)-hydroxy-5-methyl-N(6)-(2-phenoxyethyl)-5-azaspiro[2.5]octane-6,7-dicarboxamide;
N(7)-hydroxy-N(6)-[2-(4-methoxyphenyl)ethyl]-5-methyl-5-azaspiro[2.5]octane-6,7-dicarboxamide;
N(7)-hydroxy-5-methyl-N(6)-(4-phenylbutyl)-5-azaspiro[2.5]octane-6,7-dicarboxamide;
N(7)-hydroxy-5-methyl-N(6)-[3-(2-oxopyrrolidin-1-yl)propyl]-5-azaspiro[2.5]octane-6,7-dicarboxamide;
N-hydroxy-5-methyl-6-[(10a)-3,4,10,10a-tetrahydropyrazino[1,2-a]indol-2(1H)-ylcarbonyl]-5-azaspiro[2.5]octane-7-carboxamide;
(5,6-trans)-N-hydroxy-5-{[4-(2-methyl-4-nitrophenyl)piperazin-1-yl]carbonyl}spiro[2.5]octane-6-carboxamide;
(5,6-trans)-N-hydroxy-6-{[4-(3-methylphenyl)piperazin-1-yl]carbonyl}spiro[2.5]octane-5-carboxamide;
(5,6-trans)-N-hydroxy-5-[(4-phenyl-3,6-dihydropyridin-1(2H)-yl)carbonyl]spiro[2.5]octane-6-carboxamide;
(5,6-trans)-N-hydroxy-5-{[4-(3-methylphenyl)piperazin-1-yl]carbonyl}spiro[2.5]octane-6-carboxamide;
(5,6-trans)-N-hydroxy-6-[(4-phenyl-3,6-dihydropyridin-1(2H)-yl)carbonyl]spiro[2.5]octane-5-carboxamide;
N-hydroxy-6-(3,4,10,10a-tetrahydropyrazino[1,2-a]indol-2(1H)-ylcarbonyl)-5-azaspiro[2.5]octane-7-carboxamide;
6-(1,2,4,4a,5,6-hexahydro-3H-pyrazino[1,2-a]quinolin-3-ylcarbonyl)-N-hydroxy-5-methyl-5-azaspiro[2.5]octane-7-carboxamide;
Methyl 7-[(hydroxyamino)carbonyl]-6-[(4-phenyl-3,6-dihydropyridin-1(2H)-yl)carbonyl]-5-azaspiro[2.5]octane-5-carboxylate;
Benzyl 7-[(hydroxyamino)carbonyl]-6-[(4-phenyl-3,6-dihydropyridin-1(2H)-yl)carbonyl]-5-azaspiro[2.5]octane-5-carboxylate;
N-Hydroxy-5-(methylsulfonyl)-6-[(4-phenyl-3,6-dihydropyridin-1(2H)-yl)carbonyl]-5-azaspiro[2.5]octane-7-carboxamide;
N-hydroxy-6-{[3-(3-methoxyphenyl)piperidin-1-yl]carbonyl}-5-methyl-5-azaspiro[2.5]octane-7-carboxamide;
N-hydroxy-5-methyl-6-{[3-(2-phenylethyl)pyrrolidin-1-yl]carbonyl}-5-azaspiro[2.5]octane-7-carboxamide;
N-hydroxy-6-{[4-(3-methoxyphenyl)piperidin-1-yl]carbonyl}-5-methyl-5-azaspiro[2.5]octane-7-carboxamide;
6-{[4-[3-(aminocarbonyl)phenyl]-3,6-dihydropyridin-1(2H)-yl]carbonyl}-N-hydroxy-5-azaspiro[2.5]octane-7-carboxamide;
N-hydroxy-6-{[4-(2-methoxyphenyl)piperidin-1-yl]carbonyl}-5-methyl-5-azaspiro[2.5]octane-7-carboxamide;
6-{[4-(3-fluoro-2-methylphenyl)piperazin-1-yl]carbonyl}-N-hydroxy-5-azaspiro[2.5]octane-7-carboxamide;
N-hydroxy-6-{[4-(2-methyl-3-nitrophenyl)piperazin-1-yl]carbonyl}-5-azaspiro[2.5]octane-7-carboxamide;
6-(3',6'-dihydro-3,4'-bipyridin-1'(2'H)-ylcarbonyl)-N-hydroxy-5-azaspiro[2.5]octane-7-carboxamide;
N(7)-hydroxy-N(6)-(4-methoxyphenyl)-N(6)-methyl-5-azaspiro[2.5]octane-6,7-dicarboxamide;
N-hydroxy-6-{[4-(3-methoxyphenyl)piperazin-1-yl]carbonyl}-5-methyl-5-azaspiro[2.5]octane-7-carboxamide;
6-{[4-(3-chlorophenyl)piperazin-1-yl]carbonyl}-N-hydroxy-5-methyl-5-azaspiro[2.5]octane-7-carboxamide;
N-hydroxy-6-[(4-phenyl-1,4-diazepan-1-yl)carbonyl]-5-azaspiro[2.5]octane-7-carboxamide;
N-hydroxy-6-{[3-methyl-4-(3-methylphenyl)piperazin-1-yl]carbonyl}-5-azaspiro[2.5]octane-7-carboxamide;
N-hydroxy-6-{[4-(3-methoxyphenyl)piperidin-1-yl]carbonyl}-5-azaspiro[2.5]octane-7-carboxamide;
N-hydroxy-6-[(3-phenylpyrrolidin-1-yl)carbonyl]spiro[2.5]octane-5-carboxamide;
N-hydroxy-6-[(4-isobutyrylpiperazin-1-yl)carbonyl]-5-azaspiro[2.5]octane-7-carboxamide;
6-{[4-(4-cyano-2-methylphenyl)-3,6-dihydropyridin-1(2H)-yl]carbonyl}-N-hydroxy-5-azaspiro[2.5]octane-7-carboxamide;
N(7)-Hydroxy-5-methyl-N(6)-{4-[(2-methylquinolin-4-yl)methoxy]phenyl}-5-azaspiro[2.5]octane-6,7-dicarboxamide;
N(7)-Hydroxy-N(6)-{4-[(2-methylquinolin-4-yl)methoxy]phenyl}-5-azaspiro[2.5]octane-6,7-dicarboxamide;
6-{[4-(4-cyanophenyl)piperazin-1-yl]carbonyl}-N-hydroxy-5-azaspiro[2.5]octane-7-carboxamide;
N-hydroxy-7-[(4-phenylpiperidin-1-yl)carbonyl]-5-azaspiro[2.5]octane-6-carboxamide;
N-hydroxy-6-[(4-phenylpiperidin-1-yl)carbonyl]-5-azaspiro[2.5]octane-7-carboxamide;
N-Hydroxy-6-[(4-phenylpiperazin-1-yl)carbonyl]-5-azaspiro[2.5]octane-7-carboxamide;
N-hydroxy-6-({4-[3-(methoxymethyl)phenyl]piperidin-1-yl}carbonyl)-5-azaspiro[2.5]octane-7-carboxamide;
Methyl 3-[1-({7-[(hydroxyamino)carbonyl]-5-azaspiro[2.5]oct-6-yl}carbonyl)piperidin-4-yl]benzoate;
6-[(3-Cyclohexylpyrrolidin-1-yl)carbonyl]-N-hydroxy-5-azaspiro[2.5]octane-7-carboxamide;
N-Hydroxy-6-{[4-(3-isopropylphenyl)-3,6-dihydropyridin-1(2H)-yl]carbonyl}-5-azaspiro[2.5]octane-7-carboxamide;
N-hydroxy-6-{[4-(3-isopropylphenyl)piperidin-1-yl]carbonyl}-5-azaspiro[2.5]octane-7-carboxamide;
N-hydroxy-6-{[4-(4-propylphenyl)-3,6-dihydropyridin-1(2H)-yl]carbonyl}-5-azaspiro[2.5]octane-7-carboxamide;
N-hydroxy-6-{[4-(4-ethylphenyl)-3,6-dihydropyridin-1(2H)-yl]carbonyl}-5-azaspiro[2.5]octane-7-carboxamide;
N-Hydroxy-6-{[4-(4-ethylphenyl)piperidin-1-yl]carbonyl}-5-azaspiro[2.5]octane-7-carboxamide;
6-{[4-(4-cyano-2-methylphenyl)piperazin-1-yl]carbonyl}-N-hydroxy-5-azaspiro[2.5]octane-7-carboxamide;
N-Hydroxy-6-{[4-(3-isopropoxyphenyl)-3,6-dihydropyridin-1(2H)-yl]carbonyl}-5-azaspiro[2.5]octane-7-carboxamide;
N-Hydroxy-6-{[4-(3-methylphenyl)-3,6-dihydropyridin-1(2H)-yl]carbonyl}-5-azaspiro[2.5]octane-7-carboxamide;
N-Hydroxy-6-{[4-(3-methylphenyl)piperidin-1-yl]carbonyl}-5-azaspiro[2.5]octane-7-carboxamide;
6-{[4-(4-tert-butylphenyl)piperazin-1-yl]carbonyl}-N-hydroxy-5-azaspiro[2.5]octane-7-carboxamide;
N-Hydroxy-6-[(4-pyridin-4-ylpiperazin-1-yl)carbonyl]-5-azaspiro[2.5]octane-7-carboxamide;
6-[(3-Benzylpiperidin-1-yl)carbonyl]-N-hydroxy-5-azaspiro[2.5]octane-7-carboxamide;

N-hydroxy-6-[(5-methoxy-2,3-dihydro-1H-indol-1-yl)carbonyl]-5-azaspiro[2.5]octane-7-carboxamide;
N-hydroxy-6-({5-[(2-methylquinolin-4-yl)methoxy]-2,3-dihydro-1H-indol-1-yl}carbonyl)-5-azaspiro[2.5]octane-7-carboxamide;
N-hydroxy-5-methyl-6-({5-[(2-methylquinolin-4-yl)methoxy]-2,3-dihydro-1H-indol-1-yl}carbonyl)-5-azaspiro[2.5]octane-7-carboxamide;
6-{[5-(benzyloxy)-2,3-dihydro-1H-indol-1-yl]carbonyl}-N-hydroxy-5-azaspiro[2.5]octane-7-carboxamide;
6-(1,3-dihydro-1'H-spiro[indene-2,4'-piperidin]-1'-ylcarbonyl)-N-hydroxy-5-azaspiro[2.5]octane-7-carboxamide;
N-hydroxy-6-{[4-(3-isopropoxyphenyl)piperidin-1-yl]carbonyl}-5-azaspiro[2.5]octane-7-carboxamide;
Methyl 4-[1-({7-[(hydroxyamino)carbonyl]-5-azaspiro[2.5]oct-6-yl}carbonyl)-1,2,3,6-tetrahydropyridin-4-yl]-3-methylbenzoate;
N-hydroxy-6-{[4-(2-methyl-4-nitrophenyl)-3,6-dihydropyridin-1(2H)-yl]carbonyl}-5-azaspiro[2.5]octane-7-carboxamide;
6-{[4-(2-ethylphenyl)piperidin-1-yl]carbonyl}-N-hydroxy-5-azaspiro[2.5]octane-7-carboxamide;
Methyl 4-[1-({7-[(hydroxyamino)carbonyl]-5-azaspiro[2.5]oct-6-yl}carbonyl)piperidin-4-yl]-3-methylbenzoate;
6-{[4-(2,3-dihydro-1-benzofuran-5-yl)-3,6-dihydropyridin-1(2H)-yl]carbonyl}-N-hydroxy-5-methyl-5-azaspiro[2.5]octane-7-carboxamide;
N-hydroxy-6-{[4-(3-isopropylphenyl)-3,6-dihydropyridin-1(2H)-yl]carbonyl}-5-methyl-5-azaspiro[2.5]octane-7-carboxamide;
N-Hydroxy-6-{[(3R)-3-phenylpyrrolidin-1-yl]carbonyl}-5-azaspiro[2.5]octane-7-carboxamide;
N-Hydroxy-6-{[(3S)-3-phenylpyrrolidin-1-yl]carbonyl}-5-azaspiro[2.5]octane-7-carboxamide;
N-Hydroxy-6-({3-[3-(trifluoromethyl)phenyl]pyrrolidin-1-yl}carbonyl)-5-azaspiro[2.5]octane-7-carboxamide;
6-{[3-(3-chlorophenyl)pyrrolidin-1-yl]carbonyl}-N-hydroxy-5-azaspiro[2.5]octane-7-carboxamide;
6-{[3-(3-fluorophenyl)pyrrolidin-1-yl]carbonyl}-N-hydroxy-5-azaspiro[2.5]octane-7-carboxamide;
6-{[3-(4-fluorophenyl)pyrrolidin-1-yl]carbonyl}-N-hydroxy-5-azaspiro[2.5]octane-7-carboxamide;
6-{[3-(4-chlorophenyl)pyrrolidin-1-yl]carbonyl}-N-hydroxy-5-azaspiro[2.5]octane-7-carboxamide;
N-hydroxy-6-({3-[4-(trifluoromethyl)phenyl]pyrrolidin-1-yl}carbonyl)-5-azaspiro[2.5]octane-7-carboxamide;
6-{[3-(4-methoxyphenyl)pyrrolidin-1-yl]carbonyl}-N-hydroxy-5-azaspiro[2.5]octane-7-carboxamide;
6-{[3-(4-phenoxyphenyl)pyrrolidin-1-yl]carbonyl}-N-hydroxy-5-azaspiro[2.5]octane-7-carboxamide;
N-hydroxy-6-{[4-(3-methoxyphenyl)-3,6-dihydropyridin-1(2H)-yl]carbonyl}-5-azaspiro[2.5]octane-7-carboxamide;
N-hydroxy-6-{[4-(4-cyano-3-methylphenyl)-3,6-dihydropyridin-1(2H)-yl]carbonyl}-5-azaspiro[2.5]octane-7-carboxamide;
6-{[3-(3-methoxyphenyl)pyrrolidin-1-yl]carbonyl}-N-hydroxy-5-azaspiro[2.5]octane-7-carboxamide;
N-hydroxy-6-[(3-pyridin-4-ylpyrrolidin-1-yl)carbonyl]-5-azaspiro[2.5]octane-7-carboxamide;
N-hydroxy-6-{[4-(3,5-dimethylphenyl)-3,6-dihydropyridin-1(2H)-yl]carbonyl}-5-azaspiro[2.5]octane-7-carboxamide;
N-hydroxy-6-{[4-(3-trifluoromethoxyphenyl)-3,6-dihydropyridin-1(2H)-yl]carbonyl}-5-azaspiro[2.5]octane-7-carboxamide;
N-hydroxy-6-{[5-(methoxymethyl)-4-phenyl-3,6-dihydropyridin-1(2H)-yl]carbonyl}-5-azaspiro[2.5]octane-7-carboxamide;
N-hydroxy-6-(1,4,5,6-tetrahydrobenzo[f]isoquinolin-3(2H)-ylcarbonyl)-5-azaspiro[2.5]octane-7-carboxamide;
N-hydroxy-6-{[4-(5-methoxy-2-methylphenyl)-3,6-dihydropyridin-1(2H)-yl]carbonyl}-5-azaspiro[2.5]octane-7-carboxamide;
N-hydroxy-6-{[4-(4-methoxy-2-methylphenyl)-3,6-dihydropyridin-1(2H)-yl]carbonyl}-5-azaspiro[2.5]octane-7-carboxamide;
6-[(4-cyano-4-phenylpiperidin-1-yl)carbonyl]-N-hydroxy-5-azaspiro[2.5]octane-7-carboxamide;
Ethyl 7-[(hydroxyamino)carbonyl]-6-[(4-phenyl-3,6-dihydropyridin-1(2H)-yl)carbonyl]-5-azaspiro[2.5]octane-5-carboxylate;
Propyl 7-[(hydroxyamino)carbonyl]-6-[(4-phenyl-3,6-dihydropyridin-1(2H)-yl)carbonyl]-5-azaspiro[2.5]octane-5-carboxylate;
Isopropyl 7-[(hydroxyamino)carbonyl]-6-[(4-phenyl-3,6-dihydropyridin-1(2H)-yl)carbonyl]-5-azaspiro[2.5]octane-5-carboxylate;
Isobutyl 7-[(hydroxyamino)carbonyl]-6-[(4-phenyl-3,6-dihydropyridin-1(2H)-yl)carbonyl]-5-azaspiro[2.5]octane-5-carboxylate; and
N-hydroxy-6-[(5-methyl-4-phenyl-3,6-dihydropyridin-1(2H)-yl)carbonyl]-5-azaspiro[2.5]octane-7-carboxamide.
Compounds of the invention further include:
6-(1,4,4a,5,6,10b-hexahydrobenzo[f]isoquinolin-3(2H)-ylcarbonyl)-N-hydroxy-5-azaspiro[2.5]octane-7-carboxamide;
6-{[4-(4-fluorophenyl)-3-hydroxypiperidin-1-yl]carbonyl}-N-hydroxy-5-azaspiro[2.5]octane-7-carboxamide;
N-hydroxy-6-(3,3a,8,8a-tetrahydroindeno[1,2-c]pyrrol-2(1H)-ylcarbonyl)-5-azaspiro[2.5]octane-7-carboxamide;
N-hydroxy-6-{[4-(4-phenyl-1,3-thiazol-2-yl)piperidin-1-yl]carbonyl}-5-azaspiro[2.5]octane-7-carboxamide;
N-hydroxy-6-{[4-(4-tert-Butyl-1,3-thiazol-2-yl)piperidin-1-yl]carbonyl}-5-azaspiro[2.5]octane-7-carboxamide;
N-hydroxy-6-[(4-methyl-4-phenylpiperidin-1-yl)carbonyl]-5-azaspiro[2.5]octane-7-carboxamide;
N-hydroxy-6-{[4-(4-ethyl-1,3-thiazol-2-yl)piperidin-1-yl]carbonyl}-5-azaspiro[2.5]octane-7-carboxamide;
N-hydroxy-6-{[(trans)-3-methyl-4-phenylpyrrolidin-1-yl]carbonyl}-5-azaspiro[2.5]octane-7-carboxamide;
6-{[4-(2-fluorophenyl)piperazin-1-yl]carbonyl}-N-hydroxy-5-azaspiro[2.5]octane-7-carboxamide;
6-{[4-(3,5-dimethylphenyl)-3,6-dihydropyridin-1(2H)-yl]carbonyl}-N-hydroxy-5-methyl-5-azaspiro[2.5]octane-7-carboxamide;
Tetrahydro-2H-pyran-4-yl-7-((hydroxyamino)carbonyl)-6-((4-phenylpiperazin-1-yl)carbonyl-5-azaspiro(2,5)octane-5-carboxylate;
Ethyl 7-((hydroxyamino)carbonyl))-6-((4-phenylpiperazin-1-yl)carbonyl-5-azaspiro(2,5)octane-5-carboxylate;
Methyl 7-[(hydroxyamino)carbonyl]-6-[(4-phenylpiperazin-1-yl)carbonyl]-5-azaspiro[2.5]octane-5-carboxylate;
N-hydroxy-6-[(4-pyrazin-2-ylpiperazin-1-yl)carbonyl]-5-azaspiro[2.5]octane-7-carboxamide;
N-hydroxy-6-[(4-quinolin-2-ylpiperazin-1-yl)carbonyl]-5-azaspiro[2.5]octane-7-carboxamide;
N-hydroxy-6-{[3-(5,6,7,8-tetrahydronaphthalen-2-yl)pyrrolidin-1-yl]carbonyl}-5-azaspiro[2.5]octane-7-carboxamide;
N-hydroxy-5-methyl-6-{[(3R)-3-phenylpyrrolidin-1-yl]carbonyl}-5-azaspiro[2.5]octane-7-carboxamide;

Methyl 7-[(hydroxyamino)carbonyl]-6-{[(3R)-3-phenylpyrrolidin-1-yl]carbonyl}-5-azaspiro[2.5]octane-5-carboxylate;
N-hydroxy-6-[(3-pyridin-3-ylpyrrolidin-1-yl)carbonyl]-5-azaspiro[2.5]octane-7-carboxamide;
N-hydroxy-6-[(3-pyridin-2-ylpyrrolidin-1-yl)carbonyl]-5-azaspiro[2.5]octane-7-carboxamide;
N-hydroxy-6-[(3-methyl-3-phenylpyrrolidin-1-yl)carbonyl]-5-azaspiro[2.5]octane-7-carboxamide;
N-hydroxy-6-[(3-phenylazetidin-1-yl)carbonyl]-5-azaspiro[2.5]octane-7-carboxamide;
N-hydroxy-5-methyl-6-[(3-methyl-3-phenylpyrrolidin-1-yl)carbonyl]-5-azaspiro[2.5]octane-7-carboxamide;
N-hydroxy-5-methyl-6-[(3-phenylazetidin-1-yl)carbonyl]-5-azaspiro[2.5]octane-7-carboxamide;
6-(1,3,3a,4,5,9b-hexahydro-2H-benzo[e]isoindol-2-ylcarbonyl)-N-hydroxy-5-azaspiro[2.5]octane-7-carboxamide;
N-hydroxy-6-{[3-(2-naphthyl)pyrrolidin-1-yl]carbonyl}-5-azaspiro[2.5]octane-7-carboxamide;
N-hydroxy-6-{[4-(2-thienyl)-3,6-dihydropyridin-1(2H)-yl]carbonyl}-5-azaspiro[2.5]octane-7-carboxamide;
N-hydroxy-6-{[3-(3-thienyl)pyrrolidin-1-yl]carbonyl}-5-azaspiro[2.5]octane-7-carboxamide;
N-hydroxy-6-{[3-(2-thienyl)pyrrolidin-1-yl]carbonyl}-5-azaspiro[2.5]octane-7-carboxamide;
N-hydroxy-6-{[4-(2-thienyl)piperidin-1-yl]carbonyl}-5-azaspiro[2.5]octane-7-carboxamide;
N-hydroxy-6-{[3-(2-methylphenyl)pyrrolidin-1-yl]carbonyl}-5-azaspiro[2.5]octane-7-carboxamide;
N-hydroxy-6-{[3-(4-methylphenyl)pyrrolidin-1-yl]carbonyl}-5-azaspiro[2.5]octane-7-carboxamide;
5-acetyl-N-hydroxy-6-[(4-phenyl-3,6-dihydropyridin-1(2H)-yl)carbonyl]-5-azaspiro[2.5]octane-7-carboxamide;
N-hydroxy-6-{[4-(3-thienyl)-3,6-dihydropyridin-1(2H)-yl]carbonyl}-5-azaspiro[2.5]octane-7-carboxamide;
N-hydroxy-6-[(3-phenylpiperidin-1-yl)carbonyl]-5-azaspiro[2.5]octane-7-carboxamide;
N-hydroxy-6-{[4-(3-thienyl)piperidin-1-yl]carbonyl}-5-azaspiro[2.5]octane-7-carboxamide;
Methyl 6-{[4-(3,5-dimethylphenyl)-3,6-dihydropyridin-1(2H)-yl]carbonyl}-7-[(hydroxyamino)carbonyl]-5-azaspiro[2.5]octane-5-carboxylate;
6-{[4-(3,5-dimethylphenyl)-3,6-dihydropyridin-1(2H)-yl]carbonyl}-N-hydroxy-5-(methylsulfonyl)-5-azaspiro[2.5]octane-7-carboxamide;
6-{[4-(3,5-difluorophenyl)-3,6-dihydropyridin-1(2H)-yl]carbonyl}-N-hydroxy-5-azaspiro[2.5]octane-7-carboxamide;
6-{[4-(3,5-dichlorophenyl)-3,6-dihydropyridin-1(2H)-yl]carbonyl}-N-hydroxy-5-azaspiro[2.5]octane-7-carboxamide;
6-{[4-[3,5-bis (trifluoromethyl)phenyl]-3,6-dihydropyridin-1(2H)-yl]carbonyl}-N-hydroxy-5-azaspiro[2.5]octane-7-carboxamide;
N-hydroxy-5-(methylsulfonyl)-6-[(4-phenylpiperazin-1-yl)carbonyl]-5-azaspiro[2.5]octane-7-carboxamide;
5-formyl-N-hydroxy-6-[(4-phenylpiperazin-1-yl)carbonyl]-5-azaspiro[2.5]octane-7-carboxamide;
6-{[4-(3,5-difluorophenyl)piperidin-1-yl]carbonyl}-N-hydroxy-5-azaspiro[2.5]octane-7-carboxamide;
6-{[4-(2,5-dimethylphenyl)-3,6-dihydropyridin-1(2H)-yl]carbonyl}-N-hydroxy-5-azaspiro[2.5]octane-7-carboxamide;
6-{[4-(2,4,5-trimethylphenyl)-3,6-dihydropyridin-1(2H)-yl]carbonyl}-N-hydroxy-5-azaspiro[2.5]octane-7-carboxamide;
6-[(4-biphenyl-3-ylpiperidin-1-yl)carbonyl]-N-hydroxy-5-azaspiro[2.5]octane-7-carboxamide;
6-[(4-dibenzo[b,d] furan-4-ylpiperidin-1-yl)carbonyl]-N-hydroxy-5-azaspiro[2.5]octane-7-carboxamide;
6-{[4-(2,5-dimethylphenyl)piperidin-1-yl]carbonyl}-N-hydroxy-5-azaspiro[2.5]octane-7-carboxamide;
6-{[4-(2,4,5-trimethylphenyl)piperidin-1-yl]carbonyl}-N-hydroxy-5-azaspiro[2.5]octane-7-carboxamide;
Methyl 3-[1-({7-[(hydroxyamino)carbonyl]-5-azaspiro[2.5]oct-6-yl}carbonyl)-1,2,3,6-tetrahydropyridin-4-yl]-4-methylbenzoate;
6-[(5-phenyl-2,3,4,7-tetrahydro-1H-azepin-1-yl)carbonyl]-N-hydroxy-5-azaspiro[2.5]octane-7-carboxamide;
6-{[4-[3-(dimethylamino)phenyl]-3,6-dihydropyridin-1(2H)-yl]carbonyl}-N-hydroxy-5-azaspiro[2.5]octane-7-carboxamide;
Methyl 3-[1-({7-[(hydroxyamino)carbonyl]-5-azaspiro[2.5]oct-6-yl}carbonyl)piperidin-4-yl]-4-methylbenzoate;
6-[(5-phenylazepan-1-yl)carbonyl]-N-hydroxy-5-azaspiro[2.5]octane-7-carboxamide;
6-({4-[3-(dimethylamino)phenyl]piperidin-1-yl}carbonyl)-N-hydroxy-5-azaspiro[2.5]octane-7-carboxamide;
6-{[4-(2-methylphenyl)-3,6-dihydropyridin-1(2H)-yl]carbonyl}-N-hydroxy-5-azaspiro[2.5]octane-7-carboxamide;
6-[(3-phenyl-2,5-dihydro-1H-pyrrol-1-yl)carbonyl]-N-hydroxy-5-azaspiro[2.5]octane-7-carboxamide;
6-{[4-(4-cyano-2-methylphenyl)piperidin-1-yl]carbonyl}-N-hydroxy-5-azaspiro[2.5]octane-7-carboxamide;
6-[(3,3-dimethyl-4-phenyl-3,6-dihydropyridin-1(2H)-yl)carbonyl]-N-hydroxy-5-azaspiro[2.5]octane-7-carboxamide;
6-[(3,3-dimethyl-4-phenylpiperidin-1-yl)carbonyl]-N-hydroxy-5-azaspiro[2.5]octane-7-carboxamide;
N-hydroxy-5-(methylsulfonyl)-6-[(3-phenyl-2,5-dihydro-1H-pyrrol-1-yl)carbonyl]-5-azaspiro[2.5]octane-7-carboxamide;
Methyl 7-[(hydroxyamino)carbonyl]-6-[(3-phenyl-2,5-dihydro-1H-pyrrol-1-yl)carbonyl]-5-azaspiro[2.5]octane-5-carboxylate;
N-hydroxy-5-methyl-6-[(3-phenyl-2,5-dihydro-1H-pyrrol-1-yl)carbonyl]-5-azaspiro[2.5]octane-7-carboxamide;
6-{[4-(4-cyano-3-methylphenyl)piperidin-1-yl]carbonyl}-N-hydroxy-5-azaspiro[2.5]octane-7-carboxamide;
6-{[4-[3-(benzyloxy)phenyl]-3,6-dihydropyridin-1(2H)-yl]carbonyl}-N-hydroxy-5-azaspiro[2.5]octane-7-carboxamide;
6-{[4-[3-ethylphenyl]-3,6-dihydropyridin-1(2H)-yl]carbonyl}-N-hydroxy-5-azaspiro[2.5]octane-7-carboxamide;
6-{[4-[3-(ethyloxy)phenyl]-3,6-dihydropyridin-1(2H)-yl]carbonyl}-N-hydroxy-5-azaspiro[2.5]octane-7-carboxamide;
6-{[4-(3-ethylphenyl)piperidin-1-yl]carbonyl}-N-hydroxy-5-azaspiro[2.5]octane-7-carboxamide;
6-{[4-(3-ethoxyphenyl)piperidin-1-yl]carbonyl}-N-hydroxy-5-azaspiro[2.5]octane-7-carboxamide;
6-{[4-(3-cyclopropylphenyl)-3,6-dihydropyridin-1(2H)-yl]carbonyl}-N-hydroxy-5-azaspiro[2.5]octane-7-carboxamide;
6-{[4-(4-methoxy-3,5-dimethylphenyl)-3,6-dihydropyridin-1(2H)-yl]carbonyl}-N-hydroxy-5-azaspiro[2.5]octane-7-carboxamide;
6-{[4-(3,5-dimethyl-4-methoxyphenyl)piperidin-1-yl]carbonyl}-N-hydroxy-5-azaspiro[2.5]octane-7-carboxamide;

6-{[4-(4-cyano-3-ethylphenyl)-3,6-dihydropyridin-1(2H)-yl]carbonyl}-N-hydroxy-5-azaspiro[2.5]octane-7-carboxamide;

6-{[4-(4-cyano-3-ethylphenyl)piperidin-1-yl]carbonyl}-N-hydroxy-5-azaspiro[2.5]octane-7-carboxamide;

6-{[4-(4-cyano-3,5-dimethylphenyl)-3,6-dihydropyridin-1(2H)-yl]carbonyl}-N-hydroxy-5-azaspiro[2.5]octane-7-carboxamide;

6-{[4-(4-cyano-3,5-dimethylphenyl)piperidin-1-yl]carbonyl}-N-hydroxy-5-azaspiro[2.5]octane-7-carboxamide;

6-{[4-(1,3-benzothiazol-6-yl)-3,6-dihydropyridin-1(2H)-yl]carbonyl}-N-hydroxy-5-azaspiro[2.5]octane-7-carboxamide;

N-hydroxy-6-{[4-(1-methyl-1H-benzimidazol-6-yl)-3,6-dihydropyridin-1(2H)-yl]carbonyl}-5-azaspiro[2.5]octane-7-carboxamide;

N-hydroxy-6-{[4-(1-methyl-1H-benzimidazol-6-yl)piperidin-1-yl]carbonyl}-5-azaspiro[2.5]octane-7-carboxamide;

6-{[4-(4-cyano-3-isopropylphenyl)-3,6-dihydropyridin-1(2H)-yl]carbonyl}-N-hydroxy-5-azaspiro[2.5]octane-7-carboxamide;

6-{[4-(4-cyano-3-isopropylphenyl)piperidin-1-yl]carbonyl}-N-hydroxy-5-azaspiro[2.5]octane-7-carboxamide;

6-{[4-(4-cyano-3-ethylphenyl)-3,6-dihydropyridin-1(2H)-yl]carbonyl}-N-hydroxy-5-methyl-5-azaspiro[2.5]octane-7-carboxamide;

6-{[4-(4-cyano-3,5-dimethylphenyl)-3,6-dihydropyridin-1(2H)-yl]carbonyl}-N-hydroxy-5-methyl-5-azaspiro[2.5]octane-7-carboxamide;

N-hydroxy-6-{[4-(1-ethyl-1H-benzimidazol-6-yl)-3,6-dihydropyridin-1(2H)-yl]carbonyl}-5-azaspiro[2.5]octane-7-carboxamide;

N-hydroxy-6-{[4-(1-methyl-1H-indazol-5-yl)-3,6-dihydropyridin-1(2H)-yl]carbonyl}-5-azaspiro[2.5]octane-7-carboxamide;

N-hydroxy-6-{[4-(1-ethyl-1H-benzimidazol-6-yl)piperidin-1-yl]carbonyl}-5-azaspiro[2.5]octane-7-carboxamide;

N-hydroxy-6-{[4-(1-methyl-1H-indazol-5-yl)piperidin-1-yl]carbonyl}-5-azaspiro[2.5]octane-7-carboxamide;

N-hydroxy-6-{[4-(1-ethyl-1H-indazol-5-yl)-3,6-dihydropyridin-1(2H)-yl]carbonyl}-5-azaspiro[2.5]octane-7-carboxamide;

Tetrahydro-2H-pyran-4-yl 6-{[4-(1-ethyl-1H-benzimidazol-6-yl)piperidin-1-yl]carbonyl}-7-[(hydroxyamino)carbonyl]-5-azaspiro[2.5]octane-5-carboxylate;

Methyl 6-{[4-(1-ethyl-1H-benzimidazol-6-yl)-3,6-dihydropyridin-1(2H)-yl]carbonyl}-7-[(hydroxyamino)carbonyl]-5-azaspiro[2.5]octane-5-carboxylate;

6-{[4-(1-ethyl-1H-benzimidazol-6-yl)-3,6-dihydropyridin-1(2H)-yl]carbonyl}-N-hydroxy-5-(methylsulfonyl)-5-azaspiro[2.5]octane-7-carboxamide;

Methyl 6-{[4-(1-ethyl-1H-benzimidazol-6-yl)piperidin-1-yl]carbonyl}-7-[(hydroxyamino)carbonyl]-5-azaspiro[2.5]octane-5-carboxylate;

6-{[4-(1-ethyl-1H-benzimidazol-6-yl)piperidin-1-yl]carbonyl}-N-hydroxy-5-(methylsulfonyl)-5-azaspiro[2.5]octane-7-carboxamide;

6-{[4-(4-cyano-2-methylphenyl)piperidin-1-yl]carbonyl}-N-hydroxy-5-(methylsulfonyl)-5-azaspiro[2.5]octane-7-carboxamide;

Methyl 6-{[4-(4-cyano-2-methylphenyl)piperazin-1-yl]carbonyl}-7-[(hydroxyamino)carbonyl]-5-azaspiro[2.5]octane-5-carboxylate;

6-{[4-(1-ethyl-1H-benzimidazol-6-yl)piperazin-1-yl]carbonyl}-N-hydroxy-5-azaspiro[2.5]octane-7-carboxamide;

Methyl 6-{[4-(1-ethyl-1H-benzimidazol-6-yl)piperazin-1-yl]carbonyl}-7-[(hydroxyamino)carbonyl]-5-azaspiro[2.5]octane-5-carboxylate;

6-{[4-(1-ethyl-1H-benzimidazol-6-yl)piperazin-1-yl]carbonyl}-N-hydroxy-5-(methylsulfonyl)-5-azaspiro[2.5]octane-7-carboxamide;

Tetrahydro-2H-pyran-4-yl 6-{[4-(4-cyano-2-methylphenyl)piperazin-1-yl]carbonyl}-7-[(hydroxyamino)carbonyl]-5-azaspiro[2.5]octane-5-carboxylate;

Tetrahydro-2H-pyran-4-yl 6-{[4-(1-ethyl-1H-benzimidazol-6-yl)piperazin-1-yl]carbonyl}-7-[(hydroxyamino)carbonyl]-5-azaspiro[2.5]octane-5-carboxylate;

N-hydroxy-6-[(3-methyl-4-phenylpiperidin-1-yl)carbonyl]-5-azaspiro[2.5]octane-7-carboxamide;

6-{[5-(aminocarbonyl)-4-phenyl-3,6-dihydropyridin-1(2H)-yl]carbonyl}-N-hydroxy-5-azaspiro[2.5]octane-7-carboxamide;

6-{[4-(4-cyanophenyl)-5-methyl-3,6-dihydropyridin-1(2H)-yl]carbonyl}-N-hydroxy-5-azaspiro[2.5]octane-7-carboxamide;

6-{[4-(4-cyanophenyl)-3-methylpiperidin-1-yl]carbonyl}-N-hydroxy-5-azaspiro[2.5]octane-7-carboxamide;

N-hydroxy-6-{[5-methyl-4-(4-nitrophenyl)-3,6-dihydropyridin-1(2H)-yl]carbonyl}-5-azaspiro[2.5]octane-7-carboxamide;

N-hydroxy-6-{[5-methyl-4-(3-nitrophenyl)-3,6-dihydropyridin-1(2H)-yl]carbonyl}-5-azaspiro[2.5]octane-7-carboxamide;

6-[(4-dibenzo[b,d]furan-2-yl-3,6-dihydropyridin-1(2H)-yl)carbonyl]-N-hydroxy-5-azaspiro[2.5]octane-7-carboxamide;

6-[(4-dibenzo[b,d]furan-2-ylpiperidin-1-yl)carbonyl]-N-hydroxy-5-azaspiro[2.5]octane-7-carboxamide;

6-{[4-(3,3-dimethyl-2,3-dihydro-1-benzofuran-5-yl)-3,6-dihydropyridin-1(2H)-yl]carbonyl}-N-hydroxy-5-azaspiro[2.5]octane-7-carboxamide;

6-{[4-(3,3-dimethyl-2,3-dihydro-1-benzofuran-5-yl)piperidin-1-yl]carbonyl}-N-hydroxy-5-azaspiro[2.5]octane-7-carboxamide;

Isopropyl 7-[(hydroxyamino)carbonyl]-6-[(3-phenyl-2,5-dihydro-1H-pyrrol-1-yl)carbonyl]-5-azaspiro[2.5]octane-5-carboxylate;

(3S)-tetrahydrofuran-3-yl 7-[(hydroxyamino)carbonyl]-6-[(3-phenyl-2,5-dihydro-1H-pyrrol-1-yl)carbonyl]-5-azaspiro[2.5]octane-5-carboxylate;

Cyclohexyl 7-[(hydroxyamino)carbonyl]-6-[(3-phenyl-2,5-dihydro-1H-pyrrol-1-yl)carbonyl]-5-azaspiro[2.5]octane-5-carboxylate;

Tetrahydro-2H-pyran-4-yl 7-[(hydroxyamino)carbonyl]-6-[(3-phenyl-2,5-dihydro-1H-pyrrol-1-yl)carbonyl]-5-azaspiro[2.5]octane-5-carboxylate;

N-hydroxy-6-((4-phenylpiperazin-1-yl)carbonyl)spiro(2.5)octane-5-carboxamide;

N-hydroxy-6-{[(3R)-3-phenylpyrrolidin-1-yl]carbonyl}spiro[2.5]octane-5-carboxamide;

N-hydroxy-6-{[4-(2-methyl-4-nitrophenyl)piperazin-1-yl]carbonyl}spiro[2.5]octane-5-carboxamide;

N-hydroxy-6-[(4-phenyl-3,6-dihydropyridin-1(2H)-yl)carbonyl]spiro[2.5]octane-5-carboxamide;

(3S)-tetrahydrofuran-3-yl 7-[(hydroxyamino)carbonyl]-6-[(4-phenylpiperazin-1-yl)carbonyl]-5-azaspiro[2.5]octane-5-carboxylate;

(3R)-tetrahydrofuran-3-yl 7-[(hydroxyamino)carbonyl]-6-[(4-phenylpiperazin-1-yl)carbonyl]-5-azaspiro[2.5]octane-5-carboxylate;

2-Methoxyethyl 7-((hydroxyamino)carbonyl)-6-((4-phenylpiperazin-1-yl)carbonyl)-5-azaspiro(2,5)octane-5-carboxylate;

N-hydroxy-6-[(4-phenylpiperazin-1-yl)carbonyl]-5-(phenylsulfonyl)-5-azaspiro[2.5]octane-7-carboxamide;

Propyl 7-[(hydroxyamino)carbonyl)]-6-[(4-phenylpiperazin-1-yl)carbonyl]-5-azaspiro[2,5]octane-5-carboxylate;

Isopropyl 7-[(hydroxyamino)carbonyl]-6-[(4-phenylpiperazin-1-yl)carbonyl]-5-azaspiro[2.5]octane-5-carboxylate;

Methyl 6-{[4-(3,5-difluorophenyl)-3,6-dihydropyridin-1 (2H)-yl]carbonyl}-7-[(hydroxyamino)carbonyl]-5-azaspiro[2.5]octane-5-carboxylate;

Methyl 6-{[4-(3,5-difluorophenyl)-3,6-dihydropyridin-1 (2H)-yl]carbonyl}-7-[(hydroxyamino)carbonyl]-5-azaspiro[2.5]octane-5-carboxylate;

N-hydroxy-6-{[4-(4-isopropylphenyl)piperazin-1-yl]carbonyl}-5-azaspiro[2.5]octane-7-carboxamide;

6-{[4-(3,5-difluorophenyl)piperidin-1-yl]carbonyl}-N-hydroxy-5-(methylsulfonyl)-5-azaspiro[2.5]octane-7-carboxamide; and 6-{[4-(4,5-dimethyl-1,3-thiazol-2-yl)piperidin-1-yl]carbonyl}-N-hydroxy-5-azaspiro[2.5]octane-7-carboxamide.

In some embodiments, compounds of the invention include:

5-Methyl-6-(4-m-tolyl-piperazine-1-carbonyl)-5-aza-spiro [2.5]octane-7-carboxylic acid hydroxyamide;

5-Methyl-6-(4-phenyl-piperazine-1-carbonyl)-5-aza-spiro [2.5]octane-7-carboxylic acid hydroxyamide;

5-Methyl-6-[4-(3-trifluoromethyl-phenyl)-piperazine-1-carbonyl]-5-aza-spiro[2.5]octane 7-carboxylic acid hydroxyamide;

5-Methyl-6-(4-o-tolyl-piperazine-1-carbonyl)-5-aza-spiro [2.5]octane-7-carboxylic acid hydroxyamide;

6-[4-(4-Chloro-phenyl)-piperazine-1-carbonyl]-5-methyl-5-aza-spiro[2.5]octane-7-carboxylic acid hydroxyamide;

5-Methyl-6-[4-(2-methyl-4-nitro-phenyl)-piperazine-1-carbonyl]-5-aza spiro[2.5]octane-7-carboxylic acid hydroxyamide;

5-Methyl-6-(4-phenyl-piperidine-1-carbonyl)-5-aza-spiro [2.5]octane-7-carboxylic acid hydroxyamide;

6-(4-Hydroxy-4-phenyl-piperidine-1-carbonyl)-5-methyl-5-aza-spiro[2.5]octane-7-carboxylic acid hydroxyamide;

5-Methyl-6-(4-phenyl-3,6-dihydro-2H-pyridine-1-carbonyl)-5-aza-spiro[2.5]octane-7-carboxylic acid hydroxyamide;

5-Methyl-6-(4-quinolin-2-yl-piperazine-1-carbonyl)-5-azaspiro[2.5]octane-7-carboxylic acid hydroxyamide;

6-[4-(2,3-Dichloro-phenyl)-piperazine-1-carbonyl]-5-methyl-5-aza-spiro[2.5]octane-7-carboxylic acid hydroxyamide;

5-Methyl-6-(4-quinolin-4-yl-piperazine-1-carbonyl)-5-azaspiro[2.5]octane-7-carboxylic acid hydroxyamide;

5-Methyl-6-[4-(2-methyl-quinolin-4-yl)-piperazine-1-carbonyl]-5-aza-spiro[2.5]octane-7-carboxylic acid hydroxyamide;

5-Methyl-6-(4-phenethyl-piperazine-1-carbonyl)-5-azaspiro[2.5]octane-7-carboxylic acid hydroxyamide;

5-Methyl-6-(3,4,5,6-tetrahydro-2H-[4,4']bipyridinyl-1-carbonyl)-5-aza-spiro[2.5]octane-7-carboxylic acid hydroxyamide;

5-Methyl-6-[4-(4-nitro-phenyl)-piperazine-1-carbonyl]-5-aza-spiro[2.5]octane-7-carboxylic acid hydroxyamide;

6-[4-(2-Methoxy-phenyl)-piperazine-1-carbonyl]-5-methyl-5-aza-spiro[2.5]octane-7-carboxylic acid hydroxyamide;

5-Methyl-6-(4-phenoxy-piperidine-1-carbonyl)-5-aza-spiro [2.5]octane-7-carboxylic acid hydroxyamide;

6-(3,4-Dihydro-1H-isoquinoline-2-carbonyl)-5-methyl-5-aza-spiro[2.5]octane-7-carboxylic acid hydroxyamide;

6-(4,7-Dihydro-5H-thieno[2,3-c]pyridine-6-carbonyl)-5-methyl-5-aza-spiro[2.5]octane-7-carboxylic acid hydroxyamide;

6-(3-Benzyl-pyrrolidine-1-carbonyl)-5-methyl-5-aza-spiro [2.5]octane-7-carboxylic acid hydroxyamide;

5-Methyl-6-(4-pyridin-2-yl-piperazine-1-carbonyl)-5-azaspiro[2.5]octane-7-carboxylic acid hydroxyamide;

5-Methyl-6-[4-(2-pyridin-4-yl-ethyl)-piperidine-1-carbonyl]-5-aza-spiro[2.5]octane-7-carboxylic acid hydroxyamide;

5-Methyl-6-[4-(5-trifluoromethyl-pyridin-2-yl)-piperazine-1-carbonyl]-5-aza-spiro[2.5]octane-7-carboxylic acid hydroxyamide;

5-Methyl-6-[4-(3-trifluoromethyl-pyridin-2-yl)-piperazine-1-carbonyl]-5-aza-spiro[2.5]octane-7-carboxylic acid hydroxyamide;

6-([1,4']Bipiperidinyl-1'-carbonyl)-5-methyl-5-aza-spiro [2.5]octane-7-carboxylic acid hydroxyamide;

5-Methyl-6-(4-pyridin-2-ylmethyl-piperazine-1-carbonyl)-5-aza-spiro[2.5]octane-7-carboxylic acid hydroxyamide;

5-Methyl-6-(4-pyridin-4-ylmethyl-piperazine-1-carbonyl)-5-aza-spiro[2.5]octane-7-carboxylic acid hydroxyamide;

5-Methyl-6-(4-pyridin-3-ylmethyl-piperazine-1-carbonyl)-5-aza-spiro[2.5]octane-7-carboxylic acid hydroxyamide;

5-Methyl-6-(4-o-tolyl-3,6-dihydro-2H-pyridine-1-carbonyl)-5-aza-spiro[2.5]octane-7-carboxylic acid hydroxyamide;

6-(4-m-Tolyl-piperazine-1-carbonyl)-5-aza-spiro[2.5]octane-7-carboxylic acid hydroxyamide;

6-(1,3,4,9-Tetrahydro-b-carboline-2-carbonyl)-5-aza-spiro [2.5]octane-7-carboxylic acid hydroxyamide;

6-(9-Methyl-1,3,4,9-tetrahydro-b-carboline-2-carbonyl)-5-aza-spiro[2.5]octane-7-carboxylic acid hydroxyamide;

6-[4-(2-Fluoro-phenyl)-3,6-dihydro-2H-pyridine-1-carbonyl]-5-aza-spiro[2.5]octane-7-carboxylic acid hydroxyamide;

6-[4-(2-Chloro-phenyl)-3,6-dihydro-2H-pyridine-1-carbonyl]-5-aza-spiro[2.5]octane-7-carboxylic acid hydroxyamide;

6-[4-(4-Nitro-phenyl)-3,6-dihydro-2H-pyridine-1-carbonyl]-5-aza-spiro[2.5]octane-7-carboxylic acid hydroxyamide;

6-(4-Phenyl-3,6-dihydro-2H-pyridine-1-carbonyl)-5-azaspiro[2.5]octane-7-carboxylic acid hydroxyamide;

6-[4-(2-Methyl-4-nitro-phenyl)-piperazine-1-carbonyl]-5-aza-spiro[2.5]octane-7-carboxylic acid hydroxyamide;

5-Methyl-5-aza-spiro[2.5]octane-6,7-dicarboxylic acid 7-hydroxyamide 6-[methyl-(3-phenyl-propyl)-amide;

5-Methyl-5-aza-spiro[2.5]octane-6,7-dicarboxylic acid 7-hydroxyamide 6-(isobutyl-amide);

5-Methyl-6-[4-(2-nitro-phenyl)-piperazine-1-carbonyl]-5-aza-spiro[2.5]octane-7-carboxylic acid hydroxyamide;

5-Methyl-5-aza-spiro[2.5]octane-6,7-dicarboxylic acid 7-hydroxyamide 6-(isobutylmethyl-amide);

5-Methyl-5-aza-spiro[2.5]octane-6,7-dicarboxylic acid 7-hydroxyamide 6-[(2-phenoxy-ethyl)-amide];

5-Methyl-5-aza-spiro[2.5]octane-6,7-dicarboxylic acid 7-hydroxyamide 6-{[2-(4-methoxy-phenyl)-ethyl]-amide};

5-Methyl-5-aza-spiro[2.5]octane-6,7-dicarboxylic acid 7-hydroxyamide 6-[(4-phenylbutyl)-amide];

5-Methyl-5-aza-spiro[2.5]octane-6,7-dicarboxylic acid 7-hydroxyamide 6-{[3-(2-oxo pyrrolidin-1-yl)-propyl]-amide};

6-(3,4,10,10a-Tetrahydro-1H-pyrazino[1,2-a]indole-2-carbonyl)-5-aza-spiro[2.5]octane-7-carboxylic acid hydroxyamide;
5-[4-(2-Methyl-4-nitro-phenyl)-piperazine-1-carbonyl]-spiro[2.5]octane-6-carboxylic acid hydroxyamide;
6-(4-m-Tolyl-piperazine-1-carbonyl)-spiro[2.5]octane-5-carboxylic acid hydroxyamide;
5-(4-Phenyl-3,6-dihydro-2H-pyridine-1-carbonyl)-spiro[2.5]octane-6-carboxylic acid hydroxyamide;
5-(4-m-Tolyl-piperazine-1-carbonyl)-spiro[2.5]octane-6-carboxylic acid hydroxyamide;
6-(4-Phenyl-3,6-dihydro-2H-pyridine-1-carbonyl)-spiro[2.5]octane-5-carboxylic acid hydroxyamide;
6-(3,4,10,10a-Tetrahydro-1H-pyrazino[1,2-a]indole-2-carbonyl)-5-aza-spiro[2.5]octane-7-carboxylic acid hydroxyamide;
6-(1,2,4,4a,5,6-Hexahydro-pyrazino[1,2-a]quinoline-3-carbonyl)-5-methyl-5azaspiro[2.5]-octane-7-carboxylic acid hydroxyamide;
7-Hydroxycarbamoyl-6-(4-phenyl-3,6-dihydro-2H-pyridine-1-carbonyl)-5-aza-spiro[2.5]octane-5-carboxylic acid methyl ester;
7-Hydroxycarbamoyl-6-(4-phenyl-3,6-dihydro-2H-pyridine-1-carbonyl)-5-aza-spiro[2.5]octane-5-carboxylic acid benzyl ester;
5-Methanesulfonyl-6-(4-phenyl-3,6-dihydro-2H-pyridine-1-carbonyl)-5-aza-spiro[2.5]octane-7-carboxylic acid hydroxyamide;
6-[3-(3-Methoxy-phenyl)-piperidine-1-carbonyl]-5-methyl-5-aza-spiro[2.5]octane-7-carboxylic acid hydroxyamide;
5-Methyl-6-(3-phenethyl-pyrrolidine-1-carbonyl)-5-aza-spiro[2.5]octane-7-carboxylic acid hydroxyamide;
6-[4-(3-Methoxy-phenyl)-piperidine-1-carbonyl]-5-methyl-5-aza-spiro[2.5]octane-7-carboxylic acid hydroxyamide;
6-[4-(3-Carbamoyl-phenyl)-3,6-dihydro-2H-pyridine-1-carbonyl]-5-aza-spiro[2.5]octane-7-carboxylic acid hydroxyamide;
6-[4-(2-Methoxy-phenyl)-3,6-dihydro-2H-pyridine-1-carbonyl]-5-methyl-5-aza-spiro[2.5]octane-7-carboxylic acid hydroxyamide;
6-[4-(3-Fluoro-2-methyl-phenyl)-piperazine-1-carbonyl]-5-aza-spiro[2.5]octane-7-carboxylic acid hydroxyamide;
6-[4-(2-Methyl-3-nitro-phenyl)-piperazine-1-carbonyl]-5-aza-spiro[2.5]octane-7-carboxylic acid hydroxyamide;
6-(3',6'-Dihydro-2'H-[3,4']bipyridinyl-1'-carbonyl)-5-aza-spiro[2.5]octane-7-carboxylic acid hydroxyamide;
5-Aza-spiro[2.5]octane-6,7-dicarboxylic acid 7-hydroxyamide 6-[(4-methoxy-phenyl)-methyl-amide];
6-[4-(3-Methoxy-phenyl)-piperazine-1-carbonyl]-5-methyl-5-aza-spiro[2.5]octane-7-carboxylic acid hydroxyamide;
6-[4-(3-Chloro-phenyl)-piperazine-1-carbonyl]-5-methyl-5-aza-spiro[2.5]octane-7-carboxylic acid hydroxyamide;
6-(4-Phenyl-[1,4]diazepane-1-carbonyl)-5-aza-spiro[2.5]octane-7-carboxylic acid hydroxyamide
6-(3-Methyl-4-m-tolyl-piperazine-1-carbonyl)-5-aza-spiro[2.5]octane-7-carboxylic acid hydroxyamide;
6-[4-(3-Methoxy-phenyl)-piperidine-1-carbonyl]-5-aza-spiro[2.5]octane-7-carboxylic acid hydroxyamide;
6-(3-Phenyl-pyrrolidine-1-carbonyl)-spiro[2.5]octane-5-carboxylic acid hydroxyamide;
6-(4-Isobutyryl-piperazine-1-carbonyl)-5-aza-spiro[2.5]octane-7-carboxylic acid hydroxyamide;
6-[4-(4-Cyano-2-methyl-phenyl)-3,6-dihydro-2H-pyridine-1-carbonyl]-5-aza-spiro[2.5]octane-7-carboxylic acid hydroxyamide;
5-Methyl-5-aza-spiro[2.5]octane-6,7-dicarboxylic acid 7-hydroxyamide 6-{[4-(2-methyl-quinolin-4-ylmethoxy)-phenyl]-amide};
5-Aza-spiro[2.5]octane-6,7-dicarboxylic acid 7-hydroxyamide 6-{[4-(2-methyl-quinolin-4-ylmethoxy)-phenyl]-amide};
6-[4-(4-Cyano-phenyl)-piperazine-1-carbonyl]-5-aza-spiro[2.5]octane-7-carboxylic acid hydroxyamide;
7-(4-Phenyl-piperazine-1-carbonyl)-5-aza-spiro[2.5]octane-6-carboxylic acid hydroxyamide;
6-(4-Phenyl-piperidine-1-carbonyl)-5-aza-spiro[2.5]octane-7-carboxylic acid hydroxyamide;
6-(4-Phenyl-piperazine-1-carbonyl)-5-aza-spiro[2.5]octane-7-carboxylic acid hydroxyamide;
6-[4-(3-Methoxymethyl-phenyl)-piperidine-1-carbonyl]-5-aza-spiro[2.5]octane-7-carboxylic acid hydroxyamide;
3-[1-(7-Hydroxycarbamoyl-5-aza-spiro[2.5]octane-6-carbonyl)-piperidin-4-yl]-benzoic acid methyl ester;
6-(3-Cyclohexyl-pyrrolidine-1-carbonyl)-5-aza-spiro[2.5]octane-7-carboxylic acid hydroxyamide;
6-[4-(3-Isopropyl-phenyl)-3,6-dihydro-2H-pyridine-1-carbonyl]-5-aza-spiro[2.5]octane-7-carboxylic acid hydroxyamide;
6-[4-(3-Isopropyl-phenyl)-piperidine-1-carbonyl]-5-aza-spiro[2.5]octane-7-carboxylic acid hydroxyamide;
6-[4-(4-Propyl-phenyl)-3,6-dihydro-2H-pyridine-1-carbonyl]-5-aza-spiro[2.5]octane-7-carboxylic acid hydroxyamide;
6-[4-(4-Ethyl-phenyl)-3,6-dihydro-2H-pyridine-1-carbonyl]-5-aza-spiro[2.5]octane-7-carboxylic acid hydroxyamide;
6-[4-(4-Ethyl-phenyl)-piperidine-1-carbonyl]-5-aza-spiro[2.5]octane-7-carboxylic acid hydroxyamide;
6-[4-(4-Cyano-2-methyl-phenyl)-piperazine-1-carbonyl]-5-aza-spiro[2.5]octane-7-carboxylic acid hydroxyamide;
6-[4-(3-Isopropoxy-phenyl)-3,6-dihydro-2H-pyridine-1-carbonyl]-5-aza-spiro[2.5]octane-7-carboxylic acid hydroxyamide;
6-(4-m-Tolyl-3,6-dihydro-2H-pyridine-1-carbonyl)-5-aza-spiro[2.5]octane-7-carboxylic acid hydroxyamide;
6-[4-(4-tert-Butyl-phenyl)-piperazine-1-carbonyl]-5-aza-spiro[2.5]octane-7-carboxylic acid hydroxy amide;
6-(4-Pyridin-4-yl-piperazine-1-carbonyl)-5-aza-spiro[2.5]octane-7-carboxylic acid hydroxyamide;
6-(3-Benzyl-piperidine-1-carbonyl)-5-aza-spiro[2.5]octane-7-carboxylic acid hydroxyamide;
6-(5-Methoxy-2,3-dihydro-indole-1-carbonyl)-5-aza-spiro[2.5]octane-7-carboxylic acid hydroxyamide;
6-[5-(2-Methyl-quinolin-4-ylmethoxy)-2,3-dihydro-indole-1-carbonyl]-5-aza-spiro[2.5]octane-7-carboxylic acid hydroxyamide;
5-Methyl-6-[5-(2-methyl-quinolin-4-ylmethoxy)-2,3-dihydro-indole-1-carbonyl]-5-aza-spiro[2.5]octane-7-carboxylic acid hydroxyamide
6-(5-Benzyloxy-2,3-dihydro-indole-1-carbonyl)-5-aza-spiro[2.5]octane-7-carboxylic acid hydroxyamide;
6-[4-(2,2-spiroindanepiperidine-1-carbonyl]-5-aza-spiro[2.5]octane-7-carboxylic acid hydroxyamide;
6-[4-(3-Isopropoxy-phenyl)-piperidine-1-carbonyl]-5-aza-spiro[2.5]octane-7-carboxylic acid hydroxyamide;
4-[1-(7-Hydroxycarbamoyl-5-aza-spiro[2.5]octane-6-carbonyl)-1,2,3,6-tetrahydro-pyridin-4-yl]-3-methyl-benzoic acid methyl ester;
6-[4-(2-Methyl-4-nitro-phenyl)-3,6-dihydro-2H-pyridine-1-carbonyl]-5-aza-spiro[2.5]octane-7-carboxylic acid hydroxyamide;

6-[4-(2-Ethyl-phenyl)-piperidine-1-carbonyl]-5-aza-spiro[2.5]octane-7-carboxylic acid hydroxyamide;
4-[1-(7-Hydroxycarbamoyl-5-aza-spiro[2.5]octane-6-carbonyl)-piperidin-4-yl]-3-methyl-benzoic acid methyl ester;
6-[4-(2,3-Dihydro-benzofuran-5-yl)-3,6-dihydro-2H-pyridine-1-carbonyl]-5-methyl-5-aza-spiro[2.5]octane-7-carboxylic acid hydroxyamide;
6-[4-(3-Isopropyl-phenyl)-3,6-dihydro-2H-pyridine-1-carbonyl]-5-methyl-5-aza-spiro[2.5]octane-7-carboxylic acid hydroxyamide;
6-(3-Phenyl-pyrrolidine-1-carbonyl)-5-aza-spiro[2.5]octane-7-carboxylic acid hydroxyamide;
6-(3-Phenyl-pyrrolidine-1-carbonyl)-5-aza-spiro[2.5]octane-7-carboxylic acid hydroxyamide;
6-[3-(3-Trifluoromethyl-phenyl)-pyrrolidine-1-carbonyl]-5-aza-spiro[2.5]octane-7-carboxylic acid hydroxyamide;
6-[3-(3-Chloro-phenyl)-pyrrolidine-1-carbonyl]-5-aza-spiro[2.5]octane-7-carboxylic acid hydroxyamide;
6-[3-(3-Fluoro-phenyl)-pyrrolidine-1-carbonyl]-5-aza-spiro[2.5]octane-7-carboxylic acid hydroxyamide;
6-[3-(4-Fluoro-phenyl)-pyrrolidine-1-carbonyl]-5-aza-spiro[2.5]octane-7-carboxylic acid hydroxyamide;
6-[3-(4-Chloro-phenyl)-pyrrolidine-1-carbonyl]-5-aza-spiro[2.5]octane-7-carboxylic acid hydroxyamide;
6-[3-(4-Trifluoromethyl-phenyl)-pyrrolidine-1-carbonyl]-5-aza-spiro[2.5]octane-7-carboxylic acid hydroxyamide;
6-[3-(4-Methoxy-phenyl)-pyrrolidine-1-carbonyl]-5-aza-spiro[2.5]octane-7-carboxylic acid hydroxyamide;
6-[3-(4-Phenoxy-phenyl)-pyrrolidine-1-carbonyl]-5-aza-spiro[2.5]octane-7-carboxylic acid hydroxyamide;
6-[4-(3-Methoxy-phenyl)-3,6-dihydro-2H-pyridine-1-carbonyl]-5-aza-spiro[2.5]octane-7-carboxylic acid hydroxyamide;
6-[4-(4-Cyano-3-methyl-phenyl)-3,6-dihydro-2H-pyridine-1-carbonyl]-5-aza-spiro[2.5]octane-7-carboxylic acid hydroxyamide;
6-(3-Pyridin-4-yl-pyrrolidine-1-carbonyl)-5-aza-spiro[2.5]octane-7-carboxylic acid hydroxyamide;
6-[4-(3,5-Dimethyl-phenyl)-3,6-dihydro-2H-pyridine-1-carbonyl]-5-aza-spiro[2.5]octane-7-carboxylic acid hydroxyamide;
6-[4-(3-Trifluoromethoxy-phenyl)-3,6-dihydro-2H-pyridine-1-carbonyl]-5-aza-spiro[2.5]octane-7-carboxylic acid hydroxyamide;
6-(5-Methoxymethyl-4-phenyl-3,6-dihydro-2H-pyridine-1-carbonyl)-5-aza-spiro[2.5]octane-7-carboxylic acid hydroxyamide;
6-(1,4,5,6-Tetrahydro-2H-benzo[f]isoquinoline-3-carbonyl)-5-aza-spiro[2.5]octane-7-carboxylic acid hydroxyamide;
6-(4-m-Tolyl-piperidine-1-carbonyl)-5-aza-spiro[2.5]octane-7-carboxylic acid hydroxyamide;
6-[4-(5-Methoxy-2-methyl-phenyl)-3,6-dihydro-2H-pyridine-1-carbonyl]-5-aza-spiro[2.5]octane-7-carboxylic acid hydroxyamide;
6-[4-(4-Methoxy-2-methyl-phenyl)-3,6-dihydro-2H-pyridine-1-carbonyl]-5-aza-spiro[2.5]octane-7-carboxylic acid hydroxyamide;
6-(4-Cyano-4-phenyl-piperidine-1-carbonyl)-5-aza-spiro[2.5]octane-7-carboxylic acid hydroxyamide;
7-Hydroxycarbamoyl-6-(4-phenyl-3,6-dihydro-2H-pyridine-1-carbonyl)-5-aza-spiro[2.5]octane-5-carboxylic acid ethyl ester;
7-Hydroxycarbamoyl-6-(4-phenyl-3,6-dihydro-2H-pyridine-1-carbonyl)-5-aza-spiro[2.5]octane-5-carboxylic acid propyl ester;
7-Hydroxycarbamoyl-6-(4-phenyl-3,6-dihydro-2H-pyridine-1-carbonyl)-5-aza-spiro[2.5]octane-5-carboxylic acid isopropyl ester;
7-Hydroxycarbamoyl-6-(4-phenyl-3,6-dihydro-2H-pyridine-1-carbonyl)-5-aza-spiro[2.5]octane-5-carboxylic acid isobutyl ester; and
6-(5-Methyl-4-phenyl-3,6-dihydro-2H-pyridine-1-carbonyl)-5-aza-spiro[2.5]octane-7-carboxylic acid hydroxyamide.

Synthesis

The novel compounds of the present invention can be prepared in a variety of ways known to one skilled in the art of organic synthesis. The compounds of the present invention can be synthesized using the methods as hereinafter described below, together with synthetic methods known in the art of synthetic organic chemistry or variations thereon as appreciated by those skilled in the art.

The compounds of this invention can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

The processes described herein can be monitored according to any suitable method known in the art. For example, product formation can be monitored by spectroscopic means, such as nuclear magnetic resonance spectroscopy (e.g., $^1$H or $^{13}$C) infrared spectroscopy, spectrophotometry (e.g., UV-visible), or mass spectrometry, or by chromatography such as high performance liquid chromatograpy (HPLC) or thin layer chromatography.

Preparation of compounds can involve the protection and deprotection of various chemical groups. The need for protection and deprotection, and the selection of appropriate protecting groups can be readily determined by one skilled in the art. The chemistry of protecting groups can be found, for example, in Green, et al., *Protective Groups in Organic Synthesis,* 2d. Ed., Wiley & Sons, 1991, which is incorporated herein by reference in its entirety.

The reactions of the processes described herein can be carried out in suitable solvents which can be readily selected by one of skill in the art of organic synthesis. Suitable solvents can be substantially nonreactive with the starting materials (reactants), the intermediates, or products at the temperatures at which the reactions are carried out, i.e., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected.

The novel compounds of this invention may be prepared using the reaction pathways and techniques as described below.

A series of compounds of formula 12 are prepared by the methods outlined in Scheme 1 (where R1 and R2 of formulas 10-12 and R3 and R4 of formulas 11-12 correspond to appropriate substituents that would afford compounds of the invention). H-Asp(OtButyl)-OH was treated with benzyl bromide and DBU in toluene to afford compound 2, which was reacted with 3 to provide 4. The N-alkylated product was then treated with NaI in acetone to provide the corresponding iodide, which was cyclized using LiHMDS in THF to provide the desired product 6. The benzyl protecting group was switched to Cbz to afford compound 7. Cyclopropanation of 7 is accomplished by treating with diazomethane and Pd(OAc)$_2$ to provide the desired product 8. The Cbz and Bn groups of 8 were removed by hydrogenation to provide the acid 9. The resulting acid was coupled with amine using standard amide bond formation condition to provide 10. Reductive amination of 10 with aldehyde or ketone to give compound 11. The tert-butyl group was removed by treating with TFA in methylene chloride, followed by direct coupling with hydroxylamine to produce the final compound 12.

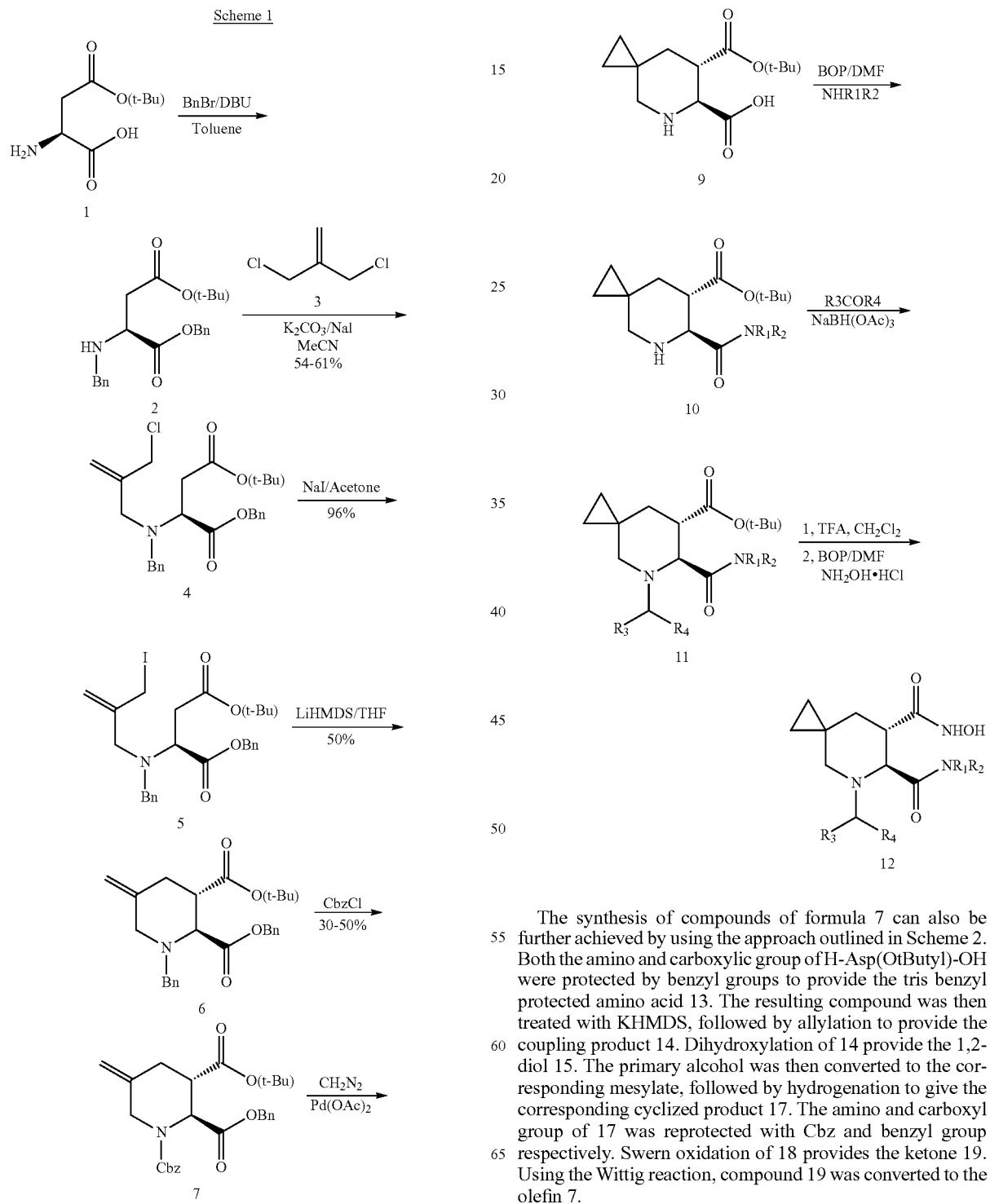

The synthesis of compounds of formula 7 can also be further achieved by using the approach outlined in Scheme 2. Both the amino and carboxylic group of H-Asp(OtButyl)-OH were protected by benzyl groups to provide the tris benzyl protected amino acid 13. The resulting compound was then treated with KHMDS, followed by allylation to provide the coupling product 14. Dihydroxylation of 14 provide the 1,2-diol 15. The primary alcohol was then converted to the corresponding mesylate, followed by hydrogenation to give the corresponding cyclized product 17. The amino and carboxyl group of 17 was reprotected with Cbz and benzyl group respectively. Swern oxidation of 18 provides the ketone 19. Using the Wittig reaction, compound 19 was converted to the olefin 7.

Scheme 2

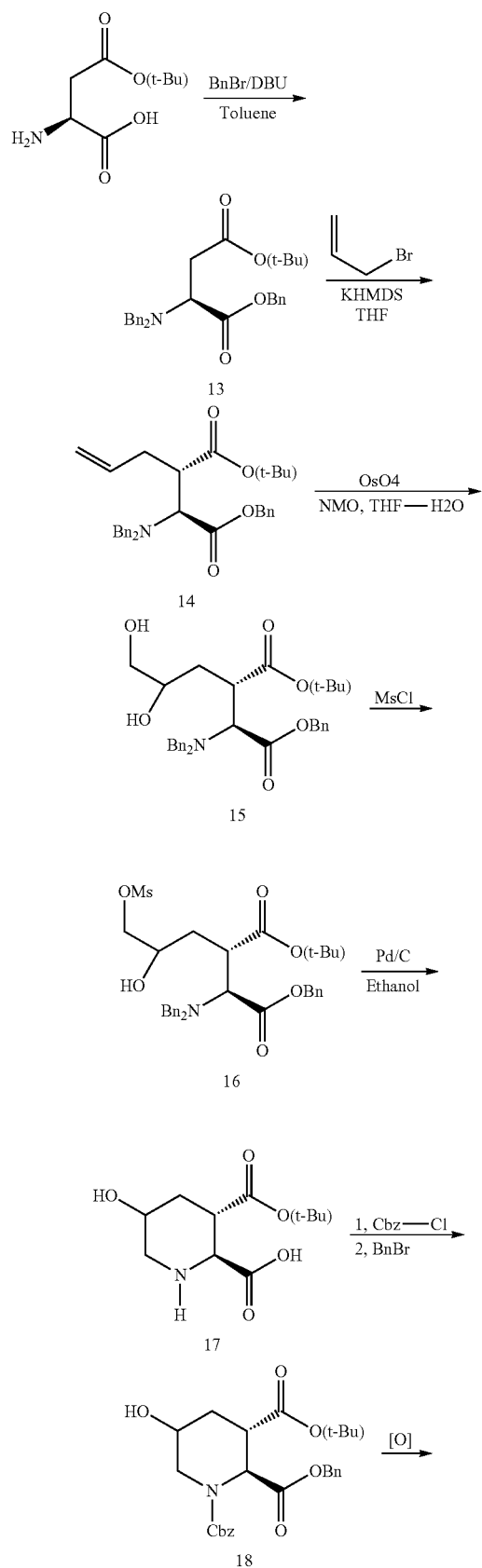

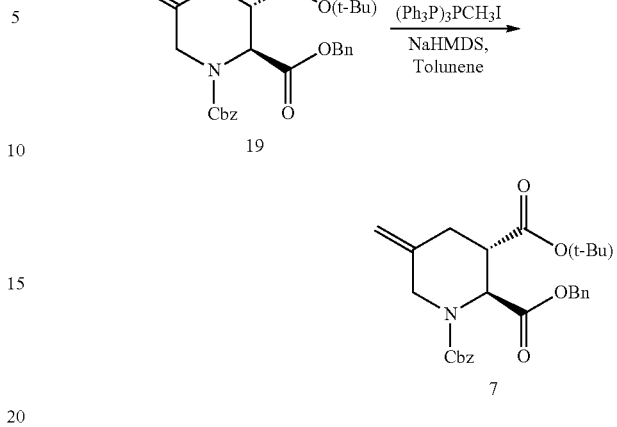

The synthesis of compounds of general structure 20 is outlined in Scheme 3 (where R1 and R2 of formulas 20 and 27 correspond to appropriate substituents that would afford compounds of the invention). Diels-Alder reaction of 21 with 22 provide 23. The TMS ether was hydrolyzed to the corresponding ketone 24. The ketone was then converted to the olefin 25. Cyclopropanation using the similar approach described in scheme 1 provides the key intermediate 26. The ethyl ester was directly converted into amide 27. The tert-butyl group of 27 was removed to give the acid. The resulting acid was converted to the final product 20 using standard synthetic conditions.

Scheme 3

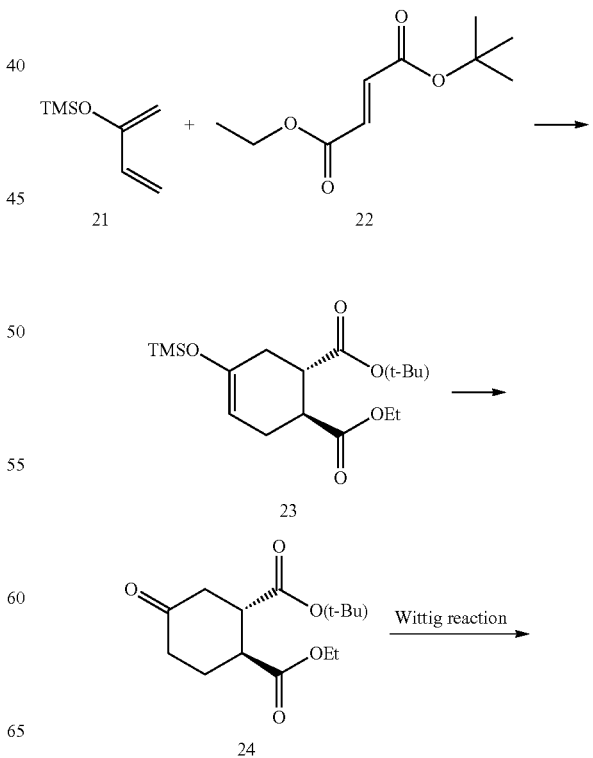

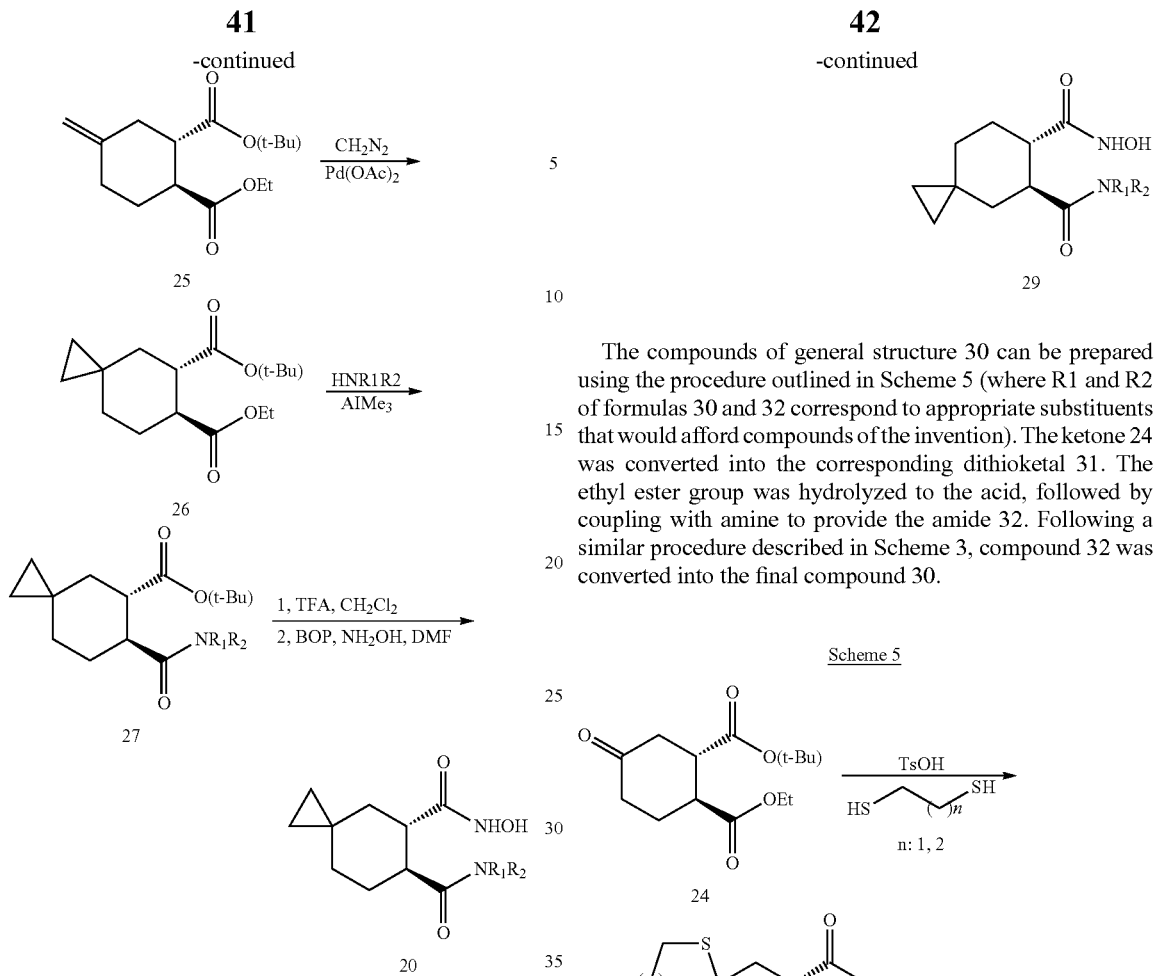

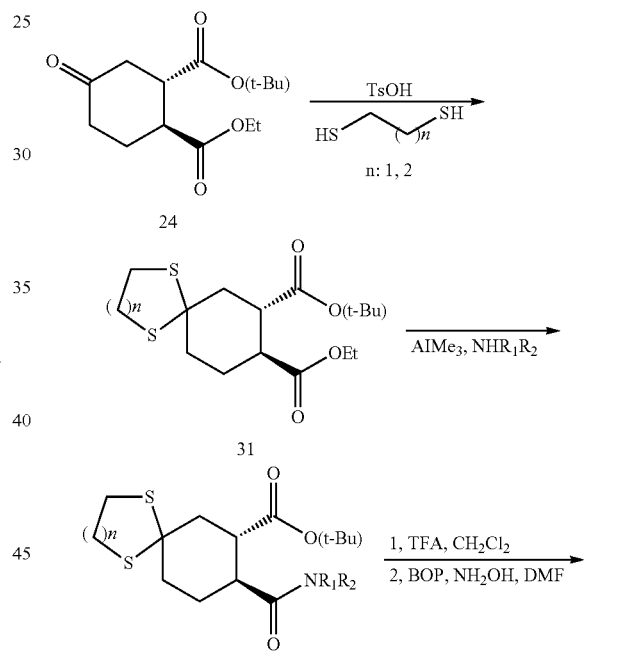

Alternatively, as shown in Scheme 4 (where R1 and R2 of formulas 28 and 29 correspond to appropriate substituents that would afford compounds of the invention), the tert-butyl group of compound 26 was removed first, followed by conventional coupling to give amide 28. Basic hydrolysis of 28 under refluxing condition provides the acid, the acid was then converted to the final compound 29 using the standard coupling procedure.

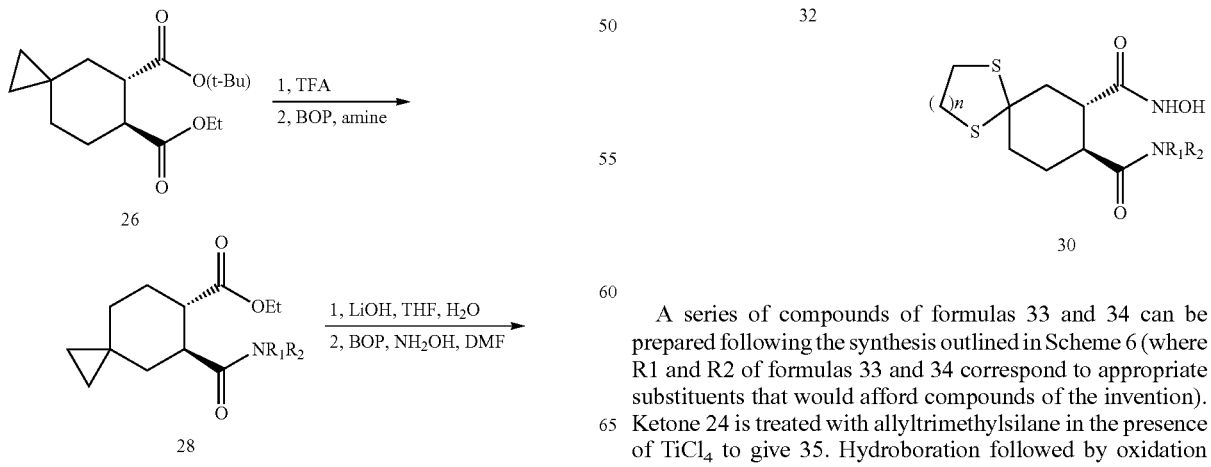

The compounds of general structure 30 can be prepared using the procedure outlined in Scheme 5 (where R1 and R2 of formulas 30 and 32 correspond to appropriate substituents that would afford compounds of the invention). The ketone 24 was converted into the corresponding dithioketal 31. The ethyl ester group was hydrolyzed to the acid, followed by coupling with amine to provide the amide 32. Following a similar procedure described in Scheme 3, compound 32 was converted into the final compound 30.

A series of compounds of formulas 33 and 34 can be prepared following the synthesis outlined in Scheme 6 (where R1 and R2 of formulas 33 and 34 correspond to appropriate substituents that would afford compounds of the invention). Ketone 24 is treated with allyltrimethylsilane in the presence of TiCl$_4$ to give 35. Hydroboration followed by oxidation provide the primary alcohol 36. The primary alcohol was activated and cyclized to the corresponding tetrahydrofuran 37. Conversion of 37 to the amide and finally hydroxamic acid 33 or 34 proceeds through the same approach as previously described.

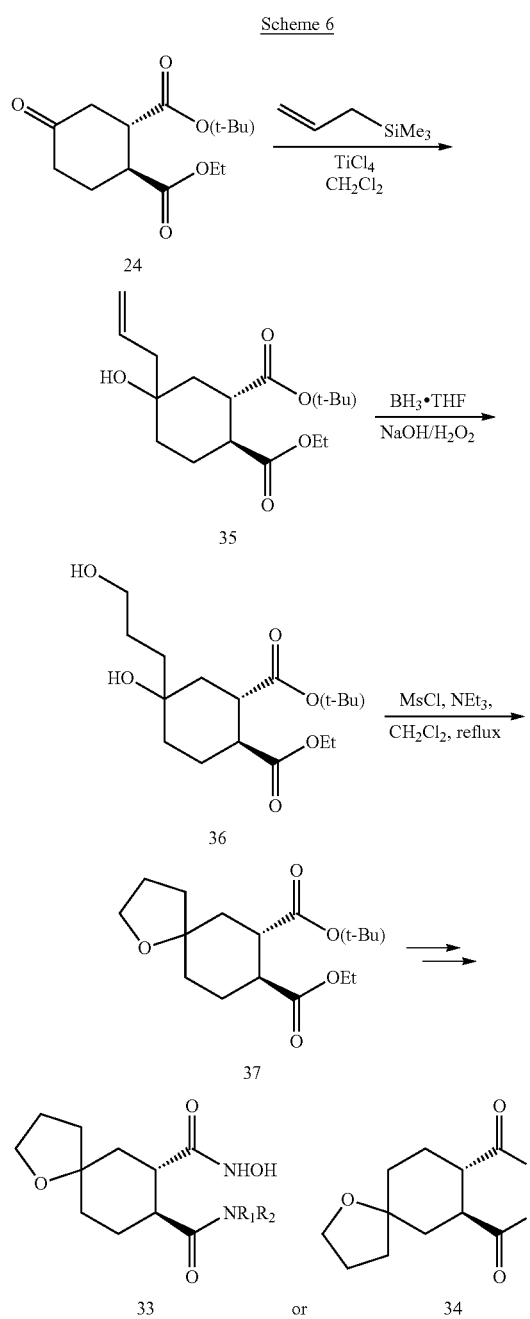

Scheme 6

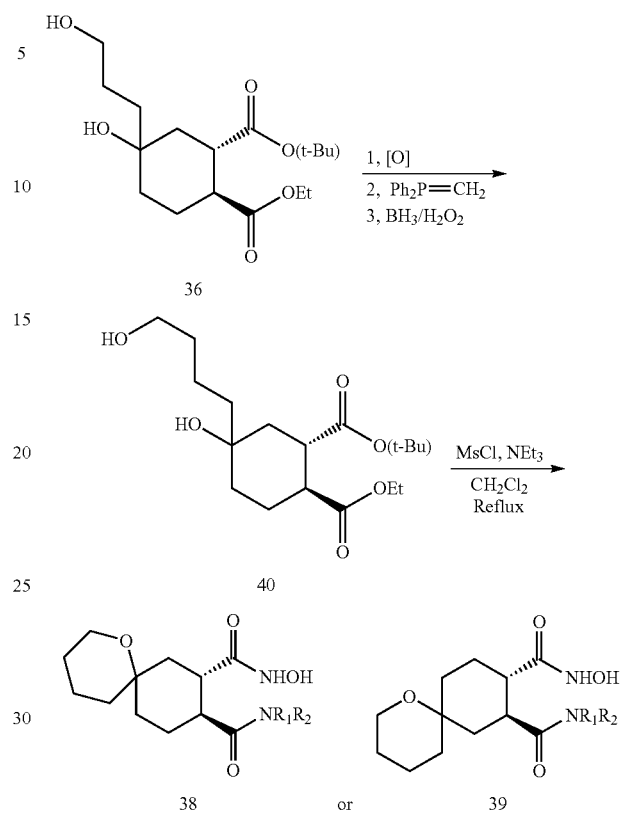

Scheme 7

A series of compounds of formula 38 or 39 are prepared following the sequence outlined in Scheme 7 (where R1 and R2 of formulas 38 and 39 correspond to appropriate substituents that would afford compounds of the invention). The primary alcohol 36 was oxidized and converted into olefin. Hydroboration and oxidation provide diol 40. Cyclization followed by a similar sequence as previously described gives 38 or 39.

A series of compounds of formula 41 are prepared following the scheme outlined in Scheme 8 (where R1 and R2 of formula 41 correspond to appropriate substituents that would afford compounds of the invention). The olefin was treated with MCPBA to provide epoxide 42. The epoxide was treated with amine to provide the ring-opening product 43. The amino alcohol was then cyclized to the spiro carbamate 44. Conversion of 44 to the amide and finally hydroxamic acid 41 proceeds through the same approach as previously described.

Scheme 8

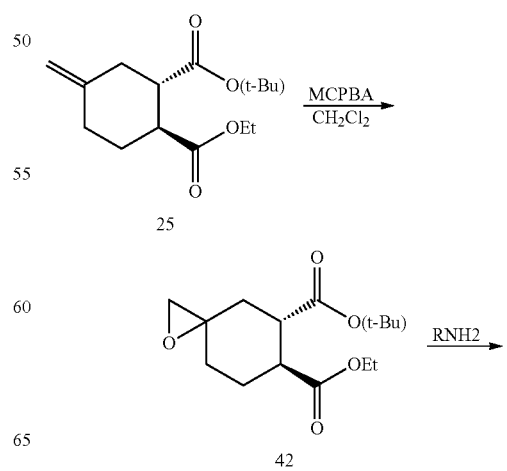

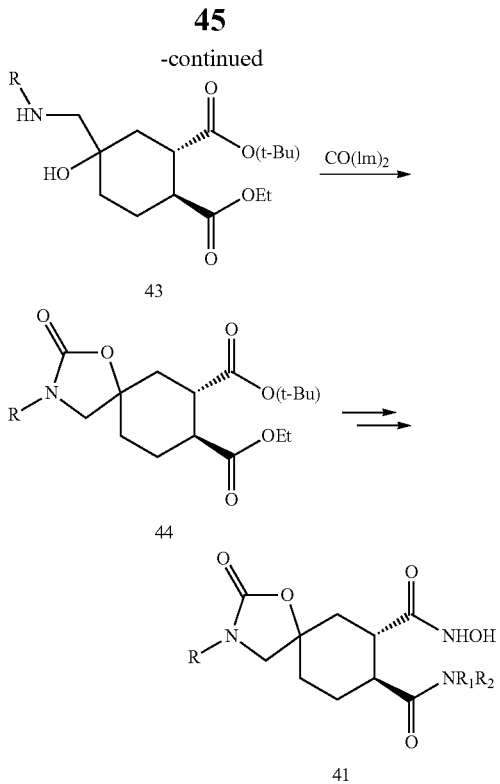

The series of 4-aryl-1,2,3,6-tetrahydro-pyridine of formula 45 and 4-aryl-piperidine of fomula 46 can be prepared following Scheme 9. For example, palladium catalyzed Suzuki coupling of 4-trifluoromethanesulfonyloxy-3,6-dihydro-2H-pyridine-1-carboxylic acid tert-butyl ester 47 with aryl boronic acid can afford compounds of formula 48 using standard procedures (e.g., Y. Deng, L. Gong, A Mi, H. Liu, Y. Jiang, *Synthesis,* 2003, 337-339). The Boc protecting group can be removed by treatment of the corresponding amine with TFA or HCl. Using a standard hydrogenation method, 4-aryl-1,2,3,6-tetrahydro-pyridine can be converted to the corresponding 4-aryl-piperidine.

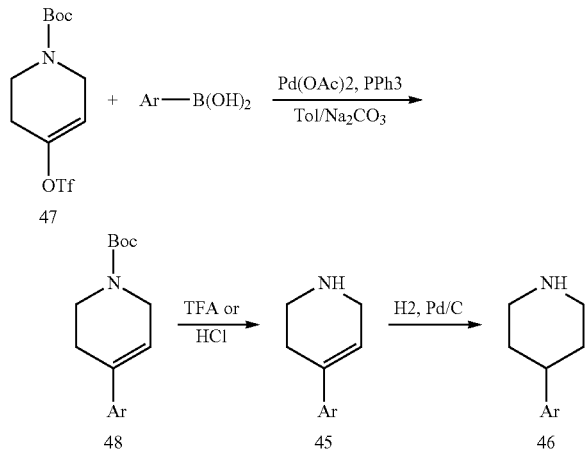

The invention is illustrated by the following examples, which are not intended to be limiting in any way.

EXAMPLES

Reagents and solvents used below can be obtained from commercial sources such as Aldrich Chemical Co. (Milwaukee, Wis., USA). Mass spectrometry results are reported as the ratio of mass over charge, followed by the relative abundance of each ion (in parentheses). In tables, a single m/e value is reported for the M+H (or, as noted, M−H) ion containing the most common atomic isotopes. Isotope patterns correspond to the expected formula in all cases.

Example 1

(6S,7S)—N-hydroxy-5-methyl-6-{[4-(3-methylphenyl)piperazin-1-yl]carbonyl}-5-azaspiro[2.5]octane-7-carboxamide Step 1a. Preparation of BnNH-L-Asp(O$^t$butyl)-OBn To a mixture of H-L-Asp(O$^t$Butyl)-OH (22 g, 106 mmol) and benzyl bromide (35 g, 205 mmol) in toluene (600 mL) was added DBU (33 g, 217 mmol). The mixture was stirred at RT for overnight, and was filtered. The filtrate was concentrated. The residue was purified by Combiflash (hexane and ethyl acetate: gradient 0 to 10% in 12 min) to afford 12.1 g (30.9%) of the desired product BnNH-L-Asp(O$^t$butyl)-OBn. MS (ESI): 370.3 (M+H$^+$).

Step 1b. Preparation of 1-benzyl 4-tert-butyl (2S)-2-{benzyl[2-(chloromethyl)prop-2-en-1-yl]amino}succinate A mixture of BnNH-L-Asp(O$^t$butyl)-Obn from step 1a (12.1 g, 32.6 mmol), K$_2$CO$_3$ (14 g, 3 eq.), NaI (3.0 g, 20 mmol) and 1-chloro-2-chloromethyl-1-propene (5.1 g, 40.8 mmol) in MeCN (150 mL) was stirred at 81° C. for 16 h. After cooling, the mixture was filtered. The filtrate was concentrated and purified by Combiflash (hexane and ethyl acetate: gradient 0 to 8% during 12 min) to give (8.7 g) 1-benzyl 4-tert-butyl (2S)-2-{benzyl[2-(chloromethyl)prop-2-en-1-yl]amino}succinate, MS (ESI): 458.3/460.3 (M+H$^+$).

Step 1c. The preparation of 1-benzyl 4-tert-butyl (2S)-2-{benzyl[2-(iodomethyl)prop-2-en-1-yl]amino}succinate A mixture of 1-benzyl 4-tert-butyl (2S)-2-{benzyl[2-(chloromethyl)prop-2-en-1-yl]amino}succinate from step 1b (8.7 g) and NaI (8.0 g) in acetone (100 mL) was stirred at RT overnight. The solid was filtered off and the filtrate concentrated. The residue was treated with methylene chloride and filtered through a pad of silica gel to give 1-benzyl 4-tert-butyl (2S)-2-{benzyl[2-(iodomethyl)prop-2-en-1-yl]amino}succinate (9.2 g). MS (ESI): 550.2 (M+H$^+$).

Step 1d. Preparation of 2-benzyl 3-tert-butyl (2S, 3S)-1-benzyl-5-methylenepiperidine-2,3-dicarboxylate To a cooled (−78° C.) solution of 1-benzyl 4-tert-butyl (2S)-2-{benzyl[2-(iodomethyl)prop-2-en-1-yl]amino}succinate from step 1c (9.2 g) in THF (50 mL) was added dropwise LiHMDS (1.0 M in THF, 20.2 mL) at −78° C. during a period of 30 min. The mixture was stirred at −78° C. for 1 h, and then was allowed to warm to −30° C. during 3 h. The reaction mixture was quenched with 10% citric acid (10 mL) and diluted with brine (100 mL). The mixture was extracted with ethyl acetate (4×75 mL). The combined organic layers were dried over MgSO$_4$ and concentrated under reduced pressure. The residue was purified through Combiflash (hexane and ethyl acetate: gradient 0 to 5% during 12 min) to give the desired 2-benzyl 3-tert-butyl (2S,3S)-1-benzyl-5-methylenepiperidine-2,3-dicarboxylate (3.45 g). MS (ESI): 422.3 (M+H$^+$).

Step 1l Preparation of 1,2-dibenzyl 3-tert-butyl (2S,3S)-5-methylenepperidine-1,2,3-tricarboxylate A mixture of 2-benzyl 3-tert-butyl (2S,3S)-1-benzyl-5-methylenepiperidine-2,3-dicarboxylate from step 1d (2.3 g) and benzyl chloroformate (3 mL) was stirred at 65° C. for 28 h. The excess of the benzyl chloroformate was removed under reduced pressure. The residue was purified through Combiflash (hexane and ethyl acetate: gradient 0 to 10% during 12 min) to give the desired compound 1,2-dibenzyl 3-tert-butyl (2S,3S)-5-methylenepiperidine-1,2,3-tricarboxylate (1.40 g). MS (ESI): 488.1 (M+Na$^+$); 366.1 (M+H$^+$—COO(t-Bu)).

Step 1f. Preparation of 5,6-dibenzyl 7-tert-butyl (6S,7S)-5-azaspiro[2.5]octane-5,6,7-tricarboxylate A solution of Diazald (5.0 g) in ethyl ether (50 mL) was added dropwise to a mixture of KOH (2.65 g), di(ethylene) ethyl ether (5 mL), water (4 mL) and ethyl ether (5 mL) at 60° C. The diazomethane formed was directly distilled into a reaction flask which contained a mixture of 1,2-dibenzyl 3-tert-butyl (2S,3S)-5-methylenepiperidine-1,2,3-tricarboxylate of step 1e (4.0 g) and palladium(II) acetate (50 mg) in ethyl ether (30 mL) at −20° C. The reaction mixture was allowed to warm to RT and stirred for 3 h. The mixture was filtered and concentrated. The residue was purified through Combiflash to afford compound 5,6-dibenzyl 7-tert-butyl (6S,7S)-5-azaspiro[2.5]octane-5,6,7-tricarboxylate (3.86 g). MS (ESI): 502.3 (M+Na$^+$); 380.3 (M+H$^+$—COO(t-Bu)).

Step 1g. Preparation of (6S,7S)-7-(tert-butoxycarbonyl)-5-azaspiro[2.5]octane-6-carboxylic acid 5,6-dibenzyl 7-tert-butyl (6S,7S)-5-azaspiro[2.5]octane-5,6,7-tricarboxylate (2.0 g) was hydrogenated in methanol (100 mL) with 5% Pd—BaSO$_4$ (750 mg) under a hydrogen atmosphere (hydrogen-balloon) at RT. The catalyst was removed by filtration. The filtrate was concentrated. The residue was dried under reduced pressure to produce (6S,7S)-7-(tert-butoxycarbonyl)-5-azaspiro[2.5]octane-6-carboxylic acid (1.06 g). MS (ESI): 256.1 (M+H$^+$); 200.1 (M+H$^+$-t-Bu).

Step 1h. Preparation of Bn$_2$N-L-Asp(O$^t$Butyl)-OBn

To a suspension of L-aspartic acid β-tert-butyl ester (12.5 g, 66 mmol) in DMF (100 ml) and DMSO (25 mL) was added benzyl bromide (39.5 mL, 236 mmol) followed by K$_2$CO$_3$ (27.5 g, 198 mmol). The mixture was stirred at 50° C. overnight. After cooling to room temperature, the salts were filtered and the filtrate was reduced to a small volume by evaporation under reduced pressure. The residue was diluted with water (200 mL) and the resulting solution was extracted with EtOAc three times. The combined organic solution was washed with brine three times, dried by MgSO$_4$ and concentrated. The residue was purified on silica gel using 10% EtOAc/Hexane as elution to provide 25.1 g of Bn$_2$N-L-Asp-(O$^t$Butyl)-OBn (83%). MS (ESI): 460.1 (M+H$^+$).

Step 1i: Preparation of 4-benzyl 1-tert-butyl (3S)-2-allyl-3-(dibenzylamino)succinate To a solution of Bn$_2$N-L-Asp-(O$^t$Butyl)-Obn from step 1h (9.7 g, 21.1 mmol) in anhydrous THF (100 mL) at −78° C. was added 0.5 M solution of KHMDS in toluene (50.7 mmol). After stirring at −78° C. for one hour, allyl iodide (2.9 mL, 31.7 mmol) was added. The temperature was increased to −30° C. and stirring was continued at this temperature for about 4 hrs. The reaction was quenched with 10% citric acid solution followed by diluting with a small amount of brine. The resulting solution was extracted with AcOEt three times. The combined solution was washed with brine three times, dried by MgSO$_4$ and concentrated. The residue was purified on silica gel using 20% EtOAc/Hexane as elution to provide a mixture of cis and anti-product 4-benzyl 1-tert-butyl (3S)-2-allyl-3-(dibenzylamino)succinate (8.1 g, 77%). MS (ESI): 500.1 (M+H$^+$).

Step 1j: Preparation of 1-benzyl 4-tert-butyl (2S,3S)-2-(dibenzylamino)-3-(2,3-dihydroxypropyl)succinate To a suspension of a mixture of cis and anti-product 4-benzyl 1-tert-butyl (3S)-2-allyl-3-(dibenzylamino)succinate from step 1i (3 g, 6.01 mmol) in acetone and water (10 mL, 1:1 v/v) at 0° C. was added NMO (0.774 g, 6.61 mmol). The suspension was stirred at 0° C. for one hour, then a solution of OsO$_4$ (4%) in water (0.15 mL) was added. The suspension was stirred at room temperature overnight. To the reaction suspension was added sodium hydrosulfite (90 mg) and stirred about 1 hour. The reaction suspension was filtered through Celite. The filtrate was extracted with EtOAc three times and the combined organic solution was washed with brine, dried by MgSO$_4$ and concentrated. The residue was purified on silica gel using 50% EtOAc/Hexane as elution to provide desired 1-benzyl 4-tert-butyl (2S,3S)-2-(dibenzylamino)-3-(2,3-dihydroxypropyl)succinate (1.78 g, 56%). MS (ESI): 534.2 (M+H$^+$).

Step 1k: Preparation of 1-benzyl 4-tert-butyl (2S, 3S)-2-(dibenzylamino)-3-{2-hydroxy-3-[(methylsulfonyl)oxy]propyl}succinate 1-benzyl 4-tert-butyl (2S,3S)-2-(dibenzylamino)-3-(2,3-dihydroxypropyl)succinate from step 1j (2.917 g, 5.47 mmol) was dissolved in pyridine (10 mL), cooled to 0° C. and MsCl (0.444 mL, 5.74 mmol) was added. The solution was stirred at 0° C. for 4 hours and diluted by 10% citric acid. The reaction mixture was extracted with EtOAc three times. The combined organic solution was washed by 10% citric acid three times, then brine, dried with MgSO$_4$ and concentrated, the residue was purified on silica gel using 50% EtOAc/Hexane as elution to provide of 1-benzyl 4-tert-butyl (2S,3S)-2-(dibenzylamino)-3-{2-hydroxy-3-[(methylsulfonyl)oxy]propyl}succinate (2.696 g, 81%). MS (ESI): 612.1.1 (M+H$^+$).

Step 1l. Preparation of (2S,3S)-3-(tert-butoxycarbonyl)-5-hydroxypiperidine-2-carboxylic acid To a solution of 1-benzyl 4-tert-butyl (2S,3S)-2-(dibenzylamino)-3-{2-hydroxy-3-[(methylsulfonyl)oxy]propyl}succinate from step 1k (5.02 g, 8.2 mmol) in methanol (40 mL) was added Pd-Black and 1M HCl (4 mL) solution. The mixture was hydrogenated under H$_2$ at 50 psi overnight. The catalyst was filtered off and the solution was concentrated to dryness. The residue was dissolved in ethanol and triethyl amine (2 mL) was added. The solution was refluxed for three hours and then concentrated to dryness to provide the crude compound (2S,3S)-3-(tert-butoxycarbonyl)-5-hydroxypiperidine-2-carboxylic acid, the compound was directly used in the next step. MS (ESI): 189.9 (M+H$^+$-t-Bu); 246.0 (M+H$^+$); 268.0 (M+Na$^+$).

Step 1m. Preparation of 1,2-dibenzyl 3-tert-butyl (2S,3S)-5-hydroxypiperidine-1,2,3-tricarboxylate To a solution of (2S,3S)-3-(tert-butoxycarbonyl)-5-hydroxypiperidine-2-carboxylic acid (2.02 g, crude from the previous step 1l in DMF was added N-(benzyloxycarbonyloxy)-succinimide (3.08 g, 12.36 mmol) followed by NMM (2.71 mL, 24.7 mmol). The mixture was stirred at room temperature overnight. The solution was acidified to a pH of 1 with 1 M HCl, extracted with EtOAc and the organic phase was washed with brine three times, dried by MgSO$_4$ and concentrated. The residue was purified on silica gel using 10% MeOH/CH$_2$Cl$_2$ as elution solvent to provide a crude mixture (2.17 g, 70%). MS (ESI): 280.0 (M+H$^+$—COO(t-Bu)); 402.0 (M+Na$^+$).

To the above material (1.28 g, 3.38 mmol) in benzene (15 mL) was added benzyl bromide (0.68 mL, 5.75 mmol) followed by DBU (1.01 mL, 6.76 mmol). The mixture was stirred at room temperature overnight. Then EtOAc was added. The solution was washed with 10% citric acid three times, then with brine, dried over MgSO$_4$ and then concentrated. The residue was purified on silica gel using 40% EtOAc/Hexane as elution solvent to provide of 1,2-dibenzyl 3-tert-butyl (2S,3S)-5-hydroxypiperidine-1,2,3-tricarboxylate (0.96 g, 61%). MS (ESI): 370.0 (M+H$^+$—COO(t-Bu)); 492.0 (M+Na$^+$).

Step 1n. Preparation of 1,2-dibenzyl 3-tert-butyl (2S,3S)-5-oxopiperidine-1,2,3-tricarboxylate To a cooled solution of oxalyl chloride (315 mg) in methylene chloride (2.5 mL) was added dropwise a solution of DMSO (0.30 mL) in methylene chloride (3.0 mL) at −78° C. The mixture was stirred at −78° C. for 30 min, 1,2-dibenzyl 3-tert-butyl (2S,3S)-5-hydroxypiperidine-1,2,3-tricarboxylate of step 1m (900 mg) in methylene chloride (4 mL) was added dropwise. The mixture was stirred at −78° C. to −60° C. for 1 h. Triethylamine (620 mg) in methylene chloride (2.5 mL) was added. The mixture was allowed to warm to RT during a period of 2 h. The mixture was diluted with ethyl acetate (75 mL) and washed with brine (2×25 mL). The organic layer was dried over Na$_2$SO$_4$ and concentrated under reduced pressure. The residue was flash chromatographed on silica gel column to afford 1,2-dibenzyl 3-tert-butyl (2S,3S)-5-oxopiperidine-1,2,3-tricarboxylate (570 mg). MS (ESI): 490.3 (M+Na$^+$); 368.2 M+H$^+$—COO(t-Bu)).

Step 1o: Preparation of 1,2-dibenzyl 3-tert-butyl (2S,3S)-5-methylenepiperidine-1,2,3-tricarboxylate To a solution of 1,2-dibenzyl 3-tert-butyl (2S,3S)-5-oxopiperidine-1,2,3-tricarboxylate of step 1n (850 mg) in toluene (10 mL) was added dropwise a solution of Ph$_3$P=CH$_2$ (0.25M in toluene/THF (3:1), 9.1 mL) at −10° C. The mixture was stirred and allowed to warm to RT during a period of 2 h. The mixture was diluted with ethyl acetate (75 mL) and washed with brine (3×25 mL). The organic layer was dried over Na$_2$SO$_4$ and concentrated under reduced pressure. The residue was flash chromatographed on silica gel column to afford 1,2-dibenzyl 3-tert-butyl (2S,3S)-5-methylenepiperidine-1,2,3-tricarboxylate (546 mg). MS (ESI): 488.1 (M+Na$^+$); 366.1 (M+H$^+$—COO(t-Bu)).

Step 1p: Preparation of tert-butyl (6S, 7S)-5-methyl-6-{[4-(3-methylphenyl)piperazin-1-yl]carbonyl}-5-azaspiro[2.5]octane-7-carboxylate A mixture of (6S,7S)-7-(tert-butoxycarbonyl)-5-azaspiro[2.5]octane-6-carboxylic acid of step 1g (25 mg), BOP (45 mg), 1-(3-methylphenyl)piperazine (176 mg) and di-isopropylethylamine (70 μL) in DMF (500 μL) was stirred at RT overnight. Formaldehyde solution (0.5 M in THF/MeCN (1:1), 600 μL) was added to the mixture followed by NaBH(OAc)$_3$ (0.25 M in THF/MeCN (1:1), 1000 μL). The resulting mixture was stirred overnight. The solvents were removed under reduced pressure. The residue was dissolved in ethyl acetate (5 mL). The solution was washed with NaHCO$_3$ (7.5%, 3×1 mL). The organic phase was dried over MgSO$_4$ and filtered and concentrated. The residue was used directly in the next step reaction without further purification.

Step 1q: Preparation of (6S,7S)—N-hydroxy-5-methyl-6-{[4-(3-methylphenyl)piperazin-1-yl]carbonyl}-5-azaspiro[2.5]octane-7-carboxamide The crude product from step 1p was dissolved in methylene chloride (3 mL). To the solution was added TFA (3 mL) followed by water (0.15 mL). The mixture was stirred at RT overnight and was concentrated under reduced pressure. The residue was dissolved in DMF (200 μL). To the solution was added BOP (45 mg) and hydroxylamine (21 mg). The mixture was adjusted to pH: 9 with di-isopropylethylamine (~80 μL), and stirred at RT for overnight, and direct RP-HPLC purification to afford the final product (6S,7S)—N-hydroxy-5-methyl-6-{[4-(3-methylphenyl)piperazin-1-yl]carbonyl}-5-azaspiro[2.5]octane-7-carboxamide. Ms(ESI): (M+H)+= 387.1

Example 2

(6S,7S)—N-hydroxy-5-methyl-6-[(4-phenylpiperazin-1-yl)carbonyl]-5-azaspiro[2.5]octane-7-carboxamide This compound was prepared using procedures analogous to those for example 1. Ms(ESI): (M+H)+=373.2

Example 3

(6S,7S)—N-hydroxy-5-methyl-6-({4-[3-(trifluoromethyl)phenyl]piperazin-1-yl}carbonyl)-5-azaspiro[2.5]octane-7-carboxamide This compound was prepared using procedures analogous to those for example 1. Ms(ESI): (M+H)+=441

Example 4

(6S,7S)—N-hydroxy-5-methyl-6-{[4-(2-methylphenyl)piperazin-1-yl]carbonyl}-5-azaspiro[2.5]octane-7-carboxamide This compound was prepared using procedures analogous to those for example 1. Ms(ESI): (M+H)+=387.1

Example 5

(6S,7S)-6-{[4-(4-chlorophenyl)piperazin-1-yl]carbonyl}-N-hydroxy-5-methyl-5-azaspiro[2.5]octane-7-carboxamide This compound was prepared using procedures analogous to those for example 1. Ms(ESI): (M+H)+=407.1

Example 6

(6S,7S)—N-hydroxy-5-methyl-6-{[4-(2-methyl-4-nitrophenyl)piperazin-1-yl]carbonyl}-5-azaspiro[2.5]octane-7-carboxamide This compound was prepared using procedures analogous to those for example 1. Ms(ESI): (M+H)+=432.0

Example 7

(6S,7S)—N-hydroxy-5-methyl-6-[(4-phenylpiperidin-1-yl)carbonyl]-5-azaspiro[2.5]octane-7-carboxamide This compound was prepared using procedures analogous to those for example 1. Ms(ESI): (M+H)+=372.2

Example 8

(6S,7S)—N-hydroxy-6-[(4-hydroxy-4-phenylpiperidin-1-yl)carbonyl]-5-methyl-5-azaspiro[2.5]octane-7-carboxamide This compound was prepared using procedures analogous to those for example 1. Ms(ESI): (M+H)+=388

Example 9

(6S,7S)—N-hydroxy-5-methyl-6-[(4-phenyl-3,6-dihydropyridin-1(2H)-yl)carbonyl]-5-azaspiro[2.5]octane-7-carboxamide This compound was prepared using procedures analogous to those for example 1. Ms(ESI): (M+H)+=370.0.

Example 11

(6S,7S)—N-hydroxy-5-methyl-6-[(4-quinolin-2-ylpiperazin-1-yl)carbonyl]-5-azaspiro[2.5]octane-7-carboxamide This compound was prepared using procedures analogous to those for example 1. Ms(ESI): (M+H)+=424.3

Example 12

(6S,7S)-6-{[4-(2,3-dichlorophenyl)piperazin-1-yl]carbonyl}-N-hydroxy-5-methyl-5-azaspiro[2.5]octane-7-carboxamide This compound was prepared using procedures analogous to those for example 1. Ms(ESI): (M+H)+=441

Example 13

(6S,7S)—N-hydroxy-5-methyl-6-[(4-quinolin-4-ylpiperazin-1-yl)carbonyl]-5-azaspiro[2.5]octane-7-carboxamide This compound was prepared using procedures analogous to those for example 1. Ms(ESI): (M+H)+=424.3

Example 14

(6S,7S)—N-hydroxy-5-methyl-6-{[4-(2-methylquinolin-4-yl)piperazin-1-yl]carbonyl}-5-azaspiro[2.5]octane-7-carboxamide This compound was prepared using procedures analogous to those for example 1. Ms(ESI): (M+H)+=438.4

Example 15

(6S,7S)—N-hydroxy-5-methyl-6-{[4-(2-phenylethyl)piperazin-1-yl]carbonyl}-5-azaspiro[2.5]octane-7-carboxamide This compound was prepared using procedures analogous to those for example 1. Ms(ESI): (M+H)+=401.3

Example 16

(6S,7S)—N-hydroxy-5-methyl-6-[(4-pyridin-4-ylpiperidin-1-yl)carbonyl]-5-azaspiro[2.5]octane-7-carboxamide This compound was prepared using procedures analogous to those for example 1. Ms(ESI): (M+H)+=373.3

Example 17

(6S,7S)—N-hydroxy-5-methyl-6-{[4-(4-nitrophenyl)piperazin-1-yl]carbonyl}-5-azaspiro[2.5]octane-7-carboxamide This compound was prepared using procedures analogous to those for example 1. Ms(ESI): (M+H)+=418.3

Example 18

(6S,7S)—N-hydroxy-6-{[4-(2-methoxyphenyl)piperazin-1-yl]carbonyl}-5-methyl-5-azaspiro[2.5]octane-7-carboxamide This compound was prepared using procedures analogous to those for example 1. Ms(ESI): (M+H)+=403

Example 19

(6S,7S)—N-hydroxy-5-methyl-6-[(4-phenoxypiperidin-1-yl)carbonyl]-5-azaspiro[2.5]octane-7-carboxamide This compound was prepared using procedures analogous to those for example 1. Ms(ESI): (M+H)+=388.3

Example 20

(6S,7S)-6-(3,4-dihydroisoquinolin-2(1H)-ylcarbonyl)-N-hydroxy-5-methyl-5-azaspiro[2.5]octane-7-carboxamide This compound was prepared using procedures analogous to those for example 1. Ms(ESI): (M+H)+=344.3

Example 21

(6S,7S)-6-(4,7-dihydrothieno[2,3-c]pyridin-6(5H)-ylcarbonyl)-N-hydroxy-5-methyl-5-azaspiro[2.5]octane-7-carboxamide This compound was prepared using procedures analogous to those for example 1. Ms(ESI): (M+H)+=350.2

Example 22

(6S,7S)-6-[(3-benzylpyrrolidin-1-yl)carbonyl]-N-hydroxy-5-methyl-5-azaspiro[2.5]octane-7-carboxamide This compound was prepared using procedures analogous to those for example 1. Ms(ESI): (M+H)+=372.3.

Example 23

(6S,7S)—N-hydroxy-5-methyl-6-[(4-pyridin-2-ylpiperazin-1-yl)carbonyl]-5-azaspiro[2.5]octane-7-carboxamide This compound was prepared using procedures analogous to those for example 1. Ms(ESI): (M+H)+=374.2

Example 24

(6S,7S)—N-hydroxy-5-methyl-6-{[4-(2-pyridin-4-ylethyl)piperidin-1-yl]carbonyl}-5-azaspiro[2.5]octane-7-carboxamide This compound was prepared using procedures analogous to those for example 1. Ms(ESI): (M+H)+=401.3

Example 25

(6S,7S)—N-hydroxy-5-methyl-6-({4-[5-(trifluoromethyl)pyridin-2-yl]piperazin-1-yl}carbonyl)-5-azaspiro[2.5]octane-7-carboxamide This compound was prepared using procedures analogous to those for example 1. Ms(ESI): (M+H)+=442.3

Example 26

(6S,7S)—N-hydroxy-5-methyl-6-({4-[3-(trifluoromethyl)pyridin-2-yl]piperazin-1-yl}carbonyl)-5-azaspiro[2.5]octane-7-carboxamide This compound was prepared using procedures analogous to those for example 1. Ms(ESI): (M+H)+=442.3

Example 27

(6S,7S)-6-(1,4'-bipiperidin-1'-ylcarbonyl)-N-hydroxy-5-methyl-5-azaspiro[2.5]octane-7-carboxamide This compound was prepared using procedures analogous to those for example 1. Ms(ESI): (M+H)+=379.3

Example 28

(6S,7S)—N-hydroxy-5-methyl-6-{[4-(pyridin-2-ylmethyl)piperazin-1-yl]carbonyl}-5-azaspiro[2.5]octane-7-carboxamide This compound was prepared using procedures analogous to those for example 1. Ms(ESI): (M+H)+=388.3

Example 29

(6S,7S)—N-hydroxy-5-methyl-6-{[4-(pyridin-4-ylmethyl)piperazin-1-yl]carbonyl}-5-azaspiro[2.5]octane-7-carboxamide This compound was prepared using procedures analogous to those for example 1. Ms(ESI): (M+H)+=388.3

Example 30

(6S,7S)—N-hydroxy-5-methyl-6-{[4-(pyridin-3-ylmethyl)piperazin-1-yl]carbonyl}-5-azaspiro[2.5]octane-7-carboxamide This compound was prepared using procedures analogous to those for example 1. Ms(ESI): (M+H)+=388.3

Example 31

(6S,7S)—N-hydroxy-5-methyl-6-{[4-(2-methylphenyl)-3,6-dihydropyridin-1(2H)-yl]carbonyl}-5-azaspiro[2.5]octane-7-carboxamide Step 1. Preparation of 4-(2-methylphenyl)-1,2,3,6-tetrahydropyridine To a solution of tert-butyl 4-{[(trifluoromethyl)sulfonyl]oxy}-3,6-dihydropyridine-1(2H)-carboxylate (500 mg, 1.51 mmol), $Na_2CO_3$ (2.1 mL, 2.0 M), LiCl (188 mg) and $Pd(PPh_3)_4$ 12 mg) was added 2-methylphenylboronic acid. The reaction mixture was refluxed for 2.0 hours, and cooled to room temperature. The solution was extracted with ethyl acetate and washed by 2N $Na_2CO_3$ and $NH_4OH$ solution and saturated brine. The crude residue was purified by flash column to give 370 mg of the pure compound.

The above material was dissolved in 4.5 mL $CH_2Cl_3$ and 0.5 mL $H_2O$, followed by addition of 5 mL of TFA. The mixture was stirred at RT for 50 min. The mixture was then concentrated to give the corresponding material.

Step 2. Preparation of (6S,7S)—N-hydroxy-5-methyl-6-{[4-(2-methylphenyl)-3,6-dihydropyridin-1(2H)-yl]carbonyl}-5-azaspiro[2.5]octane-7-carboxamide 1,4-(2-methylphenyl)-1,2,3,6-tetrahydropyridine was coupled to (6S,7S)-7-(tert-butoxycarbonyl)-5-azaspiro[2.5]octane-6-carboxylic acid using procedures analogous to those for example 1 to give the desired (6S,7S)—N-hydroxy-5-methyl-6-{[4-(2-methylphenyl)-3,6-dihydropyridin-1(2H)-yl]carbonyl}-5-azaspiro[2.5]octane-7-carboxamide Ms (ESI): (M+H)+=384.1.

Example 32

(6S,7S)—N-hydroxy-6-{[4-(3-methylphenyl)piperazin-1-yl]carbonyl}-5-azaspiro[2.5]octane-7-carboxamide This compound was prepared using procedures analogous to those for example 1. Ms(ESI): (M+H)+=373.1

Example 33

(6S,7S)—N-hydroxy-5-methyl-6-(1,3,4,9-tetrahydro-2H-β-carbolin-2-ylcarbonyl)-5-azaspiro[2.5]octane-7-carboxamide

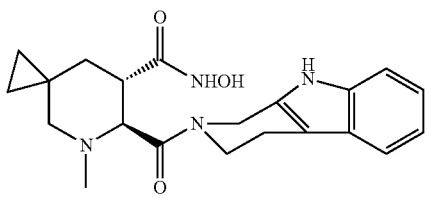

This compound was prepared using procedures analogous to those for example 1. Ms(ESI): (M+H)+=383.0.

Example 34

(6S,7S)—N-hydroxy-5-methyl-6-[(9-methyl-1,3,4,9-tetrahydro-2H-β-carbolin-2-yl)carbonyl]-5-azaspiro[2.5]octane-7-carboxamide

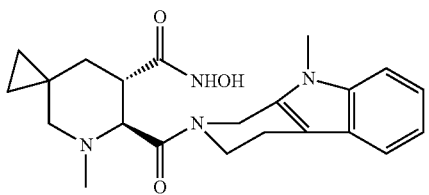

This compound was prepared using procedures analogous to those for example 1. Ms(ESI): (M+H)+=396.9.

Example 35

(6S,7S)-6-{[4-(2-fluoropfluorophenyl)-3,6-dihydropyridin-1(2H)-yl]carbonyl}-N-hydroxy-5-methyl-5-azaspiro[2.5]octane-7-carboxamide This compound was prepared using procedures analogous to those for example 31. Ms(ESI): (M+H)+=388.0

Example 36

(6S,7S)-6-{[4-(2-chlorophenyl)-3,6-dihydropyridin-1(2H)-yl]carbonyl}-N-hydroxy-5-methyl-5-azaspiro[2.5]octane-7-carboxamide This compound was prepared using procedures analogous to those for example 31. Ms(ESI): (M+H)+=404.0

Example 37

(6S,7S)-6-{[4-(4-nitrophenyl)-3,6-dihydropyridin-1(2H)-yl]carbonyl}-N-hydroxy-5-methyl-5-azaspiro[2.5]octane-7-carboxamide This compound was prepared using procedures analogous to those for example 31. Ms(ESI): (M+H)+=415.1.

Example 38

(6S,7S)-6-{[4-phenyl-3,6-dihydropyridin-1(2H)-yl]carbonyl}-N-hydroxy-5-azaspiro[2.5]octane-7-carboxamide This compound was prepared using procedures analogous to those for example 1. Ms(ESI): (M+H)+=356

Example 39

(6S,7S)-6-{[4-(2-methyl-4-nitrophenyl)-3,6-dihydropyridin-1(2H)-yl]carbonyl}-N-hydroxy-5-azaspiro[2.5]octane-7-carboxamide This compound was prepared using procedures analogous to those for example 31. Ms(ESI): (M+H)+=418.0

Example 40

(6S,7S)—N(7)-hydroxy-N(6),5-dimethyl-N(6)-(3-phenylpropyl)-5-azaspiro[2.5]octane-6,7-dicarboxamide This compound was prepared using procedures analogous to those for example 1. Ms(ESI): (M+H)+=360.1

Example 41

(6S,7S)—N(7)-hydroxy-N(6)-isobutyl-5-methyl-5-azaspiro[2.5]octane-6,7-dicarboxamide This compound was prepared using procedures analogous to those for example 1. Ms(ESI): (M+H)+=284.0

Example 42

(6S,7S)—N-hydroxy-5-methyl-6-{[4-(2-nitrophenyl)piperazin-1-yl]carbonyl}-5-azaspiro[2.5]octane-7-carboxamide This compound was prepared using procedures analogous to those for example 1. Ms(ESI): (M+H)+=418.0

Example 43

(6S,7S)—N(7)-hydroxy-N(6)-isobutyl-N(6),5-dimethyl-5-azaspiro[2.5]octane-6,7-dicarboxamide This compound was prepared using procedures analogous to those for example 1. Ms(ESI): (M+H)+=298.0

Example 44

(6S,7S)—N(7)-hydroxy-5-methyl-N(6)-(2-phenoxyethyl)-5-azaspiro[2.5]octane-6,7-dicarboxamide This compound was prepared using procedures analogous to those for example 1. Ms(ESI): (M+H)+=348.0

Example 45

(6S,7S)—N(7)-hydroxy-N(6)-[2-(4-methoxyphenyp-ethyl]-5-methyl-5-azaspiro[2.5]octane-6,7-dicarboxamide This compound was prepared using procedures analogous to those for example 1. Ms(ESI): (M+H)+=362.0

Example 46

(6S,7S)—N(7)-hydroxy-5-methyl-N(6)-(4-phenylbutyl)-5-azaspiro[2.5]octane-6,7-dicarboxamide This compound was prepared using procedures analogous to those for example 1. Ms(ESI): (M+H)+=360.0

Example 47

(6S,7S)—N(7)-hydroxy-5-methyl-N(6)-[3-(2-oxopyrrolidin-1-yl)propyl]-5-azaspiro[2.5]octane-6,7-dicarboxamide This compound was prepared using procedures analogous to those for example 1. Ms(ESI): (M+H)+=353.0

Example 48

(6S,7S)—N-hydroxy-5-methyl-6-[(10aR)-3,4,10,10a-tetrahydropyrazino[1,2-a]indol-2(1H)-ylcarbonyl]-5-azaspiro[2.5]octane-7-carboxamide

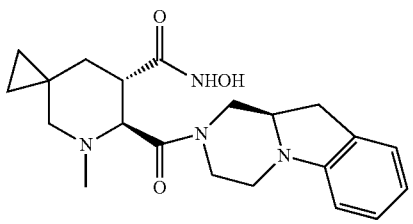

Step 1. Preparation of methyl{[(2R)-2,3-dihydro-1H-indol-2-ylcarbonyl]amino}acetate To a solution of (2R)-indoline-2-carboxylic acid (1 g, 5.64 mmol) and HCl salt of amino-acetic acid methyl ester (710 mg, 5.64 mmol) and BOP (2.75 g, 1.1 eq) in 15 mL DMF was added 2.95 mL hunig base. The mixture was stirred overnight. The mixture was diluted in sat. NaHCO$_3$, extracted with EtOAc three time, and washed with sat. NaHCO$_3$ and brine. The organic solution was dried over Na$_2$SO$_4$ and concentrated to give the desired methyl{[(2R)-2,3-dihydro-1H-indol-2-ylcarbonyl]amino}acetate. The material was used directly in the next step without further purification.

Step 2. Preparation of (10aR)-1,2,3,4,10,10a-hexahydropyrazino[1,2-a]indole methyl{[(2R)-2,3-dihydro-1H-indol-2-ylcarbonyl]amino}acetate (390 mg) was mixed with 100 mg of NaOMe in 5 mL of Ethanol. The mixture was refluxed for 2 hours and cooled to RT. The crude material was purified by flash chromatography to give the desired (10aR)-2,3, 10,10a-tetrahydropyrazino[1,2-a]indole-1,4-dione.

To a solution of (10aR)-2,3,10,10a-tetrahydropyrazino[1,2-a]indole-1,4-dione (200 mg, 0.99 mmol) in 5 mL THF was added LAH. The reaction mixture was refluxed for 1 h. Standard work up afforded 170 mg of pure (10aR)-1,2,3,4,10,10a-hexahydropyrazino[1,2-a]indole.

Step 3

Using the procedure described in Ex. 1, (10aR)-1,2,3,4,10,10a-hexahydropyrazino[1,2-a]indole was converted to the desired (6S,7S)—N-hydroxy-5-methyl-6-[(10aR)-3,4,10,10a-tetrahydropyrazino[1,2-a]indol-2(1H)-ylcarbonyl]-5-azaspiro[2.5]octane-7-carboxamide. Ms(ESI): (M+H)+=385.0.

Example 49

(5,6-trans)-N-hydroxy-5-{[4-(2-methyl-4-nitrophenyl)piperazin-1-yl]carbonyl}spiro[2.5]octane-6-carboxamide

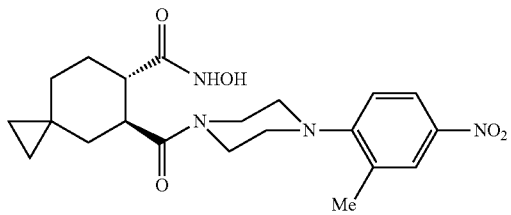

Step 1. Preparation of 2-tert-butyl 1-ethyl(1,2-trans)-4-[(trimethylsilyl)oxy]cyclohex-4-ene-1,2-dicarboxylate

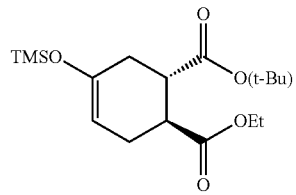

At −20° C., a 0.4 M solution in toluene of methyl aluminum bis(2,6-di-tert-butyl-4-methylphenoxide) (MAD) (50 mL, 20 mmole) was added to solvent methylenechloride (15 ml) slowly with stirring. At this temperature, a solution of tert-butyl ethyl fumarate (3.60 g, 18 mmole) in methylenechloride (4 mL) was added to MAD solution slowly with stirring. At −20° C., to the reaction mixture, a solution of 2-trimethylsilyloxy-1,3-butadiene (2.56 g, 18 mmole) in methylenechloride (4 mL) was added slowly. The reaction mixture was stirred at −20° C. for 70 hours. The reaction mixture was quenched with saturated citric acid solution, and diluted with methylenechloride. Some insoluble material came out and was filtered off After separation, the aqueous layer was extracted with methylenechloride (×2). The combined extracts were dried over $Na_2SO_4$. After filtration, the filtrate was concentrated. The resulting residue was purified by flash chromatography, 4.12 g pure product was obtained. The filtrate was re-purified by column chromatography. Another 0.56 g pure product was obtained. And 0.78 g starting material tert-butyl ethyl fumarate was recovered. Yield: 97%.

Step 2. Preparation of 2-tert-butyl 1-ethyl(1,2-trans)-4-oxocyclohexane-1,2-dicarboxylate

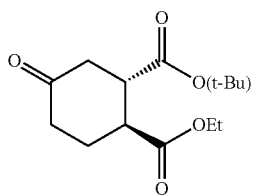

The compound 2-tert-butyl 1-ethyl(1,2-trans)-4-[(trimethylsilyl)oxy]cyclohex-4-ene-1,2-dicarboxylate of step 1(0.72 g, 2.1 mmol) was dissolved in methanol (10 ml). To the solution, saturated citric acid solution (1 mL) was added. The mixture was stirred at r.t. for 4 hours. TLC showed starting material was consumed. Methanol was removed by rotavaporation. The resulting residue was taken up into ethyl acetate and washed with water (×1), brine (×1), dried over $Na_2SO_4$. After filtration, the filtrate was concentrated to yield quantitative product.

Step 3. Preparation of 2-tert-butyl 1-ethyl(1,2)-4-methylenecyclohexane-1,2-dicarboxylate

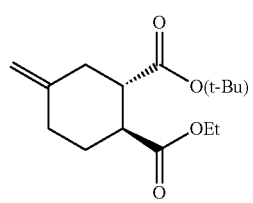

To the mixture of methyl triphenylphosponium bromide (0.87 g, 2.4 mmole) in toluene (6 mL) and THF (2 mL), 1 M of NaHMDS (2.4 mL, 2.4 mmole) in THF was added. The mixture was stirred at r.t. for 1.5 hour. This mixture was added to a pre-cold (−10° C.) solution of compound 2-tert-butyl 1-ethyl(1,2-trans)-4-oxocyclohexane-1,2-dicarboxylate of step 2 (0.57 g, 2.1 mmol) in toluene (8 mL) slowly with stirring. After completion of addition, the reaction mixture was stirred at −10° C. for 10 mins, then, at r.t. for 1.5 hour. TLC showed starting material consumed. The reaction mixture was diluted with ethyl acetate, washed with water (×1); brine (×2); dried over $Na_2SO_4$. After filtration, the filtrate was concentrated. The resulting residue was purified by flash chromatography. 0.56 g of 2-tert-butyl 1-ethyl(1,2)-4-methylenecyclohexane-1,2-dicarboxylate was obtained. Yield: 99%.

Step 4. Preparation of 5-tert-butyl 6-ethyl(5,6-trans)-spiro[2.5]octane-5,6-dicarboxylate

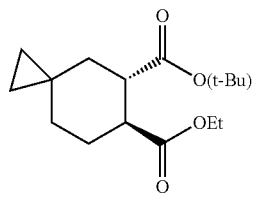

To a solution of KOH (5 g) in water (8 mL), di(ethylene glycol)ethyl ether (24 mL), and ethyl ether (25 mL) in flask A, 3 g of diazald was added in three portions. After the addition of first portion of diazald, the flask was put into a pre-heated (at 60° C.) oil bath in order to distill out $CH_2N_2$ formed with ether to another flask (B) pre-chilled to around −15° C. and containing 2-tert-butyl 1-ethyl(1,2)-4-methylenecyclohexane-1,2-dicarboxylate ster from step 3 (500 mg), and $Pd(OAc)_2$ (80 mg) in ether (15 ml). After 5 minutes, the oil bath was removed from flask A. Then, the second portion of diazald was added, and the above procedure repeated twice. After completion of the distillation of $CH_2N_2$ with ether into flask B, the cold bath was removed from flask B. The reaction mixture was stirred at r.t. for 2 hours then filtered through silica gel, rinsed with ethyl acetate and then methylenechloride. The filtrate was concentrated. The resulting residue was treated according to the above described procedures three additional times. Normal work up afforded 5-tert-butyl 6-ethyl(5,6-trans)-spiro[2.5]octane-5,6-dicarboxylate (80% yield).

Step 5. Preparation of (5,6-trans)-6-(ethoxycarbonyl)spiro[2.5]octane-5-carboxylic acid

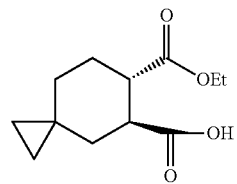 [SMILES: CCOC(=O)[C@H]1CCC2(CC2)C[C@@H]1C(=O)O]

5-tert-butyl 6-ethyl(5,6-trans)-spiro[2.5]octane-5,6-dicarboxylate (150 mg, 0.53 mmol) was dissolved in a solution of methylene chloride (2 mL)-TFA (2 mL) and water (0.1 mL). The mixture was stirred at r.t. for 3 hours. TLC showed that starting material was consumed. The reaction mixture was concentrated to yield quantitative product (5,6-trans)-6-(ethoxycarbonyl)spiro[2.5]octane-5-carboxylic acid.

Step 6. Preparation of ethyl(5, 6-trans)-5-{[4-(2-methyl-4-nitrophenyl)piperazin-1-yl]carbonyl}spiro[2.5]octane-6-carboxylate

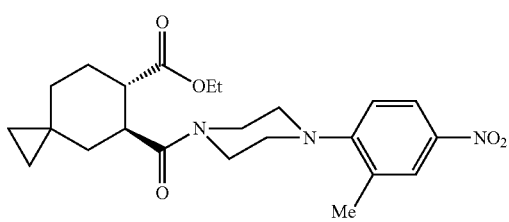 [SMILES: CCOC(=O)[C@H]1CCC2(CC2)C[C@@H]1C(=O)N1CCN(c2ccc([N+](=O)[O-])cc2C)CC1]

(5,6-trans)-6-(ethoxycarbonyl)spiro[2.5]octane-5-carboxylic acid of step 5 (27.4 mg, 0.12 mmol) and 1-(2-methyl-4-nitrophenyl)-piperazine (29.4 mg, 0.13 mmol) were dissolved in DMF (1 mL). To the resulting solution, BOP reagent (56.3 mg, 0.127 mmol) was added. After stirring 10 minutes, DIEA was added to the mixture. It was stirred at r.t. overnight then quenched with saturated citric acid solution. The product was extracted with ethyl acetate. The extract was washed with water (×1), brine (×1); dried over Na₂SO₄. After filtration, the filtrate was concentrated to afford ethyl(5,6-trans)-5-{[4-(2-methyl-4-nitrophenyl)piperazin-1-yl]carbonyl}spiro[2.5]octane-6-carboxylate.

Step 7. Preparation of compound (5,6-trans)-5-{[4-(2-methyl-4-nitrophenyl)piperazin-1-yl]carbonyl}spiro[2.5]octane-6-carboxylic acid

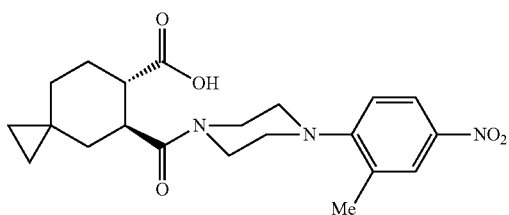 [SMILES: Cc1cc([N+](=O)[O-])ccc1N1CCN(C(=O)[C@H]2CC3(CC[C@@H]2C(=O)O)CC3)CC1]

ethyl(5,6-trans)-5-{[4-(2-methyl-4-nitrophenyl)piperazin-1-yl]carbonyl}spiro[2.5]-octane-6-carboxylate obtained from step 6 was mixed in THF (2 mL)-water (0.4 mL) and LiOH.H₂O (200 mg) and heated at reflux for 36 hours. After cooling, the reaction mixture was neutralized with saturated citric acid and extracted with ethyl acetate (×3). The combined extracts were washed with citric acid (×1), brine (×1), and dried over Na₂SO₄. After filtration, the filtrate was concentrated to give (5,6-trans)-5-{[4-(2-methyl-4-nitrophenyl)piperazin-1-yl]carbonyl}spiro[2.5]octane-6-carboxylic acid.

Step 8. Preparation of compound (5,6-trans)-N-hydroxy-5-{[4-(2-methyl-4-nitrophenyl)piperazin-1-yl]carbonyl}spiro[2.5]octane-6-carboxamide

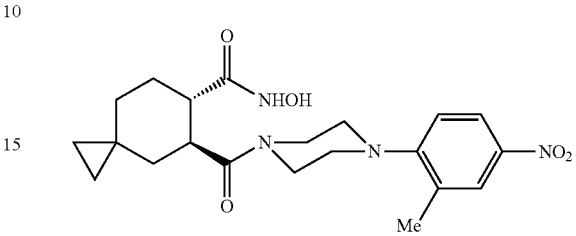

To a solution of (5,6-trans)-5-{[4-(2-methyl-4-nitrophenyl)piperazin-1-yl]carbonyl}spiro[2.5]octane-6-carboxylic acid obtained in step 7 and hydroxylamine HCl salt (30 mg, 4.3 mmol) in 1 mL DMF was added BOP coupling agent (56.3 mg, 0.13 mmol). After stirring for 10 minutes, DIEA was added to the mixture. The mixture was stirred at r.t. overnight and monitored by HPLC. The final desired product was purified by RP-HPLC to give 25.6 mg of (5,6-trans)-N-hydroxy-5-{[4-(2-methyl-4-nitrophenyl)piperazin-1-yl]carbonyl}spiro[2.5]octane-6-carboxamide in 50% yield in three steps. Ms(ESI): (M+H)+=417.2

Example 50

(5,6-trans)-N-hydroxy-6-{[4-(3-methylphenyl)piperazin-1-yl]carbonyl}spiro[2.5]octane-5-carboxamide This compound was prepared using procedures analogous to those for example 49. Ms(ESI): (M+H)+=372.2

Example 51

(5,6-trans)-N-hydroxy-5-[(4-phenyl-3,6-dihydropyridin-1(2H)-yl)carbonyl]spiro[2.5]octane-6-carboxamide This compound was prepared using procedures analogous to those for example 49. Ms(ESI): (M+H)+=355.

Example 52

(5,6-trans)-N-hydroxy-5-{[4-(3-methylphenyl)piperazin-1-yl]carbonyl}spiro[2.5]octane-6-carboxamide This compound was prepared using procedures analogous to those for example 49. Ms(ESI): (M+H)+=372.0

Example 53

(5,6-trans)-N-hydroxy-6-[(4-phenyl-3,6-dihydropyridin-1(2H)-yl)carbonyl]spiro[2.5]octane-5-carboxamide This compound was prepared using procedures analogous to those for example 49. Ms(ESI): (M+H)+=355.

Example 54

(6S,7S)—N-hydroxy-6-(3,4,10,10a-tetrahydropyrazino[1,2-a]indol-2(1H)-ylcarbonyl)-5-azaspiro[2.5]octane-7-carboxamide

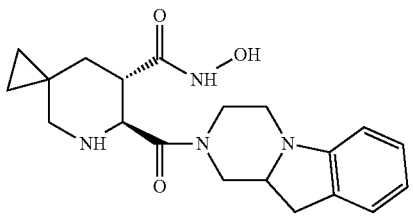 [SMILES: O=C(NO)[C@H]1CC2(CC2)CN[C@@H]1C(=O)N1CCN2c3ccccc3CC2C1]

This compound was prepared using procedures analogous to those for example 48. Ms(ESI): (M+H)+=371.2.

Example 55

(6S,7S)-6-(1,2,4,4a,5,6-hexahydro-3H-pyrazino[1,2-a]quinolin-3-ylcarbonyl)-N-hydroxy-5-methyl-5-azaspiro[2.5]octane-7-carboxamide This compound was prepared using procedures analogous to those for example 48. Ms(ESI): (M+H)+=399.4.

Example 56

Methyl (6S,7S)-7-[(hydroxyamino)carbonyl]-6-[(4-phenyl-3,6-dihydropyridin-1(2H)-yl)carbonyl]-5-azaspiro[2.5]octane-5-carboxylate This compound was prepared using procedures analogous to those for example 1. Ms(ESI): (M+H)+=414.0.

Example 57

Benzyl (6S,7S)-7-[(hydroxyamino)carbonyl]-6-[(4-phenyl-3,6-dihydropyridin-1(2H)-yl)carbonyl]-5-azaspiro[2.5]octane-5-carboxylate This compound was prepared using procedures analogous to those for example 1. Ms(ESI): (M+H)+=490.0

Example 58

(6S,7S)—N-Hydroxy-5-(methylsulfonyl)-6-[(4-phenyl-3,6-dihydropyridin-1(2H)-yl)carbonyl]-5-azaspiro[2.5]octane-7-carboxamide This compound was prepared using procedures analogous to those for example 1. Ms(ESI): (M+H)+=434.0.

Example 59

(6S,7S)—N-hydroxy-6-{[3-(3-methoxyphenyl)piperidin-1-yl]carbonyl}-5-methyl-5-azaspiro[2.5]octane-7-carboxamide This compound was prepared using procedures analogous to those for example 1. Ms(ESI): (M+H)+=402.4.

Example 60

(6S,7S)—N-hydroxy-5-methyl-6-{[3-(2-phenylethyl)pyrrolidin-1-yl]carbonyl}-5-azaspiro[2.5]octane-7-carboxamide This compound was prepared using procedures analogous to those for example 1. Ms(ESI): (M+H)+=386.0.

Example 61

(6S,7S)—N-hydroxy-6-{[4-(3-methoxyphenyl)piperidin-1-yl]carbonyl}-5-methyl-5-azaspiro[2.5]octane-7-carboxamide This compound was prepared using procedures analogous to those for example 1. Ms(ESI): (M+H)+=402.4.

Example 62

(6S,7S)-6-{[4-[3-(aminocarbonyl)phenyl]-3,6-dihydropyridin-1(2H)-yl]carbonyl}-N-hydroxy-5-azaspiro[2.5]octane-7-carboxamide This compound was prepared using procedures analogous to those for example 31. Ms(ESI): (M+H)+=398.9.

Example 63

(6S,7S)—N-hydroxy-6-{[4-(2-methoxyphenyl)piperidin-1-yl]carbonyl}-5-methyl-5-azaspiro[2.5]octane-7-carboxamide This compound was prepared using procedures analogous to those for example 31. Ms(ESI): (M+H)+=402.4.

Example 64

(6S,7S)-6-{[4-(3-fluoro-2-methylphenyl)piperazin-1-yl]carbonyl}-N-hydroxy-5-azaspiro[2.5]octane-7-carboxamide This compound was prepared using procedures analogous to those for example 1. Ms(ESI): (M+H)+=391.3.

Example 65

(6S,7S)—N-hydroxy-6-{[4-(2-methyl-3-nitrophenyl)piperazin-1-yl]carbonyl}-5-azaspiro[2.5]octane-7-carboxamide This compound was prepared using procedures analogous to those for example 1. Ms(ESI): (M+H)+=418.3.

Example 66

(6S,7S)-6-(3',6'-dihydro-3,4'-bipyridin-1'(2'H)-ylcarbonyl)-N-hydroxy-5-azaspiro[2.5]octane-7-carboxamide

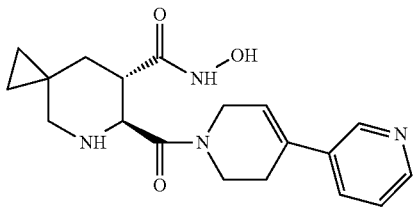 [SMILES: O=C(NO)[C@H]1CC2(CC2)CN[C@@H]1C(=O)N1CC=C(c2cccnc2)CC1]

This compound was prepared using procedures analogous to those for example 31. Ms(ESI): (M+H)+=357.4.

Example 67

(6S,7S)—N(7)-hydroxy-N(6)-(4-methoxyphenyl)-N(6)-methyl-5-azaspiro[2.5]octane-6,7-dicarboxamide This compound was prepared using procedures analogous to those for example 1. Ms(ESI): (M+H)+=334.

Example 68

(6S,7S)—N-hydroxy-6-{[4-(3-methoxyphenyl)piperazin-1-yl]carbonyl}-5-methyl-5-azaspiro[2.5]octane-7-carboxamide This compound was prepared using procedures analogous to those for example 1. Ms(ESI): (M+H)+=403.0.

Example 69

(6S,7S)-6-{[4-(3-chlorophenyl)piperazin-1-yl]carbonyl}-N-hydroxy-5-methyl-5-azaspiro[2.5]octane-7-carboxamide This compound was prepared using procedures analogous to those for example 1. Ms(ESI): (M+H)+=407.3.

Example 70

(6S,7S)—N-hydroxy-6-[(4-phenyl-1,4-diazepan-1-yl)carbonyl]-5-azaspiro[2.5]octane-7-carboxamide This compound was prepared using procedures analogous to those for example 1. Ms(ESI): (M+H)+=373.

Example 71

(6S,7S)—N-hydroxy-6-{[3-methyl-4-(3-methylphenyl)piperazin-1-yl]carbonyl}-5-azaspiro[2.5]octane-7-carboxamide This compound was prepared using procedures analogous to those for example 1. Ms(ESI): (M+H)+=387.

Example 72

(6S,7S)—N-hydroxy-6-{[4-(3-methoxyphenyl)piperidin-1-yl]carbonyl}-5-azaspiro[2.5]octane-7-carboxamide This compound was prepared using procedures analogous to those for example 1. Ms(ESI): (M+H)+=388.4.

Example 73

(5S,6S)—N-hydroxy-6-[(3-phenylpyrrolidin-1-yl)carbonyl]spiro[2.5]octane-5-carboxamide This compound was prepared using procedures analogous to those for example 1. Ms(ESI): (M+H)+=343.3.

Example 74

(6S,7S)—N-hydroxy-6-[(4-isobutyrylpiperazin-1-yl)carbonyl]-5-azaspiro[2.5]octane-7-carboxamide This compound was prepared using procedures analogous to those for example 1. Ms(ESI): (M+H)+=353.

Example 75

(6S,7S)-6-{[4-(4-cyano-2-methylphenyl)-3,6-dihydropyridin-1(2H)-yl]carbonyl}-N-hydroxy-5-azaspiro[2.5]octane-7-carboxamide This compound was prepared using procedures analogous to those for example 31. Ms(ESI): (M+H)+=395.

Example 76

(6S,7S)—N(7)-Hydroxy-5-methyl-N(6)-{4-[(2-methylquinolin-4-yl)methoxy]phenyl}-5-azaspiro[2.5]octane-6,7-dicarboxamide Step 1. Preparation of 4-(2-methylquinolin-4-ylmethoxy)phenylamine To a mixture of 2-methylquinoline (43.0 g, 0.3 mol), iron (5.04 g, 0.09 mol), $FeSO_4 \cdot 7H_2O$ (25.0 g, 0.09 mol) in methanol (400 mL) and water (200 mL) was added sulfuric acid (conc., 16.0 mL, 0.3 mol) at 0° C., and then $H_2O_2$ (160 mL) was slowly added at 0° C. The mixture was then warmed to room temperature and stirred overnight. The solution was diluted with water, basified with ammonium hydroxide, and extracted with ethyl acetate. The combined extract was washed with brine, dried and concentrated. Recrysatllization from ethyl ether/hexane to give (2-Methylquinolin-4-yl)methanol (12.0 g). ESI (M+H)+ 173.9.

(2-Methylquinolin-4-yl)methanol (7.0 g) was dissolved in chloroform (150 mL) and cooled to 0° C., the thionyl chloride (15.0 mL) was slowly added at this temperature and then the reaction mixture was allowed to warm up to room temperature while stirring overnight. The solvent was removed and the residue was triturated with ethyl acetate/ethyl ether to provide the compound 4-chloromethyl-2-methylquinoline as the HCl salt (9.0 g). ESI (M+H)+ 191.9.

The mixture of 4-chloromethyl-2-methylquinoline (6.84 g, 30.0 mmol), (4-hydroxyphenyl)carbamic acid tert-butyl ester (6.24 g, 30.0 mmol), $Cs_2CO_3$ (20.0 g, 60.0 mmol), and n-$Bu_4NI$ (11.1 g, 30.0 mmol) in DMSO (150 mL) was stirred at 80° C. for 3 h. The mixture was then cooled, dumped into cold water, and extracted with ethyl acetate. The combined extract was washed with water, brine, dried and concentrated. Chromatograph by $CH_2Cl_2$/EtOAc to provide compound [4-(2-methylquinolin-4-ylmethoxy)phenyl]-carbamic acid tert-butyl ester (8.0 g). ESI (M+H)$^+$365.3.

To a solution of compound [4-(2-methylquinolin-4-ylmethoxy)phenyl]carbamic acid tert-butyl ester (1.5 g) in ethyl acetate (5 mL) was added 4 N HCl in dioxane (20 mL) and the mixture was stirred at room temperature for 3 h. Ethyl ether was added and the precipitate was filtered and washed with ethyl ether to provide 4-(2-methylquinolin-4-ylmethoxy)phenylamine as an HCl salt (1.3 g). ESI (M+H)$^+$ 265.0.

Step 2. Preparation of tert-butyl (6S,7S)-6-[({4-[(2-methylquinolin-4-yl)methoxy]phenyl}amino)carbonyl]-5-azaspiro[2.5]octane-7-carboxylate 4-(2-Methylquinolin-4-ylmethoxy)phenylamine as an HCl salt (94.0 mg, 0.28 mmol) and (6S,7S)-7-(tert-butoxycarbonyl)-5-azaspiro[2.5]octane-6-carboxylic acid (70.0 mg, 0.27 mmol) were dissolved in DMF (2.0 mL). BOP (143.0 mg, 0.32 mmol) was added to the above solution and then cooled to 0° C. Diisopropylethylamine (0.175 mL, 1.0 mmol) was added to the above mixture at 0° C. and then the reaction was stirred at room temperature for 2 h. The mixture was diluted with water, extracted with ethyl acetate, the combined extract was washed with brine, dried and concentrated. The crude tert-butyl (6S,7S)-6-[({4-[(2-methylquinolin-4-yl)methoxy]phenyl}amino)carbonyl]-5-azaspiro[2.5]octane-7-carboxylate (140 mg) was used in the next step without purification. ESI (M+H)$^+$ 502.4.

Step 3. Preparation of tert-butyl (6S,7S)-5-methyl-6-[({4-[(2-methylquinolin-4-yl)methoxy]phenyl}amino)carbonyl]-5-azaspiro[2.5]octane-7-carboxylate To a solution of tert-butyl (6S,7S)-6-[({4-[(2-methylquinolin-4-yl)methoxy]phenyl}amino)carbonyl]-5-azaspiro[2.5]octane-7-carboxylate (140 mg, 0.27 mmol) in methanol (3.0 mL) was added formaldehyde (37% solution in water, 0.5 mL) and sodium triacetoxyborohydride (0.25 g, 1.2 mmol). The mixture was then stirred at room temperature for 2 h. The reaction was diluted with ethyl acetate, washed with saturated $NaHCO_3$, water and brine. Dried and concentrated. tert-butyl (6S,7S)-5-methyl-6-[({4-[(2-methylquinolin-4-yl)methoxy]phenyl}amino)carbonyl]-5-azaspiro[2.5]octane-7-carboxylate (105.0 mg) was obtained by column using $CH_2Cl_2$/Methanol (10%). ESI (M+H)$^+$ 516.5.

Step 4. Preparation of (6S,7S)-5-methyl-6-[({4-[(2-methylquinolin-4-yl)methoxy]phenyl}amino)carbonyl]-5-azaspiro[2.5]octane-7-carboxylic acid TFA (1.0 mL) was added to a solution of tert-butyl (6S,7S)-5-methyl-6-[({4-[(2-methylquinolin-4-yl)methoxy]phenyl}amino)carbonyl]-5-azaspiro[2.5]octane-7-carboxylate (105.0 mg) in $CH_2Cl_2$ (1.0 mL) and the mixture was stirred at room temperature for 5 h. The solvent was removed to provide (6S,7S)-5-methyl-6-[({4-[(2-methylquinolin-4-yl)methoxy]phenyl}amino)carbonyl]-5-azaspiro[2.5]octane-7-carboxylic acid (140 mg) as an TFA salt. ESI (M+H)$^+$ 460.3.

Step 5. Preparation of (6S,7S)—N(7)-hydroxy-5-methyl-N(6)-{4-[(2-methylquinolin-4-yl)methoxy]phenyl}-5-azaspiro[2.5]octane-6,7-dicarboxamide To BOP (120.0 mg, 0.24 mmol) was added to a solution of (6S,7S)-5-methyl-6-[({4-[(2-methylquinolin-4-yl)methoxy] phenyl}amino)carbonyl]-5-azaspiro[2.5]octane-7-carboxylic acid (140 mg, 0.20 mmol) in DMF (1.0 mL) at 0° C. followed by hydroxylamine hydrochloride (28.0 mg, 0.40 mmol). 4-methylmorpholine (0.07 mL, 0.70 mmol) was then added to the above mixture at 0° C. and stirred at this temperature for 2 h. The product (70 mg) was purified by preparative HPLC. ESI (M+H)$^+$ 475.4.

Example 77

(6S,7S)—N(7)-Hydroxy-N(6)-{4-[(2-methylquinolin-4-yl)methoxy]phenyl}-5-azaspiro[2.5]octane-6,7-dicarboxamide This compound was prepared using procedures analogous to those for example 77. Ms(ESI): (M+H)+=461.0.

Example 78

(6S,7S)-6-{[4-(4-cyanophenyl)piperazin-1-yl]carbonyl}-N-hydroxy-5-azaspiro[2.5]octane-7-carboxamide This compound was prepared using procedures analogous to those for example 1. Ms(ESI): (M+H)+=384.0.

Example 79

(6S,7S)—N-hydroxy-7-[(4-phenylpiperidin-1-yl)carbonyl]-5-azaspiro[2.5]octane-6-carboxamide This compound was prepared using procedures analogous to those for example 1. Ms(ESI): (M+H)+=358.0.

Example 80

(6S,7S)—N-hydroxy-6-[(4-phenylpiperidin-1-yl)carbonyl]-5-azaspiro[2.5]octane-7-carboxamide This compound was prepared using procedures analogous to those for example 1. Ms(ESI): (M+H)+=358.

Example 81

(6S,7S)—N-Hydroxy-6-[(4-phenylpiperazin-1-yl)carbonyl]-5-azaspiro[2.5]octane-7-carboxamide This compound was prepared using procedures analogous to those for example 1. Ms(ESI): (M+H)+=359.4.

Example 82

(6S,7S)—N-hydroxy-6-({4-[3-(methoxymethyl)phenyl]piperidin-1-yl}carbonyl)-5-azaspiro[2.5]octane-7-carboxamide This compound was prepared using procedures analogous to those for example 1. Ms(ESI): (M+H)+=402.

Example 83

Methyl 3-[1-({(6S,7S)-7-[(hydroxyamino)carbonyl]-5-azaspiro[2.5]oct-6-yl}carbonyl)piperidin-4-yl]benzoate This compound was prepared using procedures analogous to those for example 1. Ms(ESI): (M+H)+=416.

Example 84

(6S,7S)-6-[(3-Cyclohexylpyrrolidin-1-yl)carbonyl]-N-hydroxy-5-azaspiro[2.5]octane-7-carboxamide This compound was prepared using procedures analogous to those for example 1. Ms(ESI): (M+H)+=350.4.

Example 85

(6S,7S)—N-Hydroxy-6-{[4-(3-isopropylphenyl)-3,6-dihydropyridin-1(2H)-yl]carbonyl}-5-azaspiro[2.5]octane-7-carboxamide This compound was prepared using procedures analogous to those for example 31. Ms(ESI): (M+H)+=398.4.

Example 86

(6S,7S)—N-hydroxy-6-{[4-(3-isopropylphenyl)piperidin-1-yl]carbonyl}-5-azaspiro[2.5]octane-7-carboxamide (6S,7S)—N-hydroxy-6-{[4-(3-isopropylphenyl)-3,6-dihydropyridin-1(2H)-yl]carbonyl}-5-azaspiro[2.5]octane-7-carboxamide (10 mg) was hydrogenated at 1.0 atm over BaSO$_4$ in MeOH for one hour to give the desired product, Ms(ESI): (M+H)+=400.4.

Example 87

(6S,7S)—N-hydroxy-6-{[4-(4-propylphenyl)-3,6-dihydropyridin-1(2H)-yl]carbonyl}-5-azaspiro[2.5]octane-7-carboxamide This compound was prepared using procedures analogous to those for example 31. Ms(ESI): (M+H)+=398.

Example 88

(6S,7S)—N-hydroxy-6-{[4-(4-ethylphenyl)-3,6-dihydropyridin-1(2H)-yl]carbonyl}-5-azaspiro[2.5]octane-7-carboxamide This compound was prepared using procedures analogous to those for example 31. Ms(ESI): (M+H)+=384.4.

Example 89

(6S,7S)—N-Hydroxy-6-{[4-(4-ethylphenyl)piperidin-1-yl]carbonyl}-5-azaspiro[2.5]octane-7-carboxamide This compound was prepared using procedures analogous to those for example 86. Ms(ESI): (M+H)+=386.

Example 90

(6S,7S)-6-{[4-(4-cyano-2-methylphenyl)piperazin-1-yl]carbonyl}-N-hydroxy-5-azaspiro[2.5]octane-7-carboxamide This compound was prepared using procedures analogous to those for example 1. Ms(ESI): (M+H)+=398.

Example 91

(6S,7S)—N-Hydroxy-6-{[4-(3-isopropoxyphenyl)-3,6-dihydropyridin-1(2H)-yl]carbonyl}-5-azaspiro[2.5]octane-7-carboxamide This compound was prepared using procedures analogous to those for example 31. Ms(ESI): (M+H)+=414.4.

Example 92

(6S,7S)—N-Hydroxy-6-{[4-(3-methylphenyl)-3,6-dihydropyridin-1(2H)-yl]carbonyl}-5-azaspiro[2.5]octane-7-carboxamide This compound was prepared using procedures analogous to those for example 31. Ms(ESI): (M+H)+=370.3.

Example 93

(6S,7S)—N-Hydroxy-6-{[4-(3-methylphenyl)piperidin-1-yl]carbonyl}-5-azaspiro[2.5]octane-7-carboxamide This compound was prepared using procedures analogous to those for example 86. Ms(ESI): (M+H)+=372.4.

Example 94

(6S,7S)-6-{[4-(4-tert-butylphenyl)piperazin-1-yl]carbonyl}-N-hydroxy-5-azaspiro[2.5]octane-7-carboxamide This compound was prepared using procedures analogous to those for example 1. Ms(ESI): (M+H)+=415.4.

Example 95

(6S,7S)—N-Hydroxy-6-[(4-pyridin-4-ylpiperazin-1-yl)carbonyl]-5-azaspiro[2.5]octane-7-carboxamide This compound was prepared using procedures analogous to those for example 1. Ms(ESI): (M+H)+=360.

Example 96

(6S,7S)-6-[(3-Benzylpiperidin-1-yl)carbonyl]-N-hydroxy-5-azaspiro[2.5]octane-7-carboxamide This compound was prepared using procedures analogous to those for example 1. Ms(ESI): (M+H)+=371.9.

Example 97

(6S,7S)—N-hydroxy-6-[(5-methoxy-2,3-dihydro-1H-indol-1-yl)carbonyl]-5-azaspiro[2.5]octane-7-carboxamide This compound was prepared using procedures analogous to those for example 76. Ms(ESI): (M+H)+=346.3.

Example 98

(6S,7S)—N-hydroxy-6-({5-[(2-methylquinolin-4-yl)methoxy]-2,3-dihydro-1H-indol-1-yl}carbonyl)-5-azaspiro[2.5]octane-7-carboxamide This compound was prepared using procedures analogous to those for example 76. Ms(ESI): (M+H)+=487.4.

Example 99

(6S,7S)—N-hydroxy-5-methyl-6-({5-[(2-methylquinolin-4-yl)methoxy]-2,3-dihydro-1H-indol-1-yl}carbonyl)-5-azaspiro[2.5]octane-7-carboxamide This compound was prepared using procedures analogous to those for example 76. Ms(ESI): (M+H)+=501.4.

Example 100

(6S,7S)-6-{[5-(benzyloxy)-2,3-dihydro-1H-indol-1-yl]carbonyl}-N-hydroxy-5-azaspiro[2.5]octane-7-carboxamide This compound was prepared using procedures analogous to those for example 76. Ms(ESI): (M+H)+=422.3.

Example 101

(6S,7S)-6-(1,3-dihydro-1'H-spiro[indene-2,4'-piperidin]-1'-ylcarbonyl)-N-hydroxy-5-azaspiro[2.5]octane-7-carboxamide

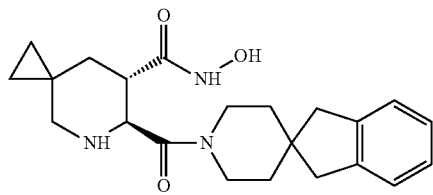 [SMILES: O=C(NO)[C@H]1CC2(CC2)CN[C@@H]1C(=O)N1CCC2(CC1)Cc1ccccc1C2]

This compound was prepared using procedures analogous to those for example 1. Ms(ESI): (M+H)+=384.4.

Example 102

(6S,7s)-N-hydroxy-6-{[4-(3-isopropoxyphenyl)piperidin-1-yl]carbonyl}-5-azaspiro[2.5]octane-7-carboxamide This compound was prepared using procedures analogous to those for example 86. Ms(ESI): (M+H)+=416.4.

Example 103

Methyl 4-[1-({(6S,7S)-7-[(hydroxyamino)carbonyl]-5-azaspiro[2.5]oct-6-yl}carbonyl)-1,2,3,6-tetrahydropyridin-4-yl]-3-methylbenzoate This compound was prepared using procedures analogous to those for example 31. Ms(ESI): (M+H)+=427.9.

Example 104

(6S,5S)—N-hydroxy-6-{[4-(2-methyl-4-nitrophenyl)-3,6-dihydropyridin-1(2H)-yl]carbonyl}-5-azaspiro[2.5]octane-7-carboxamide This compound was prepared using procedures analogous to those for example 31. Ms(ESI): (M+H)+=414.8.

Example 105

(6S,5S)-6-{[4-(2-ethylphenyl)piperidin-1-yl]carbonyl}-N-hydroxy-5-azaspiro[2.5]octane-7-carboxamide This compound was prepared using procedures analogous to those for example 86. Ms(ESI): (M+H)+=385.9.

Example 106

Methyl 4-[1-({(6S,7S)-7-[(hydroxyamino)carbonyl]-5-azaspiro[2.5]oct-6-yl}carbonyl)piperidin-4-yl]-3-methylbenzoate This compound was prepared using procedures analogous to those for example 86. Ms(ESI): (M+H)+=429.9.

Example 107

(6S,7S)-6-{[4-(2,3-dihydro-1-benzofuran-5-yl)-3,6-dihydropyridin-1(2H)-yl]carbonyl}-N-hydroxy-5-methyl-5-azaspiro[2.5]octane-7-carboxamide This compound was prepared using procedures analogous to those for example 31. Ms(ESI): (M+H)+=412.2.

Example 108

(6S,7S)—N-hydroxy-6-{[4-(3-isopropylphenyl)-3,6-dihydropyridin-1(2H)-yl]carbonyl}-5-methyl-5-azaspiro[2.5]octane-7-carboxamide This compound was prepared using procedures analogous to those for example 31. Ms(ESI): (M+H)+=412.25.

Example 109

(6S,7S)—N-Hydroxy-6-{[(3R)-3-phenylpyrrolidin-1-yl]carbonyl}-5-azaspiro[2.5]octane-7-carboxamide This compound was prepared using procedures analogous to those for example 1. Ms(ESI): (M+H)+=344.1.

Example 110

(6S,5S)—N-Hydroxy-6-{[(3S)-3-phenylpyrrolidin-1-yl]carbonyl}-5-azaspiro[2.5]octane-7-carboxamide This compound was prepared using procedures analogous to those for example 1. Ms(ESI): (M+H)+=344.1.

Example 112

(6S,7S)—N-hydroxy-6-({3-[3-(trifluoromethyl)phenyl]pyrrolidin-1-yl}carbonyl)-5-azaspiro[2.5]octane-7-carboxamide This compound was prepared using procedures analogous to those for example 1. Ms(ESI): (M+H)+=412.1.

Example 113

(6S,7S)-6-{[3-(3-chlorophenyl)pyrrolidin-1-yl]carbonyl}-N-hydroxy-5-azaspiro[2.5]octane-7-carboxamide This compound was prepared using procedures analogous to those for example 1. Ms(ESI): (M+H)+=378.1.

Example 114

(6S,7S)-6-{[3-(3-fluorophenyl)pyrrolidin-1-yl]carbonyl}-N-hydroxy-5-azaspiro[2.5]octane-7-carboxamide This compound was prepared using procedures analogous to those for example 1. Ms(ESI): (M+H)+=362.1.

Example 115

(6S,7S)-6-{[3-(4-fluorophenyl)pyrrolidin-1-yl]carbonyl}-N-hydroxy-5-azaspiro[2.5]octane-7-carboxamide This compound was prepared using procedures analogous to those for example 1. Ms(ESI): (M+H)+=362.1.

Example 116

(6S,7S)-6-{[3-(4-chlorophenyl)pyrrolidin-1-yl]carbonyl}-N-hydroxy-5-azaspiro[2.5]octane-7-carboxamide This compound was prepared using procedures analogous to those for example 1. Ms(ESI): (M+H)+=378.1.

Example 117

(6S,7S)—N-hydroxy-6-({3-[4-(trifluoromethyl)phenyl]pyrrolidin-1-yl}carbonyl)-5-azaspiro[2.5]octane-7-carboxamide This compound was prepared using procedures analogous to those for example 1. Ms(ESI): (M+H)+=412.1.

Example 118

(6S,7S)-6-{[3-(4-methoxyphenyl)pyrrolidin-1-yl]carbonyl}-N-hydroxy-5-azaspiro[2.5]octane-7-carboxamide This compound was prepared using procedures analogous to those for example 1. Ms(ESI): (M+H)+=374.1.

Example 119

(6S,7S)-6-{[3-(4-phenoxyphenyl)pyrrolidin-1-yl]carbonyl}-N-hydroxy-5-azaspiro[2.5]octane-7-carboxamide This compound was prepared using procedures analogous to those for example 1. Ms(ESI): (M+H)+=436.2.

Example 120

(6S,7S)—N-hydroxy-6-{[4-(3-methoxyphenyl)-3,6-dihydropyridin-1(2H)-yl]carbonyl}-5-azaspiro[2.5]octane-7-carboxamide This compound was prepared using procedures analogous to those for example 31. Ms(ESI): (M+H)+=386.1.

Example 121

(6S,7S)—N-hydroxy-6-{[4-(4-cyano-3-methylphenyl)-3,6-dihydropyridin-1(2H)-yl]carbonyl}-5-azaspiro[2.5]octane-7-carboxamide This compound was prepared using procedures analogous to those for example 31. Ms(ESI): (M+H)+=395.1.

Example 122

(6S,7S)-6-{[3-(3-methoxyphenyl)pyrrolidin-1-yl]carbonyl}-N-hydroxy-5-azaspiro[2.5]octane-7-carboxamide This compound was prepared using procedures analogous to those for example 1. Ms(ESI): (M+H)+=374.1.

Example 123

(6S,7S)—N-hydroxy-6-[(3-pyridin-4-ylpyrrolidin-1-yl)carbonyl]-5-azaspiro[2.5]octane-7-carboxamide This compound was prepared using procedures analogous to those for example 1. Ms(ESI): (M+H)+=345.2.

Example 124

(6S,7S)—N-hydroxy-6-{[4-(3,5-dimethylphenyl)-3,6-dihydropyridin-1(2H)-yl]carbonyl}-5-azaspiro[2.5]octane-7-carboxamide This compound was prepared using procedures analogous to those for example 31. Ms(ESI): (M+H)+=384.2.

Example 125

(6S,7S)—N-hydroxy-6-{[4-(3-trifluoromethoxyphenyl)-3,6-dihydropyridin-1(2H)-yl]carbonyl}-5-azaspiro[2.5]octane-7-carboxamide This compound was prepared using procedures analogous to those for example 31. Ms(ESI): (M+H)+=440.1.

Example 126

(6S,7S)—N-hydroxy-6-{[5-(methoxymethyl)-4-phenyl-3,6-dihydropyridin-1(2H)-yl]carbonyl}-5-azaspiro[2.5]octane-7-carboxamide This compound was prepared using procedures analogous to those for example 1. Ms(ESI): (M+H)+=400.

Example 127

(6S,7S)—N-hydroxy-6-(1,4,5,6-tetrahydrobenzo[f]isoquinolin-3(2H)-ylcarbonyl)-5-azaspiro[2.5]octane-7-carboxamide

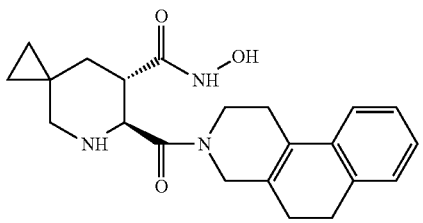 [SMILES: O=C(NO)[C@H]1CC2(CC2)CN[C@@H]1C(=O)N1CCC2=C(CCc3ccccc32)C1]

This compound was prepared using procedures analogous to those for example 1. Ms(ESI): (M+H)+=381.9.

Example 129

(6S,7S)—N-hydroxy-6-{[4-(5-methoxy-2-methylphenyl)-3,6-dihydropyridin-1(2H)-yl]carbonyl}-5-azaspiro[2.5]octane-7-carboxamide This compound was prepared using procedures analogous to those for example 31. Ms(ESI): (M+H)+=400.2.

Example 130

(6S,7S)—N-hydroxy-6-{[4-(4-methoxy-2-methylphenyl)-3,6-dihydropyridin-1(2H)-yl]carbonyl}-5-azaspiro[2.5]octane-7-carboxamide This compound was prepared using procedures analogous to those for example 31. Ms(ESI): (M+H)+=400.2.

Example 131

(6S,7S)-6-[(4-cyano-4-phenylpiperidin-1-yl)carbonyl]-N-hydroxy-5-azaspiro[2.5]octane-7-carboxamide This compound was prepared using procedures analogous to those for example 1. Ms(ESI): (M+H)+=383.2.

Example 132

Ethyl (6S,7S)-7-[(hydroxyamino)carbonyl]-6-[(4-phenyl-3,6-dihydropyridin-1(2H)-yl)carbonyl]-5-azaspiro[2.5]octane-5-carboxylate This compound was prepared using procedures analogous to those for example 1. Ms(ESI): (M−H)−=426.1.

Example 133

Propyl (6S,7S)-7-[(hydroxyamino)carbonyl]-6-[(4-phenyl-3,6-dihydropyridin-1(2H)-yl)carbonyl]-5-azaspiro[2.5]octane-5-carboxylate This compound was prepared using procedures analogous to those for example 1. Ms(ESI): (M−H)−=440.2.

Example 134

Isopropyl (6S,7S)-7-[(hydroxyamino)carbonyl]-6-[(4-phenyl-3,6-dihydropyridin-1(2H)-yl)carbonyl]-5-azaspiro[2.5]octane-5-carboxylate This compound was prepared using procedures analogous to those for example 1. Ms(ESI): (M−H)−=440.2.

Example 135

Isobutyl (6S,5S)-7-[(hydroxyamino)carbonyl]-6-[(4-phenyl-3,6-dihydropyridin-1(2H)-yl)carbonyl]-5-azaspiro[2.5]octane-5-carboxylate This compound was prepared using procedures analogous to those for example 1. Ms(ESI): (M−H)−=454.2.

Example 136

(6S,7S)—N-hydroxy-6-[(5-methyl-4-phenyl-3,6-dihydropyridin-1(2H)-yl)carbonyl]-5-azaspiro[2.5]octane-7-carboxamide This compound was prepared using procedures analogous to those for example 1. Ms(ESI): (M+H)+=370.

Example 143

(6S,7S)-6-(1,4,4a,5,6,10b-hexahydrobenzo[f]isoquinolin-3(2H)-ylcarbonyl)-N-hydroxy-5-azaspiro[2.5]octane-7-carboxamide

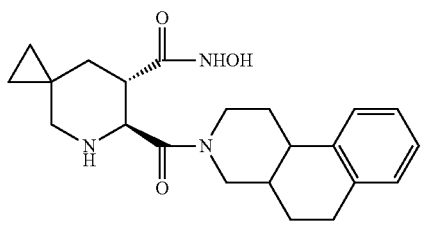

This compound was prepared using procedures analogous to those for example 1. Ms(ESI): (M+H)+=384.2.

Example 144

(6S,7S)-6-{[4-(4-fluorophenyl)-3-hydroxypiperidin-1-yl]carbonyl}-N-hydroxy-5-azaspiro[2.5]octane-7-carboxamide This compound was prepared using procedures analogous to those for example 1. Ms(ESI): (M+H)+=392.1.

Example 145

(6S,7S)—N-hydroxy-6-(3,3a,8,8a-tetrahydroindeno[1,2-c]pyrrol-2(1H)-ylcarbonyl)-5-azaspiro[2.5]octane-7-carboxamide

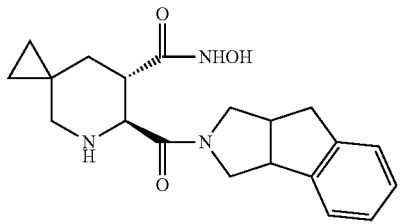

This compound was prepared using procedures analogous to those for example 1. Ms(ESI): (M+H)+=356.1.

Example 146

(6S,7S)—N-hydroxy-6-{[4-(4-phenyl-1,3-thiazol-2-yl)piperidin-1-yl]carbonyl}-5-azaspiro[2.5]octane-7-carboxamide

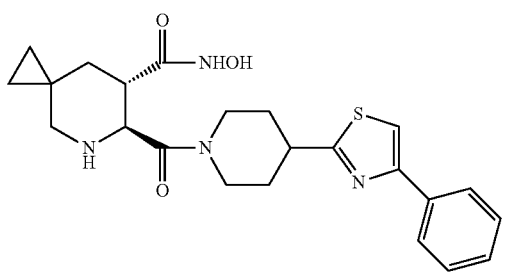

This compound was prepared using procedures analogous to those for example 1. Ms(ESI): (M+H)+=441.3.

Example 147

(6S,7S)—N-hydroxy-6-{[4-(4-tert-Butyl-1,3-thiazol-2-yl)piperidin-1-yl]carbonyl}-5-azaspiro[2.5]octane-7-carboxamide This compound was prepared using procedures analogous to those for example 1. Ms(ESI): (M+H)+=421.1.

Example 148

(6S,7S)—N-hydroxy-6-[(4-methyl-4-phenylpiperidin-1-yl)carbonyl]-5-azaspiro[2.5]octane-7-carboxamide This compound was prepared using procedures analogous to those for example 1. Ms(ESI): (M+H)+=372.2.

Example 149

(6S,7S)—N-hydroxy-6-{[4-(4-ethyl-1,3-thiazol-2-yl)piperidin-1-yl]carbonyl}-5-azaspiro[2.5]octane-7-carboxamide This compound was prepared using procedures analogous to those for example 1. Ms(ESI): (M+H)+=393.1.

Example 150

(6S,7S)—N-hydroxy-6-{[(trans)-3-methyl-4-phenylpyrrolidin-1-yl]carbonyl}-5-azaspiro[2.5]octane-7-carboxamide

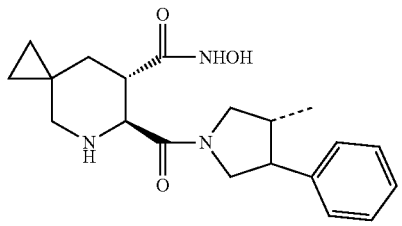

This compound was prepared using procedures analogous to those for example 1. Ms(ESI): (M+H)+=358.2.

Example 151

(6S,7S)-6-{[4-(2-fluorophenyl)piperazin-1-yl]carbonyl}-N-hydroxy-5-azaspiro[2.5]octane-7-carboxamide This compound was prepared using procedures analogous to those for example 1. Ms(ESI): (M+H)+=377.2.

Example 152

(6S,7S)-6-{[4-(3,5-dimethylphenyl)-3,6-dihydropyridin-1(2H)-yl]carbonyl}-N-hydroxy-5-methyl-5-azaspiro[2.5]octane-7-carboxamide This compound was prepared using procedures analogous to those for example 1. Ms(ESI): (M+H)+=398.1.

Example 153

Tetrahydro-2H-pyran-4-yl-(6S,7S)-7-((hydroxyamino)carbonyl)-6-((4-phenylpiperazin-1-yl)carbonyl)-5-azaspiro(2,5)octane-5-carboxylate

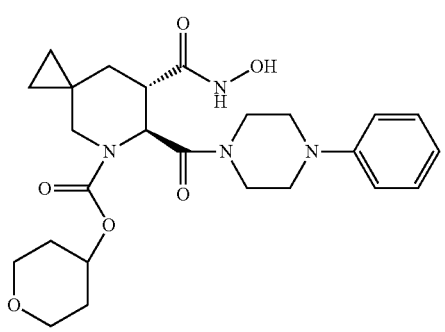 [SMILES: O=C(NO)[C@H]1CC2(CC2)CN(C(=O)OC2CCOCC2)[C@@H]1C(=O)N1CCN(c2ccccc2)CC1]

Step 1. Preparation of tert-butyl (6S,7S)-6-((4-phenyl)piperazin-1-yl)carbonyl)-5-azaspiro(2,5)octane-7-carboxylate To a solution of (6S,7S)-7-(tert-butoxycarbonyl)-5-azaspiro[2.5]octane-6-carboxylic acid (160 mg, 0.63 mmole) in DMF (1.5 ml) was added 1-phenylpiperazine (112 mg, 0.69 mmole), followed by addition of BOP (292 mg, 0.66 mmole). After stirring for 10 min, DIEA (204 mg, 1.57 mmole) was added. The mixture was stirred at r.t. for 3 hours and quenched with sat. $KH_2PO_4$ solution, extracted with ethyl acetate. The extract was washed with water, brine, and dried over $MgSO_4$. After filtration, the filtrate was concentrated. The crude material was purified with flash column. tert-butyl (6S,7S)-6-((4-phenyl)piperazin-1-yl)carbonyl)-5-azaspiro(2,5)octane-7-carboxylate was obtained quantitatively. LC-MS: m/z 400.1 (M+H)+.

Step 2. Preparation of (6S,7S-6-((4-phenyl)piperazin-1-ylcarbonyl)-5-azaspiro(2,5)octane-7-carboxylic acid The above product of tert-butyl (6S,7S)-6-((4-phenyl)piperazin-1-yl)carbonyl)-5-azaspiro(2,5)octane-7-carboxylate was stirred in 8 mL of 50% TFA in methylene chloride solution (v/v) for 4 hours. After removal of solvent, the residue was dried under high vacuum overnight to give (6S,7S)-6-((4-phenyl)piperazin-1-yl)carbonyl)-5-azaspiro(2,5)octane-7-carboxylic acid. LC-MS: m/z 344.1 (M+H)+.

Step 3. Preparation of (6S,7S)—N-(benzyloxy)-6-((4-phenyl)piperazin-1-ylcarbonyl)-5-azaspiro(2,5)octane-7-carboxamide The above resulting material of (6S,7S)-6-((4-phenyl)piperazin-1-yl)carbonyl)-5-azaspiro(2,5)octane-7-carboxylic acid (330 mg, 0.96 mmole) was dissolved in DMF (2 ml). To the resulting solution, O-benzylhydroxylamine hydrochloride (307 mg, 1.92 mmole) was added, followed by BOP (510 mg, 1.15 mmole). After stirring 5 min, at 0° C., DIEA (437 mg, 3.36 mmole) was added. The mixture was stirred at r.t for 3 hours and then quenched with sat $KH_2PO_4$ solution. The product was extracted with ethyl acetate. The extract was washed with water, brine, and dried over $MgSO_4$. After filtration, the filtrate was concentrated to afford the desired product in quantitative yield.

Step 4. Tetrahydro-2H-pyran-4-yl(6S,7S)-7-(((benzyloxy)amino)carbonyl)-6-((4-phenylpiperazin-1-ylcarbonyl)-5-azaspiro(2,5)octane-5-carboxylate (6S,7S)—N-(benzyloxy)-6-((4-phenyl)piperazin-1-yl)carbonyl)-5-azaspiro(2,5)octane-7-carboxamide (18.6 mg, 0.041 mmole) was mixed with 4-nitrophenyl-tetrahydropyran-4-yl carbonate (13.3 mg, 0.050 mmole), and DIEA (11.0 mg, 0.083 mmole) in THF and stirred at r.t. for 24 hours. After concentration, the crude material was purified with flash column to afford the desired product (6.0 mg) in quantitative yield.

Step 5. Tetrahydro-2H-pyran-4-yl(6S,7S)-7-((hydroxyamino)carbonyl)-6-((4-phenylpiperazin-1-yl)carbonyl)-5-azaspiro(2,5)octane-5-carboxylate Tetrahydro-2H-pyran-4-yl(6S,7S)-7-(((benzyloxy)amino)carbonyl)-6-((4-phenylpiperazin-1-yl)carbonyl)-5-azaspiro(2,5)octane-5-carboxylate (6.0 mg, 0.0104 mmole) was dissolved in methanol (0.3 ml) and 2 mg of 5% Pd/$BaSO_4$ was added to the resulting reaction mixture. The mixture was stirred under hydrogen (1 atm) for 1.5 hours. After filtration, the product was purified with prep. RP-HPLC. The desired fractions were collected and freeze dried to give 3.8 mg solid. LC-MS: m/z 487.1 (M+H)+; 509.0 (M+Na)+.

Example 154

Ethyl (6S,7S)-7-((hydroxyamino)carbonyl))-6-((4-phenyl)piperazin-1-yl)carbonyl-5-azaspiro(2,5)octane-5-carboxylate Step 1. 7-tert-butyl-5-ethyl (6S,7S)-6-((4-phenyl)piperazin-1-yl)carbonyl-5-azaspiro(2,5)octane-5,7-dicarboxylate The mixture of tert-butyl (6S,7S)-6-((4-phenyl)piperazin-1-yl)carbonyl)-5-azaspiro(2,5)octane-7-carboxylate prepared in example 153 (40 mg, 0.10 mmole), ethyl chloroformate (13 mg, 0.12 mmole), and DIEA (26 mg, 0.2 mmole) in acetonitrile (0.20 ml) was stirred at r.t. for 1 hour. After concentration, the residue was purified with flash column. An amount of 29 mg of 7-tert-butyl-5-ethyl (6S,7S)-6-((4-phenylpiperazin-1-yl)carbonyl-5-azaspiro(2,5)octane-5,7-dicarboxylate was obtained. Yield: 61%. MS: m/z 472.3 (M+H)+.

Step 2. (6S,7S)-5-(ethoxycarbonyl))-6-((4-phenylpiperazin-1-yl)carbonyl-5-azaspiro(2,5)octane-7-dicarboxylic acid The above material of 7-tert-butyl-5-ethyl (6S,7S)-6-((4-phenylpiperazin-1-yl)carbonyl-5-azaspiro(2,5)octane-5,7-dicarboxylate was stirred in 2 ml of 50% TFA in DCM solution (v/v) for 1.5 hours. After removal of solvent, the residue was dried under high vacuum overnight to quantitatively give the desired product. LC-MS: m/z 416.2 (M+H)+; 853.4 (2M+Na)+.

Step 3. Ethyl (6S,7S)-7-((hydroxyamino)carbonyl))-6-((4-phenylpiperazin-1-ylcarbonyl-5-azaspiro(2,5)octane-5-carboxylate To a solution of (6S,7S)-5-(ethoxycarbonyl))-6-((4-phenylpiperazin-1-yl)carbonyl-5-azaspiro(2,5)octane-7-dicarboxylic acid (30 mg, 0.072 mmole), hydroxylamine hydrochloride (15 mg, 0.217 mmole), and BOP (34 mg, 0.076 mmole) in DMF (0.30 mL), DIEA (33 mg, 0.253 mmole) was added. The mixture was stirred at r.t. for 2 hours. The final product was purified with prep. HPLC to give a solid (14.5 mg) Yield: 37%. MS: m/z 431.2 (M+H)+; 883.5 (2 M+Na)+.

Example 155

Methyl (6S,7S)-7-[(hydroxyamino)carbonyl]-6-[(4-phenylpiperazin-1-yl)carbonyl]-5-azaspiro[2.5]octane-5-carboxylate Step 1 tert-Butyl (6S,7S)-6-[(4-phenylpiperazin-1-yl)carbonyl]-5-azaspiro[2.5]octane-7-carboxylate 1-Phenylpiperazine (124 mg, 0.76 mmol) was added to a mixture of (6S,7S)-7-(tert-butoxycarbonyl)-5-azaspiro[2.5]octane-6-carboxylic acid (180 mg, 0.70 mmol) and BOP (320 mg, 0.75 mmol) in DMF (4 mL) at 0° C. The mixture was stirred at 0° C. for 10 min, then N-methylmorpholine (300 µL) was added. The resulting mixture was stirred at RT for overnight, diluted with 5% $NaHCO_3$ and extracted with ethyl acetate (3×10 mL). The combined organic layers were washed with saturated brine and dried over $Na_2SO_4$. The solution was filtered and concentrated to afford 248.4 mg of the tert-butyl (6S,7S)-6-[(4-phenylpiperazin-1-yl)carbonyl]-5-azaspiro[2.5]octane-7-carboxylate.

Step 2

7-tert-Butyl 5-methyl (6S,7S)-6-[(4-phenylpiperazin-1-yl)carbonyl]-5-azaspiro[2.5]octane-5,7-dicarboxylate Methyl chlorofomate (55 μL, 700 μL) was added to a solution of tert-butyl (6S,7S)-6-[(4-phenylpiperazin-1-yl)carbonyl]-5-azaspiro[2.5]octane-7-carboxylate (248.4 mg, 0.62 mmol) and di-isopropylethylamine (0.70 mmol, 0.125 mL) in 5 mL acetonitrile. The mixture was stirred at RT for 3 h. Solvent was removed to afford a residue which was dissolved in ethyl ether (15 mL), washed with water (3×2 mL) and dried over Na$_2$SO$_4$. The solution was filtered and concentrated to afford 281 mg of the 7-tert-butyl 5-methyl (6S,7S)-6-[(4-phenylpiperazin-1-yl)carbonyl]-5-azaspiro[2.5]octane-5,7-dicarboxylate.

Step 3

Methyl (6S,7S)-7-[(hydroxyamino)carbonyl]-6-[(4-phenylpiperazin-1-ylcarbonyl]-5-azaspiro[2.5]octane-5-carboxylate 7-tert-Butyl 5-methyl (6S,7S)-6-[(4-phenylpiperazin-1-yl)carbonyl]-5-azaspiro[2.5]octane-5,7-dicarboxylate (281 mg) was treated with a solution of 5 mL TFA in 5 mL of dichloromethane and 1.0 mL of water. The mixture was stirred at RT for overnight. Solvents were removed under reduce pressure. The residue was co-evaporated with methanol (2×3 mL), and dried under high vacuum.

The above residue was dissolved in DMF (4.0 mL) and cooled with ice-water bath. To the resulting solution, PyBOP (320 mg) and hydroxylamine hydrochloride (125 mg) and N-methylmorpholine (320 μL) were added. After 15 min, the ice-water bath was removed and stirred at RT for 2 h. The mixture was adjusted to pH 2 with TFA. The resulting solution was purified by HPLC to give 126 mg of desired product: methyl (6S,7S)-7-[(hydroxyamino)carbonyl]-6-[(4-phenylpiperazin-1-yl)carbonyl]-5-azaspiro[2.5]octane-5-carboxylate. MS(ESI): (M+H)+=417.1.

Example 156

(6S,7S)—N-hydroxy-6-[(4-pyrazin-2-ylpiperazin-1-yl)carbonyl]-5-azaspiro[2.5]octane-7-carboxamide This compound was prepared using procedures analogous to those for example 1. MS(ESI): (M+H)+=361.2.

Example 157

(6S,7S)—N-hydroxy-6-[(4-quinolin-2-ylpiperazin-1-yl)carbonyl]-5-azaspiro[2.5]octane-7-carboxamide This compound was prepared using procedures analogous to those for example 1. Ms(ESI): (M+H)+=410.1

Example 158

(6S,7S)—N-hydroxy-6-{[3-(5,6,7,8-tetrahydronaphthalen-2-yl)pyrrolidin-1-yl]carbonyl}-5-azaspiro[2.5]octane-7-carboxamide This compound was prepared using procedures analogous to those for example 1. Ms(ESI): (M+H)+=398.2

Example 159

(6S,7S)—N-hydroxy-5-methyl-6-{[(3R)-3-phenylpyrrolidin-1-yl]carbonyl}-5-azaspiro[2.5]octane-7-carboxamide This compound was prepared using procedures analogous to those for example 1. Ms(ESI): (M+H)+=358.1

Example 160

Methyl (6S,7S)-7-[(hydroxyamino)carbonyl]-6-{[(3R)-3-phenylpyrrolidin-1-yl]carbonyl}-5-azaspiro[2.5]octane-5-carboxylate This compound was prepared using procedures analogous to those for example 1. Ms(ESI): (M+H)+=402.1.

Example 161

(6S,7S)—N-hydroxy-6-[(3-pyridin-3-ylpyrrolidin-1-yl)carbonyl]-5-azaspiro[2.5]octane-7-carboxamide This compound was prepared using procedures analogous to those for example 1. Ms(ESI): (M+H)+=345.1

Example 162

(6S,7S)—N-hydroxy-6-[(3-pyridin-2-ylpyrrolidin-1-yl)carbonyl]-5-azaspiro[2.5]octane-7-carboxamide This compound was prepared using procedures analogous to those for example 1. Ms(ESI): (M+H)+=345.1

Example 163

(6S,7S)—N-hydroxy-6-[(3-methyl-3-phenylpyrrolidin-1-yl)carbonyl]-5-azaspiro[2.5]octane-7-carboxamide This compound was prepared using procedures analogous to those for example 1. Ms(ESI): (M+H)+=358.2

Example 164

(6S,7S)—N-hydroxy-6-[(3-phenylazetidin-1-yl)carbonyl]-5-azaspiro[2.5]octane-7-carboxamide This compound was prepared using procedures analogous to those for example 1. Ms(ESI): (M+H)+=330.3

Example 165

(6S,7S)—N-hydroxy-5-methyl-6-[(3-methyl-3-phenylpyrrolidin-1-yl)carbonyl]-5-azaspiro[2.5]octane-7-carboxamide This compound was prepared using procedures analogous to those for example 1. Ms(ESI): (M+H)+=372.4

Example 166

(6S,7S)—N-hydroxy-5-methyl-6-[(3-phenylazetidin-1-yl)carbonyl]-5-azaspiro[2.5]octane-7-carboxamide This compound was prepared using procedures analogous to those for example 1. Ms(ESI): (M+H)+=344.4

Example 168

(6S,7S)-6-(1,3,3a,4,5,9b-hexahydro-2H-benz[e]
isoindol-2-ylcarbonyl)-N-hydroxy-5-azaspiro[2.5]
octane-7-carboxamide

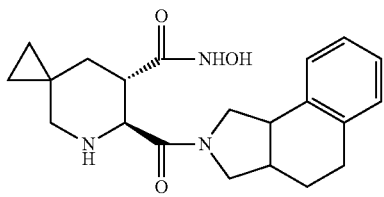

This compound was prepared using procedures analogous to those for example 1. Ms(ESI): (M+H)+=370.4

Example 169

(6S,7S)—N-hydroxy-6-{[3-(2-naphthyl)pyrrolidin-
1-yl]carbonyl}-5-azaspiro[2.5]octane-7-carboxamide This compound was prepared using procedures analogous to those for example 1. Ms(ESI): (M+H)+=394.4

Example 170

(6S,7S)—N-hydroxy-6-{[4-(2-thienyl)-3,6-dihydro-
pyridin-1(2H)-yl]carbonyl}-5-azaspiro[2.5]octane-7-
carboxamide This compound was prepared using procedures analogous to those for example 1. Ms(ESI): (M+H)+=362.1

Example 171

(6S,7S)—N-hydroxy-6-{[3-(3-thienyl)pyrrolidin-1-
yl]carbonyl}-5-azaspiro[2.5]octane-7-carboxamide This compound was prepared using procedures analogous to those for example 1. Ms(ESI): (M+H)+=350.1

Example 172

(6S,7S)—N-hydroxy-6-{[3-(2-thienyl)pyrrolidin-1-
yl]carbonyl}-5-azaspiro[2.5]octane-7-carboxamide This compound was prepared using procedures analogous to those for example 1. Ms(ESI): (M+H)+=350.2

Example 173

(6S,7S)—N-hydroxy-6-{[4-(2-thienyl)piperidin-1-
yl]carbonyl}-5-azaspiro[2.5]octane-7-carboxamide This compound was prepared using procedures analogous to those for example 1. Ms(ESI): (M+H)+=364.1

Example 174

(6S,7S)—N-hydroxy-6-{[3-(2-methylphenyl)pyrroli-
din-1-yl]carbonyl}-5-azaspiro[2.5]octane-7-carboxa-
mide This compound was prepared using procedures analogous to those for example 1. Ms(ESI): (M+H)+=358.2

Example 175

(6S,7S)—N-hydroxy-6-{[3-(4-methylphenyl)pyrroli-
din-1-yl]carbonyl}-5-azaspiro[2.5]octane-7-carboxa-
mide

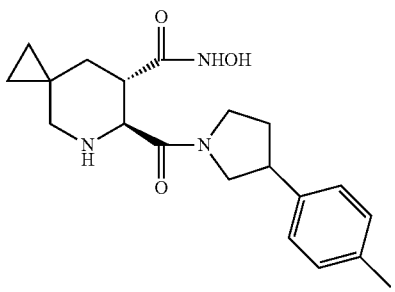

This compound was prepared using procedures analogous to those for example 1. Ms(ESI): (M+H)+=358.2

Example 176

(6S,7S)-5-acetyl-N-hydroxy-6-[(4-phenyl-3,6-dihy-
dropyridin-1(2H)-yl)carbonyl]-5-azaspiro[2.5]oc-
tane-7-carboxamide This compound was prepared using procedures analogous to those for example 154. Ms(ESI): (M−H)+=396.2

Example 177

(6S,7S)—N-hydroxy-6-{[4-(3-thienyl)-3,6-dihydro-
pyridin-1(2H)-yl]carbonyl}-5-azaspiro[2.5]octane-7-
carboxamide This compound was prepared using procedures analogous to those for example 1. Ms(ESI): (M+H)+=362.1

Example 178

(6S,7S)—N-hydroxy-6-[(3-phenylpiperidin-1-yl)
carbonyl]-5-azaspiro[2.5]octane-7-carboxamide This compound was prepared using procedures analogous to those for example 1. Ms(ESI): (M+H)+=358.2

Example 179

(6S,7S)—N-hydroxy-6-{[4-(3-thienyl)piperidin-1-
yl]carbonyl}-5-azaspiro[2.5]octane-7-carboxamide This compound was prepared using procedures analogous to those for example 1. Ms(ESI): (M+H)+=364.1

Example 180

Methyl (6S,7S)-6-{[4-(3,5-dimethylphenyl)-3,6-
dihydropyridin-1(2H)-yl]carbonyl}-7-[(hy-
droxyamino)carbonyl]-5-azaspiro[2.5]octane-5-car-
boxylate This compound was prepared using procedures analogous to those for example 154. Ms(ESI): (M+H)+=442.2

Example 181

(6S,7S)-6-{[4-(3,5-dimethylphenyl)-3,6-dihydropyridin-1(2H)-yl]carbonyl}-N-hydroxy-5-(methylsulfonyl)-5-azaspiro[2.5]octane-7-carboxamide This compound was prepared using procedures analogous to those for example 154. Ms(ESI): (M+H)+=462.1

Example 182

(6S,7S)-6-{[4-(3,5-difluorophenyl)-3,6-dihydropyridin-1(2H)-yl]carbonyl}-N-hydroxy-5-azaspiro[2.5]octane-7-carboxamide This compound was prepared using procedures analogous to those for example 1. Ms(ESI): (M+H)+=392.2

Example 183

(6S,7S)-6-{[4-(3,5-dichlorophenyl)-3,6-dihydropyridin-1(2H)-yl]carbonyl}-N-hydroxy-5-azaspiro[2.5]octane-7-carboxamide This compound was prepared using procedures analogous to those for example 1. Ms(ESI): (M+H)+=424.1

Example 184

(6S,7S)-6-{[4-[3,5-bis(trifluoromethyl)phenyl]-3,6-dihydropyridin-1(2H)-yl]carbonyl}-N-hydroxy-5-azaspiro[2.5]octane-7-carboxamide This compound was prepared using procedures analogous to those for example 1. Ms(ESI): (M+H)+=492.1

Example 185

(6S,7S)—N-hydroxy-5-(methylsulfonyl)-6-[(4-phenylpiperazin-1-yl)carbonyl]-5-azaspiro[2.5]octane-7-carboxamide This compound was prepared using procedures analogous to those for example 154. Ms(ESI): (M+H)+=437.2

Example 186

(6S,7S)-5-formyl-N-hydroxy-6-[(4-phenylpiperazin-1-yl)carbonyl]-5-azaspiro[2.5]octane-7-carboxamide This compound was prepared using procedures analogous to those for example 154. Ms(ESI): (M+H)+=387.2

Example 187

(6S,7S)-6-{[4-(3,5-difluorophenyl)piperidin-1-yl]carbonyl}-N-hydroxy-5-azaspiro[2.5]octane-7-carboxamide This compound was prepared using procedures analogous to those for example 1. Ms(ESI): (M+H)+=394.2

Example 188

(6S,7S)-6-{[4-(2,5-dimethylphenyl)-3,6-dihydropyridin-1(2H)-yl]carbonyl}-N-hydroxy-5-azaspiro[2.5]octane-7-carboxamide This compound was prepared using procedures analogous to those for example 1. Ms(ESI): (M+H)+=384.1

Example 189

(6S,7S)-6-{[4-(2,4,5-trimethylphenyl)-3,6-dihydropyridin-1(2H)-yl]carbonyl}-N-hydroxy-5-azaspiro[2.5]octane-7-carboxamide This compound was prepared using procedures analogous to those for example 1. Ms(ESI): (M+H)+=398.2

Example 190

(6S,7S)-6-[(4-biphenyl-3-ylpiperidin-1-yl)carbonyl]-N-hydroxy-5-azaspiro[2.5]octane-7-carboxamide This compound was prepared using procedures analogous to those for example 1. Ms(ESI): (M+H)+=434.2

Example 191

(6S,7S)-6-[(4-dibenzo[b,d]furan-4-ylpiperidin-1-yl)carbonyl]-N-hydroxy-5-azaspiro[2.5]octane-7-carboxamide

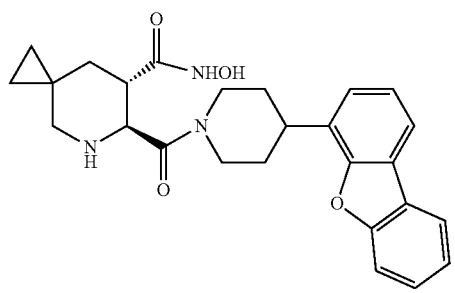

This compound was prepared using procedures analogous to those for example 1. Ms(ESI): (M+H)+=448.2

Example 192

(6S,7S)-6-{[4-(2,5-dimethylphenyl)piperidin-1-yl]carbonyl}-N-hydroxy-5-azaspiro[2.5]octane-7-carboxamide This compound was prepared using procedures analogous to those for example 1. Ms(ESI): (M+H)+=386.2

Example 193

(6S,7S)-6-{[4-(2,4,5-trimethylphenyl)piperidin-1-yl]carbonyl}-N-hydroxy-5-azaspiro[2.5]octane-7-carboxamide This compound was prepared using procedures analogous to those for example 1. Ms(ESI): (M+H)+=400.2

Example 194

Methyl 3-[1-({(6S,7S)-7-[(hydroxyamino)carbonyl]-5-azaspiro[2.5]oct-6-yl}carbonyl)-1,2,3,6-tetrahydropyridin-4-yl]-4-methylbenzoate This compound was prepared using procedures analogous to those for example 1. Ms(ESI): (M+H)+=428.2

Example 195

(6S,7S)-6-[(5-phenyl-2,3,4,7-tetrahydro-1H-azepin-1-yl)carbonyl]-N-hydroxy-5-azaspiro[2.5]octane-7-carboxamide This compound was prepared using procedures analogous to those for example 1. Ms(ESI): (M+H)$^+$=370.2

Example 196

(6S,7S)-6-{[4-[3-(dimethylamino)phenyl]-3,6-dihydropyridin-1(2H)-yl]carbonyl}-N-hydroxy-5-azaspiro[2.5]octane-7-carboxamide This compound was prepared using procedures analogous to those for example 1. Ms(ESI): (M+H)$^+$=399.2

Example 197

Methyl 3-[1-({(6S,7S)-7-[(hydroxyamino)carbonyl]-5-azaspiro[2.5]oct-6-yl}carbonyl)piperidin-4-yl]-4-methylbenzoate This compound was prepared using procedures analogous to those for example 1. Ms(ESI): (M+H)$^+$=430.2

Example 198

(6S,7S)-6-[(5-phenylazepan-1-yl)carbonyl]-N-hydroxy-5-azaspiro[2.5]octane-7-carboxamide This compound was prepared using procedures analogous to those for example 1. Ms(ESI): (M+H)$^+$=372.2

Example 199

(6S,7S)-6-({4-[3-(dimethylamino)phenyl]piperidin-1-yl}carbonyl)-N-hydroxy-5-azaspiro[2.5]octane-7-carboxamide This compound was prepared using procedures analogous to those for example 1. Ms(ESI): (M+H)$^+$=401.2

Example 200

(6S,7S)-6-{[4-(2-methylphenyl)-3,6-dihydropyridin-1(2H)-yl]carbonyl}-N-hydroxy-5-azaspiro[2.5]octane-7-carboxamide This compound was prepared using procedures analogous to those for example 1. Ms(ESI): (M+H)$^+$=370.2

Example 201

(6S,7S)-6-[(3-phenyl-2,5-dihydro-1H-pyrrol-1-yl)carbonyl]-N-hydroxy-5-azaspiro[2.5]octane-7-carboxamide This compound was prepared using procedures analogous to those for example 1. Ms(ESI): (M+H)$^+$=342.1

Example 202

(6S,7S)-6-{[4-(4-cyano-2-methylphenyl)piperidin-1-yl]carbonyl}-N-hydroxy-5-azaspiro[2.5]octane-7-carboxamide This compound was prepared using procedures analogous to those for example 1. Ms(ESI): (M+H)$^+$=397.2

Example 203

(6S,7S)-6-[(3,3-dimethyl-4-phenyl-3,6-dihydropyridin-1(2H)-yl)carbonyl]-N-hydroxy-5-azaspiro[2.5]octane-7-carboxamide This compound was prepared using procedures analogous to those for example 1. Ms(ESI): (M+H)$^+$=384.1

Example 204

(6S,7S)-6-[(3,3-dimethyl-4-phenylpiperidin-1-yl)carbonyl]-N-hydroxy-5-azaspiro[2.5]octane-7-carboxamide This compound was prepared using procedures analogous to those for example 1. Ms(ESI): (M+H)$^+$=386.2.

Example 205

(6S,7S)—N-hydroxy-5-(methylsulfonyl)-6-[(3-phenyl-2,5-dihydro-1H-pyrrol-1-yl)carbonyl]-5-azaspiro[2.5]octane-7-carboxamide This compound was prepared using procedures analogous to those for example 154. Ms(ESI): (M+H)$^+$=420.2

Example 206

Methyl (6S,7S)-7-[(hydroxyamino)carbonyl]-6-[(3-phenyl-2,5-dihydro-1H-pyrrol-1-yl)carbonyl]-5-azaspiro[2.5]octane-5-carboxylate This compound was prepared using procedures analogous to those for example 154. Ms(ESI): (M+H)$^+$=400.2

Example 207

(6S,7S)—N-hydroxy-5-methyl-6-[(3-phenyl-2,5-dihydro-1H-pyrrol-1-yl)carbonyl]-5-azaspiro[2.5]octane-7-carboxamide This compound was prepared using procedures analogous to those for example 1. Ms(ESI): (M+H)$^+$=356.2

Example 208

(6S,7S)-6-{[4-(4-cyano-3-methylphenyl)piperidin-1-yl]carbonyl}-N-hydroxy-5-azaspiro[2.5]octane-7-carboxamide This compound was prepared using procedures analogous to those for example 1. MS(ESI): (M+H)$^+$=397.2

Example 209

(6S,7S)-6-{[4-[3-(benzyloxy)phenyl]-3,6-dihydropyridin-1(2H)-yl]carbonyl}-N-hydroxy-5-azaspiro[2.5]octane-7-carboxamide To a mixture of tert-butyl 5,6-dihydro-4-(3-hydroxyphenyl)pyridine-1(2H)-carboxylate (crude, 100 mg) and potassium carbonate (300 mg) in DMF was added benzyl bromide (60 μL) at room temperature. The resulting mixture was stirred at 80° C. for 16 h. The mixture was cooled down, diluted with ethyl acetate, washed with water, brine, dried and concentrated. The product (60 mg) was purified by combiflash using hexane/ethyl acetate (max. EtOAc 10%) to afford tert-butyl 4-(3-(benzyloxy)phenyl)-5,6-dihydropyridine-1 (2H)-carboxylate which was then converted to the final compound using procedures analogous to those for example 1. MS(ESI): (M+H)⁺=462.2

Example 210

(6S,7S)-6-{[4-[3-ethylphenyl]-3,6-dihydropyridin-1 (2H)-yl]carbonyl}-N-hydroxy-5-azaspiro[2.5]octane-7-carboxamide This compound was prepared using procedures analogous to those for example 1, MS(ESI): (M+H)⁺=384.1

Example 211

(6S,7S)-6-{[4-[3-(ethyloxy)phenyl]-3,6-dihydropyridin-1(2H)-yl]carbonyl}-N-hydroxy-5-azaspiro[2.5] octane-7-carboxamide This compound was prepared using procedures analogous to those for example 1, MS(ESI): (M+H)⁺=400.1

Example 212

(6S,7S)-6-{[4-(3-ethylphenyl)piperidin-1-yl]carbonyl}-N-hydroxy-5-azaspiro[2.5]octane-7-carboxamide This compound was prepared using procedures analogous to those for example 1, MS(ESI): (M+H)⁺=386.1

Example 213

(6S,7S)-6-{[4-(3-ethoxyphenyl)piperidin-1-yl]carbonyl}-N-hydroxy-5-azaspiro[2.5]octane-7-carboxamide This compound was prepared using procedures analogous to those for example 1, MS(ESI): (M+H)⁺=402.1

Example 214

(6S,7S)-6-{[4-(3-cyclopropylphenyl)-3,6-dihydropyridin-1(2H)-yl]carbonyl}-N-hydroxy-5-azaspiro[2.5] octane-7-carboxamide This compound was prepared using procedures analogous to those for example 1, MS(ESI): (M+H)⁺=396.2

Example 215

(6S,7S)-6-{[4-(4-methoxy-3,5-dimethylphenyl)-3,6-dihydropyridin-1(2H)-yl]carbonyl}-N-hydroxy-5-azaspiro[2.5]octane-7-carboxamide This compound was prepared using procedures analogous to those for example 1, MS(ESI): (M+H)⁺=414.2

Example 216

(6S,7S)-6-{[4-(3,5-dimethyl-4-methoxyphenyl)piperidin-1-yl]carbonyl}-N-hydroxy-5-azaspiro[2.5] octane-7-carboxamide This compound was prepared using procedures analogous to those for example 1, MS(ESI): (M+H)⁺=416.2

Example 217

(6S,7S)-6-{[4-(4-cyano-3-ethylphenyl)-3,6-dihydropyridin-1(2H)-yl]carbonyl}-N-hydroxy-5-azaspiro [2.5]octane-7-carboxamide Step 1. 4-Bromo-2-ethylbenzonitrile To a solution of 4-bromo-2-methylbenzonitrile (0.4 g, 2.0 mmol) in dry THF (10 mL) was slowly added LDA (1.3 mL, 1.8 M in THF) at −78° C. and stirred at this temperature for additional 30 min. Methyl iodide (0.15 mL, 2.4 mmol) was added) at −78° C. to the above dark purple solution and the mixture was warmed to room temperature over 3 h. The reaction was quenched with water, extracted with ether, which was then was washed with brine, dried and concentrated. 4-Bromo-2-ethylbenzonitrile (0.34 g) was purified by Combiflash.

Step 2. 2-ethyl-4-(1,2,3,6-tetrahydropyridin-4-yl) benzonitrile

4-Bromo-2-ethylbenzonitrile was converted to 2-ethyl-4-(1,2,3,6-tetrahydropyridin-4-yl)benzonitrile using the standard Suzuki coupling.

Step 3. (6S,7S)-6-{[4-(4-cyano-3-ethylphenyl)-3,6-dihydropyridin-1(2H)-yl]carbonyl}-N-hydroxy-5-azaspiro[2.5]octane-7-carboxamide Using procedures analogous to those of example 1, 2-ethyl-4-(1,2,3,6-tetrahydropyridin-4-yl)benzonitrile was converted to the final compound (6S,7S)-6-{[4-(4-cyano-3-ethylphenyl)-3,6-dihydropyridin-1(2H)-yl]carbonyl}-N-hydroxy-5-azaspiro[2.5]octane-7-carboxamide, MS(ESI): (M+H)⁺=409.2.

Example 218

(6S,7S)-6-{[4-(4-cyano-3-ethylphenyl)piperidin-1-yl]carbonyl}-N-hydroxy-5-azaspiro[2.5]octane-7-carboxamide This compound was prepared using procedures analogous to those for example 1, MS(ESI): (M+H)⁺=411.2

Example 219

(6S,7S)-6-{[4-(4-cyano-3,5-dimethylphenyl)-3,6-dihydropyridin-1(2H)-yl]carbonyl}-N-hydroxy-5-azaspiro[2.5]octane-7-carboxamide This compound was prepared using procedures analogous to those for example 1, MS(ESI): (M+H)⁺=409.2

Example 220

(6S,7S)-6-{[4-(4-cyano-3,5-dimethylphenyl)piperidin-1-yl]carbonyl}-N-hydroxy-5-azaspiro[2.5]octane-7-carboxamide This compound was prepared using procedures analogous to those for example 1, MS(ESI): (M+H)⁺=411.4

Example 221

(6S,7S)-6-{[4-(1,3-benzothiazol-6-yl)-3,6-dihydro-pyridin-1(2H)-yl]carbonyl}-N-hydroxy-5-azaspiro[2.5]octane-7-carboxamide A solution of sodium nitrite (0.147 g, 2.1 mmol) in water (1.0 mL) was slowly added to a suspension of 6-aminobenzothiazole (0.30 g, 2.0 mmol) in HBr (48% in water, 3 mL) at 0° C. and then the mixture was stirred at room temperature for 30 min. The formed solution was then slowly added to a solution of copper (I) bromide (0.435 g, 3.0 mmol) in HCl (conc., 5 mL) at 0° C. After the addition, the mixture was stirred at 60° C. for 1.5 h. Cooled down, and the reaction mixture was basified with excess ammonia and extracted with diethyl ether. The combined extract was washed with water, brine, dried and concentrated. The 6-bromobenzothiazole (0.26 g) was obtained by Combiflash and then converted to the final compound using procedures analogous to those for example 1, MS(ESI): (M+H)$^+$=413.1.

Example 222

(6S,7S)—N-hydroxy-6-{[4-(1-methyl-1H-indazol-6-yl)-3,6-dihydropyridin-1(2H)-yl]carbonyl}-5-azaspiro[2.5]octane-7-carboxamide

Step 1. 5-bromo-2-methylphenyldiazonium tetrafluroborate

Sodium nitrite (0.56 g) in water(2.0 mL) was slowly added to a mixture of 2-methyl-5-bromoaniline (1.50 g) in tetrafluoroboric acid (6.0 mL) and water (4.0 mL) at 0-5° C. After addition, the reaction was stirred at room temperature for 30 min. The mixture was cooled to 0° C., filtered, washed with cold water, cold methanol and ether. The mixture was then dried to provide the product 5-bromo-2-methylphenyldiazonium tetrafluroborate (1.90 g).

Step 2. 6-bromoindazole

5-Bromo-2-methylphenyldiazonium tetrafluoroborate (1.50 g) was added to a mixture of potassium acetate (1.0 g) and 18-crown-6 (70 mg) in chloroform (50 mL) at room temperature in portions and then the reaction was stirred for 2 h. The resulting mixture was filtered and washed with chloroform. The filtrate was concentrated, and the residue was dissolved in diethyl ether, which was then washed with water, brine, dried, and the solvent was removed to give the product 6-bromoindazole (0.9 g). The product was used in the next step without further purification.

Step 3. 6-bromo-1-methylindazole

6-Bromoindazole (400 mg) was dissolved in methanol (10 mL). To this solution, potassium hydroxide (450 mg) was added followed by methyl iodide (0.50 mL) and the mixture was refluxed for 2.5 h. The reaction was cooled, diluted with diethyl ether, washed with water, brine, dried and concentrated. The product 6-bromo-1-methylindazole (160 mg) was separated from its isomer by Combiflash.

Step 4. (6S,7S)—N-hydroxy-6-{[4-(1-methyl-1H-indazol-6-yl-3,6-dihydropyridin-1(2H)-yl]carbonyl}-5-azaspiro[2.5]octane-7-carboxamide 6-Bromo-1-methylindazole was then converted into the final compound using procedures similar to those described in example 31, MS(ESI): (M+H)$^+$=410.2.

Example 223

(6S,7S)—N-hydroxy-6-{[4-(1-methyl-1H-indazol-6-yl)piperidin-1-yl]carbonyl}-5-azaspiro[2.5]octane-7-carboxamide This compound was prepared using procedures analogous to those for example 222, MS(ESI): (M+H)$^+$=412.3.

Example 224

(6S,7S)-6-{[4-(4-cyano-3-isopropylphenyl)-3,6-dihydropyridin-1(2H)-yl]carbonyl}-N-hydroxy-5-azaspiro[2.5]octane-7-carboxamide

Step 1. 4-bromo-2-isopropylphenol

To a stirred solution of 2-isopropylphenol (2.0 g) in acetic acid (20 mL) was added hydrobromic acid (48%, 10 mL) followed by dropwise addition of DMSO (10 mL). The mixture was stirred another 20 min and diluted with water, extracted with diethyl ether. The combined extract was washed with saturated NaHCO$_3$, water, brine, dried and concentrated to give the product 4-bromo-2-isopropylphenol (2.2 g, HPLC purity 95%).

Step 2. tert-butyl 4-(4-hydroxy-3-isopropylphenyl)-3,6-dihydropyridine-1(2H)-carboxylate To a solution of tert-butyl 4-(4,4,5,5-tetramethyl-1,3,2-dioxaborolan-2-yl)-3,6-dihydropyridine-1(2H)-carboxylate (0.36 g), 4-bromo-2-isopropylphenol (0.3 g) in DMF (8.0 mL) was added potassium carbonate (0.5 g) and PdCl$_2$dppf (60 mg) under nitrogen. The mixture was stirred at 80° C. for 16 h. The reaction was cooled down, diluted with ethyl acetate, washed with water, brine, dried and concentrated. The product tert-butyl 4-(4-hydroxy-3-isopropylphenyl)-3,6-dihydropyridine-1(2H)-carboxylate (0.12 g) was obtained by Combiflash.

Step 3. tert-butyl 4-(3-isopropyl-4-{[(trifluoromethyl)sulfonyl]oxy}phenyl)-3,6-dihydropyridine-1(2H)-carboxylate To a solution of tert-butyl 4-(4-hydroxy-3-isopropylphenyl)-3,6-dihydropyridine-1(2H)-carboxylate (0.10 g) in toluene (3.0 mL) at 0° C. was added triethyl amine (85 µL) followed by trifluoroacetic anhydride (60 µL). The reaction was warmed to room temperature and stirred for 2 h. The mixture was dumped to saturated solution of NaHCO$_3$ and extracted with diethyl ether. The combined extract was washed with water, brine, dried and concentrated to give the product tert-butyl 4-(3-isopropyl-4-{[(trifluoromethyl)sulfonyl]oxy}phenyl)-3,6-dihydropyridine-1(2H)-carboxylate (0.14 g, 95% purity by HPLC).

Step 4. 2-isopropyl-4-(1,2,3,6-tetrahydropyridin-4-yl)benzonitrile hydrochloride A mixture of tert-butyl 4-(3-isopropyl-4-{[(trifluoromethyl)sulfonyl]oxy}-phenyl)-3,6-dihydropyridine-1(2H)-carboxylate (0.14 g), zinc cyanide (65 mg), and tetrakis(triphenylphosphine)palladium(0) (25.0 mg) in DMF (3.0 mL) was stirred at 100° C. under nitrogen for 4 h. The reaction was cooled down, diluted with water, extracted with diethyl ether. The combined extract was washed with water, brine, dried and concentrated. tert-Butyl 4-(4-cyano-3-isopropylphenyl)-

3,6-dihydropyridine-1(2H)-carboxylate (85 mg) was isolated by Combiflash. The isolated product was dissolved in a minimum amount of ethyl acetate and 4 N HCl in dioxane (3.0 mL) was added and stirred for 1 h. Diethyl ether (10 mL) was added and the solid was filtered and washed with ether to give the product 2-isopropyl-4-(1,2,3,6-tetrahydropyridin-4-yl)benzonitrile hydrochloride (65 mg).

Step 5. (6S,7S)-6-{[4-(4-cyano-3-isopropylphenyl)-3,6-dihydropyridin-1(2H)-yl]carbonyl}-N-hydroxy-5-azaspiro[2.5]octane-7-carboxamide 2-Isopropyl-4-(1,2,3,6-tetrahydropyridin-4-yl)benzonitrile hydrochloride was then converted into the final compound using procedure similar to those described in example 1, MS(ESI): (M+H)⁺=423.2

Example 225

(6S,7S)-6-{[4-(4-cyano-3-isopropylphenyl)piperidin-1-yl]carbonyl}-N-hydroxy-5-azaspiro[2.5]octane-7-carboxamide

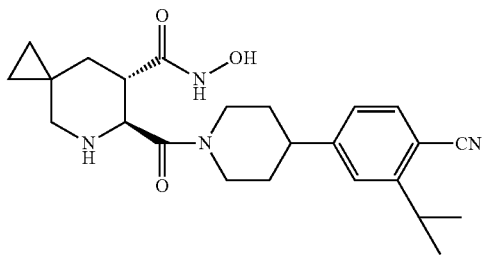 [SMILES: CC(C)c1cc(C2CCN(C(=O)[C@H]3NCC4(CC4)C[C@@H]3C(=O)NO)CC2)ccc1C#N]

This compound was prepared using procedures analogous to those for example 1, MS(ESI): (M+H)⁺=425.2

Example 236

(6S,7S)-6-{[4-(4-cyano-3-ethylphenyl)-3,6-dihydropyridin-1(2H)-yl]carbonyl}-N-hydroxy-5-methyl-5-azaspiro[2.5]octane-7-carboxamide

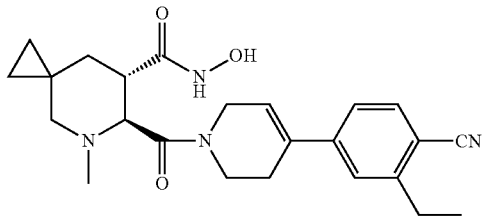 [SMILES: CCc1cc(C2=CCN(C(=O)[C@@H]3[C@@H](C(=O)NO)CC4(CC4)CN3C)CC2)ccc1C#N]

This compound was prepared using procedures analogous to those for example 1, MS(ESI): (M+H)⁺=423.2

Example 237

(6S,7S)-6-{[4-(4-cyano-3,5-dimethylphenyl)-3,6-dihydropyridin-1(2H)-yl]carbonyl}-N-hydroxy-5-methyl-5-azaspiro[2.5]octane-7-carboxamide

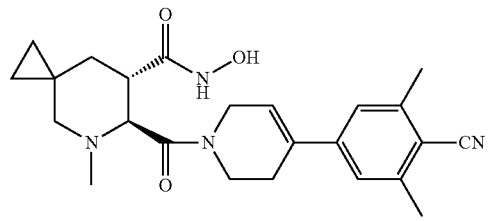 [SMILES: Cc1cc(C2=CCN(C(=O)[C@@H]3[C@@H](C(=O)NO)CC4(CC4)CN3C)CC2)cc(C)c1C#N]

This compound was prepared using procedures analogous to those for example 1, MS(ESI): (M+H)⁺=423.2

Example 238

(6S,7S)—N-hydroxy-6-{[4-(1-ethyl-1H-benzimidazol-6-yl)-3,6-dihydropyridin-1(2H)-yl]carbonyl}-5-azaspiro[2.5]octane-7-carboxamide

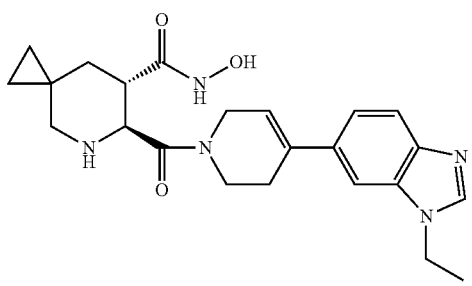 [SMILES: CCn1cnc2ccc(C3=CCN(C(=O)[C@H]4NCC5(CC5)C[C@@H]4C(=O)NO)CC3)cc21]

This compound was prepared using procedures analogous to those for example 1. MS(ESI): (M+H)⁺=424.3

Example 239

(6S,7S)—N-hydroxy-6-{[4-(1-methyl-1H-indazol-5-yl)-3,6-dihydropyridin-1(2H)-yl]carbonyl}-5-azaspiro[2.5]octane-7-carboxamide

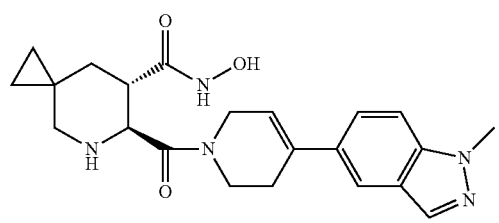 [SMILES: Cn1ncc2cc(C3=CCN(C(=O)[C@H]4NCC5(CC5)C[C@@H]4C(=O)NO)CC3)ccc21]

This compound was prepared using procedures analogous to those for example 222, MS(ESI): (M+H)⁺=410.2.

Example 240

(6S,7S)—N-hydroxy-6-{[4-(1-ethyl-1H-benzimidazol-6-yl)piperidin-1-yl]carbonyl}-5-azaspiro[2.5]octane-7-carboxamide

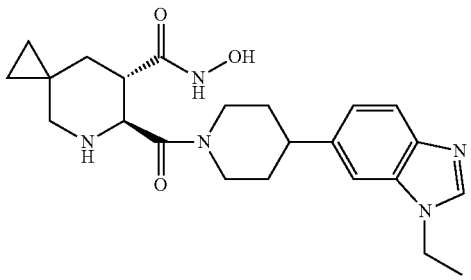 [SMILES: CCn1cnc2ccc(C3CCN(C(=O)[C@H]4NCC5(CC5)C[C@@H]4C(=O)NO)CC3)cc21]

This compound was prepared using procedures analogous to those for example 1, MS(ESI): (M+H)$^+$=426.2

Example 241

(6S,7S)—N-hydroxy-6-{[4-(1-methyl-1H-indazol-5-yl)piperidin-1-yl]carbonyl}-5-azaspiro[2.5]octane-7-carboxamide

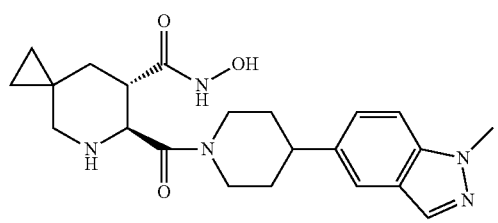 [SMILES: Cn1ncc2cc(C3CCN(C(=O)[C@H]4NCC5(CC5)C[C@@H]4C(=O)NO)CC3)ccc21]

This compound was prepared using procedures analogous to those for example 222, MS(ESI): (M+H)$^+$=412.2.

Example 242

(6S,7S)—N-hydroxy-6-{[4-(1-ethyl-1H-indazol-5-yl)-3,6-dihydropyridin-1(2H)-yl]carbonyl}-5-azaspiro[2.5]octane-7-carboxamide This compound was prepared using procedures analogous to those for example 1, MS(ESI): (M+H)$^+$=424.2

Example 243

Tetrahydro-2H-pyran-4-yl (6S,7S)-6-{[4-(1-ethyl-1H-benzimidazol-6-yl)piperidin-1-yl]carbonyl}-7-[(hydroxyamino)carbonyl]-5-azaspiro[2.5]octane-5-carboxylate This compound was prepared using procedures analogous to those for example 154, MS(ESI): (M+H)$^+$=554.3

Example 244

Methyl (6S,7S)-6-{[4-(1-ethyl-1H-benzimidazol-6-yl)-3,6-dihydropyridin-1(2H)-yl]carbonyl}-7-[(hydroxyamino)carbonyl]-5-azaspiro[2.5]octane-5-carboxylate This compound was prepared using procedures analogous to those for example 154, MS(ESI): (M+H)$^+$=482.2

Example 245

(6S,7S)-6-{[4-(1-ethyl-1H-benzimidazol-6-yl)-3,6-dihydropyridin-1(2H)-yl]carbonyl}-N-hydroxy-5-(methylsulfonyl)-5-azaspiro[2.5]octane-7-carboxamide This compound was prepared using procedures analogous to those for example 154, MS(ESI): (M+H)$^+$=502.2

Example 246

Methyl (6S,7S)-6-{[4-(1-ethyl-1H-benzimidazol-6-yl)piperidin-1-yl]carbonyl}-7-[(hydroxyamino)carbonyl]-5-azaspiro[2.5]octane-5-carboxylate This compound was prepared using procedures analogous to those for example 154, MS(ESI): (M+H)$^+$=484.2

Example 247

(6S,7S)-6-{[4-(1-ethyl-1H-benzimidazol-6-yl)piperidin-1-yl]carbonyl}-N-hydroxy-5-(methylsulfonyl)-5-azaspiro[2.5]octane-7-carboxamide This compound was prepared using procedures analogous to those for example 154 MS(ESI): (M+H)$^+$=504.2

Example 248

(6S,7S)-6-{[4-(4-cyano-2-methylphenyl)piperidin-1-yl]carbonyl}-N-hydroxy-5-(methylsulfonyl)-5-azaspiro[2.5]octane-7-carboxamide This compound was prepared using procedures analogous to those for example 154, MS(ESI): (M+H)$^+$=476.2

Example 249

Methyl (6S,7S)-6-{[4-(4-cyano-2-methylphenyl)piperazin-1-yl]carbonyl}-7-[(hydroxyamino)carbonyl]-5-azaspiro[2.5]octane-5-carboxylate This compound was prepared using procedures analogous to those for example 154, MS(ESI): (M+H)$^+$=456.2

Example 250

(6S,7S)-6-{[4-(1-ethyl-1H-benzimidazol-6-yl)piperazin-1-yl]carbonyl}-N-hydroxy-5-azaspiro[2.5]octane-7-carboxamide This compound was prepared using procedures analogous to those for example 1, MS(ESI): (M+H)$^+$=427.5

Example 251

Methyl (6S,7S)-6-{[4-(1-ethyl-1H-benzimidazol-6-yl)piperazin-1-yl]carbonyl}-7-[(hydroxyamino)carbonyl]-5-azaspiro[2.5]octane-5-carboxylate This compound was prepared using procedures analogous to those for example 154, MS(ESI): $(M+H)^+=485.3$

Example 252

(6S,7S)-6-{[4-(1-ethyl-1H-benzimidazol-6-yl)piperazin-1-yl]carbonyl}-N-hydroxy-5-(methylsulfonyl)-5-azaspiro[2.5]octane-7-carboxamide This compound was prepared using procedures analogous to those for example 154, MS(ESI): $(M+H)^+=505.2$

Example 253

Tetrahydro-2H-pyran-4-yl (6S,7S)-6-{[4-(4-cyano-2-methylphenyl)piperazin-1-yl]carbonyl}-7-[(hydroxyamino)carbonyl]-5-azaspiro[2.5]octane-5-carboxylate This compound was prepared using procedures analogous to those for example 154.

Example 254

Tetrahydro-2H-pyran-4-yl (6S,7S)-6-{[4-(1-ethyl-1H-benzimidazol-6-yl)piperazin-1-yl]carbonyl}-7-[(hydroxyamino)carbonyl]-5-azaspiro[2.5]octane-5-carboxylate This compound was prepared using procedures analogous to those for example 154, MS(ESI): $(M+H)^+=455.3$

Example 255

(6S,7S)—N-hydroxy-6-[(3-methyl-4-phenylpiperidin-1-yl)carbonyl]-5-azaspiro[2.5]octane-7-carboxamide This compound was prepared using procedures analogous to those for example 86. Ms(ESI): $(M+H)+=372.1$

Example 256

(6S,7S)-6-{[5-(aminocarbonyl)-4-phenyl-3,6-dihydropyridin-1(2H)-yl]carbonyl}-N-hydroxy-5-azaspiro[2.5]octane-7-carboxamide This compound was prepared using procedures analogous to those for example 31.

Example 257

(6S,7S)-6-{[4-(4-cyanophenyl)-5-methyl-3,6-dihydropyridin-1(2H)-yl]carbonyl}-N-hydroxy-5-azaspiro[2.5]octane-7-carboxamide This compound was prepared using procedures analogous to those for example 31. Ms(ESI): $(M+H)+=395.2$

Example 258

(6S,7S)-6-{[4-(4-cyanophenyl)-3-methylpiperidin-1-yl]carbonyl}-N-hydroxy-5-azaspiro[2.5]octane-7-carboxamide This compound was prepared using procedures analogous to those for example 86. Ms(ESI): $(M+H)+=397.1$

Example 259

(6S,7S)—N-hydroxy-6-{[5-methyl-4-(4-nitrophenyl)-3,6-dihydropyridin-1(2H)-yl]carbonyl}-5-azaspiro[2.5]octane-7-carboxamide This compound was prepared using procedures analogous to those for example 31. Ms(ESI): $(M+H)+=415.2$

Example 260

(6S,7S)—N-hydroxy-6-{[5-methyl-4-(3-nitrophenyl)-3,6-dihydropyridin-1(2H)-yl]carbonyl}-5-azaspiro[2.5]octane-7-carboxamide This compound was prepared using procedures analogous to those for example 31. Ms(ESI): $(M+H)+=415.1$

Example 262

(6S,7S)-6-[(4-dibenzo[b,d]furan-2-yl-3,6-dihydropyridin-1(2H)-yl)carbonyl]-N-hydroxy-5-azaspiro[2.5]octane-7-carboxamide This compound was prepared using procedures analogous to those for example 31. Ms(ESI): $(M+H)+=446.1$

Example 263

(6S,7S)-6-[(4-dibenzo[b,d]furan-2-ylpiperidin-1-yl)carbonyl]-N-hydroxy-5-azaspiro[2.5]octane-7-carboxamide This compound was prepared using procedures analogous to those for example 86. Ms(ESI): $(M+H)+=448.1$

Example 264

(6S,7S)-6-{[4-(3,3-dimethyl-2,3-dihydro-1-benzofuran-5-yl-3,6-dihydropyridin-1(2H)-yl]carbonyl}-N-hydroxy-5-azaspiro[2.5]octane-7-carboxamide This compound was prepared using procedures analogous to those for example 31. Ms(ESI): $(M+H)+=426.1$

Example 265

(6S,7S)-6-{[4-(3,3-dimethyl-2,3-dihydro-1-benzofuran-5-yl)piperidin-1-yl]carbonyl}-N-hydroxy-5-azaspiro[2.5]octane-7-carboxamide This compound was prepared using procedures analogous to those for example 86. Ms(ESI): $(M+H)+=428.1$

Example 266

Isopropyl (6S,7S)-7-[(hydroxyamino)carbonyl]-6-[(3-phenyl-2,5-dihydro-1H-pyrrol-1-yl)carbonyl]-5-azaspiro[2.5]octane-5-carboxylate This compound was prepared using procedures analogous to those for example 56. Ms(ESI): (M+H)+=428.1

Example 267

(3S)-tetrahydrofuran-3-yl (6S,7S)-7-[(hydroxyamino)carbonyl]-6-[(3-phenyl-2,5-dihydro-1H-pyrrol-1-yl)carbonyl]-5-azaspiro[2.5]octane-5-carboxylate This compound was prepared using procedures analogous to those for example 56. Ms(ESI): (M+H)+=456.1

Example 268

Cyclohexyl (6S,7S)-7-[(hydroxyamino)carbonyl]-6-[(3-phenyl-2,5-dihydro-1H-pyrrol-1-yl)carbonyl]-5-azaspiro[2.5]octane-5-carboxylate This compound was prepared using procedures analogous to those for example 56. Ms(ESI): (M+H)+=468.2

Example 269

Tetrahydro-2H-pyran-4-yl (6S,7S)-7-[(hydroxyamino)carbonyl]-6-[(3-phenyl-2,5-dihydro-1H-pyrrol-1-yl)carbonyl]-5-azaspiro[2.5]octane-5-carboxylate This compound was prepared using procedures analogous to those for example 56. Ms(ESI): (M+H)+=470.2

Example 270

(5S,6S)—N-hydroxy-6-((4-phenylpiperazin-1-yl)carbonyl)spiro(2.5) octane-5-carboxamide Step 1. Preparation of (1S,2S,5S)-2-(tert-butoxycarbonyl)-5-hydroxycyclohexanecarboxylic acid tert-Butyl (1S,2S,5S)-7-oxo-6-oxabicyclo(3,2,1)octane-2-carboxylate was dissolved in THF-H$_2$O. At 0° C., LiOH (3 eq.) was added and the resulting mixture was stirred at 0° C. for 2 hours. TLC showed starting material was consumed. The mixture was then acidified to pH of about 2. The product was extracted with EtOAc (×3). The combined extracts were washed with brine (×1); dried over MgSO$_4$. After filtration, the filtrate was concentrated to give (1S,2S,5S)-2-(tert-butoxycarbonyl)-5-hydroxycyclohexanecarboxylic acid (quantitative).

Step 2. Preparation of 2-Benzyl-1-tert-butyl(1S,2S,4S)-4-hydroxycyclohexane-1,2-dicarboxylate (1S,2S,5S)-2-(tert-butoxycarbonyl)-5-hydroxycyclohexanecarboxylic acid (1.07 g, 4.38 mmole) was dissolved in benzene (20 ml). To the solution, benzyl bromide was added ar r.t., followed by DBU. The mixture was stirred at r.t. for 3 hours. The resulting mixture was quenched with 1N HCl solution and extracted with EtOAc (×2). The combined extracts were washed with 10% citric acid (×1); brine (×1); and dried over MgSO$_4$. After filtration, the filtrate was concentrated to afford 2-Benzyl-1-tert-butyl(1S,2S,4S)-4-hydroxycyclohexane-1,2-dicarboxylate.

Step 3. Preparation of 2-Benzyl-1-tert-butyl(1S,2S)-4-oxocyclohexane-1,2-dicarboxylate (1S,2S,4S)-1-tert-butyl 2-benzyl 4-hydroxycyclohexane-1,2-dicarboxylate (1.47 g, 4.40 mmole) was dissolved in DCM (30 ml). Dess-Martin reagent was added at r.t. to the solution with stirring. After 2 hours, TLC showed starting material was consumed. The mixture was quenched with sat'd Na$_2$S$_2$O$_3$ solution and then extracted with EtOAc (×2). The combined extracts were washed with water (×1), brine (×1); and dried over MgSO$_4$. After filtration, the filtrate was concentrated. The resulting residue was purified with combi-flash and eluted with EtOAc/Hexane to give 2-Benzyl-1-tert-butyl(1S,2S)-4-oxocyclohexane-1,2-dicarboxylate.

Step 5. Preparation of 2-Benzyl-1-tert-butyl(1S,2S)-4-methylenecyclohexane-1,2-dicarboxylate Methyl triphenylphosphonium bromide (1.9 g, 5.32 mmole) and sodium bis(trimethylsilyl)amide (1.0 M in THF, 5.32 ml, 5.32 mmole) in toluene (15 ml)/THF (5 mL) solution was combined with a solution of (1S,2S)-1-tert-butyl 2-benzyl 4-oxocyclohexane-1,2-dicarboxylate (1.0 g, 4.09 mmole) in toluene (15 mL) at −10° C. The resulting mixture was stirred at r.t. for 2 hours at −10° C. and at r.t for 2 hours. TLC showed starting material was consumed. The mixture was diluted with EtOAc, and the resulting solution was washed with water (×1); brine (×2); and dried over MgSO$_4$. After filtration, the filtrate was concentrated. The crude product was purified with combi-flash to afford (1S,2S)-1-tert-butyl 2-benzyl 4-methylenecyclohexane-1,2-dicarboxylate (0.65 g; 1.97 mmole).

Step 6. Preparation of 5-Benzyl-6-tert-butyl (5S,6S)-spiro(2,5)octane-5,6-dicarboxylate To a solution of KOH (1.9 g) in water (3 ml), di(ethylene glycol) ethyl ether (9 ml), and ethyl ether (10 ml) in flask A, 1.0 g of diazald was added in three portions. After addition of the first portion, the flask was put into a pre-heated (at 60° C.) oil bath in order to distill out CH$_2$N$_2$ which was transferred to flask B pre-chilled to around −15° C. and containing the compound (1S,2S)-1-tert-butyl 2-benzyl 4-methylenecyclohexane-1,2-dicarboxylate (200 mg), and Pd(OAc)$_2$ (80 mg) in ether (10 ml). After 5 minutes, the oil bath was removed from flask A. Then, the second portion of diazald was added, and the above procedure was repeated twice. After completion of the distillation of CH$_2$N$_2$ with ether into flask B, the cold bath was removed from Flask B. The reaction mixture was stirred at r.t. for 2 hours, then filtered through silica gel and rinsed with ethyl acetate and methylenechloride. The filtrate was concentrated. The resulting residue is the desired product 5-Benzyl-6-tert-butyl (5S,6S)-spiro(2,5)octane-5,6-dicarboxylate, confirmed by $^1$H NMR. The product was directly used in next step reaction without further purification.

Step 7. Preparation of (5S,6S)-5-((benzyloxy)carbonyl)spiro(2,5)octane-6-carboxylic acid The product of the previous step 6 was stirred in DCM/TFA (1:1) overnight and then concentrated to yield (5S,6S)-5-((benzyloxy)carbonyl)spiro(2,5)octane-6-carboxylic acid.

Step 8. Preparation of Benzyl (5S,6S)-64(4-phenylpiperazin-1-ylcarbonyl)spiro(2.5) octane-5-carboxylate (5S,6S)-5-((benzyloxy)carbonyl)spiro(2,5)octane-6-carboxylic acid from step 7 (47 mg, 0.16 mmole) was dissolved in DMF (0.7 mL). To the solution, 1-phenylpiperazine (29 mg, 0.18 mmole) was added, followed by BOP (76 mg, 0.17 mmole). DIEA (53 mg, 0.41 mmole) was added after the mixture was stirred at r.t. for 10 min. The mixture was then stirred at r.t. overnight and quenched with sat'd NaHCO₃ solution, extracted with EtOAc. The extract was washed with NaHCO₃ sat'd solution, brine; dried over MgSO₄. After filtration, the filtrate was concentrated. The resulting residue was purified by column chromatography to afford Benzyl (5S,6S)-6-((4-phenylpiperazin-1-yl)carbonyl)spiro(2.5) octane-5-carboxylate.

Step 9. Preparation of (5S,6S)-6-((4-phenylpiperazin-1-yl)carbonyl)spiro(2.5) octane-5-carboxylic acid The product of the previous step 8 was dissolved in methanol. To the solution, 5% Pd—BaSO₄ was added. The mixture was stirred under a hydrogen atmosphere at r.t. for 2 hours. After removal of solid, the solution was concentrated to dryness (yield: 30%) to give (5S,6S)-6-((4-phenylpiperazin-1-yl)carbonyl)spiro(2.5) octane-5-carboxylic acid.

Step 10. Preparation of (5S,6S)—N-hydroxy-6-((4-phenylpiperazin-1-yl)carbonyl)spiro(2.5) octane-5-carboxamide The product from step 9 (36 mg, 0.105 mmole), and hydroxylamine hydrochloride (22 mg, 0.315 mmole) were dissolved in DMF (0.70 ml). To the solution, BOP (49 mg, 0.11 mmole) was added with stirring at r.t. for 10 min. DIEA (61 mg, 0.47 mmole) was added. The mixture was stirred at r.t. for 2 hours. The product was purified with preparative HPLC providing 22 mg of (5S,6S)—N-hydroxy-6-((4-phenylpiperazin-1-yl)carbonyl)spiro(2.5) octane-5-carboxamide. Yield: 44%. MS: M/Z 358.2 (M+H)+; 380.2 (M+Na)+; 737.2 (2M+Na)+.

Example 271

(6S)—N-hydroxy-6-{[(3R)-3-phenylpyrrolidin-1-yl]carbonyl}spiro[2.5]octane-5-carboxamide This compound was prepared using procedures analogous to those of the preparation of example 270. MS:M/Z 343.3 (M+H)+; 365.2 (M+Na)+; 707.3 (2M+Na)+.

Example 272

(5S,6S)—N-hydroxy-6-{[4-(2-methyl-4-nitrophenyl)piperazin-1-yl]carbonyl}spiro[2.5]octane-5-carboxamide This compound was prepared using procedures analogous to those of the preparation of example 270. MS:M/Z 417.2 (M+H)+.

Example 273

(5S,6S)—N-hydroxy-6-[(4-phenyl-3,6-dihydropyridin-1(2H)-yl)carbonyl]spiro[2.5]octane-5-carboxamide This compound was prepared using procedures analogous those for the preparation of example 270. MS: M/Z 355.2 (M+H)+; 377.2 (M+Na)+; 731.4 (2M+Na)+.

Example 274

(3S)-tetrahydrofuran-3-yl (6S,7S)-7-[(hydroxyamino)carbonyl]-6-[(4-phenylpiperazin-1-yl)carbonyl]-5-azaspiro[2.5]octane-5-carboxylate This compound was prepared using procedures analogues to the example 154. MS: m/z 473.2 (M+H)+; 495.0 (M+Na)+.

Example 275

(3R)-tetrahydrofuran-3-yl(6S,7S)-7-[(hydroxyamino)carbonyl]-6-[(4-phenylpiperazin-1-yl)carbonyl]-5-azaspiro[2.5]octane-5-carboxylate This compound was prepared using procedures analogues to the example 154. MS: m/z 473.2 (M+H)+; 495.2 (M+Na)+.

Example 276

2-Methoxyethyl (6S,7S)-7-((hydroxyamino)carbonyl)-6-((4-phenylpiperazin-1-yl)carbonyl)-5-azaspiro(2,5)octane-5-carboxylate This compound was prepared using procedures analogues to the example 154. MS: m/z 461.1 (M+H)+; 483.1 (M+Na)+.

Example 277

(6S,7S)—N-hydroxy-6-[(4-phenylpiperazin-1-yl)carbonyl]-5-(phenylsulfonyl)-5-azaspiro[2.5]octane-7-carboxamide This compound was prepared using procedures analogues to the example 154. MS: m/z 499.1 (M+H)+.

Example 278

Propyl (6S,7S)-7-[(hydroxyamino)carbonyl)]-6-[(4-phenylpiperazin-1-yl)carbonyl]-5-azaspiro[2,5]octane-5-carboxylate This compound was prepared using procedures analogues to the example 154. MS: m/z 445.2 (M+H)+.

Example 279

Isopropyl (6S,7S)-7-[(hydroxyamino)carbonyl]-6-[(4-phenylpiperazin-1-yl)carbonyl]-5-azaspiro[2.5]octane-5-carboxylate This compound was prepared using procedures analogues to the example 154. MS: m/z 445.2 (M+H)+; 467.2 (M+Na)+.

Example 280

Methyl (6S,7S)-6-{[4-(3,5-difluorophenyl)-3,6-dihydropyridin-1(2H)-yl]carbonyl}-7-[(hydroxyamino)carbonyl]-5-azaspiro[2.5]octane-5-carboxylate This compound was prepared using procedures analogous to those for example 1. Ms(ESI): (M+H)+=450.2.

Example 281

(6S,7S)-6-(4-(3,5-difluorophenyl)-1,2,3,6-tetrahydropyridine-1-carbonyl)-N-hydroxy-5-(methylsulfonyl)-5-azaspiro[2.5]octane-7-carboxamide This compound was prepared using procedures analogous to those for example 154. Ms(ESI): (M+H)+=470.2

Example 282

(6S,7S)—N-hydroxy-6-{[4-(4-isopropylphenyl)piperazin-1-yl]carbonyl}-5-azaspiro[2.5]octane-7-carboxamide This compound was prepared using procedures analogous to those for example 1.

Example 283

(6S,7S)-6-{[4-(3,5-difluorophenyl)piperidin-1-yl]carbonyl}-N-hydroxy-5-(methylsulfonyl)-5-azaspiro[2.5]octane-7-carboxamide This compound was prepared using procedures analogous to those for example 154. Ms(ESI): (M+H)+=472.1

Example 284

(6S,7S)-6-{[4-(4,5-dimethyl-1,3-thiazol-2-yl)piperidin-1-yl]carbonyl}-N-hydroxy-5-azaspiro[2.5]octane-7-carboxamide This compound was prepared using procedures analogous to those for example 1. Ms(ESI): (M+H)+=393.1.

Compounds of the Examples are listed below in Table 1.

TABLE 1

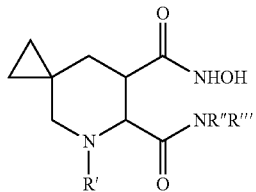

A

Ex. 1-48, 54-78, 80-136,
143-225, 236-269, 271-284

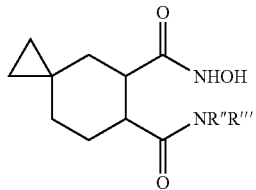

B

Ex. 50, 53, 270-273

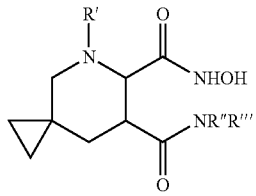

C

Ex. 79

TABLE 1-continued

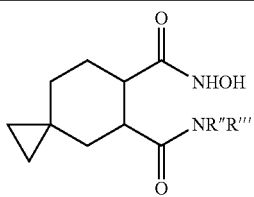

D
Ex. 49, 51, 52

| Exp. | Core | NR"R''' | R' | MS: M + H |
|---|---|---|---|---|
| 1 | A | 4-(3-methylphenyl)piperazin-1-yl | Me | 387.1 |
| 2 | A | 4-phenylpiperazin-1-yl | Me | 373.2 |
| 3 | A | 4-[3-(trifluoromethyl)phenyl]piperazin-1-yl | Me | 441 |
| 4 | A | 4-(2-methylphenyl)piperazin-1-yl | Me | 387.1 |
| 5 | A | 4-(4-Chlorophenyl)piperazin-1-yl | Me | 407.1 |
| 6 | A | 4-(2-methyl-4-nitrophenyl)piperazin-1-yl | Me | 432 |
| 7 | A | 4-phenylpiperidin-1-yl | Me | 372.2 |
| 8 | A | 4-hydroxy-4-phenylpiperidin-1-yl | Me | 388 |
| 9 | A | 4-phenyl-3,6-dihydropyridin-1(2H)-yl | Me | 370 |
| 11 | A | 4-quinolin-2-ylpiperazin-1-yl | Me | 424.3 |
| 12 | A | 4-(2,3-dichlorophenyl)piperazin-1-yl | Me | |
| 13 | A | 4-quinolin-4-ylpiperazin-1-yl | Me | 424.3 |
| 14 | A | 4-(2-methylquinolin-4-yl)piperazin-1-yl | Me | 438.4 |
| 15 | A | 4-(2-phenylethyl)piperazin-1-yl | Me | 401.3 |
| 16 | A | 4-pyridin-4-ylpiperidin-1-yl | Me | 373.3 |
| 17 | A | 4-(4-nitrophenyl)piperazin-1-yl | Me | 418.3 |
| 18 | A | 4-(2-methoxyphenyl)piperazin-1-yl | Me | 403 |
| 19 | A | 4-phenoxypiperidin-1-yl | Me | 388.3 |
| 20 | A | 3,4-dihydroisoquinolin-2(1H)-yl | Me | 344.3 |
| 21 | A | 4,7-dihydrothieno[2,3-c]pyridin-6(5H)-yl | Me | 350.2 |
| 22 | A | 3-benzylpyrrolidin-1-yl | Me | 372.3 |
| 23 | A | 4-pyridin-2-ylpiperazin-1-yl | Me | 374.2 |
| 24 | A | 4-(2-pyridin-4-ylethyl)piperidin-1-yl | Me | 401.3 |
| 25 | A | 4-[5-(trifluoromethyl)pyridin-2-yl]piperazin-1-yl | Me | 442.3 |
| 26 | A | 4-[3-(trifluoromethyl)pyridin-2-yl]piperazin-1-yl | Me | 442.3 |
| 27 | A | 1,4'-bipiperidin-1'-yl | Me | 379.3 |
| 28 | A | 4-(pyridin-2-ylmethyl)piperazin-1-yl | Me | 388.3 |
| 29 | A | 4-(pyridin-4-ylmethyl)piperazin-1-yl | Me | 388.3 |
| 30 | A | 4-(pyridin-3-ylmethyl)piperazin-1-yl | Me | 388.3 |
| 31 | A | 4-(2-methylphenyl)-3,6-dihydropyridin-1(2H)-yl | Me | 384.1 |
| 32 | A | 4-(3-methylphenyl)piperazin-1-yl | H | 373.1 |
| 33 | A | 1,3,4,9-tetrahydro-2H-β-carbolin-2-yl | Me | 383 |
| 34 | A | 9-methyl-1,3,4,9-tetrahydro-2H-β-carbolin-2-yl | Me | 396.9 |
| 35 | A | 4-(2-fluorophenyl)-3,6-dihydropyridin-1(2H)-yl | Me | 388 |
| 36 | A | 4-(2-chlorophenyl)-3,6-dihydropyridin-1(2H)-yl | Me | 404 |
| 37 | A | 4-(4-nitrophenyl)-3,6-dihydropyridin-1(2H)-yl | Me | 415.1 |
| 38 | A | 4-phenyl-3,6-dihydropyridin-1(2H)-yl | H | 356 |
| 39 | A | 4-(2-methyl-4-nitrophenyl)piperazin-1-yl | H | |
| 40 | A | N-methyl-N'-(3-phenylpropyl)amino | Me | 360.1 |
| 41 | A | isobutylamino | Me | 284 |
| 42 | A | 4-(2-nitrophenyl)piperazin-1-yl | Me | 418 |
| 43 | A | N-methyl-N'-(isobutyl)amino | Me | 298 |
| 44 | A | (2-phenoxyethyl)-amino | Me | 348 |
| 45 | A | 2-(4-methoxyphenyl)ethylamino | Me | 362 |
| 46 | A | 4-phenylbutylamino | Me | 360 |
| 47 | A | 3-(2-oxopyrrolidin-1-yl)propylamino | Me | 353 |
| 48 | A | 3,4,10,10a-tetrahydropyrazino[1,2-a]indol-2(1H)-yl | H | 385 |
| 49 | D | 4-(2-methyl-4-nitrophenyl)piperazin-1-yl | | 417.2 |
| 50 | B | 4-(3-methylphenyl)piperazin-1-yl | | 372.2 |
| 51 | D | 4-phenyl-3,6-dihydropyridin-1(2H)-yl | | 355 |
| 52 | D | 4-(3-methylphenyl)piperazin-1-yl | | 372 |
| 53 | B | 4-phenyl-3,6-dihydropyridin-1(2H)-yl | | 355 |
| 54 | A | 3,4,10,10a-tetrahydropyrazino[1,2-a]indol-2(1H)-yl | H | 371.2 |
| 55 | A | 1,2,4,4a,5,6-hexahydro-3H-pyrazino[1,2-a]quinolin-3-yl | Me | 399.4 |
| 56 | A | 4-phenyl-3,6-dihydropyridin-1(2H)-yl | methoxycarbonyl | 414 |
| 57 | A | 4-phenyl-3,6-dihydropyridin-1(2H)-yl | benzyloxycarbonyl | 490 |
| 58 | A | 4-phenyl-3,6-dihydropyridin-1(2H)-yl | methylsulfonyl | 434 |
| 59 | A | 3-(3-methoxyphenyl)piperidin-1-yl | Me | 402.4 |
| 60 | A | 3-(2-phenylethyl)pyrrolidin-1-yl | Me | 386 |
| 61 | A | 4-(3-methoxyphenyl)piperidin-1-yl | Me | 402.4 |
| 62 | A | 4-[3-(aminocarbonyl)phenyl]-3,6-dihydropyridin-1(2H)-yl | H | 398.9 |

TABLE 1-continued

| | | | | |
|---|---|---|---|---|
| 63 | A | 4-(2-methoxyphenyl)piperidin-1-yl | Me | 402.4 |
| 64 | A | 4-(3fFluoro-2-methylphenyl)piperazin-1-yl | H | 391.3 |
| 65 | A | 4-(2-methyl-3-nitrophenyl)piperazin-1-yl | H | 418.3 |
| 66 | A | 3',6'-dihydro-3,4'-bipyridin-1'(2'H)-yl | H | 357.4 |
| 67 | A | N-(4-methoxyphenyl)-N'-methylamino | H | 334 |
| 68 | A | 4-(3-methoxyphenyl)piperazin-1-yl | Me | 403 |
| 69 | A | 4-(3-Chlorophenyl)piperazin-1-yl | Me | 407.3 |
| 70 | A | 4-Phenyl-[1,4]diazepan-1-yl | H | 373 |
| 71 | A | 3-methyl-4-(3-methylphenyl)piperazin-1-yl | H | 387 |
| 72 | A | 4-(3-methoxyphenyl)piperidin-1-yl | H | 388.4 |
| 73 | B | 3-phenylpyrrolidin-1-yl | | 343.3 |
| 74 | A | 4-isobutyrylpiperazin-1-yl | H | 353 |
| 75 | A | 4-(4-cyano-2-methylphenyl)-3,6-dihydropyridin-1(2H)-yl | H | 395 |
| 76 | A | 4-[(2-methylquinolin-4-yl)methoxy]phenylamino | Me | 475.4 |
| 77 | A | 4-[(2-methylquinolin-4-yl)methoxy]phenylamino | H | 461 |
| 78 | A | 4-(4-cyanophenyl)piperazin-1-yl | H | 384 |
| 79 | C | 4-phenylpiperidin-1-yl | H | 358 |
| 80 | A | 4-phenylpiperidin-1-yl | H | 358 |
| 81 | A | 4-phenylpiperazin-1-yl | H | 359 |
| 82 | A | 4-[3-(methoxymethyl)phenyl]piperidin-1-yl | H | 402 |
| 83 | A | 4-(3-methoxycarbonylphenyl)piperidin-1-yl | H | 416 |
| 84 | A | 3-cyclohexylpyrrolidin-1-yl | H | 350.4 |
| 85 | A | 4-(3-isopropylphenyl)-3,6-dihydropyridin-1(2H)-yl | H | 398.4 |
| 86 | A | 4-(3-Isopropylphenyl)piperidin-1-yl | H | 400.4 |
| 87 | A | 4-(4-propylphenyl)-3,6-dihydropyridin-1(2H)-yl | H | |
| 88 | A | 4-(4-ethylphenyl)-3,6-dihydropyridin-1(2H)-yl | H | 384.4 |
| 89 | A | 4-(4-ethylphenyl)piperidin-1-yl | H | 386 |
| 90 | A | 4-(4-cyano-2-methylphenyl)piperazin-1-yl | H | 398 |
| 91 | A | 4-(3-isopropoxyphenyl)-3,6-dihydropyridin-1(2H)-yl | H | 414.4 |
| 92 | A | 4-(3-methylphenyl)-3,6-dihydropyridin-1(2H)-yl | H | 370.3 |
| 93 | A | 4-(3-methylphenyl)piperazin-1-yl | H | 372.4 |
| 94 | A | 4-(4-tert-butylphenyl)piperazin-1-yl | H | 415.4 |
| 95 | A | 4-pyridin-4-ylpiperazin-1-yl | H | 360 |
| 96 | A | 3-benzylpiperidin-1-yl | H | 371.9 |
| 97 | A | 5-methoxy-2,3-dihydro-1H-indol-1-yl | H | 346.3 |
| 98 | A | 5-[(2-methylquinolin-4-yl)methoxy]-2,3-dihydro-1H-indol-1-yl | H | 487.4 |
| 99 | A | 5-[(2-methylquinolin-4-yl)methoxy]-2,3-dihydro-1H-indol-1-yl | Me | 501.4 |
| 100 | A | 5-(benzyloxy)-2,3-dihydro-1H-indol-1-yl | H | 422.3 |
| 101 | A | 1,3-dihydro-1'H-spiro[indene-2,4'-piperidin]-1'-yl | H | 384.4 |
| 102 | A | 4-(3-isopropoxyphenyl)piperidin-1-yl | H | 416.4 |
| 103 | A | 4-(2-methyl-4-methoxycarbonylphenyl)-3,6-dihydropyridin-1(2H)-yl | H | 427.9 |
| 104 | A | 4-(2-methyl-4-nitrophenyl)-3,6-dihydropyridin-1(2H)-yl | H | 414.8 |
| 105 | A | 4-(2-ethylphenyl)piperidin-1-yl | H | 385.9 |
| 106 | A | 4-(2-methyl-4-methoxycarbonylphenyl)piperidin-1-yl | H | 429.9 |
| 107 | A | 4-(2,3-dihydro-1-benzofuran-5-yl)-3,6-dihydropyridin-1(2H)-yl | Me | 412.2 |
| 108 | A | 4-(3-isopropylphenyl)-3,6-dihydropyridin-1(2H)-yl | Me | 412.2 |
| 109 | A | (3R)-3-phenylpyrrolidin-1-yl | H | 344.1 |
| 110 | A | (3S)-3-phenylpyrrolidin-1-yl | H | 344.1 |
| 112 | A | 3-[3-(trifluoromethyl)phenyl]pyrrolidin-1-yl | H | 412.1 |
| 113 | A | 3-(3-chlorophenyl)pyrrolidin-1-yl | H | 378.1 |
| 114 | A | 3-(3-fluorophenyl)pyrrolidin-1-yl | H | 362.1 |
| 115 | A | 3-(4-fluorophenyl)pyrrolidin-1-yl | H | 362.1 |
| 116 | A | 3-(4-chlorophenyl)pyrrolidin-1-yl | H | 378.1 |
| 117 | A | 3-[4-(trifluoromethyl)phenyl]pyrrolidin-1-yl | H | 412.1 |
| 118 | A | 3-(4-methoxyphenyl)pyrrolidin-1-yl | H | 374.1 |
| 119 | A | 3-(4-phenoxyphenyl)pyrrolidin-1-yl | H | 436.2 |
| 120 | A | 4-(3-methoxyphenyl)-3,6-dihydropyridin-1(2H)-yl | H | 386.1 |
| 121 | A | 4-(4-cyano-3-methylphenyl)-3,6-dihydropyridin-1(2H)-yl | H | 395.1 |
| 122 | A | 3-(3-methoxyphenyl)pyrrolidin-1-yl | H | 374.1 |
| 123 | A | 3-pyridin-4-ylpyrrolidin-1-yl | H | 345.2 |
| 124 | A | 4-(3,5-dimethylphenyl)-3,6-dihydropyridin-1(2H)-yl | H | 384.2 |
| 125 | A | 4-(3-trifluoromethoxyphenyl)-3,6-dihydropyridin-1(2H)-yl | H | 440.1 |
| 126 | A | 5-(methoxymethyl)-4-phenyl-3,6-dihydropyridin-1(2H)-yl | H | 400 |
| 127 | A | 1,4,5,6-tetrahydrobenzo[f]isoquinolin-3(2H)-yl | H | 381.9 |

TABLE 1-continued

| | | | | |
|---|---|---|---|---|
| 129 | A | 4-(5-methoxy-2-methylphenyl)-3,6-dihydropyridin-1(2H)-yl | H | 400.2 |
| 130 | A | 4-(4-methoxy-2-methylphenyl)-3,6-dihydropyridin-1(2H)-yl | H | 400.2 |
| 131 | A | 4-cyano-4-phenylpiperidin-1-yl | H | 383.2 |
| 132 | A | 4-phenyl-3,6-dihydropyridin-1(2H)-yl | Ethoxycarbonyl | 426.1* |
| 133 | A | 4-phenyl-3,6-dihydropyridin-1(2H)-yl | Propionoxycarbonyl | 440.2* |
| 134 | A | 4-phenyl-3,6-dihydropyridin-1(2H)-yl | iso-propionoxycarbonyl | 440.2* |
| 135 | A | 4-phenyl-3,6-dihydropyridin-1(2H)-yl | iso-butoxycarbonyl | 454.2* |
| 136 | A | 5-methyl-4-phenyl-3,6-dihydropyridin-1(2H)-yl | H | 370 |
| 143 | A | 1,4,4a,5,6,10b-hexahydrobenzo[f]isoquinolin-3(2H)-yl | H | 384.2 |
| 144 | A | 4-(4-fluorophenyl)-3-hydroxypiperidin-1-yl | H | 392.1 |
| 145 | A | 3,3a,8,8a-tetrahydroindeno[1,2-c]pyrrol-2(1H)-yl | H | 356.1 |
| 146 | A | 4-(4-phenyl-1,3-thiazol-2-yl)piperidin-1-yl | H | 441.3 |
| 147 | A | 4-(4-tert-Butyl-1,3-thiazol-2-yl)piperidin-1-yl | H | 421.1 |
| 148 | A | 4-methyl-4-phenylpiperidin-1-yl | H | 372.2 |
| 149 | A | 4-(4-ethyl-1,3-thiazol-2-yl)piperidin-1-yl | H | 393.1 |
| 150 | A | 3-methyl-4-phenylpyrrolidine-1-yl | H | 358.2 |
| 151 | A | 4-(2-fluorophenyl)piperazin-1-yl | H | 377.2 |
| 152 | A | 4-(3,5-dimethylphenyl)-3,6-dihydropyridin-1(2H)-yl | Me | 398.1 |
| 153 | A | 4-phenylpiperazin-1-yl | tetrahydro-2H-pyran-4-oxycarbonyl | 487.1 |
| 154 | A | 4-phenylpiperazin-1-yl | ethoxycarbonyl | 431.2 |
| 155 | A | 4-phenylpiperazin-1-yl | methoxycarbonyl | 417.1 |
| 156 | A | 4-pyrazin-2-ylpiperazin-1-yl | H | 361.2 |
| 157 | A | 4-quinolin-2-ylpiperazin-1-yl | H | 410.1 |
| 158 | A | 3-(5,6,7,8-tetrahydronaphthalen-2-yl)pyrrolidin-1-yl | H | 398.2 |
| 159 | A | (3R)-3-phenylpyrrolidin-1-yl | Me | 358.1 |
| 160 | A | (3R)-3-phenylpyrrolidin-1-yl | methoxycarbonyl | 402.1 |
| 161 | A | 3-pyridin-3-ylpyrrolidin-1-yl | H | 345.1 |
| 162 | A | 3-pyridin-2-ylpyrrolidin-1-yl | H | 345.1 |
| 163 | A | 3-methyl-3-phenylpyrrolidine-1-yl | H | 358.2 |
| 164 | A | 3-phenylazetidin-1-yl | H | 330.3 |
| 165 | A | 3-methyl-3-phenylpyrrolidine-1-yl | Me | 372.4 |
| 166 | A | 3-phenylazetidin-1-yl | Me | 344.4 |
| 168 | A | 1,3,3a,4,5,9b-hexahydro-2H-benzo[e]isoindol-2-yl | H | 370.4 |
| 169 | A | 3-(2-naphthyl)pyrrolidin-1-yl | H | 394.4 |
| 170 | A | 4-(2-thienyl)-3,6-dihydropyridin-1(2H)-yl | H | 362.1 |
| 171 | A | 3-(3-thienyl)pyrrolidin-1-yl | H | 350.1 |
| 172 | A | 3-(2-thienyl)pyrrolidin-1-yl | H | 350.2 |
| 173 | A | 4-(2-thienyl)piperidin-1-yl | H | 364.1 |
| 174 | A | 3-(2-methylphenyl)pyrrolidin-1-yl | H | 358.2 |
| 175 | A | 3-(4-methylphenyl)pyrrolidin-1-yl | H | 358.2 |
| 176 | A | 4-phenyl-3,6-dihydropyridin-1(2H)-yl | Ac | |
| 177 | A | 4-(3-thienyl)-3,6-dihydropyridin-1(2H)-yl | H | 362.1 |
| 178 | A | 3-phenylpiperidin-1-yl | H | 358.2 |
| 179 | A | 4-(3-thienyl)piperidin-1-yl | H | 364.1 |
| 180 | A | 4-(3,5-dimethylphenyl)-3,6-dihydropyridin-1(2H)-yl | methoxycarbonyl | 442.2 |
| 181 | A | 4-(3,5-dimethylphenyl)-3,6-dihydropyridin-1(2H)-yl | methanesulfonyl | 462.1 |
| 182 | A | 4-(3,5-difluorophenyl)-3,6-dihydropyridin-1(2H)-yl | H | 392.2 |
| 183 | A | 4-(3,5-dichlorophenyl)-3,6-dihydropyridin-1(2H)-yl | H | 424.1 |
| 184 | A | 4-[3,5-bis(trifluoromethyl)phenyl]-3,6-dihydropyridin-1(2H)-yl | H | 492.1 |
| 185 | A | 4-phenylpiperazin-1-yl | methanesulfonyl | 437.2 |
| 186 | A | 4-phenylpiperazin-1-yl | formyl | 387.2 |
| 187 | A | 4-(3,5-difluorophenyl)piperidin-1-yl | H | 394.2 |
| 188 | A | 4-(2,5-dimethylphenyl)-3,6-dihydropyridin-1(2H)-yl | H | 384.1 |
| 189 | A | 4-(2,4,5-trimethylphenyl)-3,6-dihydropyridin-1(2H)-yl | H | 398.2 |
| 190 | A | 4-biphenyl-3-ylpiperidin-1-yl | H | 434.2 |
| 191 | A | 4-dibenzo[b,d]furan-4-ylpiperidin-1-yl | H | 448.2 |
| 192 | A | 4-(2,5-dimethylphenyl)piperidin-1-yl | H | 386.2 |
| 193 | A | 4-(2,4,5-trimethylphenyl)piperidin-1-yl | H | 400.2 |
| 194 | A | 4-(3-methoxycarbonyl-6-methylphenyl)-3,6-dihydropyridin-1(2H)-yl | H | 428.2 |
| 195 | A | 5-phenyl-2,3,4,7-tetrahydro-1H-azepin-1-yl | H | 370.2 |
| 196 | A | 4-[3-(dimethylamino)phenyl]-3,6-dihydropyridin-1(2H)-yl | H | 399.2 |
| 197 | A | 4-(3-methoxycarbonyl-6-methylphenyl)piperidin-1-yl | H | 430.2 |

TABLE 1-continued

| | | | | |
|---|---|---|---|---|
| 198 | A | 5-phenylazepan-1-yl | H | 372.2 |
| 199 | A | 4-[3-(dimethylamino)phenyl]piperidin-1-yl | H | 401.2 |
| 200 | A | 4-(2-methylphenyl)-3,6-dihydropyridin-1(2H)-yl | H | 370.2 |
| 201 | A | 3-phenyl-2,5-dihydro-1H-pyrrol-1-yl | H | 342.1 |
| 202 | A | 4-(4-cyano-2-methylphenyl)piperidin-1-yl | H | 397.2 |
| 203 | A | 3,3-dimethyl-4-phenyl-3,6-dihydropyridin-1(2H)-yl | H | 384.1 |
| 204 | A | 3,3-dimethyl-4-phenylpiperidin-1-yl | H | 386.2 |
| 205 | A | 3-phenyl-2,5-dihydro-1H-pyrrol-1-yl | methanesulfonyl | 420.2 |
| 206 | A | 3-phenyl-2,5-dihydro-1H-pyrrol-1-yl | methoxycarbonyl | 400.2 |
| 207 | A | 3-phenyl-2,5-dihydro-1H-pyrrol-1-yl | Me | 356.2 |
| 208 | A | 4-(4-cyano-3-methylphenyl)piperidin-1-yl | H | 397.2 |
| 209 | A | 4-[3-(benzyloxy)phenyl]-3,6-dihydropyridin-1(2H)-yl | H | 462.2 |
| 210 | A | 4-[3-ethylphenyl]-3,6-dihydropyridin-1(2H)-yl | H | 384.1 |
| 211 | A | 4-[3-(ethyloxy)phenyl]-3,6-dihydropyridin-1(2H)-yl | H | 400.1 |
| 212 | A | 4-(3-ethylphenyl)piperidin-1-yl | H | 386.1 |
| 213 | A | 4-(3-ethoxyphenyl)piperidin-1-yl | H | 402.1 |
| 214 | A | 4-(3-cyclopropylphenyl)-3,6-dihydropyridin-1(2H)-yl | H | 396.2 |
| 215 | A | 4-(4-methoxy-3,5-dimethylphenyl)-3,6-dihydropyridin-1(2H)-yl | H | 414.2 |
| 216 | A | 4-(3,5-dimethyl-4-methoxyphenyl)piperidin-1-yl | H | 416.2 |
| 217 | A | 4-(4-cyano-3-ethylphenyl)-3,6-dihydropyridin-1(2H)-yl | H | 409.2 |
| 218 | A | 4-(4-cyano-3-ethylphenyl)piperidin-1-yl | H | 411.2 |
| 219 | A | 4-(4-cyano-3,5-dimethylphenyl)-3,6-dihydropyridin-1(2H)-yl | H | 409.2 |
| 220 | A | 4-(4-cyano-3,5-dimethylphenyl)piperidin-1-yl | H | 411.4 |
| 221 | A | 4-(1,3-benzothiazol-6-yl)-3,6-dihydropyridin-1(2H)-yl | H | 413.1 |
| 222 | A | 4-(1-methyl-1H-indazol-6-yl)-3,6-dihydropyridin-1(2H)-yl | H | 410.2 |
| 223 | A | 4-(1-methyl-1H-indazol-6-yl)piperidin-1-yl | H | 412.3 |
| 224 | A | 4-(4-cyano-3-isopropylphenyl)-3,6-dihydropyridin-1(2H)-yl | H | 423.2 |
| 225 | A | 4-(4-cyano-3-isopropylphenyl)piperidin-1-yl | H | 425.2 |
| 236 | A | 4-(4-cyano-3-ethylphenyl)-3,6-dihydropyridin-1(2H)-yl | Me | 423.2 |
| 237 | A | 4-(4-cyano-3,5-dimethylphenyl)-3,6-dihydropyridin-1(2H)-yl | Me | 423.2 |
| 238 | A | 4-(1-ethyl-1H-benzimidazol-6-yl)-3,6-dihydropyridin-1(2H)-yl | H | 424.3 |
| 239 | A | 4-(1-methyl-1H-indazol-5-yl)-3,6-dihydropyridin-1(2H)-yl | H | 410.2 |
| 240 | A | 4-(1-ethyl-1H-benzimidazol-6-yl)piperidin-1-yl | H | 426.2 |
| 241 | A | 4-(1-methyl-1H-indazol-5-yl)piperidin-1-yl | H | 412.2 |
| 242 | A | 4-(1-ethyl-1H-indazol-5-yl)-3,6-dihydropyridin-1(2H)-yl | H | 424.2 |
| 243 | A | 4-(1-ethyl-1H-benzimidazol-6-yl)piperidin-1-yl | tetrahydro-2H-pyran-4-oxycarbonyl | 554.3 |
| 244 | A | 4-(1-ethyl-1H-benzimidazol-6-yl)-3,6-dihydropyridin-1(2H)-yl | methoxycarbonyl | 482.2 |
| 245 | A | 4-(1-ethyl-1H-benzimidazol-6-yl)-3,6-dihydropyridin-1(2H)-yl | methanesulfonyl | 502.2 |
| 246 | A | 4-(1-ethyl-1H-benzimidazol-6-yl)piperidin-1-yl | methoxycarbonyl | 484.2 |
| 247 | A | 4-(1-ethyl-1H-benzimidazol-6-yl)piperidin-1-yl | methanesulfonyl | 504.2 |
| 248 | A | 4-(4-cyano-2-methylphenyl)piperidin-1-yl | methanesulfonyl | 476.2 |
| 249 | A | 4-(4-cyano-2-methylphenyl)piperazin-1-yl | methoxycarbonyl | 456.2 |
| 250 | A | 4-(1-ethyl-1H-benzimidazol-6-yl)piperazin-1-yl | H | 427.5 |
| 251 | A | 4-(1-ethyl-1H-benzimidazol-6-yl)piperazin-1-yl | methoxycarbonyl | 485.3 |
| 252 | A | 4-(1-ethyl-1H-benzimidazol-6-yl)piperazin-1-yl | methanesulfonyl | 505.2 |
| 253 | A | 4-(4-cyano-2-methylphenyl)piperazin-1-yl | tetrahydro-2H-pyran-4-oxycarbonyl | 526.3 |
| 254 | A | 4-(1-ethyl-1H-benzimidazol-6-yl)piperazin-1-yl | tetrahydro-2H-pyran-4-oxycarbonyl | |
| 255 | A | 3-methyl-4-phenylpiperidin-1-yl | H | 372.1 |
| 256 | A | 5-(aminocarbonyl)-4-phenyl-3,6-dihydropyridin-1(2H)-yl | H | |
| 257 | A | 4-(4-cyanophenyl)-5-methyl-3,6-dihydropyridin-1(2H)-yl | H | 395.2 |
| 258 | A | 4-(4-cyanophenyl)-3-methylpiperidin-1-yl | H | 397.1 |
| 259 | A | 5-methyl-4-(4-nitrophenyl)-3,6-dihydropyridin-1(2H)-yl | H | 415.2 |
| 260 | A | 5-methyl-4-(3-nitrophenyl)-3,6-dihydropyridin-1(2H)-yl | H | 415.1 |
| 262 | A | 4-dibenzo[b,d]furan-2-yl-3,6-dihydropyridin-1(2H)-yl | H | 446.1 |
| 263 | A | 4-dibenzo[b,d]furan-2-ylpiperidin-1-yl | H | 448.1 |

TABLE 1-continued

| | | | | |
|---|---|---|---|---|
| 264 | A | 4-(3,3-dimethyl-2,3-dihydro-1-benzofuran-5-yl)-3,6-dihydropyridin-1(2H)-yl | H | 426.1 |
| 265 | A | 4-(3,3-dimethyl-2,3-dihydro-1-benzofuran-5-yl)piperidin-1-yl | H | 428.1 |
| 266 | A | 3-phenyl-2,5-dihydro-1H-pyrrol-1-yl | iso-propionoxycarbonyl | 428.1 |
| 267 | A | 3-phenyl-2,5-dihydro-1H-pyrrol-1-yl | (3S)-tetrahydrofuran-3-oxycarbonyl | 456.1 |
| 268 | A | 3-phenyl-2,5-dihydro-1H-pyrrol-1-yl | cyclohexoxycarbonyl | 468.2 |
| 269 | A | 3-phenyl-2,5-dihydro-1H-pyrrol-1-yl | tetrahydro-2H-pyran-4-oxycarbonyl | 470.2 |
| 270 | B | 4-phenylpiperazin-1-yl | | 358.2 |
| 271 | B | (3R)-3-phenylpyrrolidin-1-yl | | 343.3 |
| 272 | B | 4-(2-methyl-4-nitrophenyl)piperazin-1-yl | | 417.2 |
| 273 | B | 4-phenyl-3,6-dihydropyridin-1(2H)-yl | | 355.2 |
| 274 | A | 4-phenylpiperazin-1-yl | (3S)-tetrahydrofuran-3-oxycarbonyl | 473.2 |
| 275 | A | 4-phenylpiperazin-1-yl | (3R)-tetrahydrofuran-3-oxycarbonyl | 473.2 |
| 276 | A | 4-phenylpiperazin-1-yl | 2-methoxyethoxycarbonyl | 461.1 |
| 277 | A | 4-phenylpiperazin-1-yl | phenylsulfonyl | 499.1 |
| 278 | A | 4-phenylpiperazin-1-yl | propionoxycarbonyl | 445.2 |
| 279 | A | 4-phenylpiperazin-1-yl | iso-propionoxycarbonyl | 445.2 |
| 280 | A | 4-(3,5-difluorophenyl)-3,6-dihydropyridin-1(2H)-yl | methoxycarbonyl | 450.2 |
| 281 | A | 4-(3,5-difluorophenyl)-3,6-dihydropyridin-1(2H)-yl | methanesulfonyl | 470.2 |
| 282 | A | 4-(4-isopropylphenyl)piperazin-1-yl | H | — |
| 283 | A | 4-(3,5-difluorophenyl)piperidin-1-yl | methanesulfonyl | 472.1 |
| 284 | A | 4-(4,5-dimethyl-1,3-thiazol-2-yl)piperidin-1-yl | H | 393.1 |

*M—H

The capacity of the novel compounds of the invention to inhibit metalloproteases can be determined using a suitable screen such as a high through-put assay. For example, an agent can be tested in an extracellular acidification assay, calcium flux assay, ligand binding assay or chemotaxis assay. Below are example assays.

TNFα Assay

In some embodiments, the capacity of the compounds of the invention to act as inhibitors of the production of TNFα can be determined using the following procedure. A 100 µM solution of the inhibitor being tested or dilutions thereof is incubated at 37° C. in an atmosphere of 5% $CO_2$ with THP-1 cells (human monocytes) suspended in RPM1 1640 medium and 20 µM β-mercaptoethanol at a cell density of $1 \times 10^6$/ml and stimulated with LPS. After 18 hours the supernatant is assayed for the levels of TNFα using a commercially available ELISA kit. The activity in the presence of 0.1 mM inhibitor or dilutions thereof is compared to activity in a control devoid of inhibitor and results reported as that inhibitor concentration effecting 50% inhibition of the production of TNFα.

PBMC Assay Measuring TNFα Activity

A leukophoresis is obtained from (Biological Specialties, Colmar Pa.) from normal drug free (no aspirin, ibuprofen, NSAIDs) etc.) donors. In a 50 mL conical tube (VWR, NJ), add 20 mL of blood and 20 mL of sterile 0.9% saline (Baxter Healthcare, Dearfield, Ill.) and mix well. Underlay 10 mL of endotoxin free ficoll paque (Pharmacia, Uppsala, Sweden) and spin at 3000 RPM for 30 minutes. Remove the layer of white blood cells and wash with 50 mls 0.9% saline. Count cells and add 0.250 mL to 96 well plate (Costar/Corning VWR, NJ) at 2×10 6 c/ml, in RPMI 1640 medium (Gibco BRL). Add compounds and preincubate with cells for 10 min before adding LPS (Calbiochem, Calif.) at 1 ug/ml for 5 hours. Collect supernatent and assay for TNFα production by standard sandwich ELISA (R&D Systems, Minneapolis, Minn.). Compound inhibition was determined relative to cells cultured with LPS alone.

Assay for Her-2 Sheddase Activity

A human breast cell cancer line BT474 (ATCC, Manassas, Va.), is seeded at $2 \times 10^4$ cells/well in 100 µL in a 96 well plate (Costar/Corning VWR, NJ) in RPMI 1640 media (In Vitrogen, Carlsbad, Calif.) containing 10% fetal bovine serum (Hyclone, Lenexa, Kans.), and incubated overnight at 37° C., 5% $CO_2$. The following morning media is removed and fresh media is added back at 100 µL/well. Compounds are added at appropriate concentrations and the cells are incubated for 72 hour at 37° C., 5% $CO_2$. Supernatants are then removed and either tested immediately or stored at −20° C. until testing can be performed. Supernatants are tested at a 1/20 dilution for inhibition of Her-2 sheddase by commercial ELISA (Oncogene Research, San Diego, Calif.)). Compound inhibition was determined relative to cells cultured alone.

ADAM and MMP In Vitro Assays

Except for ADAM17 and MT1-MMP, all recombinant human MMPs and ADAMs were obtained from R&D Systems (Minneapolis, Minn.). Their catalog numbers are as following: MMP1 (901-MP), MMP2 (902-MP), MMP3 (513-MP), MMPI (907-MP), MMP8 (908-MP), MMP9 (911-MP), MMP10 (910-MP), MMP12 (919-MP), MMP13 (511-MM), ADAMS (939-AD), and ADAM10 (936-AD). MT1-MMP was obtained from US Biological (Swampscott, Mass.) with a catalog number of M2429. Porcine ADAM17 was purified in house from porcine spleen.

Fluorogenic Peptide substrate, (7-methoxycoumarin-4-yl) acetyl-Pro-Leu-Gly-Leu-(3-[2, 4-dinitrophenyl]-L-2, 3-diaminopropionyl)-Ala-Arg-$NH_2$, was obtained from R&D Systems with a catalog number of ES001. It was used as substrate for MMP1, MMP2, MMP7, MMP8, MMP9, MMP12, MMP13, and MT1-MMP assays. Fluorogenic Peptide substrate, (7-methoxycoumarin-4-yl) acetyl-Arg-Pro-Lys-Pro-Val-Glu-Nva-Trp-Arg-Lys(2,4-dinitrophenyl)-NH$_2$, was obtained from R&D Systems with a catalog number of ES002. It was used as substrate for MMP3 and MMP10 assays. Fluorogenic Peptide substrate, (7-methoxy-courmarin-4-yl)-acetyl-Pro-Leu-Ala-Gln-Ala-Val-(3-[2,4-dinitrophenyl]-L-2,3-diaminopropionyl)-Arg-Ser-Ser-Ser-Arg-NH$_2$, was obtained from R&D Systems with a catalog number of ES003. It was used as substrate for ADAM9, ADAM10, and ADAM17 assays.

Assay Buffer Conditions: In general, assay buffer condition was chosen based on obtaining optimal enzymatic activities. The specific assay buffer conditions are summarized as following. For MMP1, MMP2, MMP3, MMP7, and MMP12, the assay buffer contains 50 mM Tricine, 10 mM NaCl, 10 mM CaCl$_2$, 1.0 mM ZnCl$_2$, pH 7.4. For MMP8 and MMP13, the assay buffer contains 50 mM Tricine, 10 mM NaCl, 10 mM CaCl$_2$, 1.0 mM ZnCl$_2$, 0.001% Brij35, pH 7.4. For MMP9 and MMP10, the assay buffer contains 50 mM Tris-HCl, 150 mM NaCl, 10 mM CaCl$_2$, 0.001% Brij35, pH 7.5. For MT1-MMP, the assay buffer contains 100 mM Tris-HCl, 100 mM NaCl, 10 mM CaCl$_2$, 0.001 Brij35, pH 7.5. For ADAM9, the assay buffer contains 25 mM Tris, 2.5 µM ZnCl2, and 0.001% Brij35, 0.1 mg/mL BSA, pH 9.0. For ADAM10, the assay buffer contains 25 mM Tris, 2.5 µM ZnCl$_2$, and 0.005% Brij35, pH 9.0. For ADAM17, the assay buffer contains 25 mM Tris, 2.5 µM ZnCl$_2$, and 0.001% Brij35, pH 9.0.

To activate MMP enzymes, 10 or 20 µg of lyophilized Pro-MMPs were dissolved in 100 µL of water. 100 mM p-aminophenylmercuric acetate (APMA) stock in DMSO was added to Pro-MMPs to give 1.0 mM final concentration. Pro-MMPs were incubated with APMA at 37° C. for a period time specified below. For MMP1, MMP7, and MMP8, the incubation time was 1 hour. For MMP10 and MMP13, the incubation time was 2 hours. For MMP3 and MMP9, the incubation time was 24 hours.

In general, 5 mM compound stock was prepared in DMSO. 2-Fold serial dilution starting with a specific concentration was performed to give the compound plate. 1.0 µL of compound in DMSO was transferred from compound plate to the assay plate. Enzyme solution was prepared in assay buffer with a concentration specified below. Substrate solution was prepared in assay buffer with a concentration of 20 µM. 50 µL of enzyme solution was added to the assay plate. The assay plate was incubated for 5 minutes. 50 µL of substrate solution was then added to the assay plate. Protect the plate from the light and incubate the reaction at room temperature or 37° C. for a period of time specified below. The reaction was stopped by adding 10 µL of 500 mM EDTA solution. The plate was read on a plate reader with excitation of 320 nm and emission of 405 nm. Percentage of inhibition was calculated for each concentration and IC50 value was generated from curve fitting. Specific conditions for each assay are as following: MMP1 enzyme concentration 1000 ng/mL, room temperature, 1 hour incubation; MMP2 enzyme concentration 200 ng/mL, room temperature, 1 hour incubation; MMP3 enzyme concentration 1000 ng/mL, room temperature 1 hour incubation; MMPI enzyme concentration 100 ng/mL, room temperature 1 hour incubation; MMP8 enzyme concentration 500 ng/mL, room temperature, 2 hours incubation; MMP9 enzyme concentration 100 ng/mL, room temperature, 1 hour incubation; MMP10 enzyme concentration 1000 ng/mL, room temperature, 2 hours incubation; MMP12 enzyme concentration 200 ng/mL, room temperature, 1 hour incubation; MMP13 enzyme concentration 200 ng/mL, room temperature, 1.5 hours incubation; MT1-MMP enzyme concentration 200 ng/mL, room temperature, 1 hour incubation; ADAMS enzyme concentration 4000 ng/mL, incubated at 37° C. 6 hours; ADAM10 enzyme concentration 700 ng/mL, incubated at 37° C. 6 hours; ADAM17 enzyme concentration 600 ng/mL, incubated at 37° C. 1 hour.

MMP2 Assay 5 mM compound stock was prepared in DMSO. Compound plate was prepared by 2-fold dilution for 11-point curve, with highest concentration of 500 uM. 1 µL of compound in DMSO was transferred from compound plate to the assay plate. Enzyme solution was prepared in assay buffer with a concentration of 10 ng/50 µL. Substrate solution was prepared in assay buffer with a concentration of 20 µM. 50 µL of enzyme solution was added to the assay plate. The assay plate was incubated for 5 minutes. 50 µL of substrate solution was then added to the assay plate. Protect the plate from the light and incubate the reaction at room temperature for 1 hour. The reaction was stopped by adding 10 µL of 500 mM EDTA solution. Read the plate on a plate reader with excitation of 320 nm and emission of 405 nm.

MMP3 Assay 5 mM compound stock was prepared in DMSO. Compound plate was prepared by 2-fold dilution for 11-point curve, with highest concentration of 500 uM. 1 µL of compound in DMSO was transferred from compound plate to the assay plate. Enzyme solution was prepared in assay buffer with a concentration of 50 ng/50 µL. Substrate solution was prepared in assay buffer with a concentration of 20 µM. 50 µL of enzyme solution was added to the assay plate. The assay plate was incubated for 5 minutes. Add 10 µL of 500 mM EDTA to background wells. 50 µL of substrate solution was then added to the assay plate. Protect the plate from the light and incubate the reaction at room temperature for 1 hour. The reaction was stopped by adding 10 µL of 500 mM EDTA solution. Read the plate on a plate reader with excitation of 320 nm and emission of 405 nm.

MMP12 Assay 5 mM compound stock was prepared in DMSO. Compound plate was prepared by 2-fold dilution for 11-point curve, with highest concentration of 500 µM. 1 µL of compound in DMSO was transferred from compound plate to the assay plate. Enzyme solution was prepared in assay buffer with a concentration of 10 ng/50 µL. Substrate ((7-methoxy-coumarin-4-yl) acetyl-Pro-Leu-Gly-Leu-(3-[2,4-dinitrophenyl]-L-2, 3-diaminopropionyl)-Ala-Arg-NH$_2$) solution was prepared in assay buffer with a concentration of 20 µM. 50 µL of enzyme solution was added to the assay plate. The assay plate was incubated for 5 minutes. Add 10 µL of 500 mM EDTA in the background well. 50 µL of substrate solution was then added to the assay plate. Protect the plate from the light and incubate the reaction at room temperature for 1 hour. The reaction was stopped by adding 10 µL of 500 mM EDTA solution. Read the plate on a plate reader with excitation of 320 nm and emission of 405 nm.

ADAM10 Assay 5 mM Compound stock was prepared in DMSO. Compound plate was prepared by 2-fold dilution for 11-point curve, with highest concentration of 500 uM. 1 µL of compound in DMSO was transferred from compound plate to the assay plate. Enzyme solution was prepared in assay buffer with a concentration of 100 ng/50 µL. Substrate ((7-methoxy-courmarin-4-yl)-acetyl-Pro-Leu-Ala-Gln-Ala-Val-(3-[2,4-dinitrophenyl]-L-2,3-diaminopropionyl)-Arg-Ser-Ser-Ser-Arg-NH$_2$) solution was prepared in assay buffer with a concentration of 20 µM. 50 µL of enzyme solution was added to the assay plate. The assay plate was incubated for 5 minutes. 50 µL of substrate solution was then added to the assay plate. The plate was protected from light and incubated at 37° C. for 4 hours. The reaction was stopped by adding 10 uL of 500 mM EDTA solution. The plate was read on a plate reader with excitation of 320 nm and emission of 405 nm.

ADAM15 Assay

ADAM15 can be assayed in a similar fashion to ADAM10 (see, e.g., Fourie et al., *J Biol Chem.* 2003, 278(33), 30469-77). In brief, a fluorescence quenched peptide substrate is made by labeling one terminus with a fluorescent dye and the other terminus with a quencher dye. Cleavage of the peptide by ADAM15 can be measured by the increase in fluorescence intensity as a result of the decrease in proximity of the quencher dye to the fluorescent dye.

Compound Activity

The compounds of the present invention have $IC_{50}$ values in the range of about 5 nM to about 10 µM for target inhibition when tested by at least one of the above in vitro assays.

In Vivo Assay

To measure the antineoplastic activity of metalloprotease inhibitors, both estrogen dependent (MCF-7 and BT-474) and independent (MDA-MB-435) human breast cancer cell lines were used in immune compromised mouse (BALB/c nude and SCID/bg) xenograft experiments. The BT-474 tumors were from a subclone of the parental BT-474 cells from ATCC (BT-474-SC1) that were selected based on their increased tumor take and growth rates but are referred to herein as BT-474 for simplicity sake. In the BT-474 and MCF-7 tumor models, slow-release estrogen pellets (Innovative Research of America) were inserted subcutaneously (s.c.) into the flank of each mouse 24 hours prior to tumor cell inoculation. For all models, the indicated number of cells is combined with BD Matrigel™ at a 1:1 ratio immediately prior to implantation. The day after estrogen pellet implantation, $2 \times 10^7$ BT-474 cells were injected s.c. into the upper flank of each mouse. MCF-7 tumors were generated by s.c. implantation of $5 \times 10^6$ cells injected in similar fashion. For the MDA-MB-435 tumor cells, $2 \times 10^6$ cells were inject s.c. into the flank of BALB/c nude mice. For all models, tumors were measured on a weekly basis and their volumes calculated using the formula [volume=(length×width$^2$)÷2]. Once the mean tumor volume of the required number of mice reached the desired size (usually >150 mm$^3$), they were randomized into treatment groups usually containing between 6 and 10 mice. Animals were then treated with test compound or vehicle by mini-osmotic pump implated i.p. or s.c. for 7 to 28 days to achieve the desired compound exposure—controlled by altering the pump flow rate and/or the concentration of compound inside the pumps. Tumor size and body weights (a measure of animal health) were monitored weekly. Blood samples were also drawn while the osmotic pumps were functional and plasma was separated (by centrifugation) and stored at −80° C. for later pharmacokinetic analysis.

Methods of Treatment, Dosages and Formulations

The compounds of the invention can be administered to a mammal, such as a human, but can also be administered to other mammals such as an animal in need of veterinary treatment, e.g., domestic animals (e.g., dogs, cats, and the like), farm animals (e.g., cows, sheep, pigs, horses, and the like) and laboratory animals (e.g., rats, mice, guinea pigs, and the like). The mammal treated in the methods of the invention is a mammal, male or female, in whom modulation of matrix metalloprotease activity is desired. The term modulation is intended to encompass antagonism, agonism, partial antagonism and/or partial agonism.

In the present specification, the term "therapeutically effective amount" means the amount of the subject compound that will elicit the biological or medical response of a tissue, system, animal or human that is being sought by the researcher, veterinarian, medical doctor or other clinician.

The compounds of the invention are administered in therapeutically effective amounts to treat a disease for example such as rheumatoid arthritis. A therapeutically effective amount of a compound is that amount which results in the inhibition of one or more of the processes mediated by metalloproteases in a subject with a disease associated with aberrant metalloprotease activity. Alternatively, a therapeutically effective amount of a compound is the quantity required to achieve a desired therapeutic and/or prophylactic effect, such as an amount which results in the prevention of or a decrease in the symptoms associated with a disease associated with aberrant metalloprotease activity.

The present invention provides a method for treating a disease associated with unwanted metalloprotease activity in a mammalian subject. In some embodiments, the unwanted metalloprotease activity is associated with arthritis, cancer (such as breast cancer, ovarian cancer, prostate cancer, non-small cell lung cancer, colon cancer, gastric cancer, pancreatic cancer, glioma, and the like), cardiovascular disorders, skin disorders, inflammation or allergic conditions. In further embodiments, the present invention provides a method of inhibiting pathological changes mediated by elevated levels of metalloproteases in mammals.

The compounds herein are useful in treating diseases, pathologic conditions and disorders associated with metalloprotease activity such as by modulation (e.g., inhibition or antagonism) of metalloproteases including matrix metalloproteases (MMPs), ADAMs, ADAM-TSs, and sheddases which can pathologically involve aberrant extracellular matrix degradation, shedding of cell surface protein ectodomains, and/or TNF synthesis. In further embodiments, the compounds of the invention modulate matrix metalloproteases (e.g., MMP12, MMP14, MMP3, MMP2, or MMP9), members of the ADAMs family of enzymes including TNF α-convertase, ADAM10, ADAM15, ADAM17 and sheddases such as Her-2 sheddase, heparin-binding EGF sheddase. The compounds of the invention can modulate activity of ADAMs which are believed responsible for the release or shedding of soluble receptors (for example, CD30 and receptors for TNF), adhesion molecules (for example, L-selectin, ICAM-1, fibronectin), growth factors and cytokines (for example Fas ligand, TGF-α, EGF, HB-EGF, SCF IL-6, IL-1, TSH and M-CSF), and growth factor receptors (for example EGFR family members, such as Her-2 and Her-4) which have been implicated in the pathogenesis of different types of cancer, including breast cancer, ovarian cancer, prostate cancer, non-small cell lung cancer, colon cancer, gastric cancer, pancreatic cancer and glioma. Accordingly, the compounds of the invention can be useful in the treatment of diseases and disorders related to activity of any of the above-named targets.

Diseases or conditions of human or other species which can be treated with the metalloprotease modulators of the invention, include, but are not limited to: inflammatory or allergic diseases and conditions, including respiratory allergic diseases such as asthma, allergic rhinitis, hypersensitivity lung diseases, hypersensitivity pneumonitis, eosinophilic cellulitis (e.g., Well's syndrome), eosinophilic pneumonias (e.g., Loeffler's syndrome, chronic eosinophilic pneumonia), eosinophilic fasciitis (e.g., Shulman's syndrome), delayed-type hypersensitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies (e.g., to penicillin, cephalosporins), eosinophilia-myalgia syndrome due to the ingestion of contaminated tryptophan, insect sting allergies; autoimmune diseases, such as rheumatoid arthritis, psoriatic arthritis, multiple sclerosis, systemic lupus erythematosus, myasthenia gravis, juvenile onset diabetes; glomerulonephritis, autoimmune thyroiditis, Behcet's disease; graft rejection (e.g., in transplantation), including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such as an dermatitis, eczema, atopic dermatitis, allergic contact dermatitis, urticaria; vasculitis (e.g., necrotizing, cutaneous, and hypersensitivity vasculitis); eosinophilic myositis, eosinophilic fasciitis; neoplastic diseases such as breast cancer and cancers with leukocyte infiltration of the skin or organs. Other diseases or conditions in which undesirable inflammatory responses are to be inhibited can be treated, including, but not limited to, reperfusion injury, atherosclerosis, certain hematologic malignancies, cytokine-induced toxicity (e.g., septic shock, endotoxic shock), polymyositis, and dermatomyositis.

The compounds represented of the invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the metabolic stability, rate of excretion, drug combination, and length of action of that compound the species, age, sex, health, medical condition, and weight of the recipient; the nature and extent of the symptoms; the kind of concurrent treatment; the frequency of treatment; the specific route of administration, the renal and hepatic function of the patient, and the desired effect. A physician or veterinarian can determine and prescribe the effective amount of the drug required to prevent, counter, or arrest the progress of the specific disorder for which treatment is necessary.

Generally, the daily oral dosage of each active ingredient, when used for the indicated effects, will range between about 0.0001 to 1000 mg/kg of body weight, preferably between about 0.001 to 100 mg/kg of body weight per day, and most preferably between about 0.1 to 20 mg/kg/day. For intravenous use, the most preferred doses will range from about 0.1 to about 10 mg/kg/minute during a constant rate infusion. For oral administration, the compositions are preferably provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

The compounds of the instant invention can also be administered in intranasal form via topical use of suitable intranasal vehicles, or via transdermal routes, using transdermal skin patches. When administered in the form of a transdermal delivery system, the dosage administration-will, of course, be continuous rather than intermittent throughout the dosage regimen.

The compounds of the invention are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like. For oral administration in liquid form, the oral drug components can be combined with any oral, non-toxic, pharmaceutically acceptable inert carrier such as ethanol, glycerol, water, and the like. Additionally, when desired or necessary, suitable binders, lubricants, disintegrating agents, and coloring agents can also be incorporated into the mixture. Suitable binders include starch, gelatin, natural sugars such as glucose or β-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be provided to a patient in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

The compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or poly-ethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, and crosslinked or amphipathic block copolymers of hydrogels.

Dosage forms for the compounds of the invention suitable for administration may contain from about 0.1 milligram to about 100 milligrams of active ingredient per dosage unit. In these pharmaceutical compositions the active ingredient will ordinarily be present in an amount of about 0.5-95% by weight based on the total weight of the composition.

Gelatin capsules can also be used as dosage forms and may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

When using liquid dosage forms for oral administration they can contain coloring and flavoring to increase patient acceptance.

Generally, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol. Suitable pharmaceutical carriers are described in Remington's Pharmaceutical Sciences, Mack Publishing Company, a standard reference text in the field of pharmacology.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the present invention are employed. As used herein, topical application is also meant to include the use of mouth washes and gargles.

The pharmaceutical compositions and methods of the present invention may further comprise other therapeutically active compounds which are usually applied in the treatment of the above mentioned pathological conditions.

Representative useful pharmaceutical dosage-forms for administration of the compounds of this invention can be illustrated as follows:

Capsules

A large number of unit capsules can be prepared by filling standard two-piece hard gelatin capsules each with 50 milligrams of powdered active ingredient, 100 milligrams of lactose, 25 milligrams of cellulose, and 3 milligrams magnesium stearate.

Soft Gelatin Capsules

A mixture of active ingredient in a digestible oil such as soybean oil, cottonseed oil or olive oil may be prepared and injected by means of a positive displacement pump into gelatin to form soft gelatin capsules containing 75 milligrams of the active ingredient. The capsules should be washed and dried.

Tablets

Tablets may be prepared by conventional procedures so that the dosage unit is 75 milligrams of active ingredient, 0.15 milligrams of colloidal silicon dioxide, 4 milligrams of magnesium stearate, 250 milligrams of microcrystalline cellulose, 9 milligrams of starch and 75 milligrams of lactose. Appropriate coatings well known to one skilled in the art may be applied to increase palatability or delay absorption.

Injectable

A parenteral composition suitable for administration by injection may be prepared by stirring 1.0% by weight of active ingredient in 8% by volume propylene glycol and water. The solution should be made isotonic with sodium chloride and sterilized.

Suspension

An aqueous suspension can be prepared for oral administration so that each 5 mL contain 75 mg of finely divided active ingredient, 150 mg of sodium carboxymethyl cellulose, 3.75 mg of sodium benzoate, 0.75 g of sorbitol solution, U.S.P., and 0.015 mL of vanillin.

All patents, patent applications and publications cited in this application are hereby incorporated by reference in their entirety for all purposes to the same extent as if each individual patent, patent application or publication were so individually denoted.

While the many forms of the invention herein disclosed constitute presently preferred embodiments, many others are possible and further details of the preferred embodiments and other possible embodiments are not to be construed as limitations. It is understood that the terms used herein are merely descriptive rather than limiting and that various changes many equivalents may be made without departing from the spirit or scope of the claimed invention.

What is claimed is:

1. A compound having the formula:

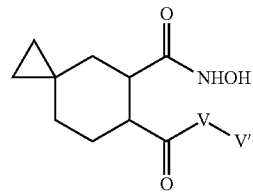

or an enantiomer, diastereomer, solvate, or pharmaceutically acceptable salt thereof, wherein:

V is heterocyclyl substituted with 0-5 $R_e$;

V' is $C_{3-13}$ carbocyclyl substituted with 0-5 $R_e$;

$R_e$ is H, T, $C_{1-8}$alkylene-T, $C_{2-8}$alkenylene-T, $C_{2-6}$alkynylene-T, $C(O)NR_a'(CR_b'R_c')_r$-T, $C(O)O(CR_b'R_c')_r$-T, $S(O)_p(CR_b'R_c')_r$-T, $(CR_b'R_c')_r$—O—$(CR_b'R_c')_r$-T, OH, Cl, F, Br, I, CN, $NO_2$, $NR^IR^{II}$, $COR^{III}$, $COOR^{IV}$, $OR^{IV}$, $CONR^IR^{II}$, $NR^ICONR^IR^{II}$, $OCONR^IR^{II}$, $NR^ICOR^{II}$, $SO_2NR^IR^{II}$, $NR^ISO_2R^{II}$, $NR^ISO_2NR^IR^{II}$, $OSO_2NR^IR^{II}$, $SO_pR^V$, $C_{1-8}$ haloalkyl, $C_{3-13}$ carbocyclyl, heterocyclyl, carbocyclylalkyl, or heterocyclylalkyl, wherein each of said carbocyclyl, heterocyclyl, carbocyclylalkyl, and heterocylcylalkyl groups is optionally substituted by one or more $C_{1-8}$ alkyl, alkoxy, halo, haloalkyl, haloalkoxy, cyano, nitro, amino, alkylamino, dialkylamino, carboxy, carboxy alkyl ester, carboxy aryl ester, aminocarbonyl, alkylaminocarbonyl, dialkylaminocarbonyl, sulfonyl, aminosulfonyl, alkylaminosulfonyl, dialkylaminosulfonyl, arylsulfonyl, arylsulfinyl, alkylsulfonyl or arylsulfonyl;

T is H, $C_{1-10}$ alkyl substituted with 0 to 5 $R_b'$; $C_{2-10}$ alkenyl substituted with 0 to 5 $R_b'$, $C_{2-10}$ alkynyl substituted with 0 to 5 $R_b'$, $C_{3-13}$ carbocyclyl substituted with 0-3 $R_b'$, heterocyclyl substituted with 0-5 $R_b'$;

$R_a'$, $R_b'$ and $R_c'$ are each, independently, H, $C_{1-6}$ alkyl, $C_{2-6}$ alkenyl, $C_{2-6}$ alkynyl, OH, Cl, F, Br, I, CN, $NO_2$, $NR^IR^{II}$, $COR^{III}$, $COOR^{IV}$, $OR^{IV}$, $CONR^IR^{II}$, $R^INCONR^IR^{II}$, $OCONR^IR^{II}$, $R^INCOR^{II}$, $SO_2NR^IR^{II}$, $NR^ISO_2R^{II}$, $NR^ISO_2NR^IR^{II}$, $OSO_2NR^IR^{II}$, $SO_pR^V$, $C_{1-8}$ haloalkyl, carbocyclyl, heterocyclyl, carbocyclylalkyl, heterocyclylalkyl, carbocyclyloxy or heterocarbocyclyloxy, wherein each of said carbocyclyl, heterocyclyl, carbocyclylalkyl, heterocyclylalkyl, carbocyclyloxy or heterocarbocyclyloxy groups is optionally substituted by one or more $C_{1-8}$ alkyl, alkoxy, halo, haloalkyl, haloalkoxy, cyano, nitro, amino, alkylamino, dialkylamino, carboxy, carboxy alkyl ester, carboxy aryl ester, aminocarbonyl, alkylaminocarbonyl, dialkylaminocarbonyl, sulfonyl, aminosulfonyl, alkylaminosulfonyl, dialkylaminosulfonyl, arylsulfonyl, arylsulfinyl, alkylsulfonyl or arylsulfonyl;

$R^I$ and $R^{II}$ are each, independently, H, $C_{1-6}$ alkyl or $C_{3-13}$ carbocyclyl;

$R^{III}$ and $R^{IV}$ are each, independently, H, $C_{1-6}$ alkyl, haloalkyl, carbocyclyl, heterocyclyl, carbocyclylalkyl or heterocyclylalkyl, wherein said carbocyclyl, heterocyclyl, carbocyclylalkyl or heterocyclylalkyl are each optionally substituted by one or more halo, $C_{1-4}$ alkyl or $C_{1-4}$ alkoxy;

$R^V$ is $C_{1-6}$ alkyl, haloalkyl, carbocyclyl or heterocyclyl;

p=1 or 2; and r=0, 1, 2, 3, 4 or 5;

with the proviso that the spiro ring is a stable chemical entity.

2. The compound of claim 1 wherein V is azetidin-1-yl, 2,5-dihydro-1H-pyrrol-1-yl, piperindin-1yl, piperazin-1-yl, pyrrolidin-1-yl, isoquinol-2-yl, pyridin-1-yl, 3,6-dihydropyridin-1-yl, 2,3-dihydroindol-1-yl, 1,3,4,9-tetrahydrocarbolin-2-yl, thieno[2,3-c]pyridin-6-yl, 3,4,10,10a-tetrahydro-1H-pyrazino[1,2-a]indol-2-yl, 1,2,4,4a,5,6-hexahydropyrazino[1,2-a] quinolin-3-yl, pyrazino[1,2-a]quinolin-3-yl, diazepan-1-yl, 1,4,5,6-tetrahydro-2H-benzo[f]isoquinolin-3-yl, 1,4,4a,5,6,10b-hexahydro-2H-benzo[f]isoquinolin-3-yl, 3,3 a,8,8a-tetrahydro-1H-2-aza-cyclopenta[a]inden-2-yl, or 2,3,4,7-tetrahydro-1H-azepin-1-yl, azepan-1-yl.

3. The compound of claim 1 wherein V' is phenyl substituted with 0-5 T, $C_{1-8}$alkylene-T, $(CR_b'R_c')_r$—O—$(CR_b'R_c')_r$-T, OH, Cl, F, Br, I, CN, $NO_2$, $OR^{IV}$, $CONR^IR^{II}$ or $NR^ICOR^{II}$.

4. The compound of claim 1 wherein V' is phenyl.

5. The compound of claim 1 wherein:
V is piperindin-1yl, piperazin-1-yl, pyrrolidin-1-yl, pyridin-1-yl or 3,6-dihydropyridin-1-yl and
V' is phenyl substituted with 0-3 $R_e$.

6. A composition comprising a compound of claim 1 and a pharmaceutically acceptable carrier.

7. A method for treating breast cancer in a mammal comprising administering to said mammal in need of such treatment a therapeutically effective amount of a compound according to claim 1.

8. A method for treating a cancer associated with activity of Her-2 sheddase in a mammal comprising administering to said mammal a therapeutically effective amount of a compound of claim 1, wherein said cancer is breast cancer, ovarian cancer, prostate cancer, non-small cell lung cancer, colon cancer, gastric cancer, pancreatic cancer or glioma.

9. The compound of claim 1, selected from:
(5,6-trans)-N-hydroxy-6-{[4-(3-methylphenyl)piperazin-1-yl]carbonyl}spiro[-2.5]octane-5-carboxamide;
(5,6-trans)-N-hydroxy-6-[(4-phenyl-3,6-dihydropyridin-1(2H)-yl)carbonyl]spiro[2.5]octane-5-carboxamide;
(5S,6S)—N-hydroxy-6-((4-phenylpiperazin-1-yl)carbonyl)spiro(2.5) octane-5-carboxamide;
(6S)—N-hydroxy-6-(((3R)-3-phenylpyrrolidin-1-yl)-carbonyl)spiro[2.5]octane-5-carboxamide;
(5S,6S)—N-hydroxy-6-{[4-(2-methyl-4-nitrophenyl)piperazin-1-yl]carbonyl}spiro[2.5]octane-5-carboxamide; and
(5S,6S)—N-hydroxy-6-[(4-phenyl-3,6-dihydropyridin-1(2H)-yl)carbonyl]spiro[2.5]octane-5-carboxamide,
or an enantiomer, diastereomer, solvate, or pharmaceutically acceptable salt thereof.

10. The compound of claim 1 wherein:
V is piperazin-1-yl, pyrrolidin-1-yl, or 3,6-dihydropyridin-1-yl and
V' is phenyl substituted with 0-3 $R_e$.

* * * * *

UNITED STATES PATENT AND TRADEMARK OFFICE
CERTIFICATE OF CORRECTION

PATENT NO. : 8,637,497 B2  
APPLICATION NO. : 13/184860  
DATED : January 28, 2014  
INVENTOR(S) : Wenqing Yao et al.

Page 1 of 1

It is certified that error appears in the above-identified patent and that said Letters Patent is hereby corrected as shown below:

On the Title Page:

Page 2, column 2, line 23 (Other Publications): delete "Brest" and insert -- Breast --

Page 3, column 2, line 13 (Other Publications): delete "Appin." and insert -- Appln. --

In the Claims:

Column 122, line 60 (Claim 1): "heterocylcylalkyl" and insert -- heterocyclylalkyl --

Column 123, line 36 (Claim 1): "piperidin-1yl" and insert -- piperidin-1-yl --

Column 124, line 1 (Claim 2): "3,3 a,8,8a" and insert -- 3,3a,8,8a --

Column 124, line 8 (Claim 2): "piperidin-1yl" and insert -- piperidin-1-yl --

Signed and Sealed this  
Seventh Day of July, 2015

Michelle K. Lee  
*Director of the United States Patent and Trademark Office*